(12) United States Patent
De Maio Domingos

(10) Patent No.: US 11,602,303 B2
(45) Date of Patent: Mar. 14, 2023

(54) METHODS AND SYSTEMS FOR PREVENTING, CORRECTING, TRANSFORMING, AND MODIFYING FACIAL, AESTHETICS, AND CONSULTING PATIENTS REGARDING THE SAME

(71) Applicant: Mauricio De Maio Domingos, São Paulo (BR)

(72) Inventor: Mauricio De Maio Domingos, São Paulo (BR)

(73) Assignee: MAURICIO DE MAIO DOMINGOS, São Paulo (BR)

( * ) Notice: Subject to any disclaimer, the term of this patent is extended or adjusted under 35 U.S.C. 154(b) by 750 days.

(21) Appl. No.: 16/483,400

(22) PCT Filed: Feb. 10, 2018

(86) PCT No.: PCT/IB2018/000207
§ 371 (c)(1),
(2) Date: Aug. 2, 2019

(87) PCT Pub. No.: WO2018/146550
PCT Pub. Date: Aug. 16, 2018

(65) Prior Publication Data
US 2020/0146615 A1    May 14, 2020

Related U.S. Application Data

(60) Provisional application No. 62/479,150, filed on Mar. 30, 2017, provisional application No. 62/479,139, (Continued)

(51) Int. Cl.
*A61B 5/00* (2006.01)
*G16H 20/40* (2018.01)
(Continued)

(52) U.S. Cl.
CPC .............. *A61B 5/442* (2013.01); *A61Q 19/00* (2013.01); *G06T 7/0012* (2013.01); *G16H 10/60* (2018.01);
(Continued)

(58) Field of Classification Search
CPC ........ A61B 5/442; G16H 20/40; G16H 10/60; G16H 50/20; G16H 40/63; A61Q 19/00;
(Continued)

(56) References Cited

U.S. PATENT DOCUMENTS 6,358,917 B1   3/2002  Carruthers et al.
8,286,639 B2 * 10/2012  Seckel .................... A61Q 19/08
601/17

(Continued)

FOREIGN PATENT DOCUMENTS

WO   WO 2008/143680 A1   11/2008
WO   WO 2012/112940 A1    8/2012

OTHER PUBLICATIONS

International Preliminary Report on Patentability of PCT/IB2018/000207 dated Aug. 22, 2019, 12 pages.
(Continued)

*Primary Examiner* — Gregory M Desire
(74) *Attorney, Agent, or Firm* — Squire Patton Boggs (US) LLP

(57) ABSTRACT

Provided herein are MD Codes, MD DYNA Codes, MD ASA, and Next Human system, and the methods of using them to diagnose and treat aesthetic conditions or disorders.

45 Claims, 155 Drawing Sheets

Related U.S. Application Data filed on Mar. 30, 2017, provisional application No. 62/477,312, filed on Mar. 27, 2017, provisional application No. 62/457,761, filed on Feb. 10, 2017.

(51) Int. Cl.

| | | |
|---|---|---|
| *G16H 10/60* | (2018.01) | |
| *G16H 50/20* | (2018.01) | |
| *G16H 40/63* | (2018.01) | |
| *A61Q 19/00* | (2006.01) | |
| *G06T 7/00* | (2017.01) | |
| *A61K 8/65* | (2006.01) | |
| *A61K 8/73* | (2006.01) | |
| *A61K 31/728* | (2006.01) | |
| *A61K 38/48* | (2006.01) | |

(52) U.S. Cl.
CPC ............. *G16H 20/40* (2018.01); *G16H 40/63* (2018.01); *G16H 50/20* (2018.01); *A61K 8/65* (2013.01); *A61K 8/735* (2013.01); *A61K 31/728* (2013.01); *A61K 38/4893* (2013.01); *G06T 2207/30088* (2013.01); *G06T 2207/30201* (2013.01)

(58) Field of Classification Search
CPC ......... G06T 7/0012; G06T 2207/30088; G06T 2207/30201; A61K 8/65; A61K 8/735; A61K 31/728; A61K 38/4893
See application file for complete search history.

(56) References Cited

U.S. PATENT DOCUMENTS

| | | | | |
|---|---|---|---|---|
| 8,871,184 B2* | 10/2014 | Tamarkin | ............... | A61P 1/00 |
| | | | | 552/202 |
| 9,579,057 B2* | 2/2017 | Bradu | ............... | A61B 5/4839 |
| 9,706,778 B2* | 7/2017 | Berkes | ............... | A61P 3/00 |
| 2007/0009555 A1* | 1/2007 | Borodic | ............. | A61K 38/4893 |
| | | | | 424/239.1 |
| 2009/0155314 A1 | 6/2009 | Tezel et al. | | |
| 2009/0156982 A1* | 6/2009 | Petrie | ..................... | A61K 9/127 |
| | | | | 604/290 |
| 2013/0123647 A1 | 5/2013 | Bhatnagar et al. | | |
| 2014/0039451 A1 | 2/2014 | Bangera et al. | | |
| 2014/0121636 A1 | 5/2014 | Boyden et al. | | |
| 2015/0126907 A1 | 5/2015 | Yu et al. | | |
| 2017/0259013 A1 | 9/2017 | Boyden et al. | | |

OTHER PUBLICATIONS

Unlocking the code to facial revitalization: A step-by-step approach to using injectables, Allergan Medical Institute, Produced by Allergan-EAME/0109/2015, Mar. 2015, 85 pages.

Interantional Search Report and Written Opinion of PCT/IB2018/000207 dated Jun. 29, 2018, 16 pages.

Mauricio De Maio et al., "Multi-Dimensional Aesthetic Scan Assessment (MD ASA™): Initial experience with a novel consultation, facial assessment, and treatment planning tool", J Cosmet Dermatol, Apr. 2021;00:1-14; DOI: 10.1111/jocd.14216.

Mauricio De Maio, "Myomodulation with Injectable Fillers: An Update", Aesthetic Plastic Surgery, published online Aug. 5, 2020, DOI 10.1007/s00266-020-01768-1.

Mauricio De Maio, "Myomodulation with Injectable Fillers: An Innovative Approach to Addressing Facial Muscle Movement", Aesth Plast Surg, Published online Mar. 16, 2018; https://doi.org/10.1007/s00266-018-1116-z.

Mauricio De Maio, "Correction to: MD Codes™ : A Methodological Approach to Facial Aesthetic Treatment with Injectable Hyaluronic Acid Fillers", Aesth Plast Surg, published online Feb. 17, 2021; https://doi.org/10.1007/s00266-020-01762-7.

Mauricio De Maio, "MD Codes™: A Methodological Approach to Facial Aesthetic Treatment with Injectable Hyaluronic Acid Fillers", Aesth Plast Surg, published online May 22, 2020; https://doi.org/10.1007/s00266-020-01762-7.

* cited by examiner

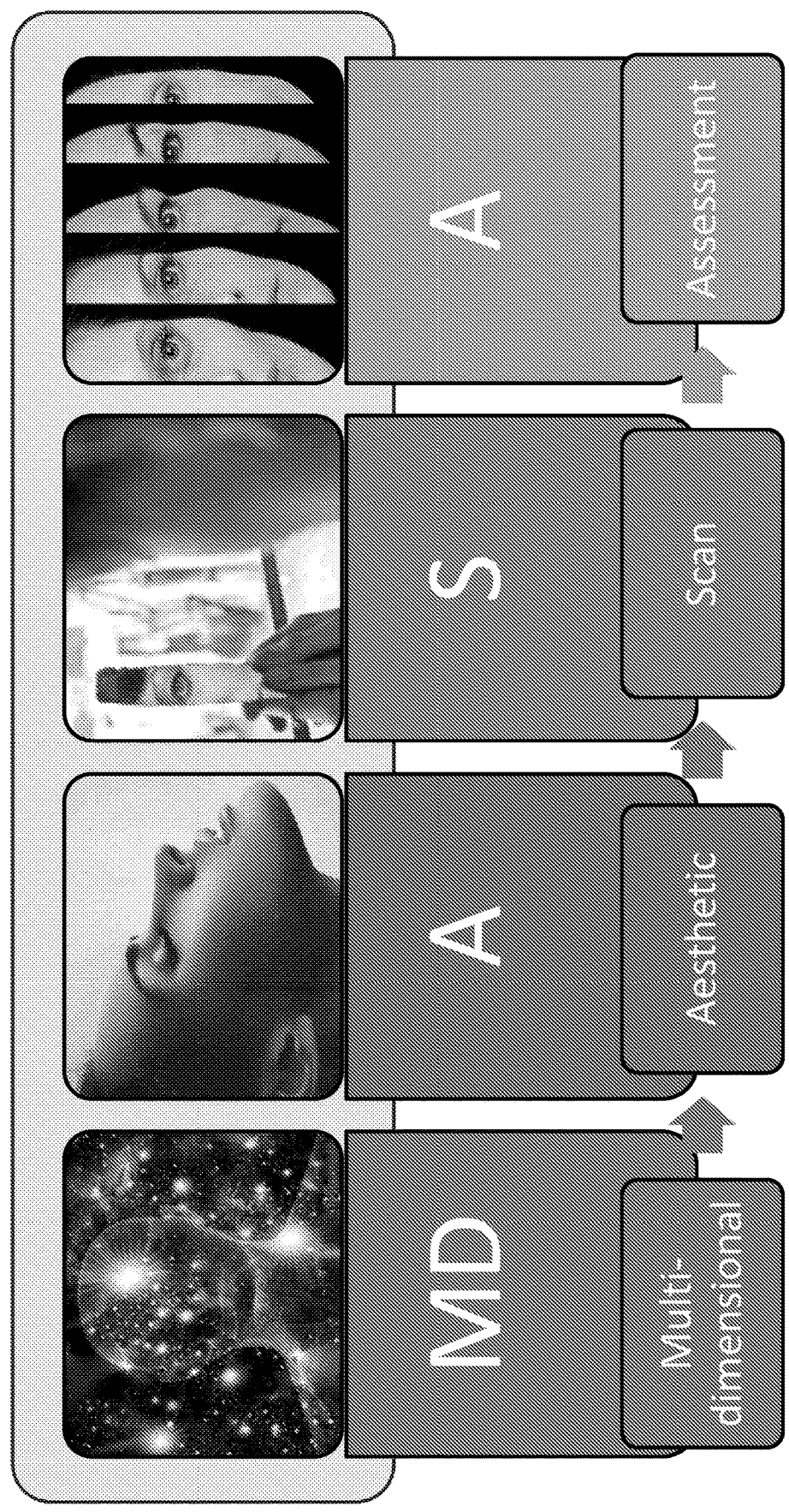
FIG. 1. – MD ASA acronym and meaning

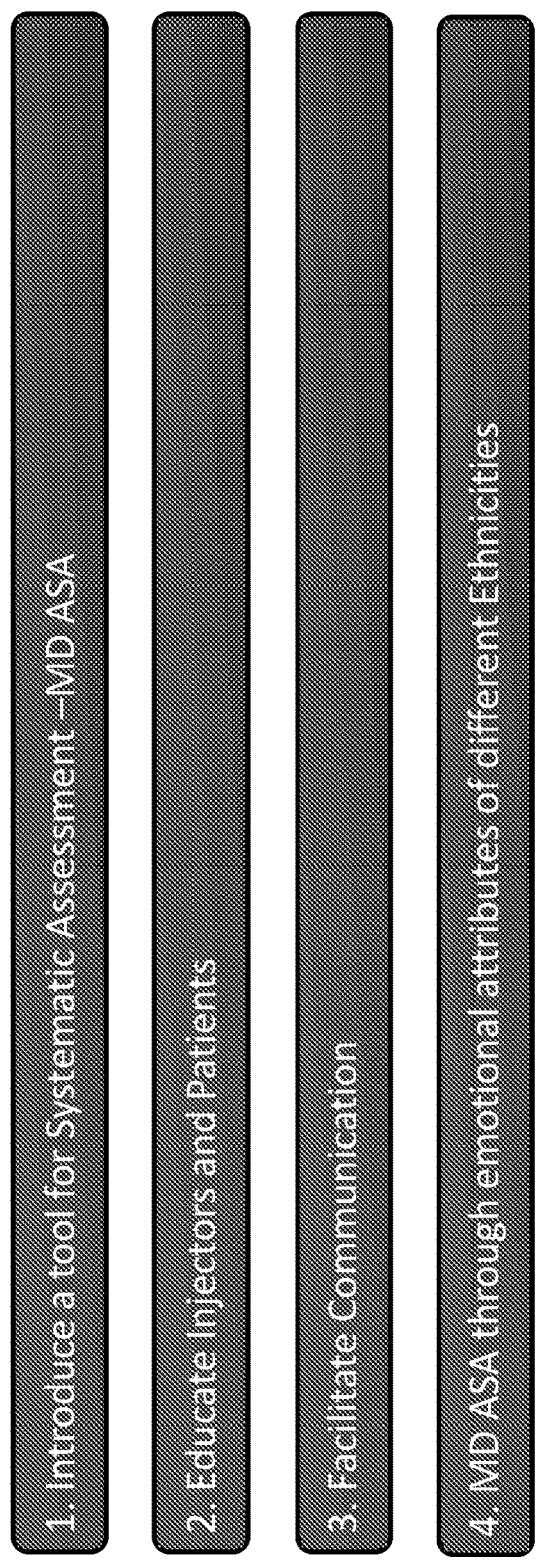
FIG. 2. – MD ASA objectives

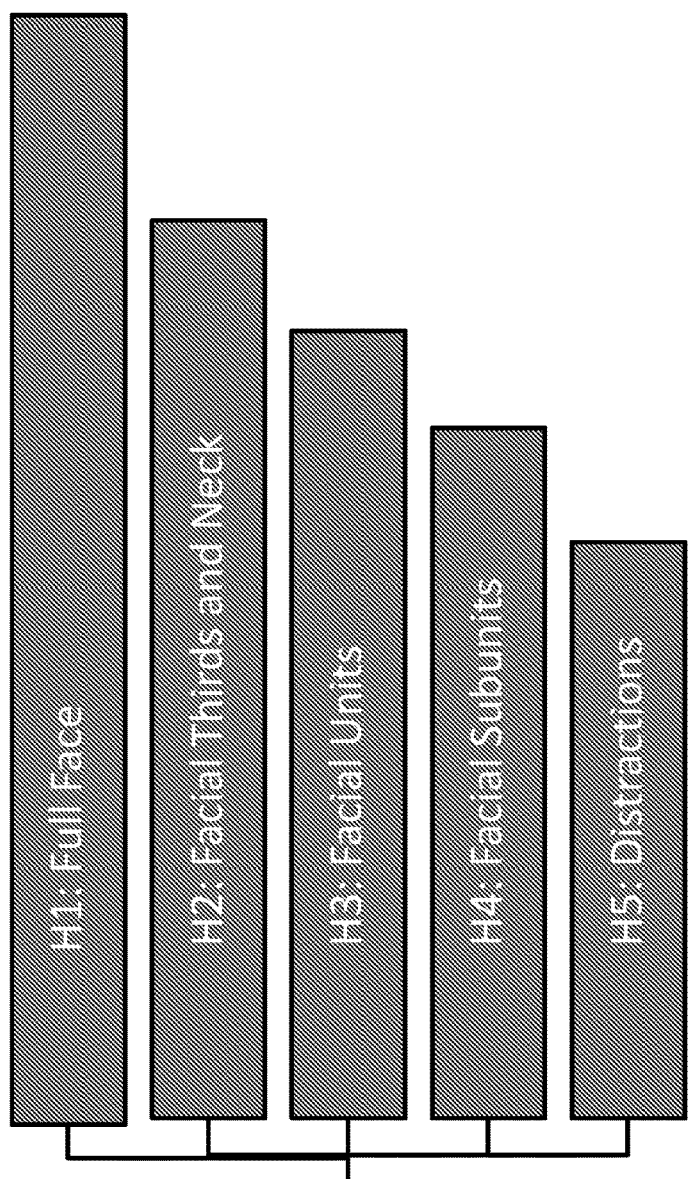
FIG. 3. – MD ASA through aesthetic hierarchy

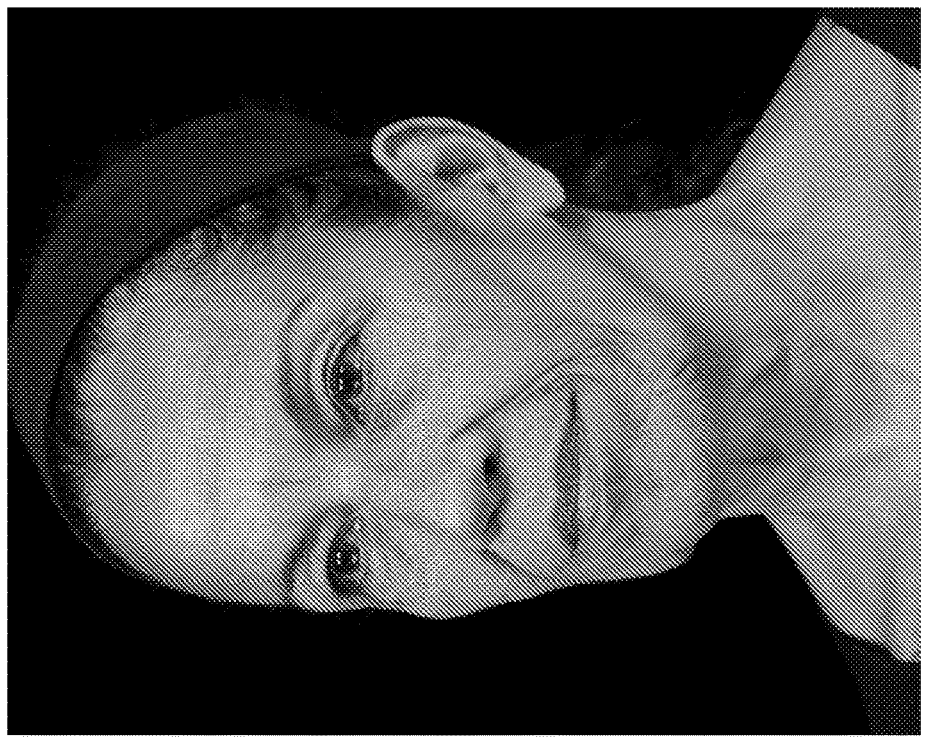
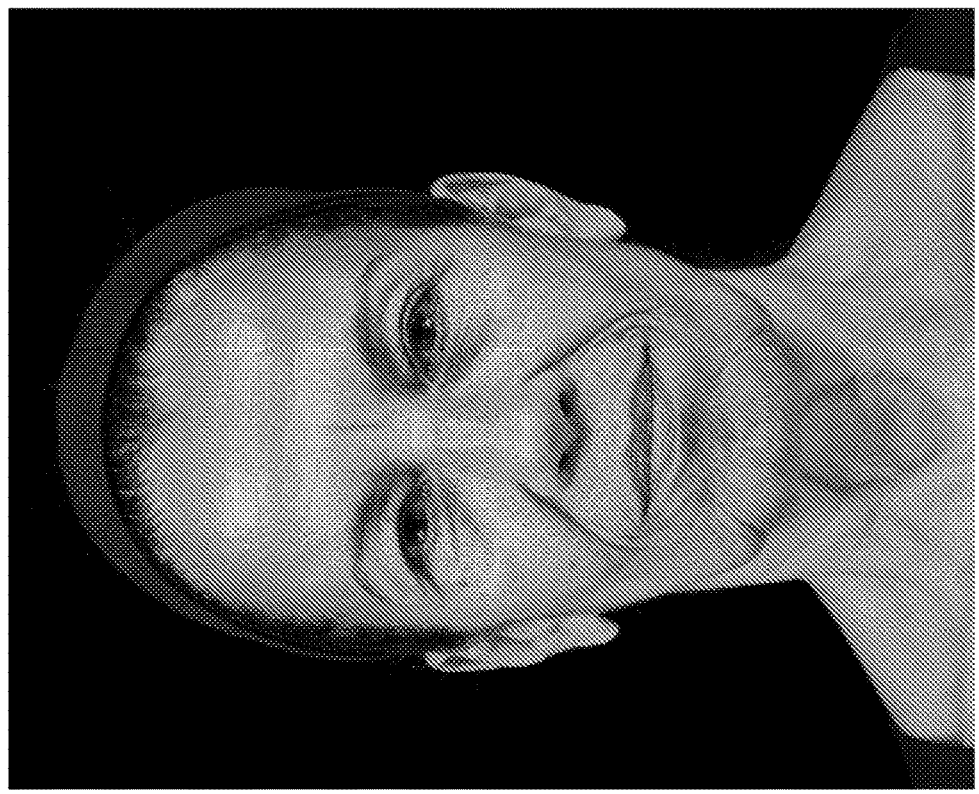
FIG. 4. — MD ASA through aesthetic hierarchy: H1 — Full face

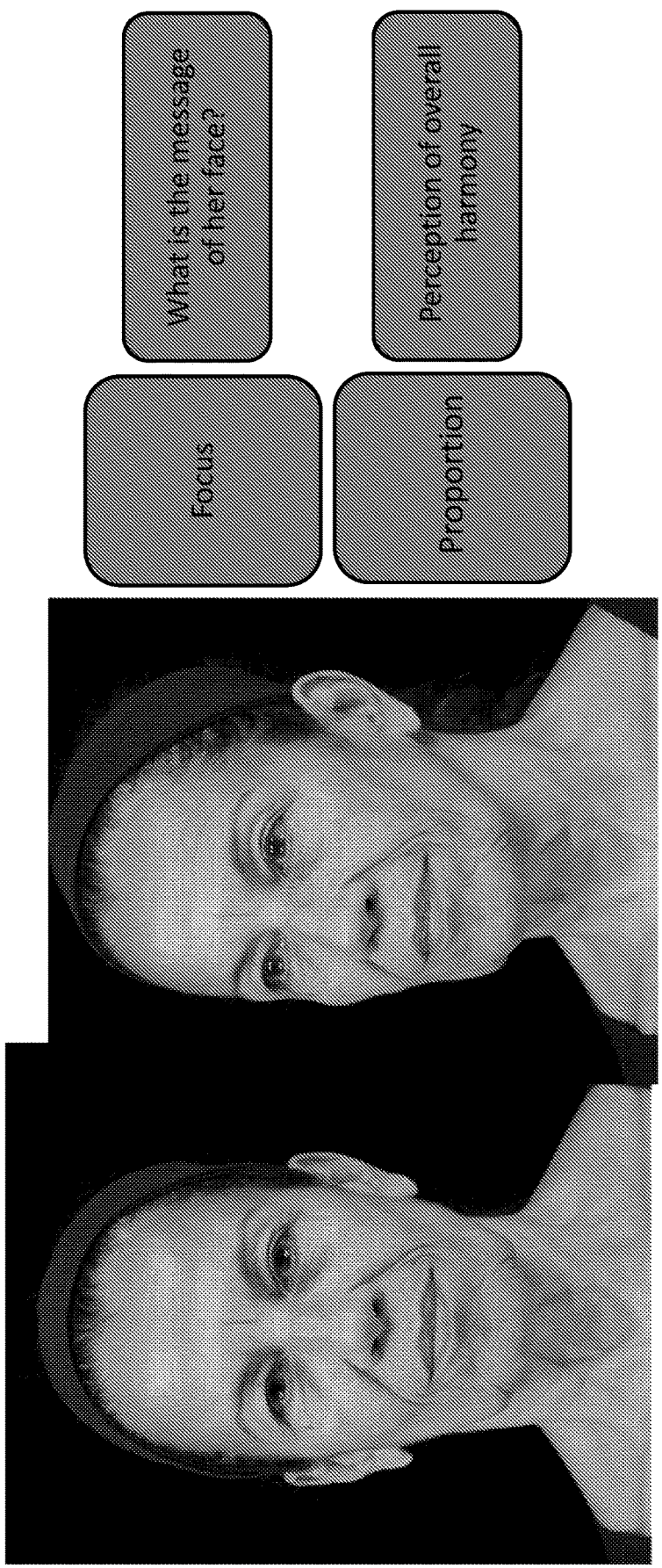
FIG. 5. — MD ASA through aesthetic hierarchy: H1 – Full face

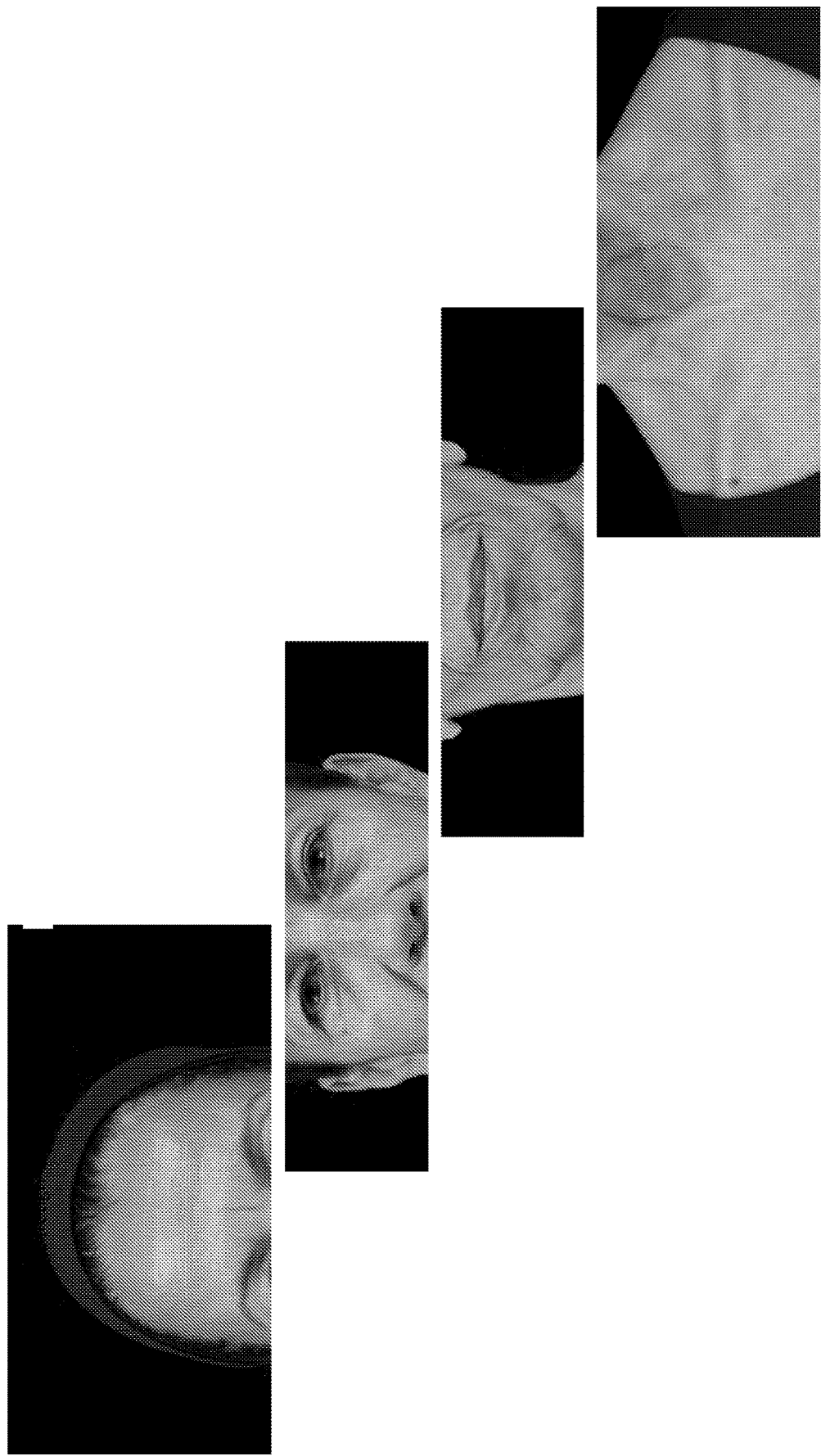
FIG. 6. - MD ASA through aesthetic hierarchy: H2 - Facial thirds and neck

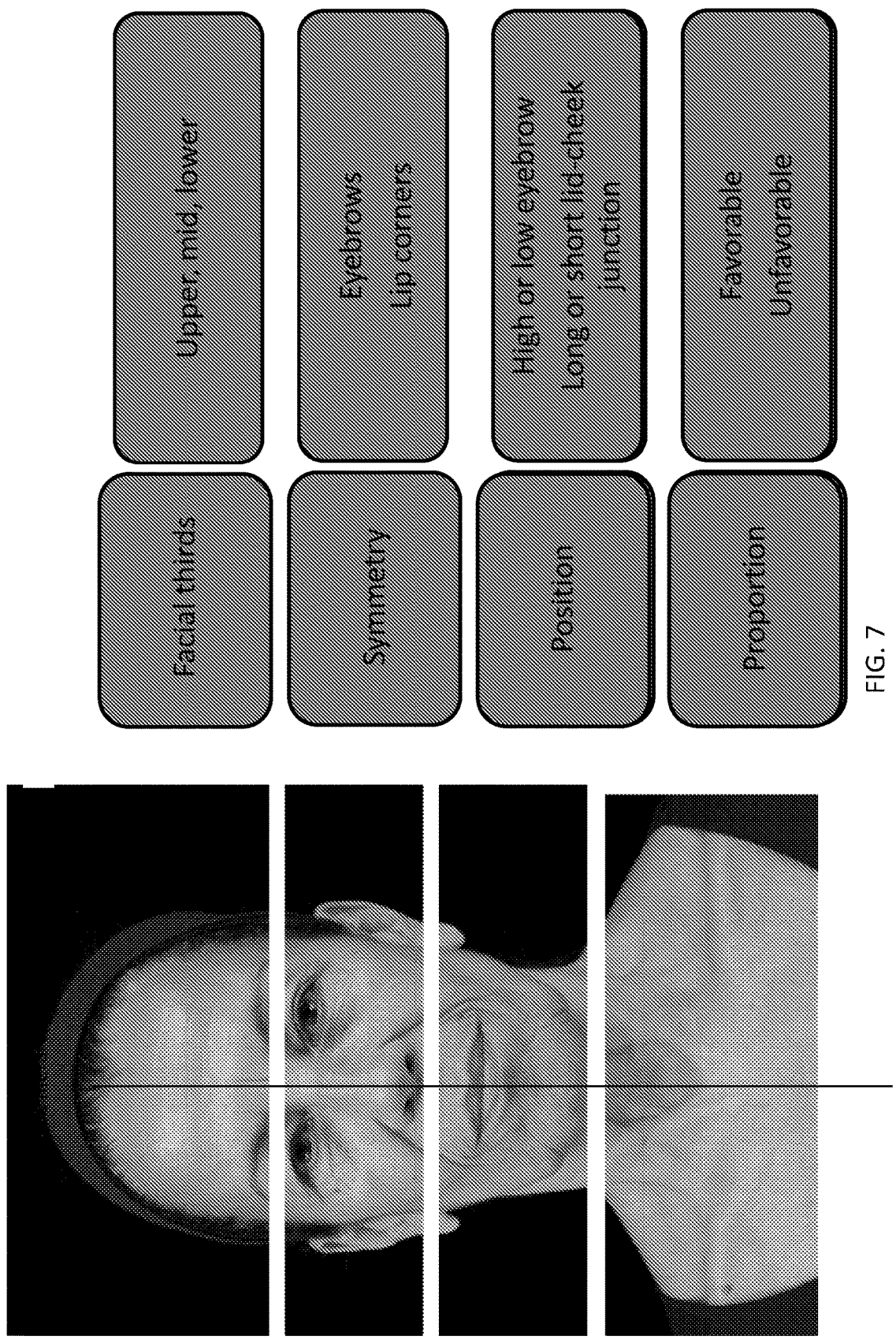
FIG. 7. - MD ASA through aesthetic hierarchy: H2 - Facial thirds and neck

FIG. 8. – MD ASA through aesthetic hierarchy: H3 – Facial units

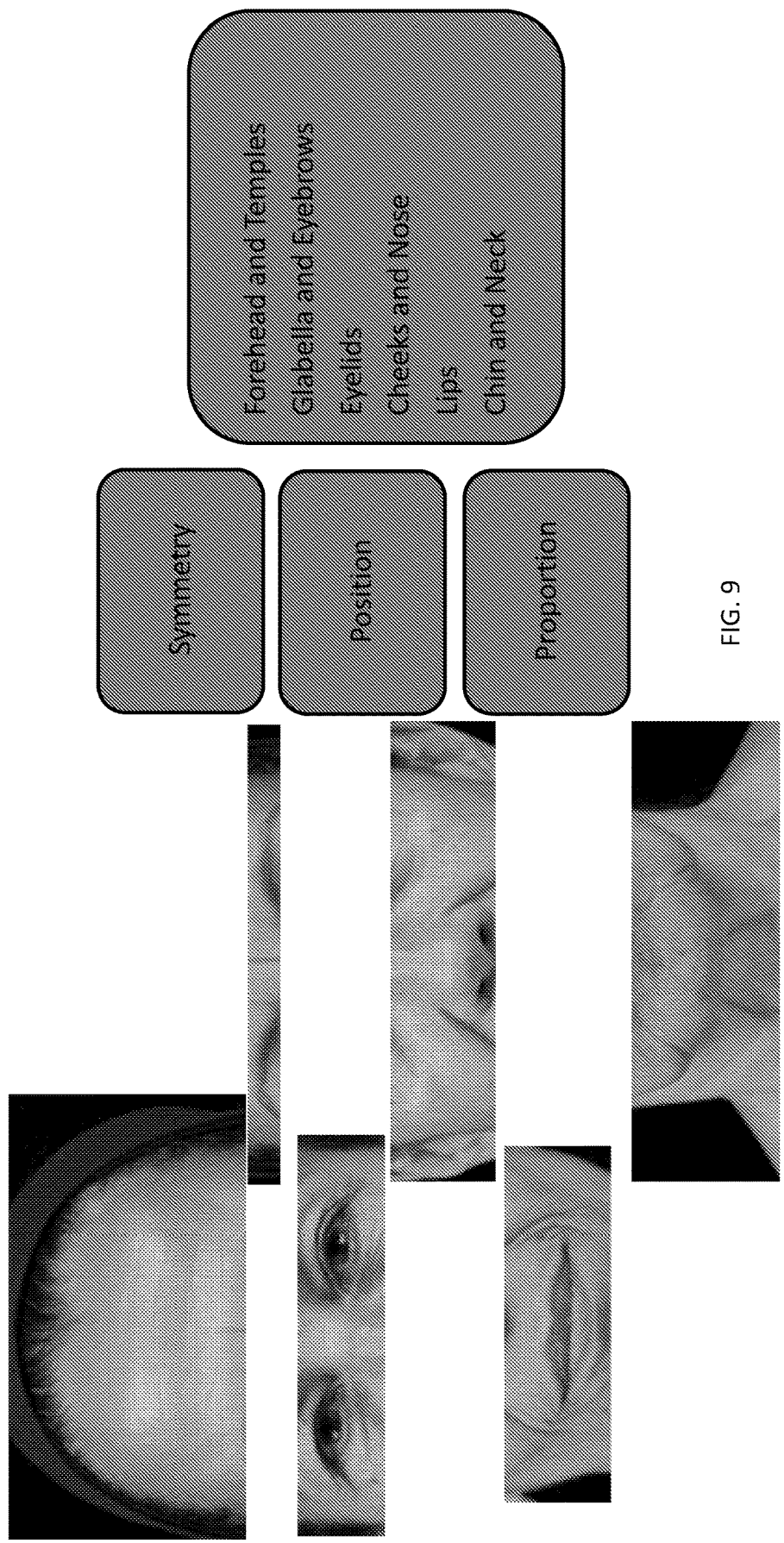
FIG. 9. – MD ASA through aesthetic hierarchy: H3 – Facial units

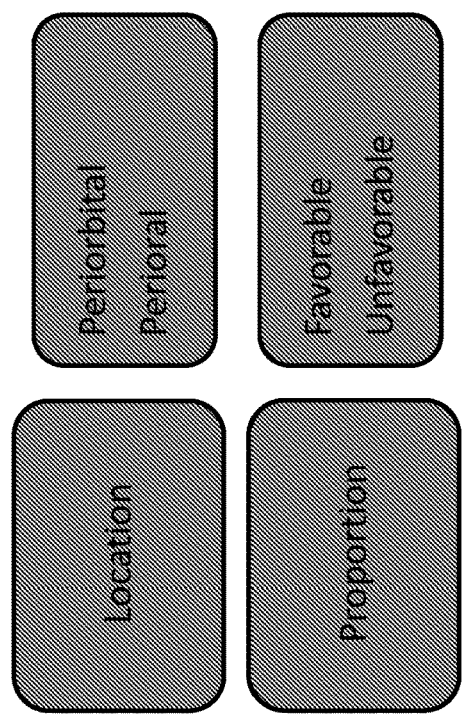
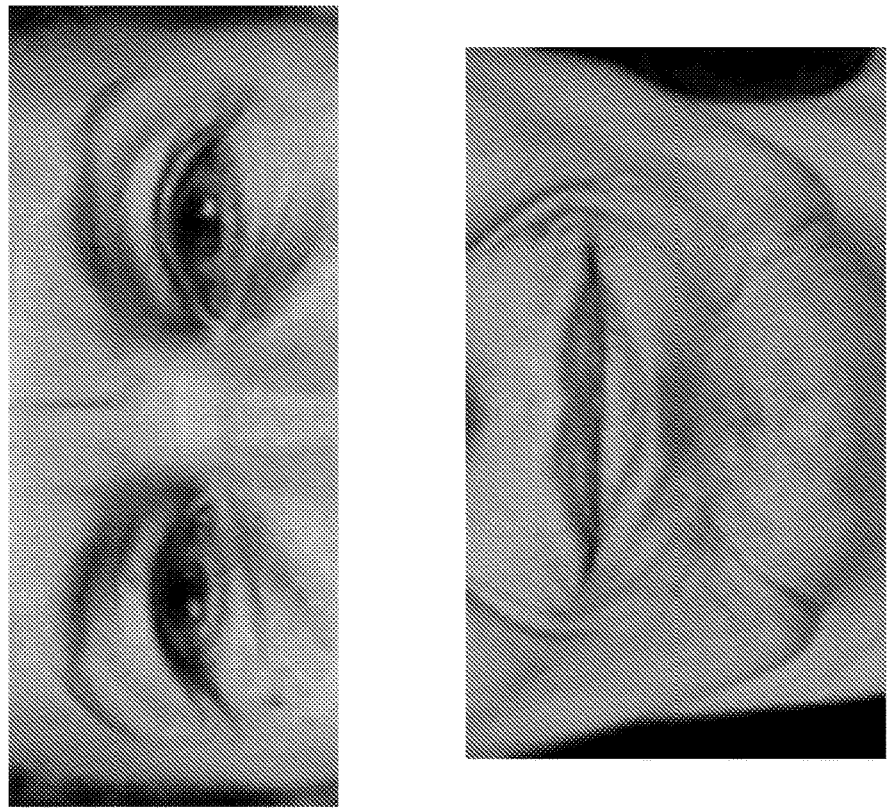
FIG. 10. – MD ASA through aesthetic hierarchy: H3 – Facial units
FIG. 10

FIG. 11.– MD ASA through aesthetic hierarchy: H4 – Facial Subunits

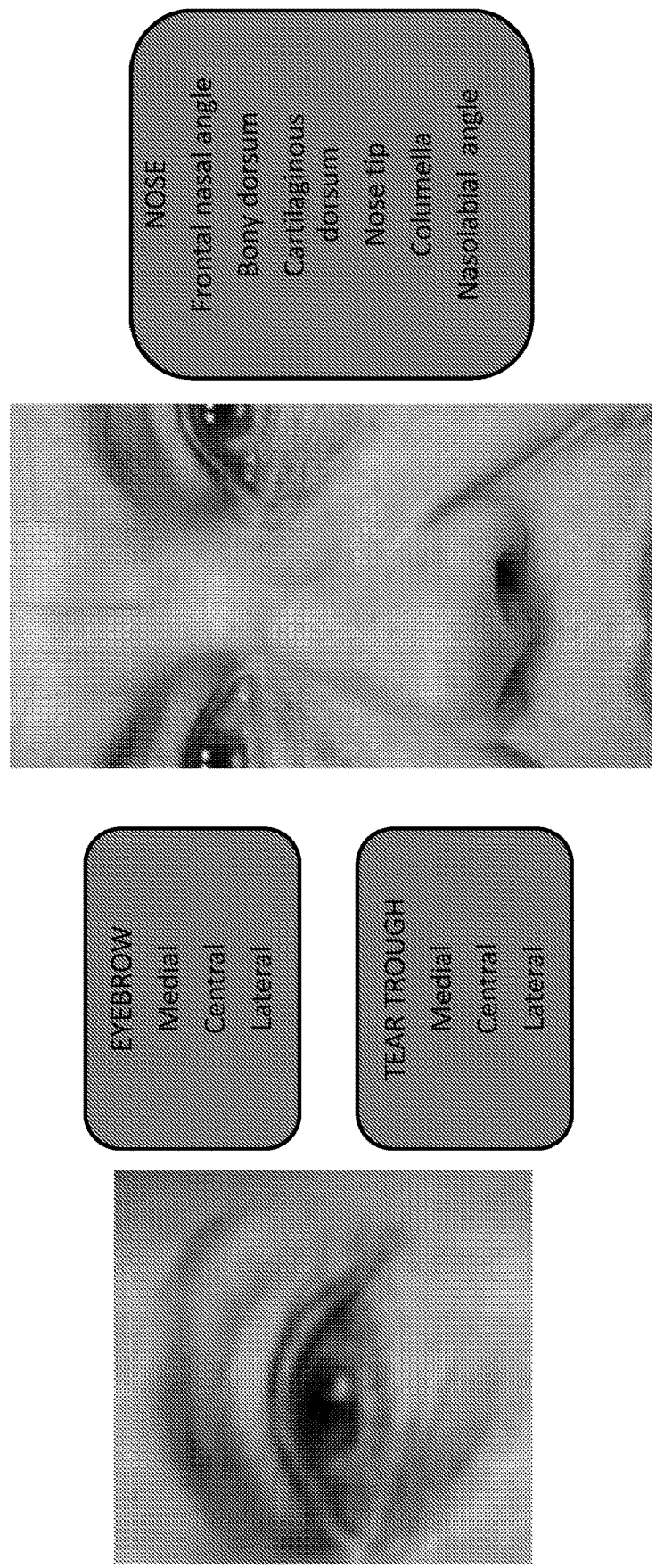
FIG. 12. – MD ASA through aesthetic hierarchy: H4 – Facial Subunits

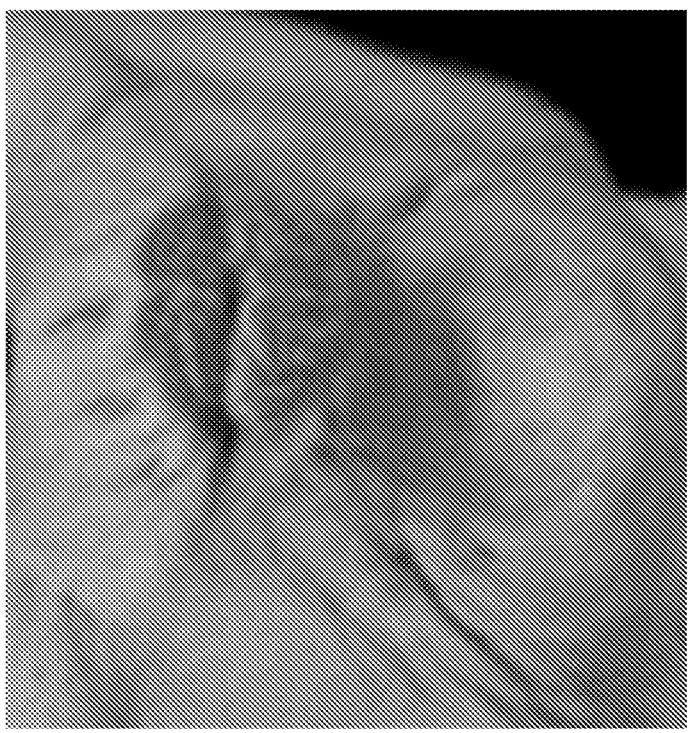
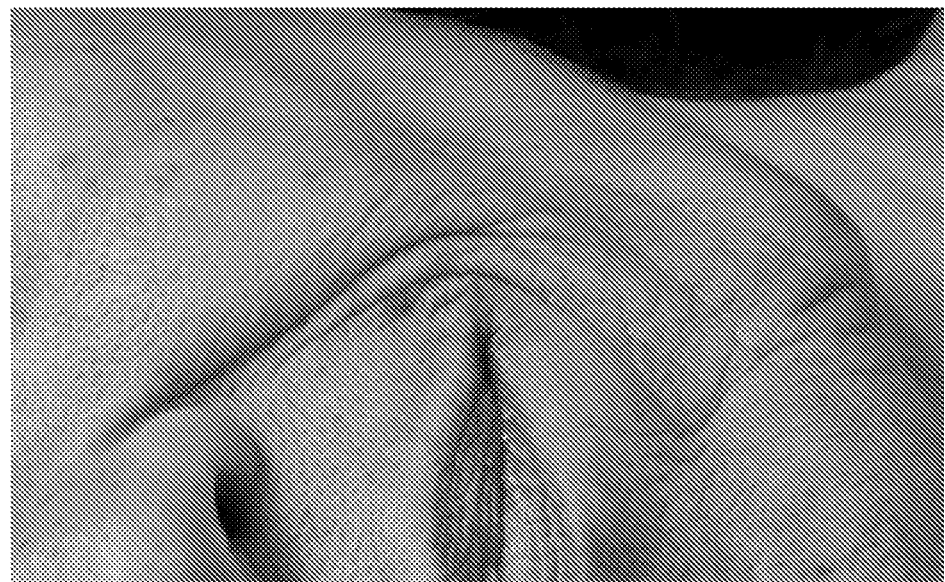
FIG. 13. – MD ASA through aesthetic hierarchy: H5 – Distractions
FIG. 13

FIG. 14. – MD ASA through aesthetic hierarchy: H5 – Distractions

FIG. 15. – MD ASA through aesthetic hierarchy: Clinical example

FIG. 16. – MD ASA through horizontal scanning: H2 – facial thirds and neck – focus on upper third

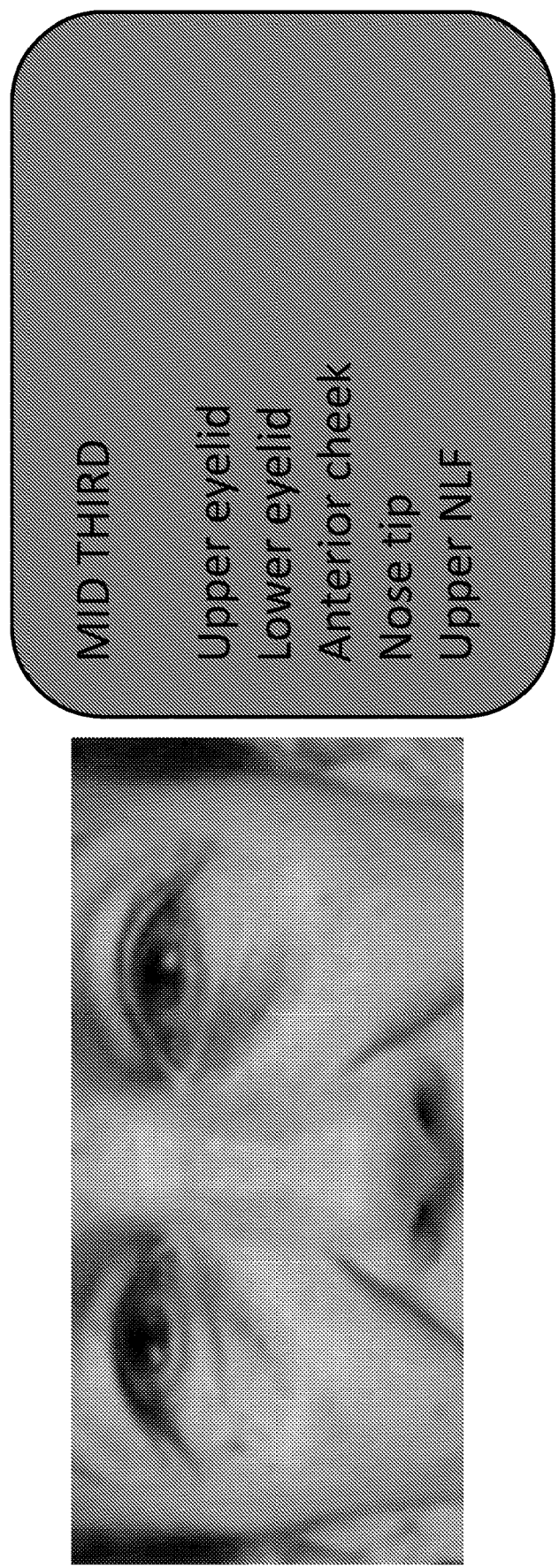
FIG. 17 – MD ASA through horizontal scanning: H2 – facial thirds and neck – focus on mid third

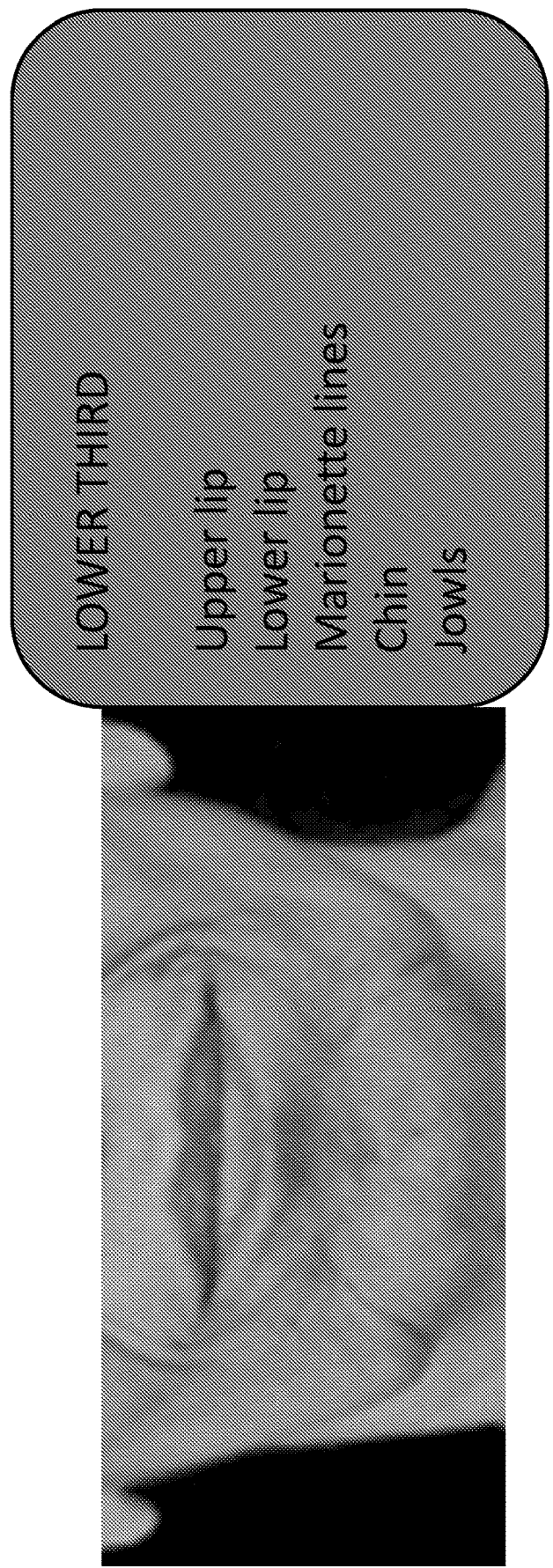
FIG. 18. — MD ASA through horizontal scanning: H2 – facial thirds and neck – focus on lower third

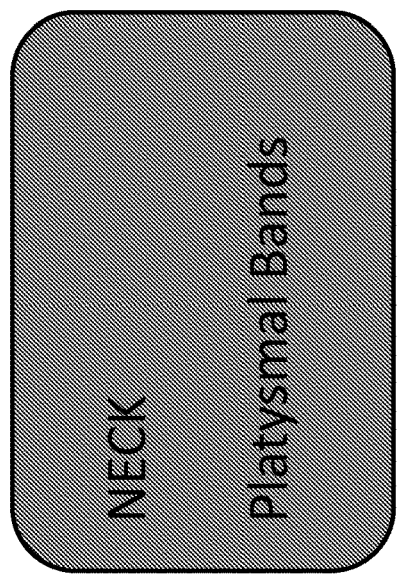
FIG. 19. – MD ASA through horizontal scanning: H2 – facial thirds and neck – focus on the neck

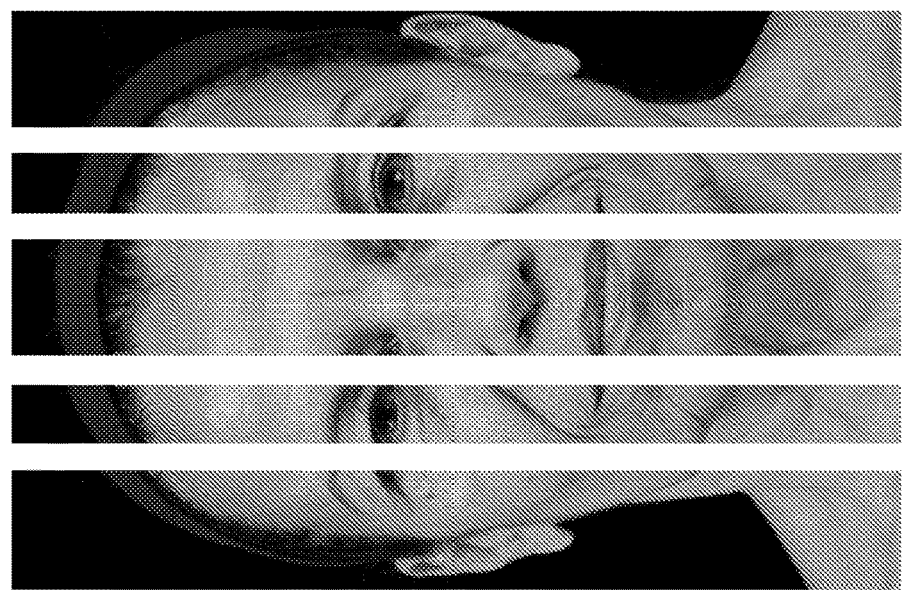
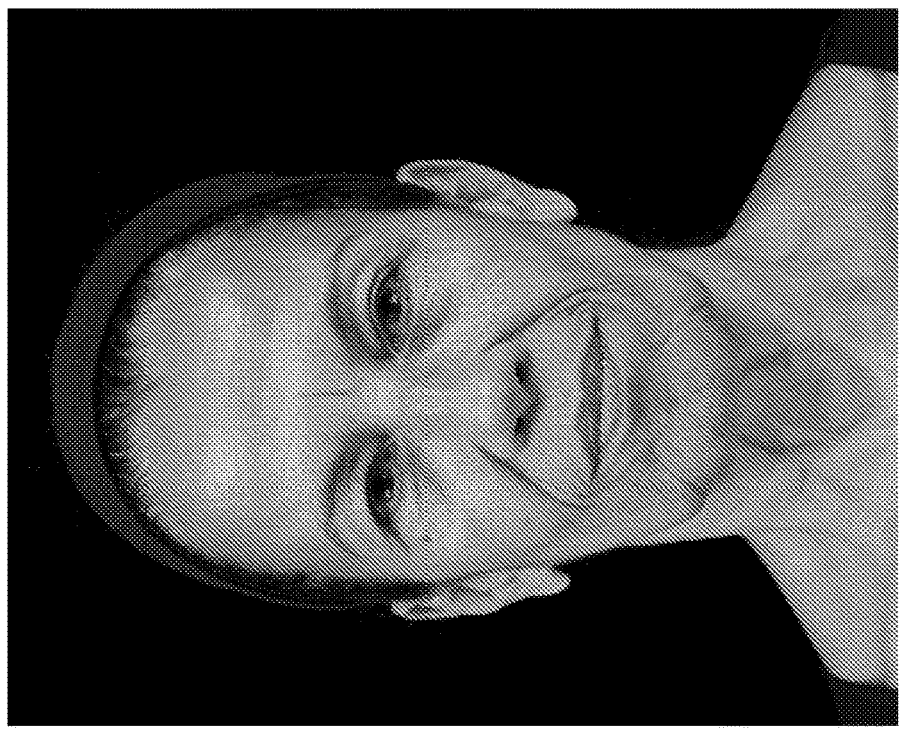
FIG. 20. – MD ASA through vertical scanning
FIG. 20

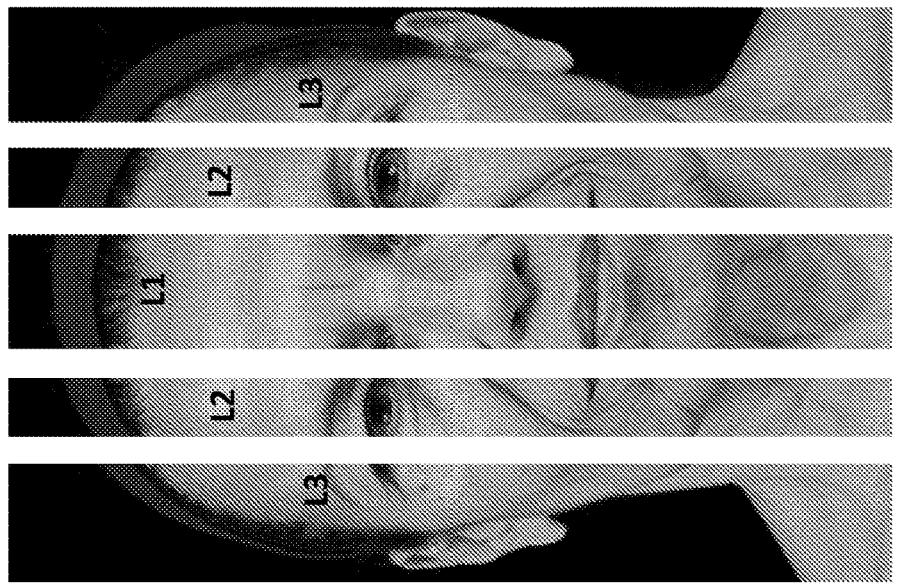
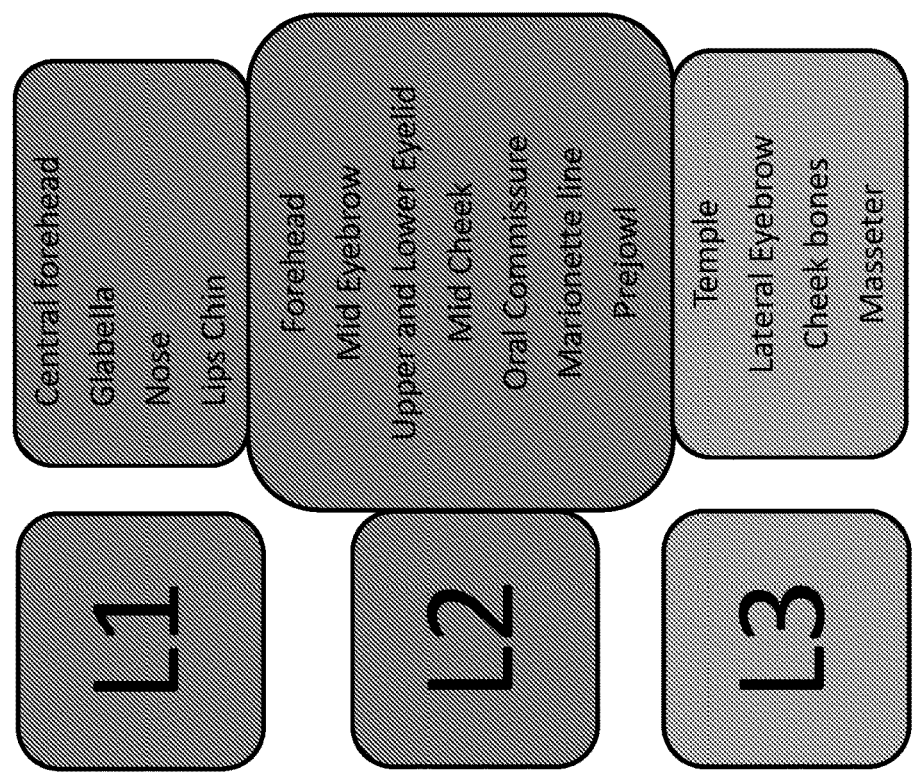
FIG. 21. – MD ASA through vertical scanning: L1 to L3
FIG. 21

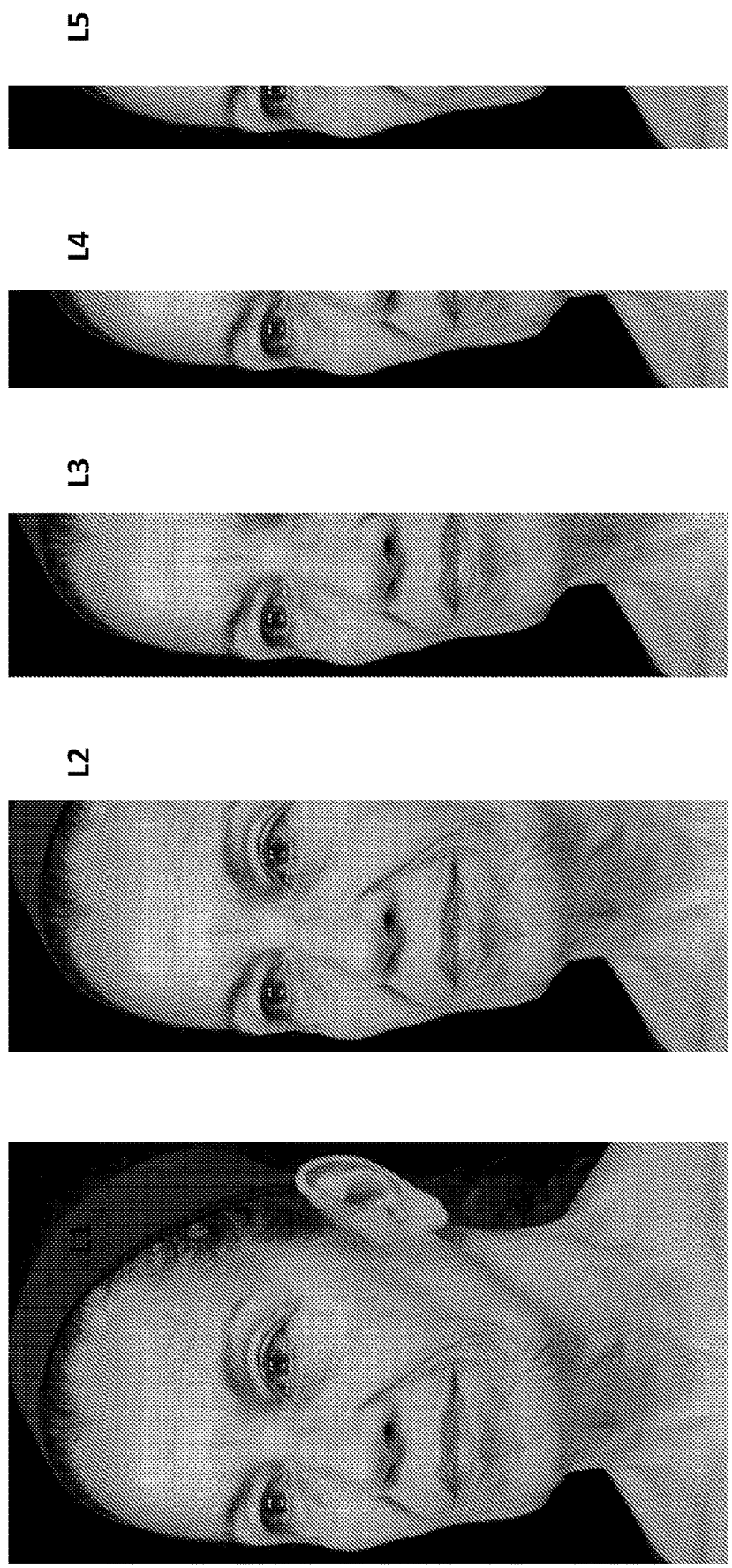
FIG. 22. – MD ASA through vertical scanning: Oblique view

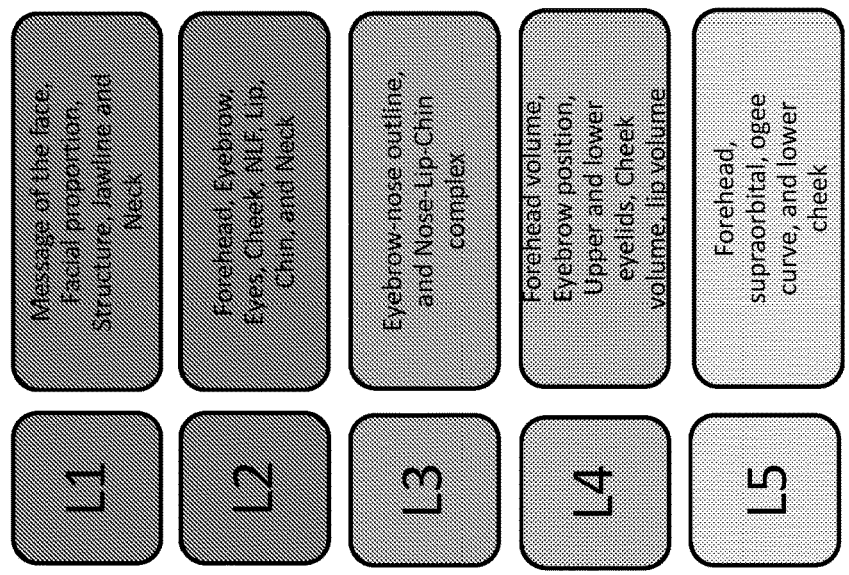
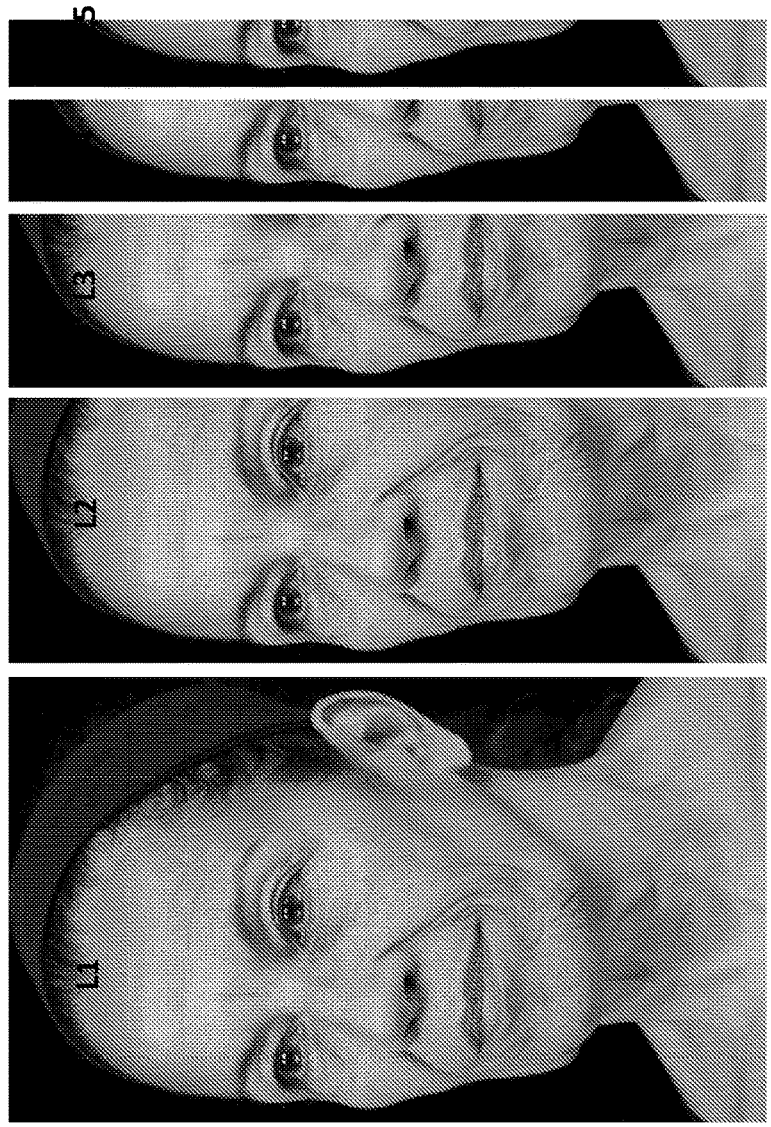
FIG. 23. – MD ASA through vertical scanning: Oblique view – L1 to L5

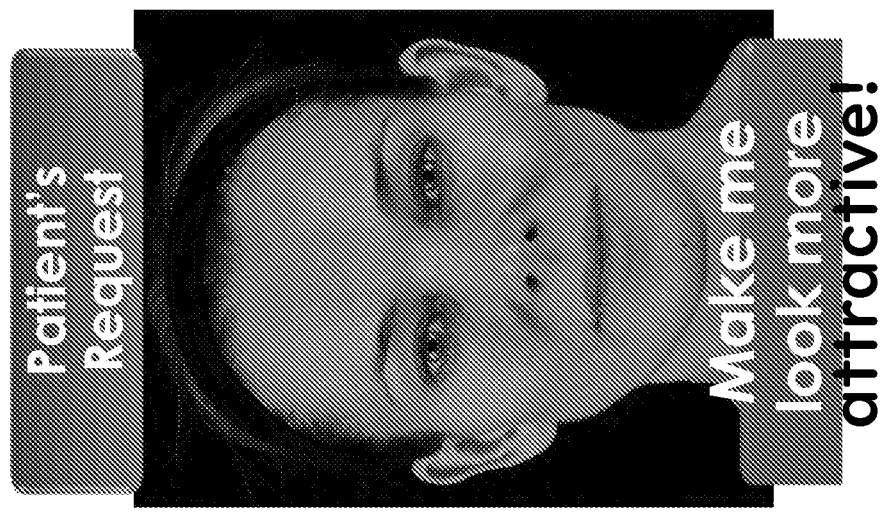
FIG. 24. – MD ASA: Assessing attractiveness in young patients

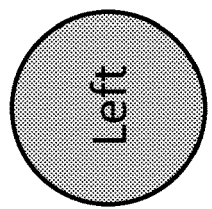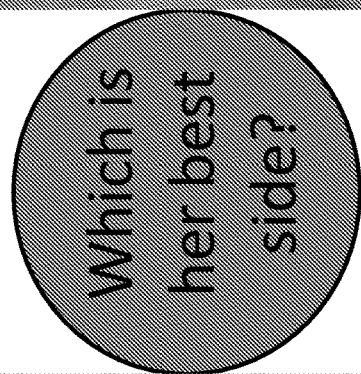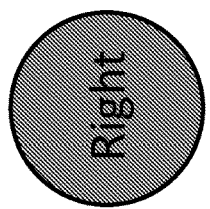
FIG. 25. - MD ASA: Assessing attractiveness in young patients
FIG. 25

FIG. 26. - MD ASA: Assessing attractiveness in young patients

FIG. 27. – MD ASA: Assessing attractiveness in young patients

FIG. 28. - MD ASA: Assessing attractiveness in young patients

FIG. 29. - MD ASA: Assessing attractiveness in young patients

FIG. 30. - MD ASA: Assessing attractiveness in young patients

FIG. 31. — MD ASA: Assessing attractiveness in young patients

Figure 32. – MD ASA: Assessing attractiveness in mature patients

Figure 33. – MD ASA: Assessing attractiveness in mature patients

FIG. 34. - MD ASA: Assessing attractiveness in mature patients

Figure 35. – MD ASA: Assessing attractiveness in mature patients

Figure 36. – Assessing genetic aging: Putting MD ASA into practice
Frontal view
Full Face Assessment at rest – H1
Analysis focusing on the messages of the face
Overall perception of proportion and harmony
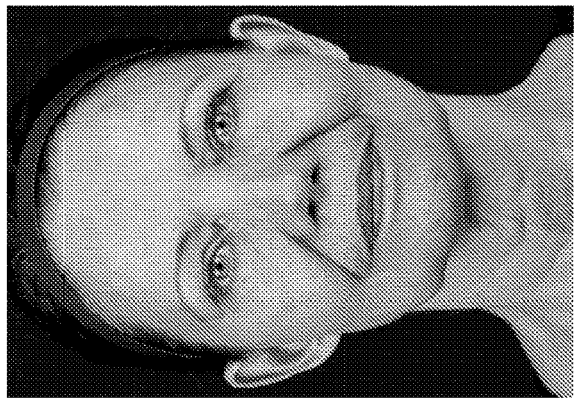
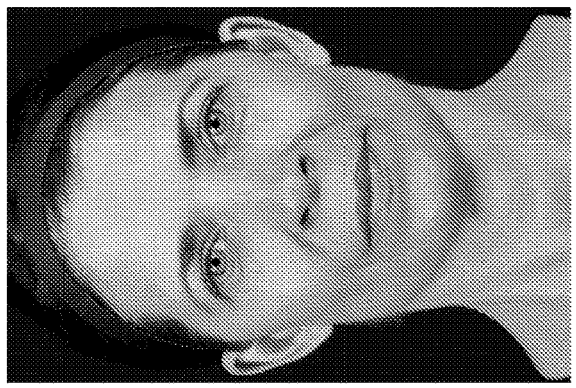
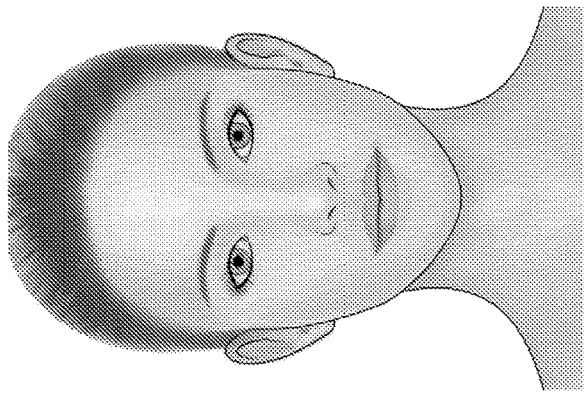
FIG. 36

Figure 37.– Assessing genetic aging: Putting MD ASA into practice

Frontal view

Upper Third Assessment - H2

Relationship of forehead height and width temples

Positon of eyebrows

Forehead lines

Glabella lines

Figure 39. – Assessing genetic aging: Putting MD ASA into practice
Frontal view
Lower Third Assessment - H2
Central and lower NLF
Upper lip
Philtrum columns
Vermillion
Oral commissure
Marionette lines
Chin
Prejowl
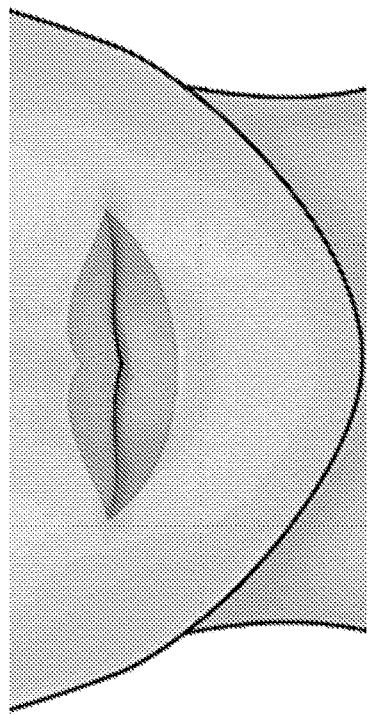
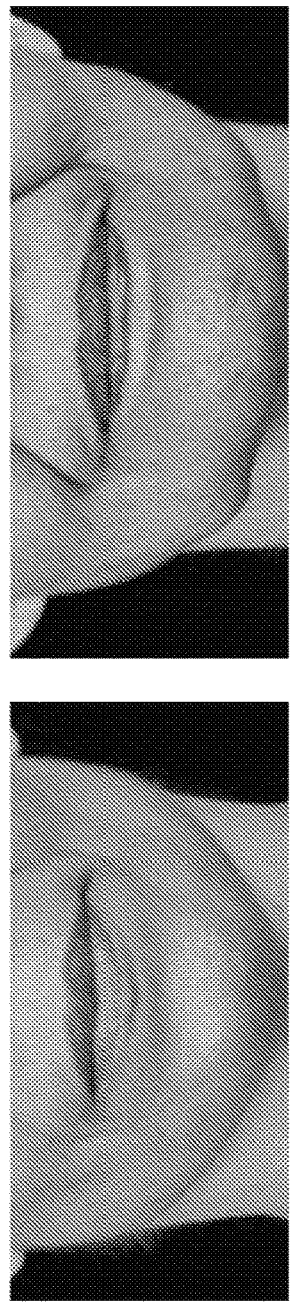
FIG. 39

Figure 40. – Assessing genetic aging: Putting MD ASA into practice

Frontal view

Neck Assessment - H2

Saggy Skin
Submental fat
Medial platysmal bands
Lateral platysmal bands
Horizontal neck lines Figure 41. – Assessing genetic aging: Putting MD ASA into practice
Vertical Scanning Assessment at rest – L3
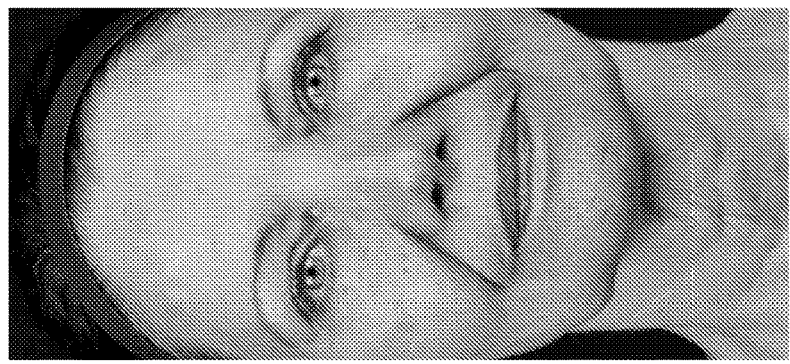
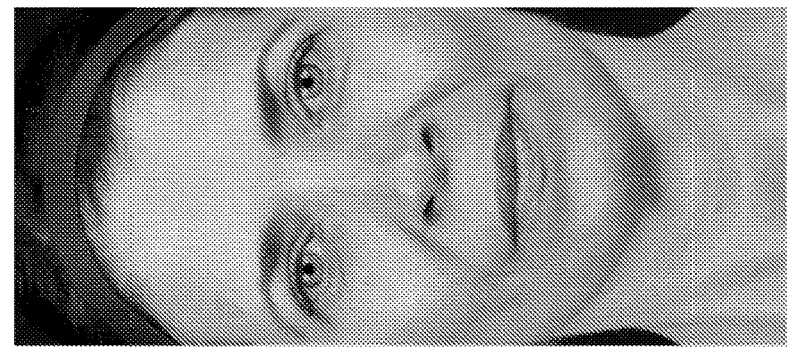
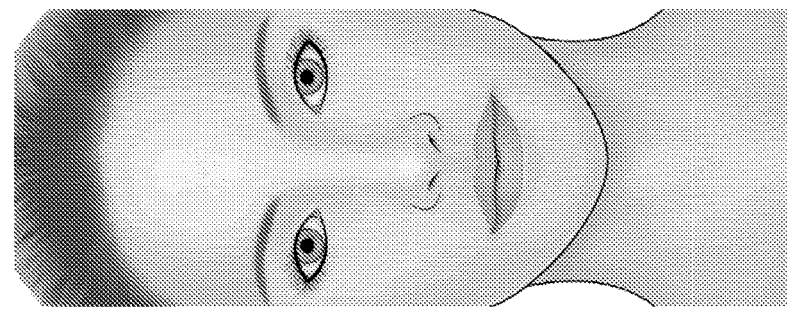
Analysis focus on the impact of central part of the face showing the relationship of cheeks and nasolabial folds
Focus on the relationship of eyes-nose-chin complex
FIG. 41

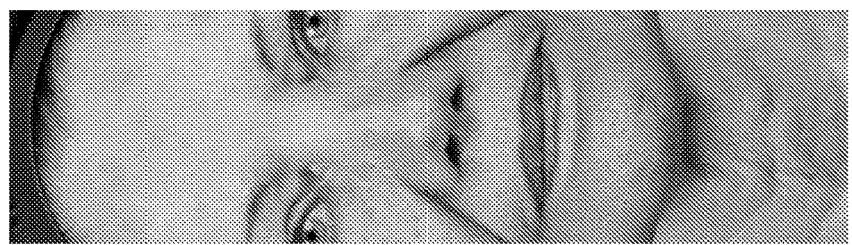
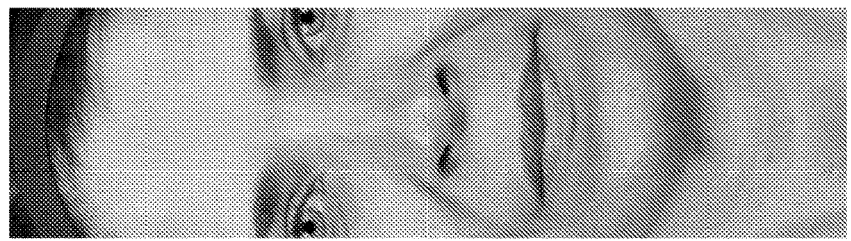
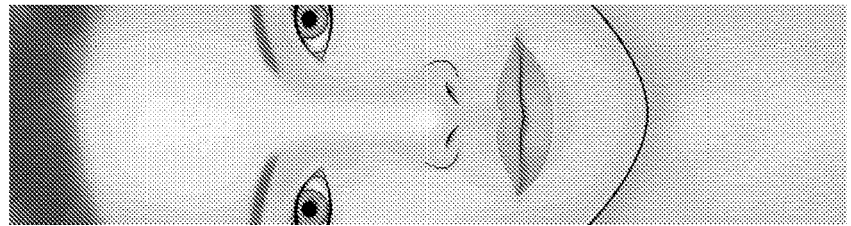
Figure 42. – Assessing genetic aging: Putting MD ASA into practice
Vertical Scanning Assessment at rest – L2
Analysis focus on central forehead and glabella areas
Relationship of the nose and mouth width
Focus on chin apex and central neck
FIG. 42

Figure 44. – Assessing genetic aging: Putting MD ASA into practice
Full Face Assessment at rest
Symmetry assessment
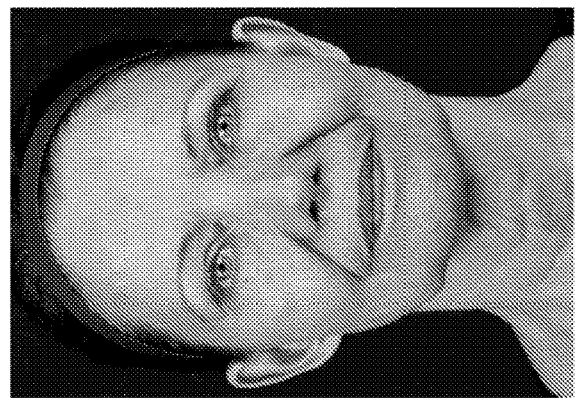
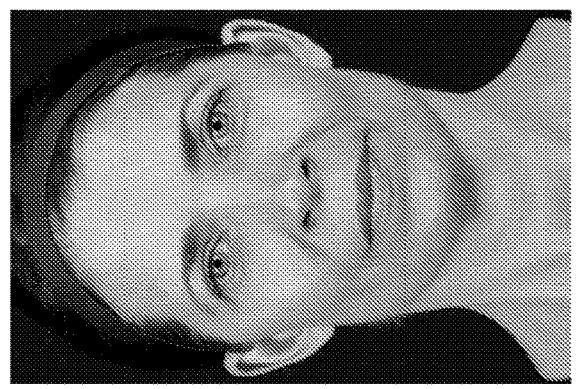
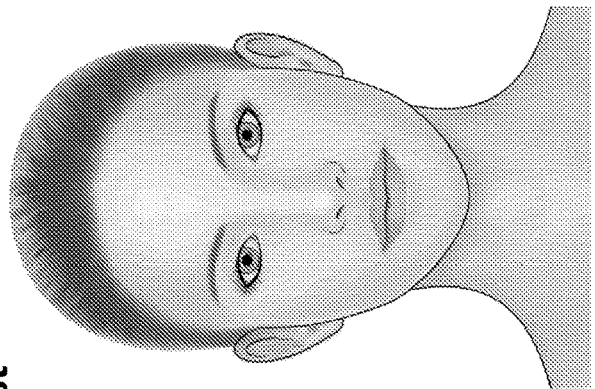
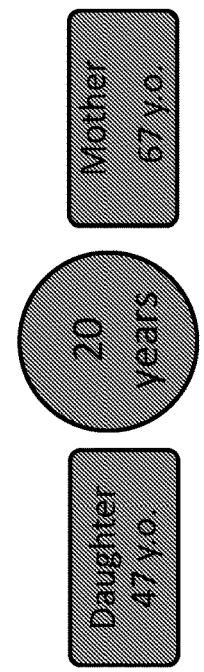
FIG. 44

Figure 45. – Assessing genetic aging: Putting MD ASA into practice
Full Face Assessment at rest
Symmetry assessment
Focus on
- Eyebrow position
- Nose deviation
- Chin deviation
- Platysmal bands
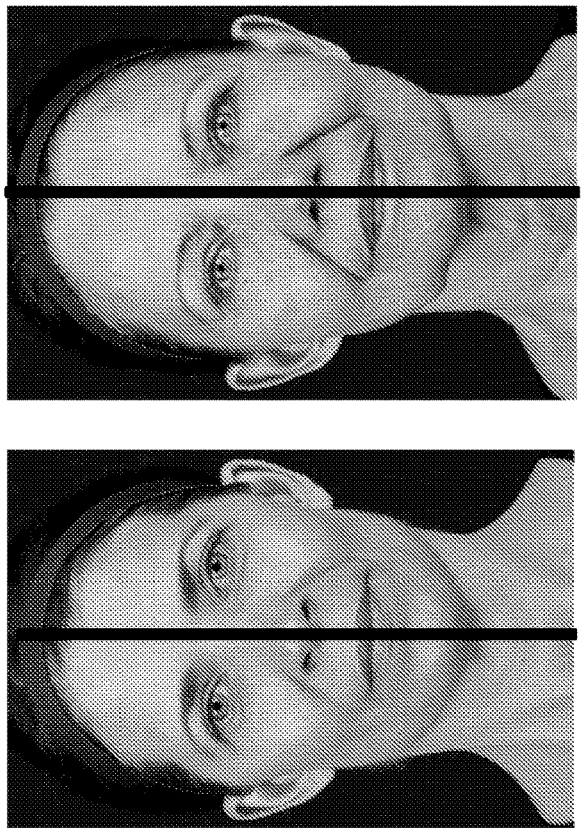
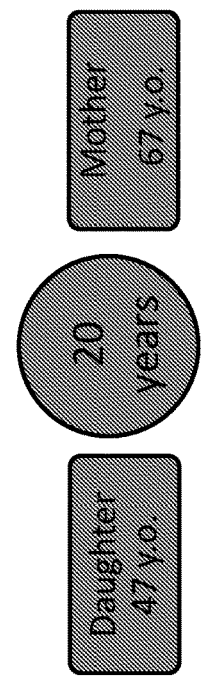
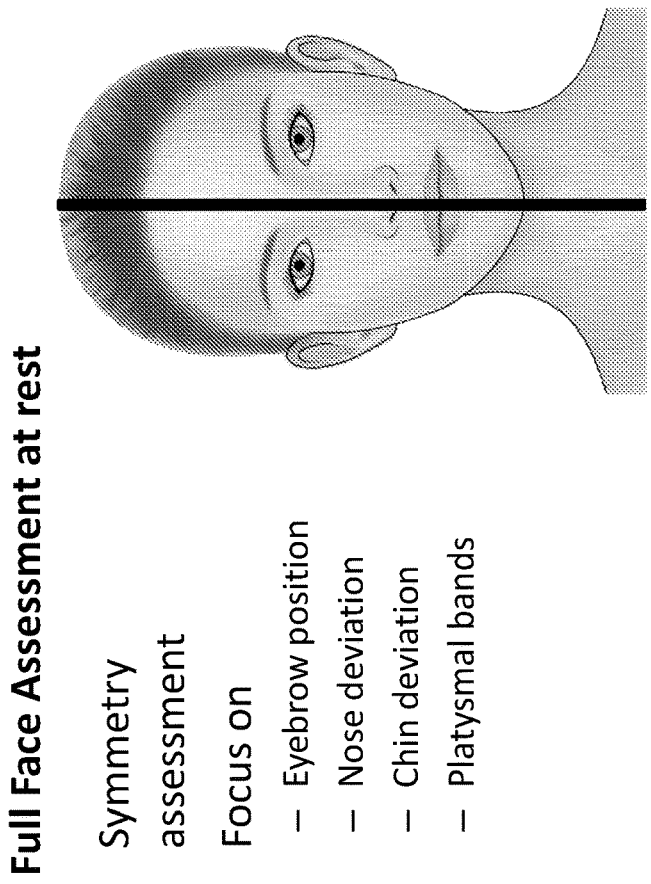
FIG. 45

Figure 46. – Assessing genetic aging: Putting MD ASA into practice
Full Face Assessment at rest
Symmetry assessment
Focus on:
- Medial eyebrow
- Medial canthus
- Nasal flare
- NLF
- Vermillion volume
- Prejowl sulcus
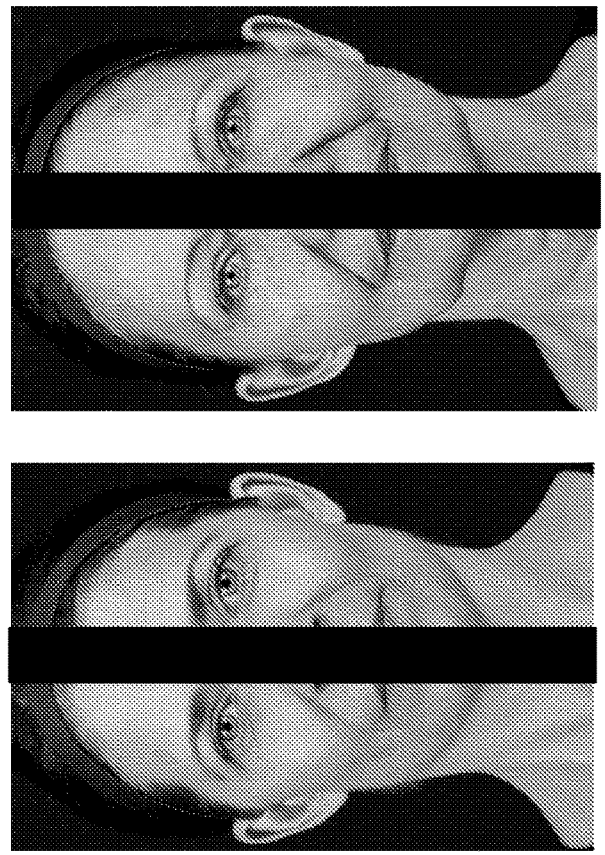
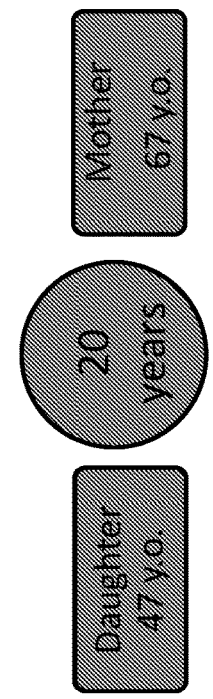
FIG. 46

Figure 47. – Assessing genetic aging: Putting MD ASA into practice
Full Face Assessment at rest
Symmetry assessment
Focus on:
- Central and lateral eyebrow
- Upper eyelid
- Lateral canthus
- Cheek
- Masseter
- Jawline
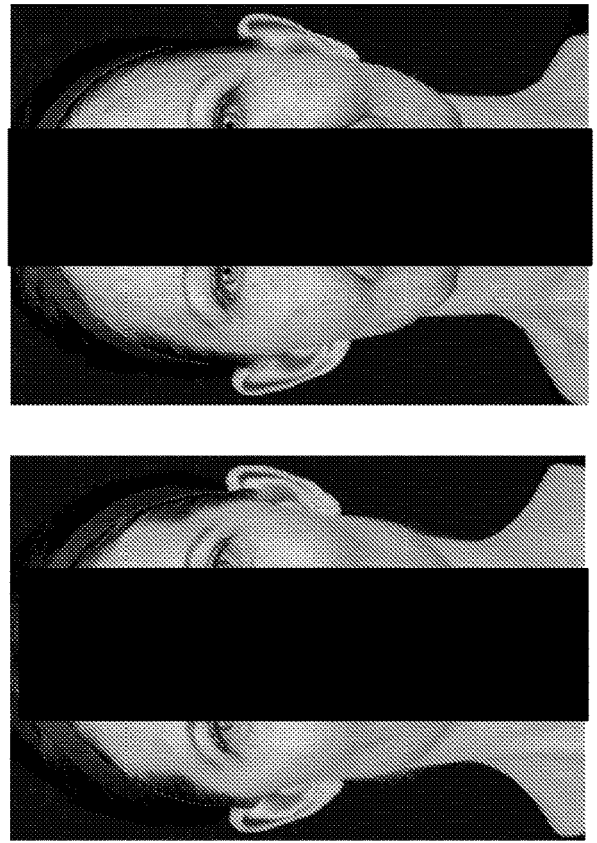
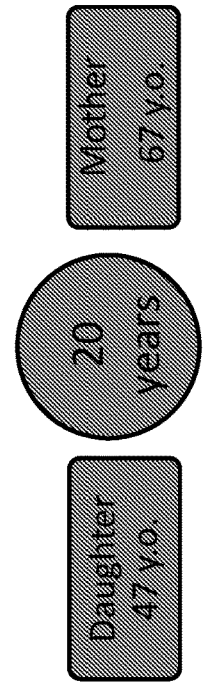
FIG. 47

Figure 48. – Assessing genetic aging: Putting MD ASA into practice
Full Face Assessment at rest
Symmetry
assessment
Focus on:
- Temples
- Zygomatic arch
- Ear
- Masseter
Facial widths
- Bitemporal
- Bizygomatic
- bigonial
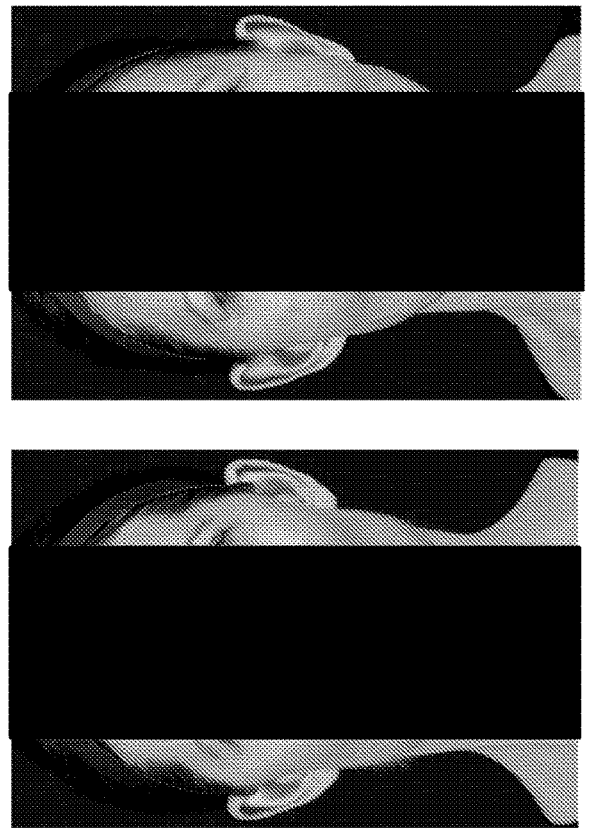
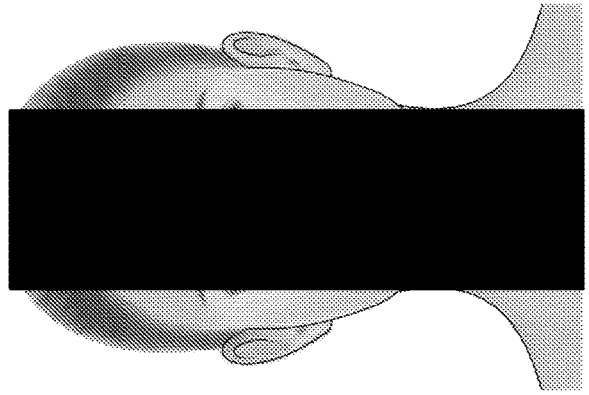
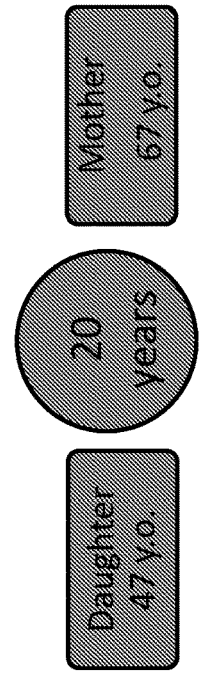
FIG. 48

Figure 49. – Assessing genetic aging: Putting MD ASA into practice
Vertical Assessment at rest – Hemiface
Analysis focus on relationships among structures
- Temples
- Lateral brow
- Zygomatic arc
- Ear
- Masseter
- Neck
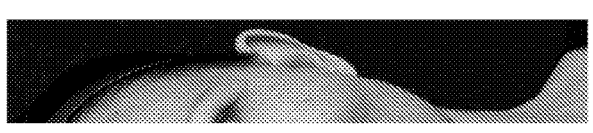
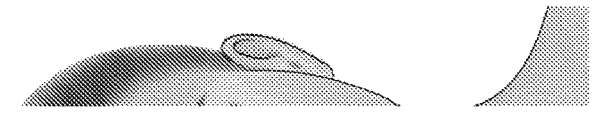
FIG. 49

Figure 50.– Assessing genetic aging: Putting MD ASA into practice
Vertical Assessment at rest – Hemiface
Analysis focus on relationships among structures
— Forehead
— Central brow
— Lateral canthus
— Midpupillary line
— Anterior cheek
— Jawline
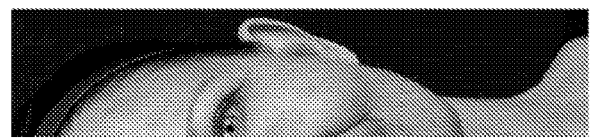
FIG. 50

Figure 51. – Assessing genetic aging: Putting MD ASA into practice
Vertical Assessment at rest – Hemiface
Analysis focus on
relationships among
structures
- Forehead height
- medial canthus
- Midpupillary line
- NLF
- Oral commissure
- Pre-jowl
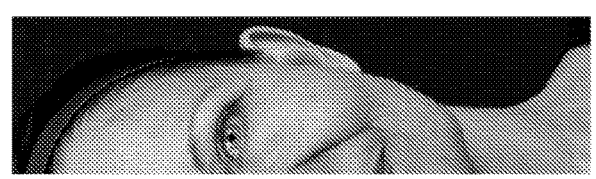
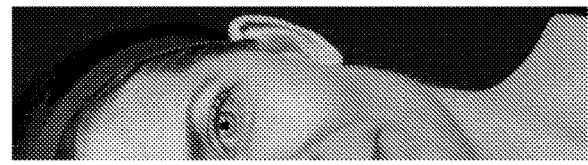
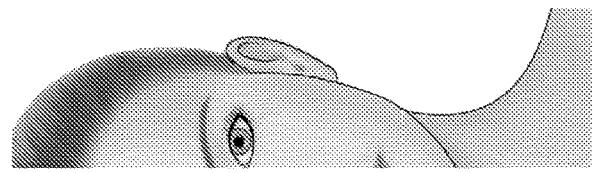
FIG. 51

Figure 52. – Assessing genetic aging: Putting MD ASA into practice
Vertical Assessment at rest – Hemiface
Analysis focus on relationships among structures
- Forehead height
- medial brow
- medial canthus
- Nasal flare
- NLF
- Upper lip
- Oral commissure
- Lower lip
- Chin
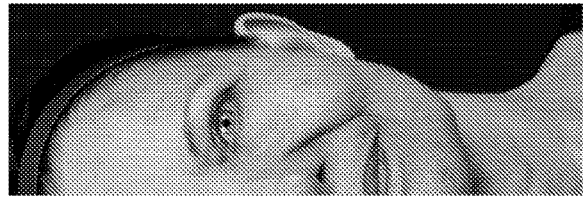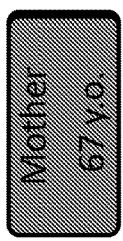
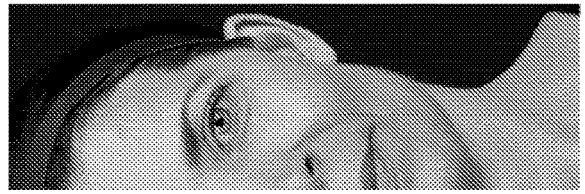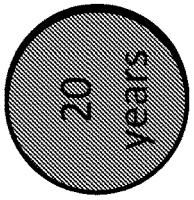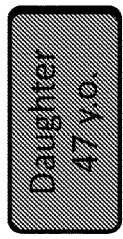
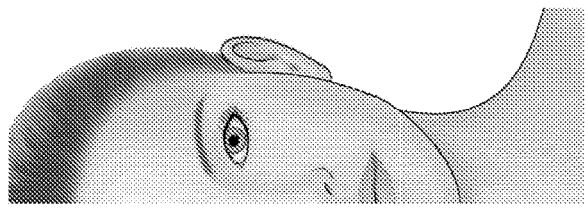
FIG. 52

Figure 53. – Assessing genetic aging: Putting MD ASA into practice

Triangular Central Assessment

Relationship of central face

- Eyes
- Nose
- Lips
- Chin

Figure 54. – Assessing genetic aging: Putting MD ASA into practice

Oval Central Assessment

Relationship of Central Face

- Eyes
- Nose
- Lips
- Chin

Figure 55. – Assessing genetic aging: Putting MD ASA into practice
Full Face Assessment at rest – best side of the face
Symmetry assessment
— Best side of the face
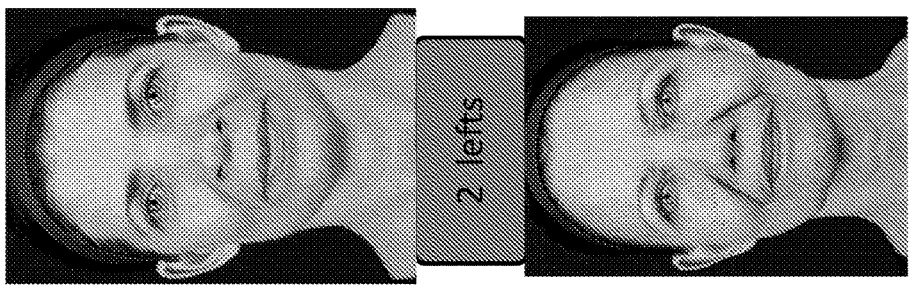
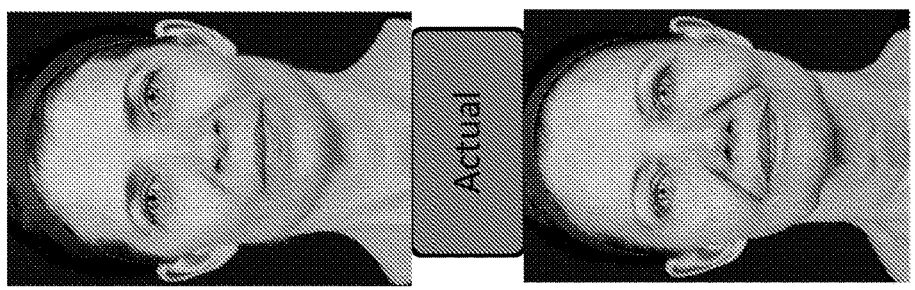
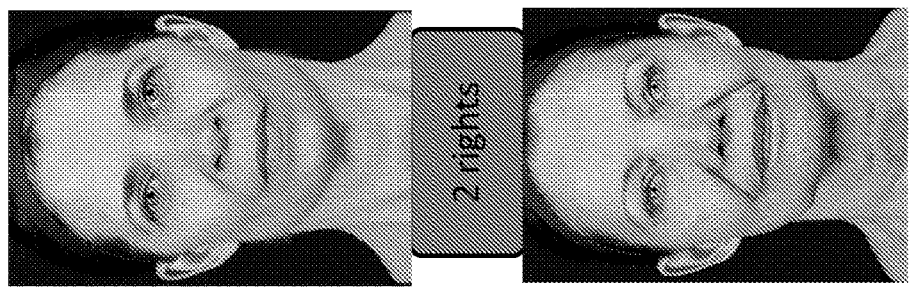
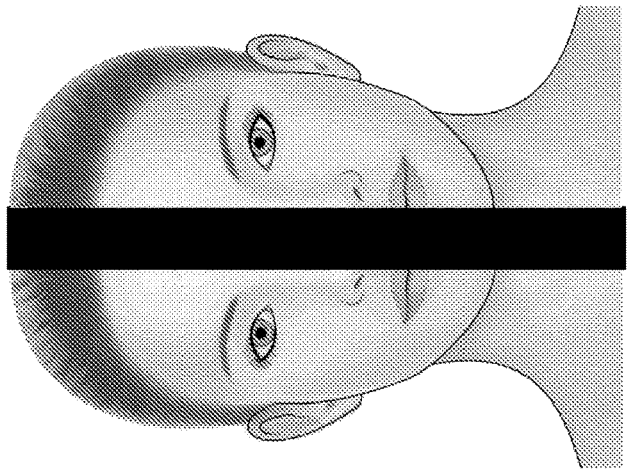
FIG. 55

Figure 56. – Assessing genetic aging: Putting MD ASA into practice

L1 – Oblique view: full face assessment at rest

Analysis focus on the messages of the face

Overall perception of proportion and harmony

Facial thirds

Jawline and neck

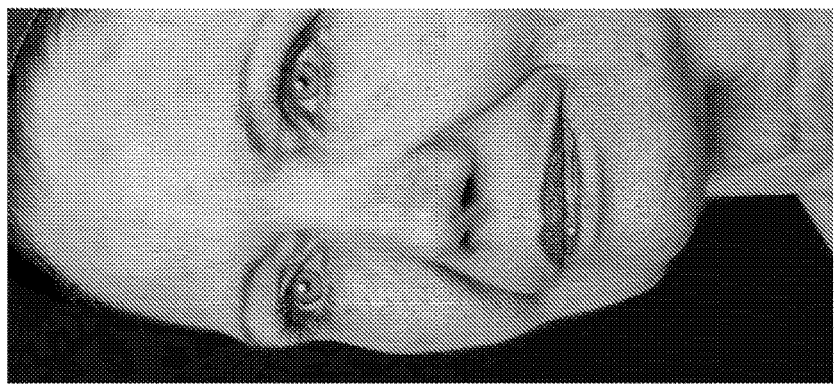
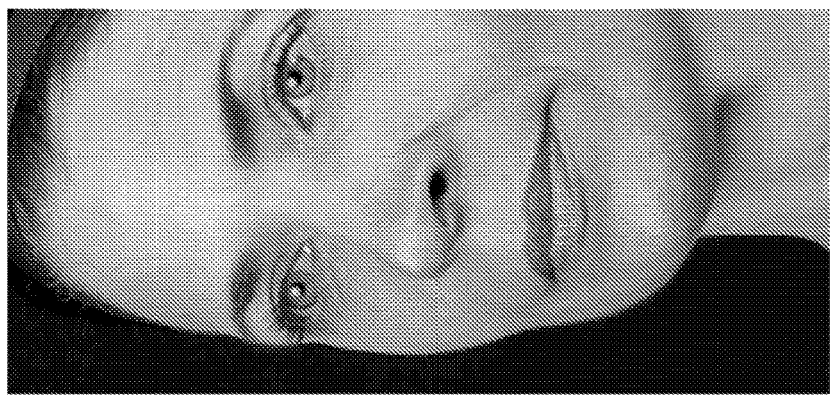
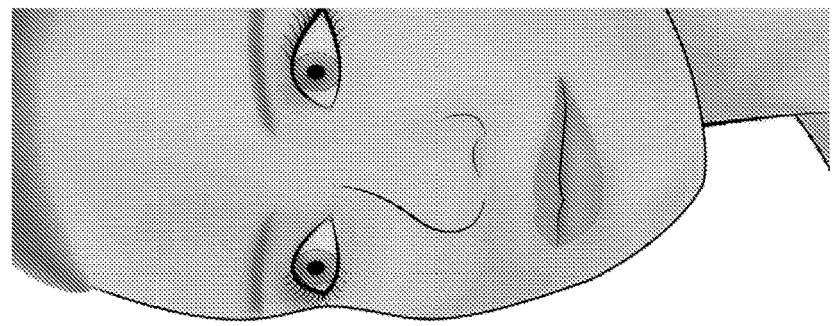
Figure 57. – Assessing genetic aging: Putting MD ASA into practice
L2 – Oblique view: partial vertical assessment at rest
Focus on:
— Forehead
— Eyebrow
— Eyes
— Cheek
— NLF
— Lip
— Chin
— Neck
FIG. 57

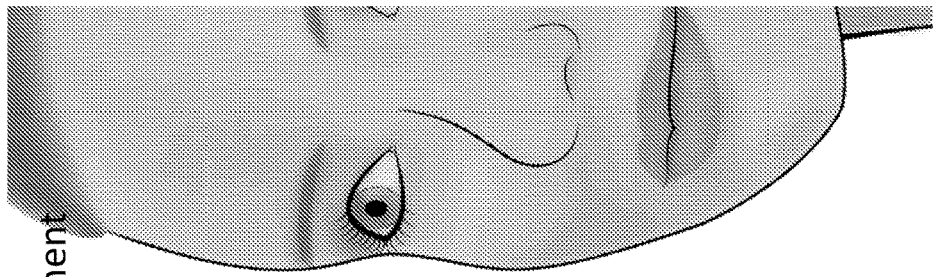
Figure 58. – Assessing genetic aging: Putting MD ASA into practice
L3 – Oblique view: partial vertical assessment at rest
Focus on:
— Eyebrow-nose outline
— Nose-Lip-Chin Complex
FIG. 58

Figure 59. – Assessing genetic aging: Putting MD ASA into practice

L4 – Oblique view: partial vertical assessment at rest

Focus on details:
— Forehead volume
— Eyebrow position
— Upper eyelid
— Lower eyelid
— Cheek volume
— Lip volume and contour

Figure 60. – Assessing genetic aging: Putting MD ASA into practice

L5 – Oblique view: partial vertical assessment at rest

Oblique view Outlines:
— Forehead
— Supraorbital
— Ogee curve
— Lower cheek

Figure 61. – Assessing genetic aging: Putting MD ASA into practice
Profile view  Face Assessment at rest – H1
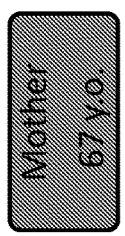
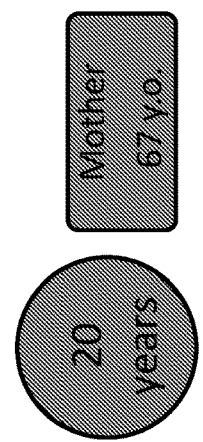
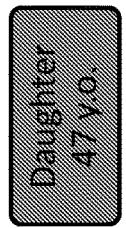
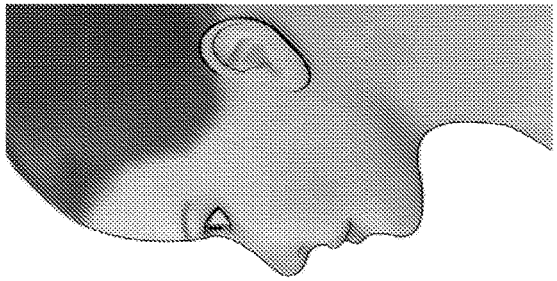
Analysis focus on
the messages of
the face
Overall perception
of proportion and
harmony
FIG. 61

Figure 62. – Assessing genetic aging: Putting MD ASA into practice

Figure 63. – Assessing genetic aging: Putting MD ASA into practice

Profile view Face Assessment at rest – H1

Forehead outline
Nose breakpoint
Eye position
Cheek projection and position
NLF
Oral commissure
Marionette lines
Submental area Figure 64. – Assessing genetic aging: Putting MD ASA into practice

Profile view Face Assessment at rest – H1

Forehead outline
Frontal nasal angle
Nose projection
Nasal labial angle
Upper lip projection
Lower lip projection
Labial mental angle
Chin projection Figure 65. – MD ASA through emotional attributes

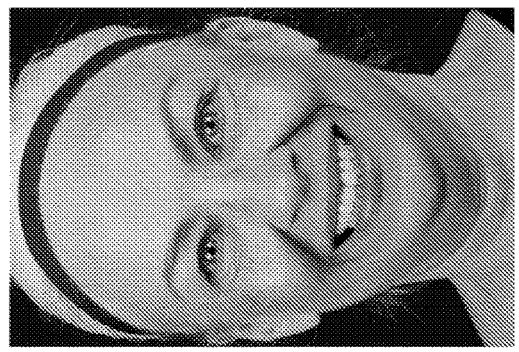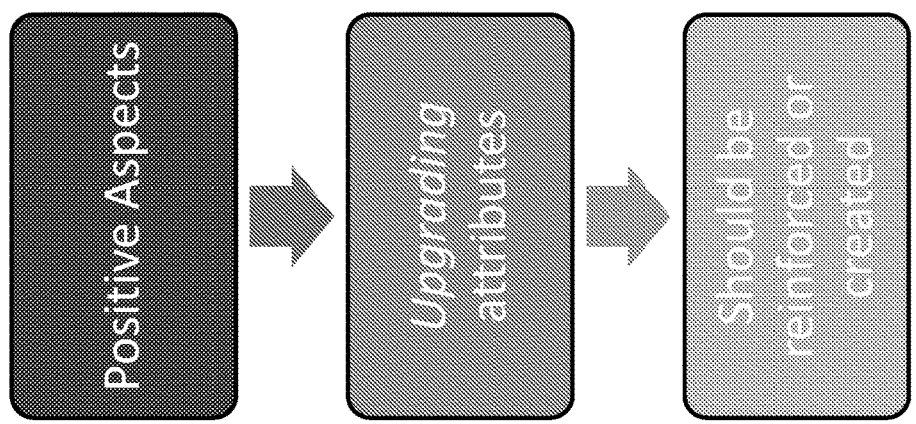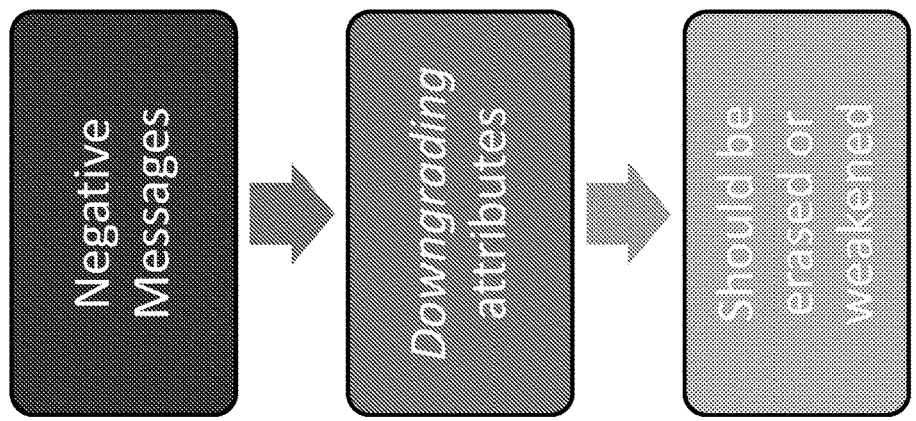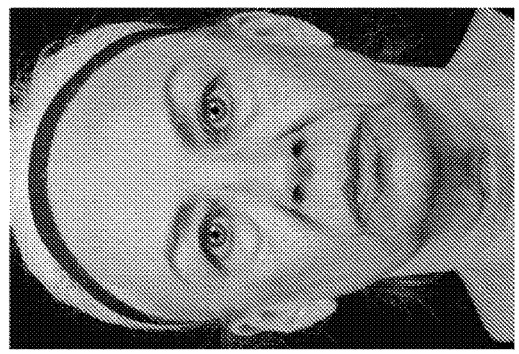
Figure 66. – MD ASA through emotional attributes: Assessment flow

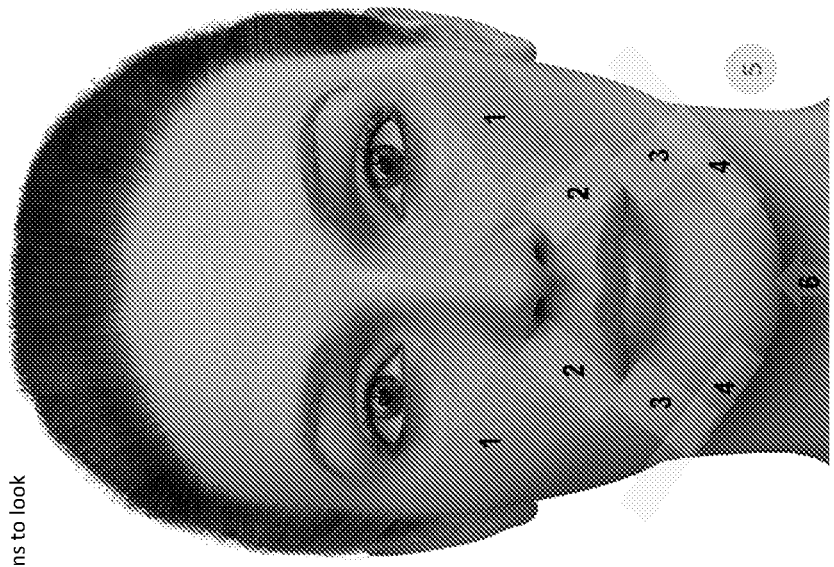
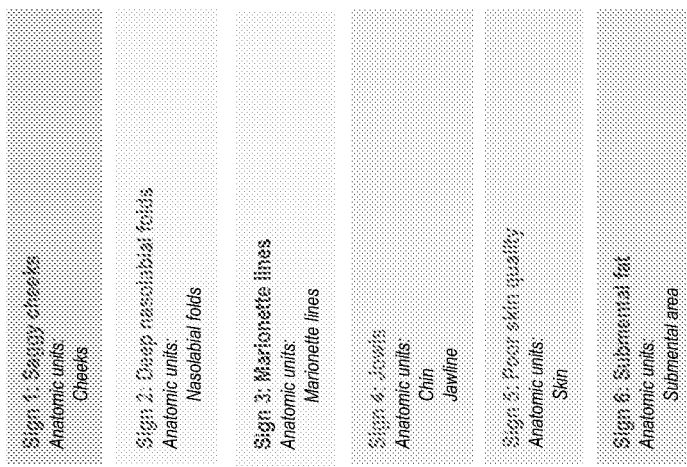
Figure 68. – Example of MD ASA diagram: Key facial signs to look less saggy
Sign 1: Saggy cheeks
Anatomic units:
Cheeks
Sign 2: Deep nasolabial folds
Anatomic units:
Nasolabial folds
Sign 3: Marionette lines
Anatomic units:
Marionette lines
Sign 4: Jowls
Anatomic units:
Chin
Jawline
Sign 5: Poor skin quality
Anatomic units:
Skin
Sign 6: Submental fat
Anatomic units:
Submental area
FIG. 68

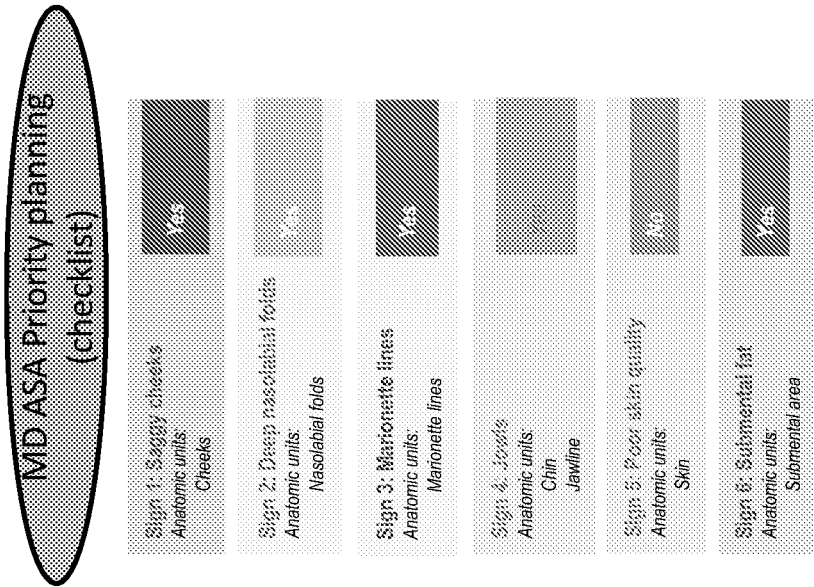
Figure 69. – Example of MD ASA diagram
Case study (50 y.o.) – I want to look less saggy
Assessment (before treatment)
Key facial signs
*In this patient*
FIG. 69

Figure 70. – Example of MD ASA diagram
Case study (50 y.o.) – I want to look less saggy Assessment (before treatment)
Key facial signs
*In this patient*

Figure 71. – MD ASA Case study (50 y.o.) – I want to look less saggy

Figure 72. – Example of MD ASA diagram: Key facial signs to look less sad in the periorbital area Sign 1: Low brows
Anatomic units:
 Eyebrows
 Temples Sign 2: Downturn of corner of the eye
Anatomic units:
 Cheeks
 Tear trough Sign 3: Lines around the eyes
Anatomic units:
 Glabellar lines
 Lateral canthal/orbital lines Sign 4: Poor skin quality
Anatomic units:
 Periorbital skin Figure 73. – Example of MD ASA diagram: Key facial signs to look less sad in the perioral area Figure 74. – Example of MD ASA diagram
Case study (42 y.o.) – I want to look less sad Figure 75. — MD ASA Case study (42 y.o.) – I want to look less sad

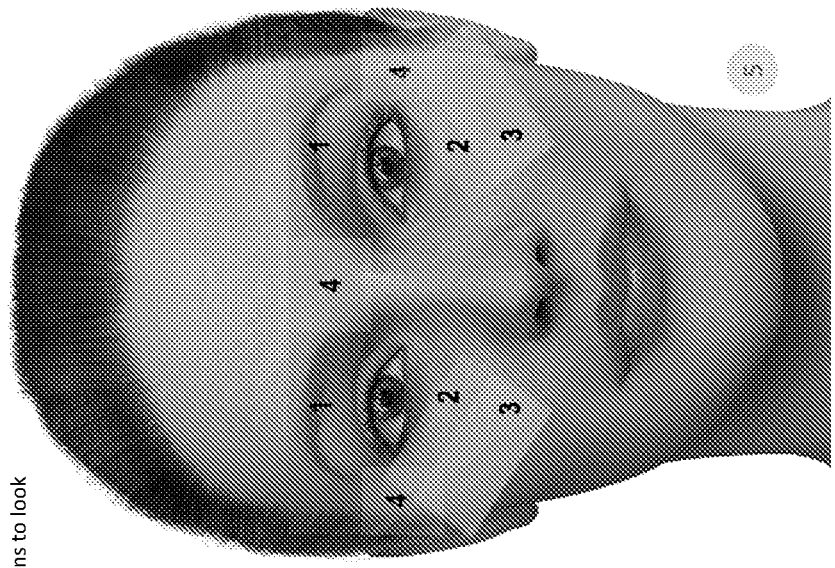
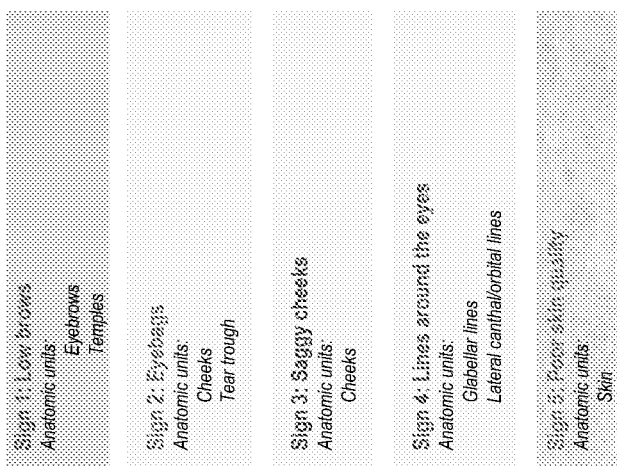
Figure 76. – Example of MD ASA diagram: Key facial signs to look less tired
Sign 1: Low brows
Anatomic units:
  Eyebrows
  Temples
Sign 2: Eyebags
Anatomic units:
  Cheeks
  Tear trough
Sign 3: Saggy cheeks
Anatomic units:
  Cheeks
Sign 4: Lines around the eyes
Anatomic units:
  Glabellar lines
  Lateral canthal/orbital lines
Sign 5: Poor skin quality
Anatomic units:
  Skin
FIG. 76

Figure 77. – Example of MD ASA diagram
Case study (27 y.o.) – I want to look less tired Figure 78. – MD ASA Case study (27 y.o.) – I want to look less tired

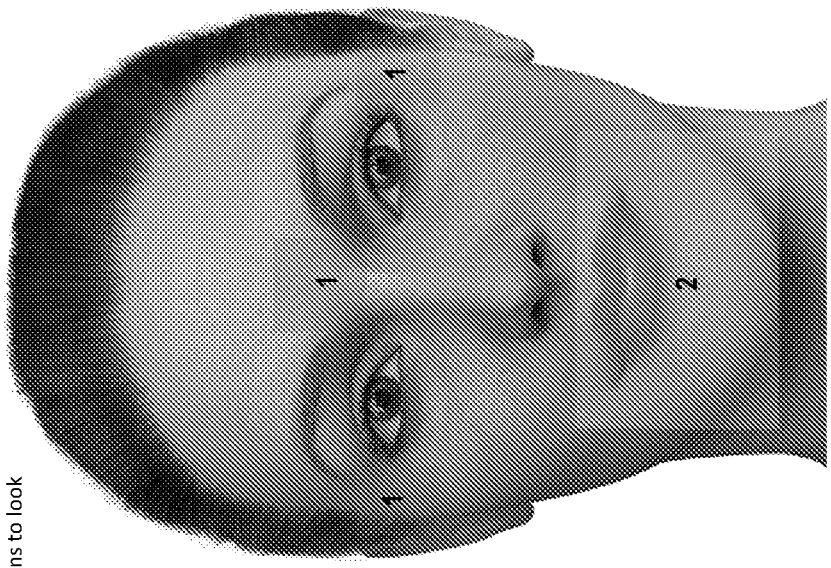
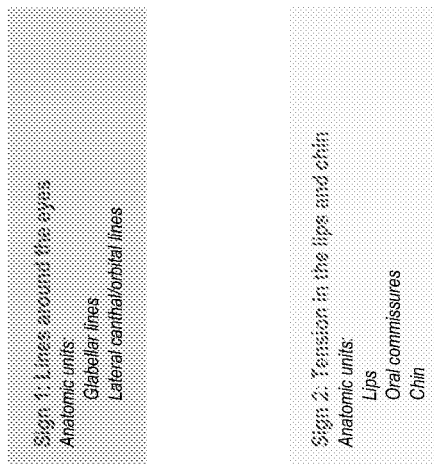
Figure 79. – Example of MD ASA diagram: Key facial signs to look less angry
FIG. 79

Figure 81. – MD ASA Case study (32 y.o.) – I want to look less angry

Figure 82. – MD ASA Case study (32 y.o.) – I want to look less angry

Figure 83. – Example of MD ASA diagram: Key facial signs to look slimmer

Figure 85. —MD ASA Case study (37 y.o.) – I want to look slimmer

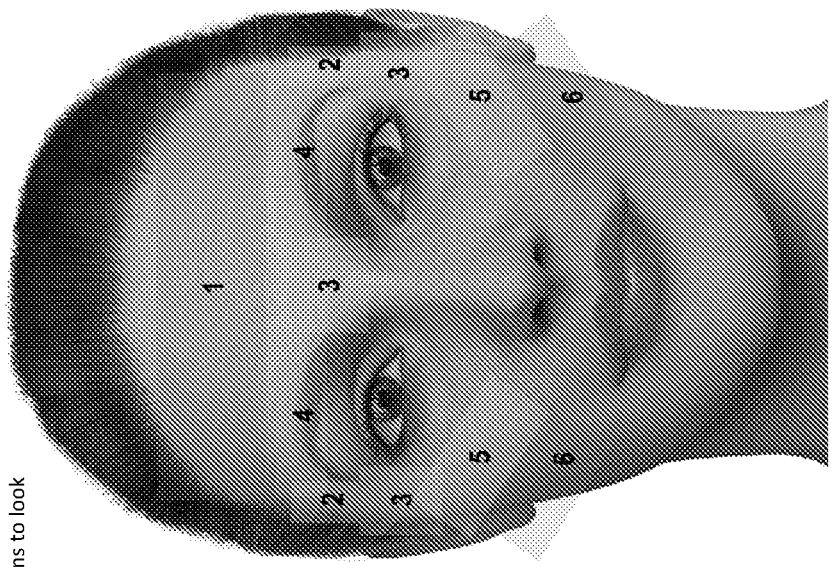

Figure 86. – Example of MD ASA diagram: Key facial signs to look more feminine/softer *(for female patients)*

Sign 1: Prominent forehead
Anatomic units:
　Forehead

Sign 2: Sunken temples
Anatomic units:
　Temples

Sign 3: Lines around the eyes
Anatomic units:
　Glabellar lines
　Lateral canthal/orbital lines Sign 4: To create higher brows
Anatomic units:
　Eyebrows Sign 5: To create fullness in the upper cheek
Anatomic units:
　Upper cheek Sign 6: To create definition/fullness in the lower cheek
Anatomic units:
　Lower cheek

FIG. 86

Figure 87. – Example of MD ASA diagram: Key facial signs to look more feminine/softer *(for female patients)* (cont.)

Sign 7: To create full and defined lips
Anatomic units:
 Lips

Sign 8: To create a triangular chin
Anatomic units:
 Chin

Sign 9: Poor skin quality
Anatomic units:
 Skin

Sign 10: Submental fat
Anatomic units:
 Submental area

Figure 88. – Example of MD ASA diagram
Case study (48 y.o.) – I want to look more feminine FIG. 89. - Example of MD ASA Case study (48 y.o.) - I want to look more feminine

Figure 90. – Example of MD ASA diagram: Key facial signs to look more masculine *(for male patients)*

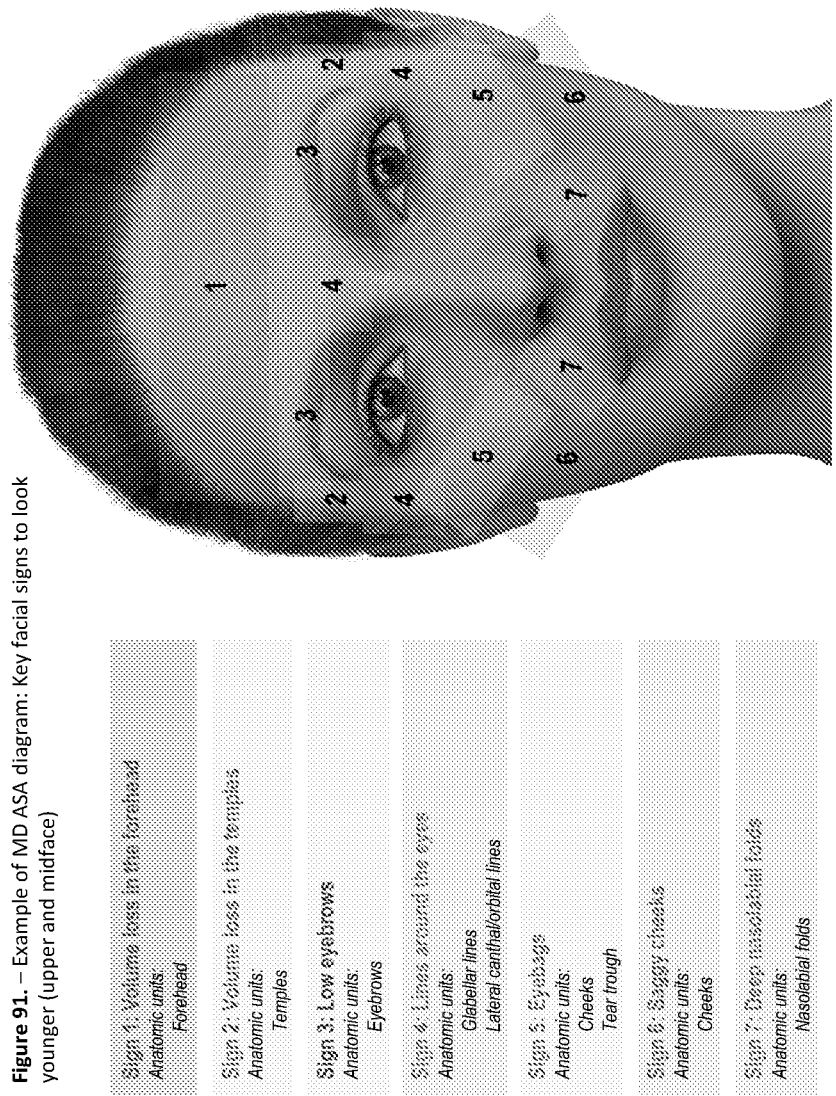

Figure 91. – Example of MD ASA diagram: Key facial signs to look younger (upper and midface)

Sign 1: Volume loss in the forehead
Anatomic units:
  Forehead

Sign 2: Volume loss in the temples
Anatomic units:
  Temples

Sign 3: Low eyebrows
Anatomic units:
  Eyebrows

Sign 4: Lines around the eyes
Anatomic units:
  Glabellar lines
  Lateral canthal/orbital lines Sign 5: Eyebags
Anatomic units:
  Cheeks
  Tear trough Sign 6: Saggy cheeks
Anatomic units:
  Cheeks Sign 7: Deep nasolabial folds
Anatomic units:
  Nasolabial folds

FIG. 91

Figure 92. – Example of MD ASA diagram: Key facial signs to look younger (lower face and neck)

Figure 94. – MD ASA Case study (52 y.o.) – I want to look younger

Figure 95. – Example of MD ASA diagram: Key facial signs to look more attractive (upper and midface)

Figure 99. – Example of MD ASA diagram: Key facial signs to look more attractive (for Asian patients)

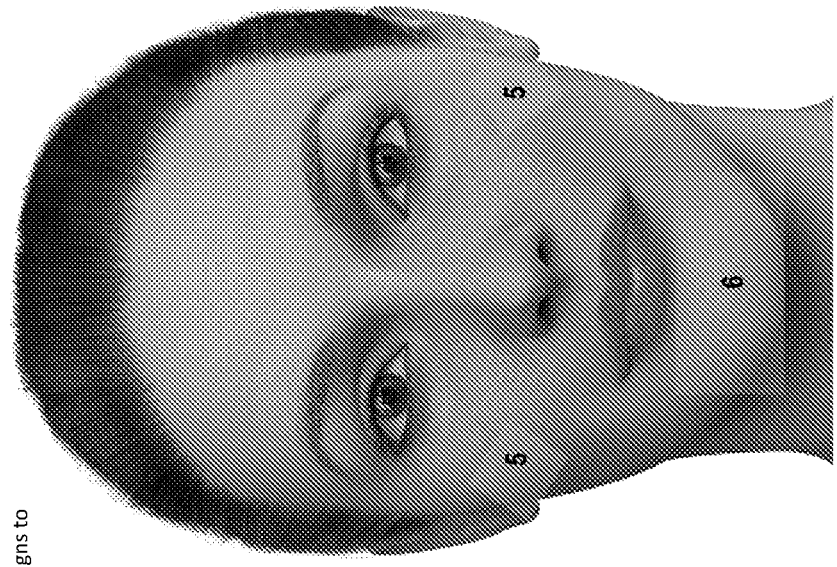
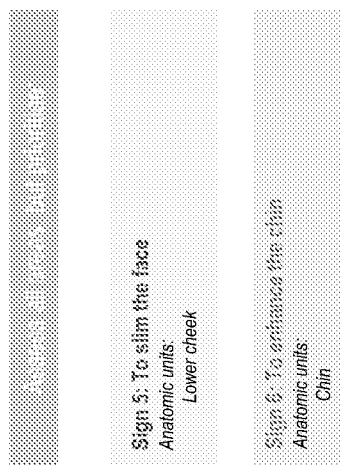
Figure 100. – Example of MD ASA diagram: Key facial signs to look more attractive (for Asian patients) *(cont.)*
Sign 5: To slim the face
*Anatomic units:*
  Lower cheek
Sign 6: To enhance the chin
*Anatomic units:*
  Chin
FIG. 100

Figure 102. – MD ASA Case study (33 y.o., Asian patient) – I want to look more attractive

Figure 103. – MD ASA Case study (33 y.o., Asian patient) – I want to look more attractive Figure 104. – Example of MD ASA diagram: Key facial signs to look more attractive (for Middle Eastern patients)

Figure 105. – Example of MD ASA diagram
Case study (39 y.o., Middle Eastern patient) – I want to look more attractive Figure 106. – MD ASA Case study (39 y.o., Middle Eastern patient) – I want to look more attractive

Figure 107. – Example of MD ASA diagram: Key facial signs to look more attractive (for Afro descent patients)

Figure 108 - Dyna Codes frontal view muscle location

Figure 109 - Dyna Codes frontal view split face muscles vs surface topography

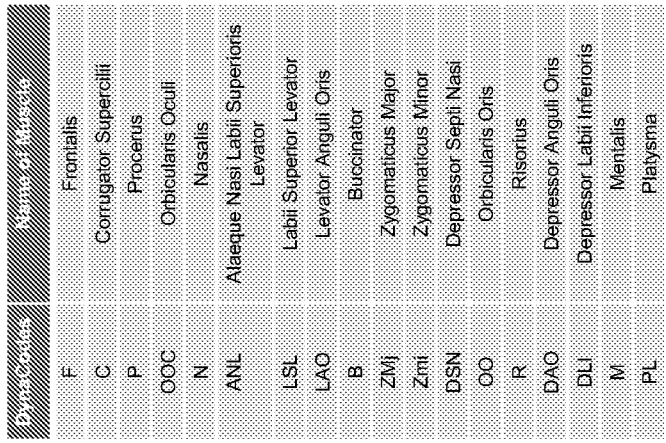
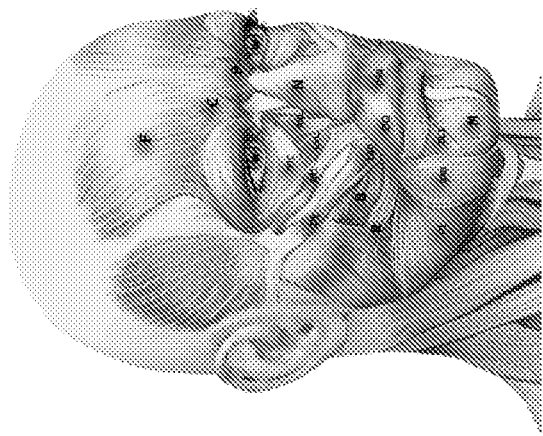
Figure 110 - Dyna Codes oblique view muscle location
FIG. 110

Figure 111 - Dyna Codes oblique view

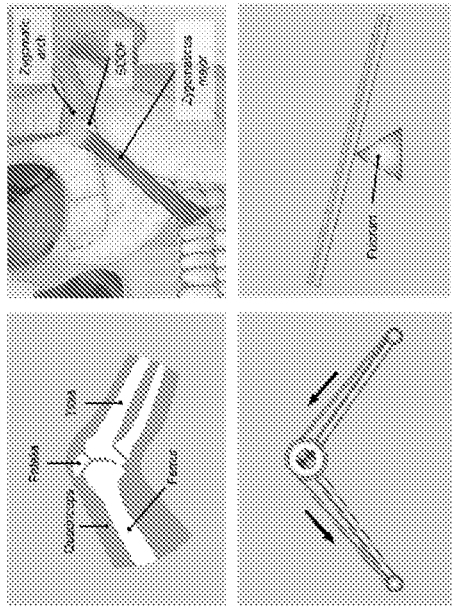

Figure 112 - Muscle pulley and lever systems.

In the knee (upper left), the patella functions as a pulley glide plane (lower left) and a lever fulcrum (lower right), increasing the mechanical advantage of the quadriceps muscle and reducing the amount of force required to extend the leg.
Similarly, the lateral sub-orbicularis oculi fat pad (SOOF) and bone support acts as a glide plane for zygomaticus major (upper right). The SOOF and underlying bone also function together as a lever fulcrum, providing mechanical advantage to the zygomaticus major as it lifts the corners of the mouth in a smile. Deflation of the SOOF and loss of bone in aging can reduce the lever effect and consequently the lifting power of the muscle.

FIG. 112

Figure 113 - Aging and treatment effects on muscle action.

Normal youthful facial structure (underlying bone and fat) gives muscle fibers convexity, which allows powerful contraction of levator muscles. The levator and depressor muscles are balanced and structures are in their normal position.

In aging, underlying support for muscle is lost with deflation of facial structure. The mechanical advantage provided by the lever fulcrum is diminished and the levator loses lifting power to counteract gravity. Muscle fibers are stretched as skin sags. With reduced opposition, the depressor increases in tone over time and pulls facial structures downward in a domino effect.

A filler bolus replaces lost structure (fulcrum), increasing mechanical advantage of the levator muscle. The levator's power of contraction is strengthened. This reduces sagging and balances contraction of the depressor, halting the chain of events triggered by aging.

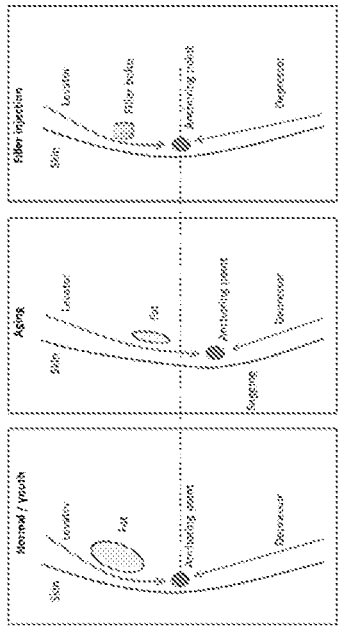

FIG. 113

Figure 114 - Dyna Code symbol : muscle letters, side location, and injection above the muscle fibers Figure 115 - Dyna Code symbol : muscle letters, side location, and injection under the muscle fibers Figure 116 - Dyna Code symbol : muscle letters, side location, and injection within the muscle fibers

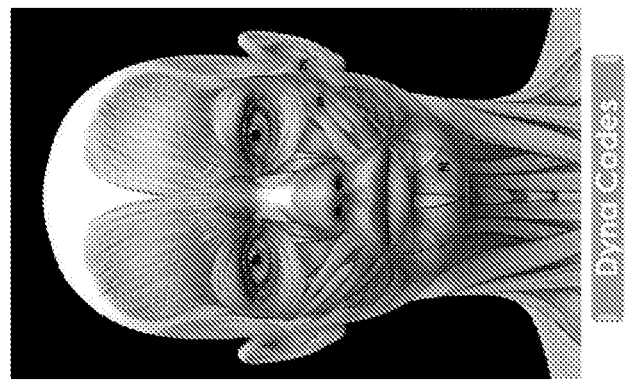
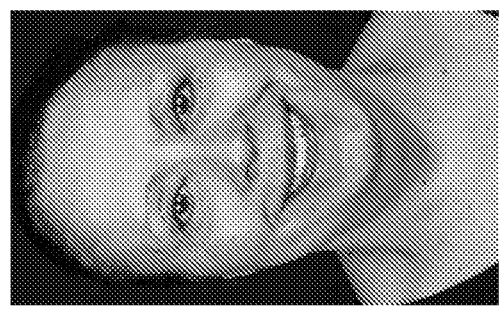
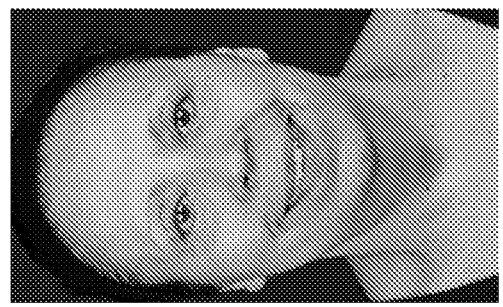
FIG. 117

Figure 122 – The four consultation questions

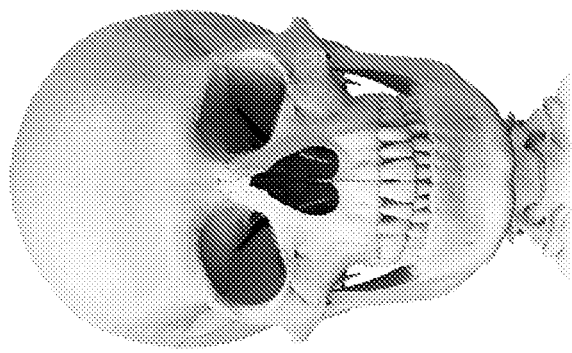
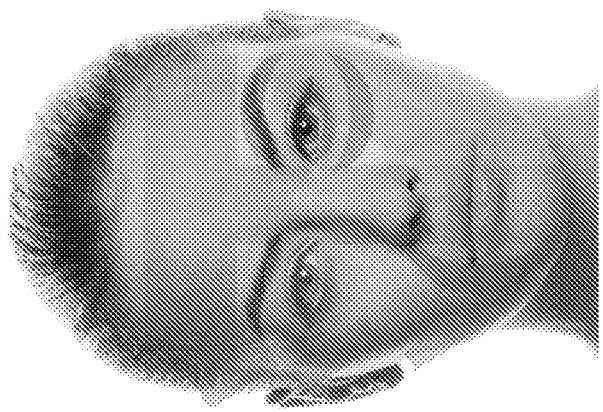

Figure 123 – Human face: Surface and bone levels

Humans are very similar at the Bone level and only specialists can differentiate skulls of different age, gender and ethnicity. However, on the surface, the differentiation is immediate. One can easily see that figure on the left is from a young Caucasian female. Hard to attest by the skull. Patients will refer to distraction only at the skin surface level. Structural deficiencies at the bone level will occur at an earlier stage. Usually, they are neither assessed or treated leading to a domino effect with exponential aging.

FIG. 123

Figure 125– The 16 SATP: Right oblique view

| SATP | Abbr | Description |
|---|---|---|
| 1 | FN | Fronto Nasal angle |
| 2 | NP | Nasal Prominence |
| 3 | NA | Nasal Labial Angle |
| 4 | LP | Labial Prominence |
| 5 | LM | Labial Mental angle |
| 6 | FP | Frontal Prominence |
| 7 | SO | Supra Orbital |
| 8 | IO | Infra Orbital |
| 9 | Mx | Maxilla |
| 10 | CF | Canine Fossa |
| 11 | Mo | Modioulus |
| 12 | PJ | PreJowl |
| 13 | TF | Temporal Fossa |
| 14 | LC | Lateral Canthus |
| 15 | ZA | Zygomatic Arch |
| 16 | MA | Mandible Angle |

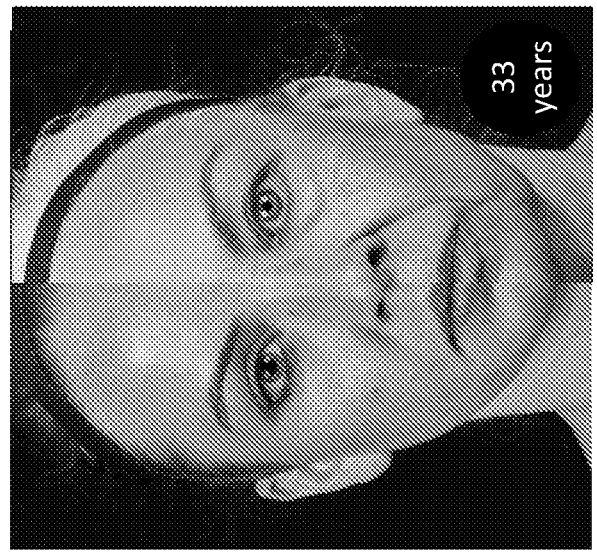

Figure 127 – Identifying the SATP through genetic aging

Patient assessment with mother (58 y.o.) and daughter (25 y.o.). Both are genetically similar and 33 years apart. The daughter is 25 y.o. hardly present any visible aging sign. However, with more attention, she already presents a mild tear trough concavity and downturn of the oral commissure which are represented by SATP Tt and M, respectively. The mother already shows severe SATP for her age. The prominent eye-bags and marionette lines are too prominent for her age. The daughter should be aware that if treated at an early stage, she will not develop those aging features found in the mother. The daughter still presents the fat pads in proper location and the mother already presents gravitational displacement of soft tissue landmarks.

FIG. 127

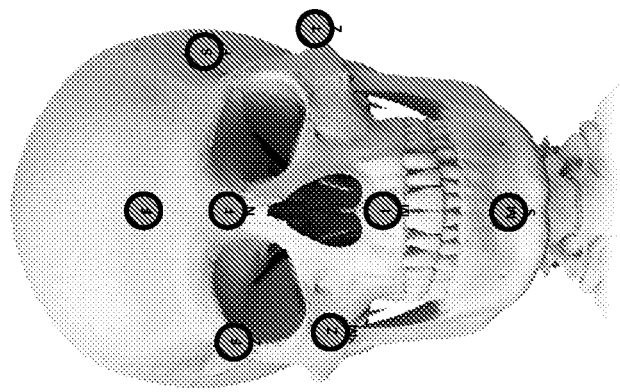

FIG. 128

Figure 128 – The 8 BAPT: Front view. BATP refer to Bone Aging Point Triggers and are anatomically related to bone sutures (regions that bone fuse during embryologic and skeletal development post birth.

| BATP | Abbreviation | Description |
|---|---|---|
| 1 | F | Frontal (metopic) suture |
| 2 | SF | Sphenofrontal suture |
| 3 | FZ | Frontozygomatic suture |
| 4 | FN | Frontonasal suture |
| 5 | TZ | Temporozygomatic suture |
| 6 | ZM | Zygomaticomaxillary suture |
| 7 | IM | Intermaxillary suture |
| 8 | MS | Mandibular Symphisis (medial suture) |

Figure 129 – The 8 BAPT: Right oblique view

| BATP | Abbreviation | Description |
|---|---|---|
| 1 | F | Frontal (Metopic) suture |
| 2 | SF | Sphenofrontal suture |
| 3 | FZ | Frontozygomatic suture |
| 4 | FN | Frontonasal suture |
| 5 | TZ | Temporozygomatic suture |
| 6 | ZM | Zygomaticomaxillary suture |
| 7 | IM | Intermaxillary suture |
| 8 | MS | Mandibular Symphisis (medial suture) |

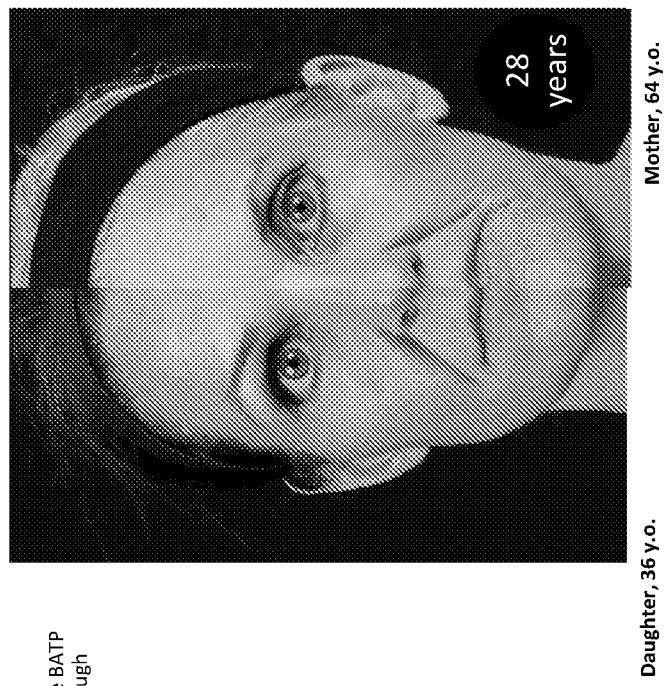

Figure 131 – Identifying the BATP and SATP through genetic aging

Patient assessment with mother (64 y.o.) and daughter (36 y.o.). Both are genetically similar and 28 years apart. The daughter already presents a very visible nasolabial fold for her age due to retruded upper maxilla. The BATP that are compromised at an early stage are ZM and IM and the SATP include N, NL and Lp, both of the around the perioral area. The mother present an incremented number of lines and skin fractures around the lips and chin. It is much easier to revert the aging condition in the daughter than in the mother. The degree of severity of SATP and BATP is much higher in the mother.

FIG. 131

Figure 132 – A more detailed table containing statistics on the main death causes worldwide

FIG. 132

Figure 133 – The eight HM

Figure 134 – The eight HM and reference ranges

| # | Category | Details |
|---|---|---|
| 1 | Metabolic | Total cholesterol < 200 mg/dL; LDL < 130 mg/dL; HDL > 40 mg/dL; triglycerides < 150 mg/dL |
| 2 | Metabolic | Fasting blood sugar < 100 mg/dL, glycated Hemoglobin < 5,6% |
| 3 | Sexual Hormones | Estrone (E1)<br>Adult Male: 10-60 pg/mL<br>Adult Female:<br>Premenopausal - 17-200 pg/mL<br>Postmenopausa - 7-40 pg/mL<br><br>17-Hydroxyprogesterone, Serum (OHPG)<br>Adult Male: <220 ng/dL<br>or =19 years: 240-950 ng/dL<br>Adult Female<br>ng/dL<br>Follicular - <80 ng/dL<br>Luteal - 285 ng/dL<br>Postmenopausal - <51 ng/dL<br><br>Estradiol (E2)<br>Adult Male: 10-40 pg/mL<br>Adult Female:<br>Premenopausal - 15-350 pg/mL<br>Postmenopausal - <10 pg/mL<br><br>Testosterone, Total, Serum (TTST)<br>Male: ><br>Female > or =19 years: 8-60 |
| 4 | Cardiovascular | Blood pressure < 120/80 mmHg |

Hormone reference ranges source:
http://www.mayomedicallaboratories.com/test-catalog/Clinical+and+Interpretive/84230
http://www.mayomedicallaboratories.com/test-catalog/Clinical+and+Interpretive/9231
http://www.mayomedicallaboratories.com/test-catalog/Clinical+and+Interpretive/8533

FIG. 134

Figure 135 – The eight HM and reference ranges (cont.)

| | | |
|---|---|---|
| 5 | Metabolic | BMI<br><25 |
| 6 | Habit | Alcohol Limit<br>1 serving for women or 2 servings for men per day |
| 7 | Habit | Smoking<br>Light smoker: <10 cigarettes per day<br>Moderate smoker: 10-19 cigarettes per day<br>Heavy smoker: ≥20 cigarettes per day |
| 8 | Fitness | Physical activity<br>> 18 > 64 y.o. - 150 minutes of moderate-intensity aerobic physical activity throughout the week, or at least 75 minutes of vigorous-intensity aerobic physical activity throughout the week or an equivalent combination of moderate- and vigorous-intensity activity.<br>Muscle-strengthening activities should be done involving major muscle groups on 2 or more days a week. |

Cigarette smoking source: Lawrence D, Fagan P, Backinger CL, Gibson JT, Hartman A. Cigarette smoking patterns among young adults aged 18-24 years in the United States. Nicotine & Tobacco Research. 2007;9(6):687–97.
Recommendation for Physical Activity: http://www.who.int/dietphysicalactivity/factsheet_adults/en/

FIG. 135

Figure 136 – Decades of life: The evolution of aging signs in non-related female individuals. Note that the degree of aging signs increase

Figure 137 – The evolution of aging signs in non-related female individuals. The chin down with eyes up position helps with the diagnosis of BATP and SATP. Both tend to worsen with time and make more evident which facial signs will be mostly visible in upright position in the years to come. SATP are visible on the skin surface and hence the name Surface Aging Trigger Points. The diagnosis of BATP is made through palpation of the specific bone structure or visually when an specific aging sign is visible at an early stage like the presence of eye-bags

FIG. 137

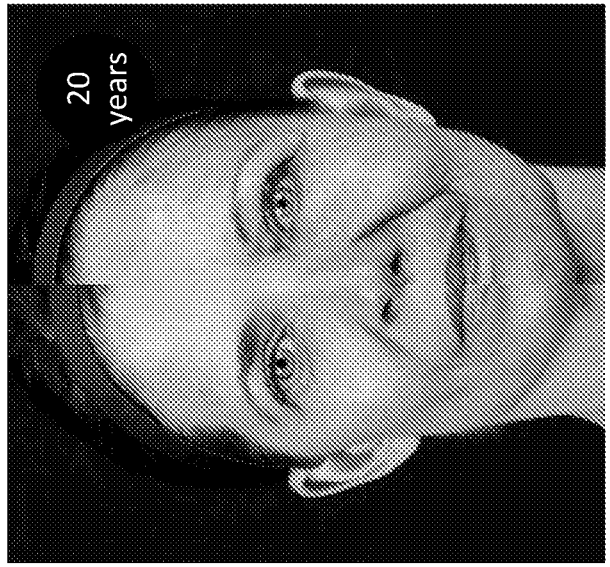

Figure 138 - Patient assessment with mother (67 y.o.) and daughter (47 y.o.). They are genetically similar and 20 years apart. Note that the daughter present mild aging signs such as prominent nasolabial fold and some minimal dark spots on the skin. The mother presents a more severe nasolabial fold with heavy and saggy anterior cheek and jawline. She also present more static lines and dark spots. The ATP in the mother have already reached exponential speed. The degree of sagginess in the mother will evolve much faster than in the daughter and correction is challenging. The worse the distractions are, even worse and faster they get. Reverting the mother to 30's pattern is impossible

FIG. 138

Figure 139 – Genetic Aging Diagram

Figure 140 – Aging process impacted by gravity

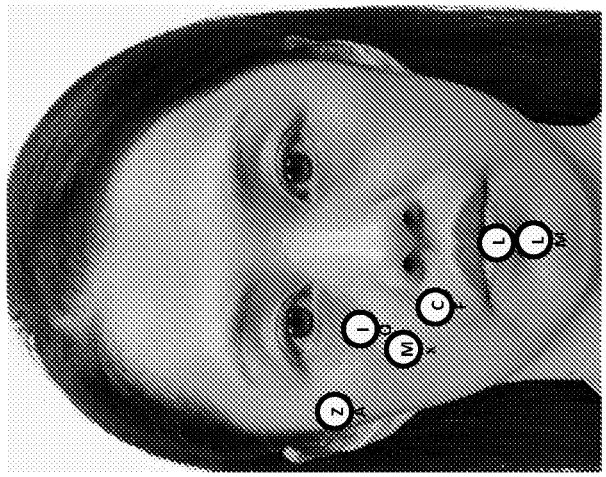

Figure 141 - Assessment of the potential SATP to be corrected. Before treatment photo showed the need to correct 6 out of 16 points

| SATP | Abbr | Description |
|---|---|---|
| 1 | FN | Fronto Nasal angle |
| 2 | NP | Nasal Prominence |
| 3 | NA | Nasal Labial Angle |
| 4 | LP | Labial Prominence |
| 5 | LM | Labial Mental angle |
| 6 | FP | Frontal Prominence |
| 7 | SO | Supra Orbital |
| 8 | IO | Infra Orbital |
| 9 | Mx | Maxilla |
| 10 | CF | Canine Fossa |
| 11 | Mo | Modiolus |
| 12 | PJ | PreJowl |
| 13 | TF | Temporal Fossa |
| 14 | LC | Lateral Canthus |
| 15 | ZA | Zygomatic Arch |
| 16 | MA | Mandible Angle |

FIG. 141

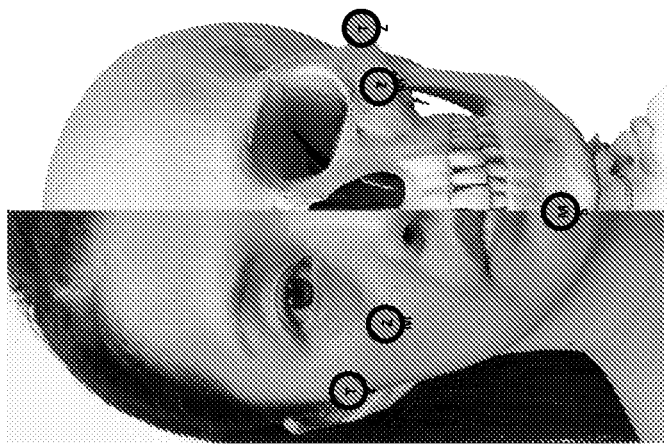

Figure 143 - Assessment of the potential BATP to be corrected. Before treatment photo showed the need to correct 3 out of 8 points. The split face photo show the location at the bone level and the topography on the skin

| BATP | Abbreviation | Description |
|---|---|---|
| 1 | F | Frontal (Metopic) suture |
| 2 | SF | Sphenofrontal suture |
| 3 | FZ | Frontozygomatic suture |
| 4 | FN | Frontonasal suture |
| 5 | TZ | Temporozygomatic suture |
| 6 | ZM | Zygomaticomaxillary suture |
| 7 | IM | Intermaxillary suture |
| 8 | MS | Mandibular Symphisis (medial suture) |

FIG. 143

Figure 144 - Assessment of the potential BATP to be corrected: Profile view.

Figure 145 - Before and After the treatment with Hyaluronic acid-based injectable. This patient (38 y.o.) was treated according to BATP and SATP. The negative messages of her face were changed. Before the treatment, she looked tired and angry and older for her age. After 2 hours that the treatment ended, she was back to a youthful appearance and the ATP were weakened leading to a more favorable aging process

FIG. 145

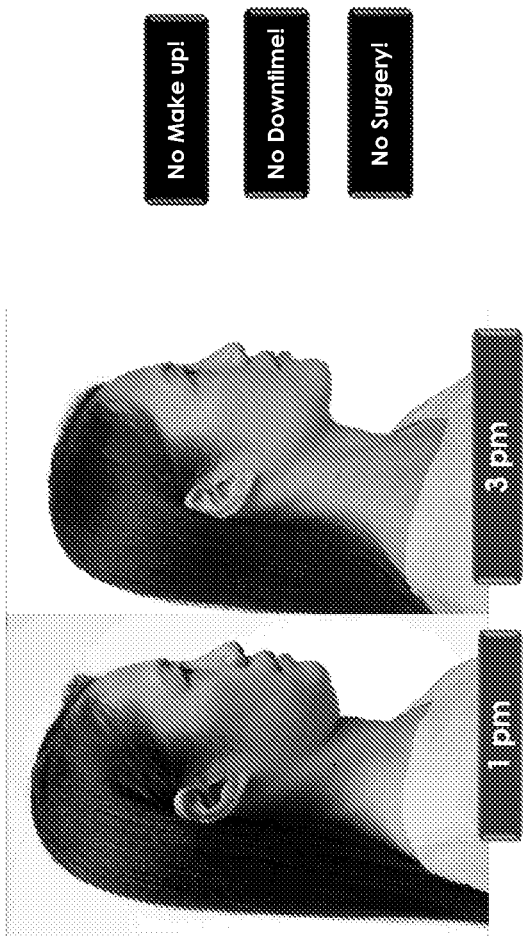

Figure 147 – Observe the chin profile before the treatment. The skin excess would worsen exponentially with time. Natural reversion (without treatment) of the saggy skin condition along the jawline is impossible at this age. The BATP in the mid and lower face were corrected with HA-based injectables. The correction of the BATP led to a structured jawline and correction of the sagginess at this level

FIG. 147

Figure 148 – B&A diagram example: Profile view

Figure 149 – Evolution of the treatment of the ATP. Firstly, the some BATP were addressed and then, some SATP were weakened. Note that the negative messages were gradually improved Figure 151 – Treatment's planning flow

Figure 152 - Palpation is very important to assess the BATP. Differences in symmetry on palpation may be perceived and indicate unfavorable points. The more asymmetrical an individual is, the faster and more asymmetrical one gets with aging process A: Palpating BATP 6 – ZM B: Palpating BATP 4 FN Figure 153– The ATP (SATP and BATP) 5-point scale Figure 154 – Treatment planning of the NEXT HUMAN system for this 38 y.o. The SATP and BATP are defined to provide foundation, shape and proportion and lastly-refinement.

Figure 155 – Next Human's follow up plan: On the oblique view, the SATP that are to be addressed in subsequent sessions to revert even more the aging signs. On the full profile view, the SATP will also need to be corrected to project her low nose and the nasal labial angle

METHODS AND SYSTEMS FOR PREVENTING, CORRECTING, TRANSFORMING, AND MODIFYING FACIAL, AESTHETICS, AND CONSULTING PATIENTS REGARDING THE SAME

CROSS-REFERENCE TO RELATED APPLICATIONS

This application is the U.S. national-stage entry of International Application No. PCT/IB2018/00207 (filed Feb. 10, 2018), which claims priority to U.S. Provisional Application No. 62/457,761 (filed Feb. 10, 2017), U.S. Provisional Application No. 62/479,139 (filed Mar. 30, 2017), U.S. Provisional Application No. 62/479,150 (filed Mar. 30, 2017), and U.S. Provisional Application No. 62/477,312 (filed Mar. 27, 2017), the disclosures of which are incorporated by reference in their entirety herein.

FIELD

The present disclosure concerns methods and systems for injecting or delivering pharmaceutical compositions, cosmetic compositions, or combinations thereof.

The present disclosure concerns methods and systems for diagnosing a subject in need of aesthetic treatments and method of treating such a subject with injectables including injecting said injectables at specific injection sites on the facial muscles or neck of a subject in need thereof.

The present disclosure concerns methods and systems for diagnosing a subject in need of aesthetic and reconstructive treatments and method of identifying treatments and treatment areas which should be addresses and threated for the patient with injectables.

The present disclosure concerns methods and systems for modulating the aging process in a human, including, but not limited to, injecting or delivering pharmaceutical compositions, cosmetic compositions, or combinations thereof.

BACKGROUND

Prior to the effective filing date of the instant application, standardized methods of treating patients with injectable fillers and botulinum toxin type A in aesthetics were not established and a variety of different techniques were introduced in the medical practice with inconsistent and varied results. Recipients of these non-standardized methods of treatment had, after their treatments, undesirable results such as unnatural appearances, frozen looks, big deformed lips, and other related undesirable results.

What is therefore needed in the progression of facial medical aesthetic are improved methods and systems for using injectables.

Current methods of treating facial aesthetic conditions or disorders are inadequate. Methods currently known do not properly consider the dynamic, expressive nature of the face when treating facial conditions and disorders. Over time, the current methods of treating result in unnatural appearances. With respect to methods of rehabilitating or repairing facial aesthetic conditions after an impairment or injury, the currently known methods are also inadequate for providing satisfactory results because these methods do not consider the underlying face dynamics including the muscle and bone structure. There are other problems in the relevant field which render the currently known methods of treating facial aesthetic conditions or disorders or of rehabilitating repairing facial aesthetic conditions after an impairment or injury in adequate.

For example, injectables are typically delivered as a filler treatment. Injectable filler treatments are normally used to fill static wrinkles, folds, and localized areas of volume loss, whereas neuromodulators (botulinum toxin type A) are used to address excessive muscle activity. However, a more comprehensive understanding of the role of muscle function in facial appearance, taking into account biomechanical concepts such as the balance of activity among synergistic and antagonistic muscle groups, is critical to achieving an attractive, youthful appearance with facial aesthetic treatments. The currently known methods do not take these factors into account.

Deficits in facial structure—whether related to changes with age, congenital abnormalities or nerve or muscle disorders—can yield aberrant muscle action reflected at the skin and across the face. Every line that we see in the face is a manifestation of structural deficiencies and the loss of balance between muscle antagonist pairs and synergist groups. As a face ages over time, structural support is lost due to bone loss, reduction of facial angles, and fat pad volume loss and displacement. Muscle action is altered, which affects the balance in activity between muscles. Antagonists may overcompensate for the reduced power of the muscle resulting in other negative side effects. The aforementioned currently known methods do not consider the interactions between facial structure and muscle action, which shows an unbalanced activity in muscle synergists and antagonists.

The classical treatment for dynamic lines is the injection of botulinum toxin type A. This approach leads to the temporary block of release of acetylcholine at the level of the neuro motor plaque. As a result, interruption of muscle contraction is achieved. Although it is the conventional tool to combat dynamic lines, undesirable results are typical including the frozen look appearance, potential of asymmetries and a sensation of heaviness in specific areas such as forehead and around the mouth. In case of any inadvertent reaction such as excessive muscle weakening, there is no antidote that can revert the clinical issue completely. In patients suffering from facial palsy, botulinum toxin type A is used to weaken the hemi facial normal side that tends to become overactive due to lack of movement on the paralyzed side. Nerve reconstructive methods have been helpful to animate the paralyzed side with very complex surgical procedures delivered by specialized surgeons. The presence of scars and downtime may impact the adherence of treatment by patients.

Yet missing from the facial aesthetic literature is a comprehensive discussion both of how aging affects the numerous synergist and antagonist groups in the facial musculature and how those changing interactions should be considered in the methods of treating facial aesthetic treatments. An understanding of the biomechanics of facial muscles and the effects of loss of stability on muscle action will help physicians better assess the underlying etiology of the characteristics of an individual aging face, and will allow that physician to more appropriately plan a course of treatment with neuromodulators and fillers to achieve an aesthetically pleasing outcome. Conversely, failure to fully understand the effects of loss of support (due to aging or congenital structural deficiency) on muscle action and interaction, and failure to take those interactions into account in a developing a treatment plan, can result in inadequate or inappropriate treatment, which produces an unnatural appearance with negative secondary effects distant from the site of injection. Theories of facial aging have largely focused on changes in skin, underlying fat, and bone that result in sagging and folds, while the role of muscle aging has generally been neglected. The complementary and distinct ways in which injectable fillers and neuromodulators have generally been used for rejuvenation and improvement of facial aesthetics illustrate how changes in aging skin and fat are considered separately from muscle action. Injectable fillers are customarily used to fill static wrinkles, folds, and localized areas of volume loss. Neuromodulators are used to reduce muscle movement in overacting muscles, for example to diminish hyperdynamic lines or correct position or asymmetry by reducing muscle activity. Experience treating patients with structural facial deficits has demonstrated, however, that structural support for stable muscle contraction together with balanced muscle activity across the face are reflected at the skin surface and are essential for the appearance of a typical youthful individual.

Health care providers tend to inject injectable in a person's face using the person's skin lines, wrinkles and concavities as the guide as to where to inject. However, no system is yet known for guiding where to inject these injectable, at least not one which includes a method of analyzing a face's proportions, volume, symmetry and intrinsic characteristics and which provides a method of treatment based on the patient's unique features. Without such a system, patients are often unsatisfied with their results or the results do not look natural.

Moreover, there is yet to be a system which accounts for the unique aesthetic differences between ethnicities. See FIG. 2.

People age differently, some better than others, primarily due to two factors: intrinsic (genetic) and extrinsic (environmental) aging. Environmental aging, for example, relates to sun damage, smoking, alcohol intake and poor nutrition. Genetic aging, for example, relates to aging side effects caused by genetic factors.

What is needed in the relevant art is, for example, an easy-to-use, simple and friendly diagnostic tool for assessing facial features, for example, based on key facial signs and indicators, and identifying the correct injectable treatment plan. What is also needed is a diagnostic tool for assessing facial features and identifying the correct injectable treatment plan which a patient can be treated with at an early enough time to effectively prevent, reverse, or delay the side effects of the aging process. What is needed is as a diagnostic tool to clarify the key facial signs on the face's aesthetic assessment to provide a correct treatment planning and thus maintain a youthful facial appearance, slow down and reverse the symptoms and negative side effects of aging.

With the advent of new technology, medicine, advances in healthcare and our understanding of biology underling health, as well as other multifactor reasons, humans are living longer than ever. Although the exception, it is not uncommon for persons to live at least one-hundred years old.

In developing countries, interestingly, the human lifespan is also increasing due to a variety of factors. Some factors include an improving economy and educational system, a reduction in deaths from infectious diseases, improved nutrition and other reasons. For example, women born in South Korea in the year 2030 are expected to have an average lifespan of about ninety (90) years. Women born in France in the year 2030 are expected to have an average lifespan of about eight-eight and four-tenths (88.4) years. Women born in Japan in the year 2030 are expected to have an average lifespan of about eight-eight and six-tenths (88.6) years. See https://medicalxpress.com/news/2017-02-average-life-countries.html.

Despite humans living longer, humans are not necessarily living longer well. For example, see the study by S. Jay Olshansky (http://www.npr.org/sections/health-shots/2016/10/05/496532976/has-the-human-lifespan-hit-the-ceiling), which highlights certain genetic factors involved with aging that result in negative aging side effects. For example, aging includes accumulating damaged DNA and other cellular molecules. In order to continue to age but to live longer well, it would be desirable to slow down the aging process.

Current medical treatments focus on treating diseases after symptoms manifest. However, with the aging process, treating aging side effects after they manifest is insufficient as many of these effects are permanent. Therefore, what is needed are methods for treating aging before the symptoms of aging are observed.

For example, facial aging side effects can be ameliorated to some extent by treating patients with injectable fillers, botulinum toxin type A, lasers, chemical peels, plastic surgery among others secondary methods. However, this treatment is insufficient to completely reverse these effects because the treatment is delivered too late in time.

Once a disease is diagnosed, proper treatment is delivered. The limitation is timing. Mature and senior individuals are much more complex to improve and impossible to revert the damage caused by the aging process in most cases.

One challenge with treating aging is that many indicators of aging are difficult to identify. Unlike a painful tooth which might direct a patient to seek the help of a dentist, aging problems are not pre-empted by painful signals which alert a person to take corrective action. Instead, persons usually become aware that the negative side effects of aging have occurred too late in time to completely reverse or ameliorate the effect.

Some aging negative side effects include the following. Skin is negatively affecting in most humans starting around twenty (20) years of age due to a reduction in collagen production and skin elasticity as well as problems shedding and regenerating new skin. Lung capacity significantly decreases with age after forty (40) years old. Bone densities decrease around twenty (20) years of age, and do so particularly for post-menopausal women—a bone-thinning condition known as osteoporosis. Around the age of thirty-five (35), women's breasts lose tissue and fat, reduce in size and fullness, and around the age of forty (40) sagging may occur and the areola may shrink considerably. Kidney functions decrease around fifty (50) years of age or more. Male hair loss and hair-color fading usually begins in when they are about thirty (30) years old, which may be due to changes in testosterone levels and hair follicles shrinking, both an effect of aging. Each new hair is thinner than the previous one. Eventually, all that remains is a much smaller hair follicle and a thin stump of hair that does not grow out to the skin surface. Female fertility begins to decline around the age of thirty-five (35). Some men experience benign prostatic hyperplasia around the age of fifty (50). Bladder control begins to decline around the age of sixty-five (65). Aging problems include many other negative side effects known in the relevant field.

With this in mind, while people are living longer than ever before, people do not age well and suffer from the side effects of aging, particularly at the oldest ages. What is needed, therefore, are systems and methods for treating patients, or preventing the negative side effects of aging from manifesting, so they can live longer and better than they otherwise would without such treatment. In particular, what is needed are systems and methods for treating facial aesthetics and health. Set forth herein are such systems and methods, as well as other solutions to unmet problems in the relevant field.

SUMMARY

In an embodiment, set forth herein is a method of treating a subject having a condition or disorder, including providing a subject having a condition or disorder; selecting at least one or more MD Codes to treat the condition or disorder, wherein the MD Codes indicate injection sites on the face or neck of the subject; and injecting a therapeutically effective amount of a pharmaceutical composition at the injection sides.

In another embodiment, set forth herein is a method of providing a subject with a consultation, including identifying a condition or disorder in the subject; identifying at least one or more MD Codes useful for treating the condition or disorder, wherein the MD Codes indicate injection sites on the face or neck of the subject; generating a treatment plan to inject a therapeutically effective amount of a pharmaceutical composition at the injection sides identified by the MD Codes; and optionally visualizing the treatment plan on a graphical display.

In another embodiment, set forth herein is a method of developing a treatment plan using the MD Codes.

In another embodiment, set forth herein is software which models the interaction of the MD Codes with a particular patient.

Set forth herein is a system for treating aesthetic conditions and myomodulation (i.e., facial muscle dynamics), wherein the system includes using the DYNA Codes which are injection sites used to guide the treatment of a patient's aesthetic conditions by providing specific injection sites at which to inject certain injectable compositions. Set forth herein is a system for modulating myomodulation (i.e., facial muscle dynamics), wherein the system includes using the DYNA Codes which are injection sites used to guide the treatment of a patient's aesthetic conditions by providing specific injection sites at which to inject certain injectable compositions. In some embodiments, the systems and methods, herein, include any of the disclosure in U.S. Provisional Patent Application No. 62/457,761, filed Feb. 10, 2017, entitled METHODS AND SYSTEMS FOR PREVENTING, CORRECTING, TRANSFORMING, AND MODIFYING FACIAL AESTHETICS, AND CONSULTING PATIENTS REGARDING THE SAME, the entire contents of which are herein incorporated by reference in their entirety for all purposes. In some embodiments, including any of the foregoing, the systems and methods, herein, include any of the disclosure in U.S. Provisional Patent Application No. 62/477,312, filed Mar. 27, 2017, entitled NEXT HUMAN METHODS AND SYSTEMS, the entire contents of which are herein incorporated by reference in their entirety for all purposes.

In an embodiment, set forth herein is a method of treating an aesthetic condition or disorder in a subject having such a condition or disorder, including providing a subject having an aesthetic condition or disorder; selecting at least one or more injection sites using the DYNA Codes set forth herein and in the Figures, to treat the condition or disorder, wherein the injection sites are on the face or neck of the subject; and injecting a therapeutically effective amount of a pharmaceutical composition at the injection sides.

In another embodiment, set forth herein is a method of providing a subject with a consultation, including identifying an aesthetic condition or disorder in the subject; identifying at least one or more injection sites useful for treating the aesthetic condition or disorder, wherein the injection sites are on the face or neck of the subject; generating a treatment plan to inject a therapeutically effective amount of a pharmaceutical composition at the injection sides; and optionally visualizing the treatment plan on a graphical display.

In another embodiment, set forth herein is a method of developing a treatment plan using the DYNA Codes described herein.

In another embodiment, set forth herein is software which models the interaction of the methods of treating a subject described herein with a particular patient.

Set forth herein is a system for identifying aesthetic conditions and aging conditions, wherein the system includes an MD ASA diagram or series of MD ASA diagrams which are used to assess a patient's aesthetic conditions and used to treat the patient in order to address, ameliorate or improve their aesthetic condition. In some embodiments, the systems and methods, herein, include any of the disclosure in U.S. Provisional Patent Application No. 62/457,761, filed Feb. 10, 2017, entitled METHODS AND SYSTEMS FOR PREVENTING, CORRECTING, TRANSFORMING, AND MODIFYING FACIAL AESTHETICS, AND CONSULTING PATIENTS REGARDING THE SAME, the entire contents of which are herein incorporated by reference in their entirety for all purposes.

Set forth herein is a system for treating an aesthetic conditions and aging conditions, wherein the system includes an MD ASA diagram or series of MD ASA diagrams which are used to assess a patient's aesthetic conditions and used to treat the patient in order to address, ameliorate or improve their aesthetic condition. In some embodiments, the systems and methods, herein, include any of the disclosure in U.S. Provisional Patent Application No. 62/457,761, filed Feb. 10, 2017, entitled METHODS AND SYSTEMS FOR PREVENTING, CORRECTING, TRANSFORMING, AND MODIFYING FACIAL AESTHETICS, AND CONSULTING PATIENTS REGARDING THE SAME, the entire contents of which are herein incorporated by reference in their entirety for all purposes.

In an embodiment, set forth herein is a method for identifying an aesthetic condition or disorder in a subject having such a condition or disorder, including providing a subject having an aesthetic condition or disorder; selecting at least one or more injection sites, set forth herein using the MD ASA diagram, to treat the condition or disorder, wherein the injection sites are on the face or neck of the subject.

In an embodiment, set forth herein is a method for treating an aesthetic condition or disorder in a subject having such a condition or disorder, including providing a subject having an aesthetic condition or disorder; selecting at least one or more injection sites, set forth herein using the MD ASA diagram, to treat the condition or disorder, wherein the injection sites are on the face or neck of the subject.

In another embodiment, set forth herein is a method of providing a subject with a consultation, including identifying an aesthetic condition or disorder in the subject; identifying at least one or more injection sites useful for treating the aesthetic condition or disorder, wherein the injection sites are on the face or neck of the subject; generating a treatment plan to inject a therapeutically effective amount of a pharmaceutical composition at the injection sides; and optionally visualizing the treatment plan on a graphical display.

In another embodiment, set forth herein is a method of developing a treatment plan using the MD ASA diagrams described herein.

Set forth herein is a system to assess aesthetic and health indicators and using these indicators to maintain or preserve a youthful appearance while aging. Also set forth herein is a system to assess aesthetic and health indicators and for using these indicators to generate beneficial aging responses. Some of the indicators are associated with negatively affecting the aesthetics and health status of an aging human. These are called aesthetic and health indicators. If these indicators are identified and addressed (e.g., corrected), at a sufficiently early stage, the treatments set forth herein perpetuate optimal conditions for physical appearance and health. Using the treatment methods set forth herein, humans who are in need of such treatment are able to age without experiencing the natural aging process and instead will be comparatively healthier and younger-looking than they otherwise would be in the absence of this treatment. In some embodiments, the systems and methods, herein, include any of the disclosure in U.S. Provisional Patent Application No. 62/457,761, filed Feb. 10, 2017, entitled METHODS AND SYSTEMS FOR PREVENTING, CORRECTING, TRANSFORMING, AND MODIFYING FACIAL AESTHETICS, AND CONSULTING PATIENTS REGARDING THE SAME, the entire contents of which are herein incorporated by reference in their entirety for all purposes.

In an embodiment, set forth herein is a method of treating aging in a subject having an aging condition or disorder, including providing a subject having an aging condition or disorder; selecting at least one or more injection sites, set forth herein, to treat the condition or disorder, wherein the injection sites are on the face or neck of the subject; and injecting a therapeutically effective amount of a pharmaceutical composition at the injection sides.

In another embodiment, set forth herein is a method of providing a subject with a consultation, including identifying an aging condition or disorder in the subject; identifying at least one or more injection sites useful for treating the aging condition or disorder, wherein the injection sites are on the face or neck of the subject; generating a treatment plan to inject a therapeutically effective amount of a pharmaceutical composition at the injection sides; and optionally visualizing the treatment plan on a graphical display.

In another embodiment, set forth herein is a method of developing a treatment plan using the Aging Trigger Point (ATP) and health markers (HM) described herein.

In another embodiment, set forth herein is software which models the interaction of the methods of treating a subject described herein with a particular patient.

BRIEF DESCRIPTION OF DRAWINGS

FIG. 1 describes the acronym MD ASA: Multi-dimensional Aesthetic Scan Assessment.
FIG. 2 shows that MD ASA is a new tool for an aesthetic systematic assessment.
FIG. 3 shows the aesthetic hierarchy: H1 to H5.
FIGS. 4 and 5 show H1:Full face.
FIGS. 6 and 7 show H2: Facial thirds and neck.
FIGS. 8 to 10 show H3: Facial units.
FIGS. 11 and 12 show H4: Facial subunits.
FIGS. 13 and 14 show H5: Distractions.
FIGS. 16 to 19 show H2: Facial thirds and neck.
FIGS. 20 and 21 show Vertical scanning of the front face.
FIGS. 22 and 23 show Vertical scanning of the oblique face into five levels.
FIGS. 24 to 31 show "Best side of the face" symmetry analysis on a young woman.
FIGS. 36 to 64 show how to assess the genetic aging in frontal, oblique, and profile views.
FIG. 66 shows an assessment flow: weakening the downgrading attributes and reinforcing the upgrading ones.
FIGS. 67 to 107 show case studies.
FIGS. 67 to 71: How to defeat the saggy appearance.
FIGS. 72 to 75: How to defeat the sad appearance.
FIGS. 76 to 78: How to defeat the tired appearance.
FIGS. 79 to 82: How to defeat the angry appearance.
FIGS. 83 to 85: How to enhance the slimmer appearance.
FIGS. 86 to 89: How to enhance a more feminine (softer) appearance.
FIG. 90: How to enhance a more masculine appearance [for male patients].
FIGS. 91 to 94: How to enhance a youthful appearance.
FIGS. 95 to 98: How to enhance a more attractive appearance.
FIGS. 99 to 103: How to enhance a more attractive appearance in an Asian patient.
FIGS. 104 to 106: How to enhance a more attractive appearance in a Middle Eastern patient.
FIG. 107: How to enhance a more attractive appearance for Afro descent patients.
FIGS. 110 and 111 show Dyna Codes Muscle location—Oblique view.
FIG. 112 shows the Muscle pulley and lever systems.
FIG. 113 shows the aging and treatment effects on muscle action.
FIG. 117 shows the results of Example 1.
FIG. 123 shows the human face: Surface and bone levels.
FIG. 127 identifies the SATP through genetic aging.
FIG. 128 shows the eight (8) BAPT: Front view.
FIG. 131 shows the BATP and SATP through genetic aging.
FIG. 132 shows a more detailed table of statistics of the main death causes worldwide.

FIGS. 134 and 135 show the eight (8) HM and reference ranges.

FIG. 137 shows an example of aging sign evolution in non-related female individuals—oblique view.

FIG. 138 shows an example of patient assessment which includes overlaying a picture of a mother and a daughter.

FIG. 141 shows SATP locations suitable for use herein.

FIG. 143 shows BATP locations suitable for use herein.

FIG. 145 shows before and after images of a subject treated with a Hyaluronic acid-based injectable. The details are discussed in Example 2.

FIG. 147 shows before and after images of a subject treated with a Hyaluronic acid-based injectable: Profile view. The details are discussed in Example 2.

FIG. 147 shows before and after images of a subject treated with a Hyaluronic acid-based injectable: Profile view. The details are discussed in Example 2.

DETAILED DESCRIPTION

Figure 14:
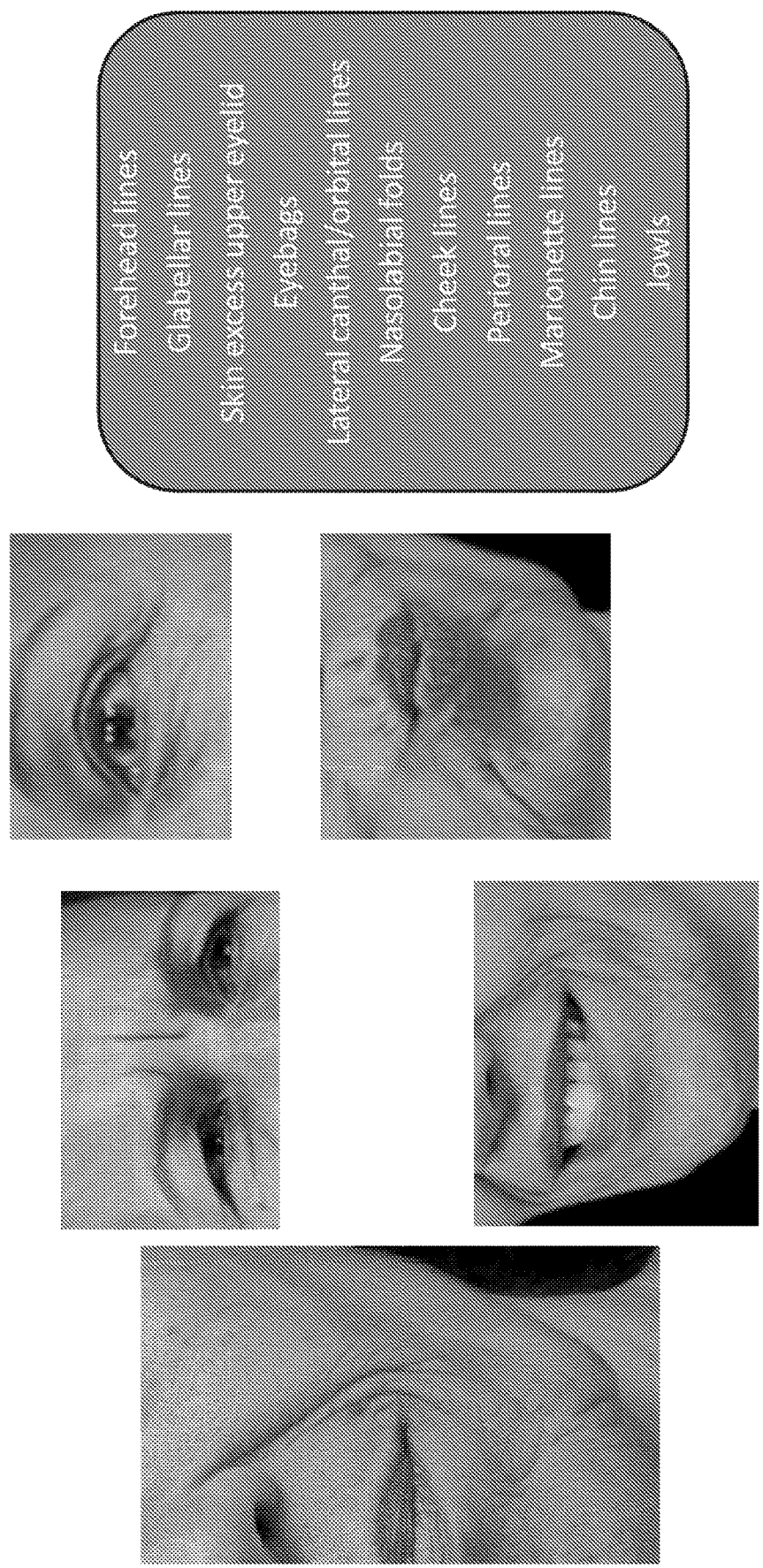

Set forth herein are MD Codes. These MD Codes provide unique injection patterns, injection sites, and related injection instructions for injecting various compositions into aesthetic facial unit (e.g., cheek, chin, lips, etc.) and subunits thereof. By injecting the compositions described herein using the injection sites provided by the MD Codes, different and improved treatment results are possible.

The MD CODES provide a method for injecting treatments and for providing treatment plans. The purpose of the instant disclosure is to expand from the treatment of isolated facial areas, and expand the treatment of conditions to include emotional conditions/attributes using the MD Codes equations, MD Codes formulas, MD Codes for long chains of hyaluronic acid (HA) polymers, MD Codes for toxin protein derived from the bacterium *Clostridium botulinum* (botulinum toxin type A), MD Codes for HA-based skin boosters, and/or MD Codes for deoxycholic acid (for reduction of submental fat). Also set forth herein are methods for consulting a patient, and developing a treatment plan, or developing a financial plan, related to the use of the MD Codes.

The MD Codes are a series of precise sites that were created to guide injections on the face. The injection sites are divided into anatomical areas. Each injection site is represented by letters and numbers. The letters represent the anatomical area and the numbers refer to subunits and may also indicate the sequence in which the injections may be potentially delivered.

With reference to the Figures filed herewith, the letters in the figures represent the name of the anatomical area. The numbers in the figures represent the subunits of the anatomical unit. For example, number 1 represents the priority area and number 3 usually represents the alert zone. The number positions are as follows. Superscript ($x^2$) refers to upper area such as in upper lip, and subscript ($x_2$) refers to lower area such as lower lip. Right (r) or left (l) refers to the left or right areas of the treated site, respectively. The colors represent priority areas, alert areas, need of support, and the like. The shapes represent the technical delivery of the product.

Each MD Code for botulinum toxin type A is depicted with a combination of the following. The letters refer for the anatomical unit (e.g., G=*glabella*). The numbers correspond to the anatomical subunit (e.g., G1=subunit 1 of the *glabella*). The number location indicates the side of the face (e.g., G1toxR is the injection site on the right-hand side). The number positions are as follows. Superscript ($X"$) refers to upper areas (e.g., F2=upper part of forehead unit 2), and subscript ($X_n$) refers to lower areas (e.g., F2=lower part of forehead unit 2).

In some examples, the MD Codes include a system for injecting facial treatments into a subject. In some example, the MD Codes provide a unique treatment of the facial areas by providing a unique site or pattern or sites in which to inject a facial treatment. The MD Codes can be tailored to individual patients or to particular conditions. The MD Codes can be used to provide an individualized, holistic treatment plan. In some examples, the MD Codes provide an injection guide that may prevent, correct and transform the facial aging.

In some examples, set forth herein are methods of consulting a patient about the use of the MD Codes. In these examples, the MD Codes are a helpful tool to be used during communication between injectors, doctors, and other related health care or cosmetic provides, and patients to understand the patient's treatment plan, motivation, and expected results. In these examples, the MD Codes are a helpful tool to be used during communication between injectors, doctors, and other related health care or cosmetic provides, and patients to evaluate a given product, volume and budget calculations, with respect to the treatment plan with the patients.

Set forth herein are MD Codes, Equations and Formulas.

The MD Codes equations focus on a specific unit of the face and consist of the MD Codes that guide treatments of a specific facial sign or deficiency. The MD Codes formulas combine all of the MD Codes equations that commonly define a specific emotional attribute. There is one Formula per emotional attribute. Each Formula includes all of the facial units that should be assessed and considered for treatment, and the product options available. In other words, each MD Codes formula is a recipe that will guide treatment of the key facial signs that are usually present in patients with a specific emotional attribute. While treatment should always be tailored to the individual needs of the patient, the MD Codes formulas provide a starting point that can be individualized during clinical assessment. Most of the MD Codes formulas may be applied universally to patients of all ethnicities and genders, but there are some formulas where specific guidance is given for different gender and patient populations.

In some examples, the formula for Botulinum Toxin—Type A are the 3-point forehead reshape: F1, F2, and F3. In some examples, the formula are the 2-point glabellar reshape: G1, G2. In some examples, the formula are the 3-point tear through shape: Tt1, Tt2, and Tt3. In some examples, the formula are the 8-point lip reshape: Lp1, Lp2, Lp3, Lp4, Lp5, Lp6, Lp7, and Lp8. In some examples, the formula are the 6-point chin reshape: C1, C2, C3, C4, C5, C6.

In some examples, the formula for the long-chain Hyaluronic Acid products are the 3-point eyebrow reshape: E1, E2, E3. In some examples, the formula for the long-chain Hyaluronic Acid products are the 2-point temple reshape: T1, T2. 3-point lateral periorbital reshape: O1, O2, O3. In some examples, the formula for the long-chain Hyaluronic Acid products are the 5-point cheek reshape: Ck1, Ck2, Ck3, Ck4, Ck5. In some examples, the formula for the long-chain Hyaluronic Acid products are the 3-point nasolabial reshape: NL1, NL2, NL3. In some examples, the formula for the long-chain Hyaluronic Acid products are the 3-point marionette line reshape: M1, M2, M3. In some examples, the formula for the long-chain Hyaluronic Acid products are the 5-point jawline reshape: Jw1, Jw2, Jw3, Jw4, Jw5.

In some examples, the methods of treatment using the MD Codes for HA (hyaluronic acid) provide structure, correct lines and folds in the face and provide a non-surgical option for the saggy skin. In other examples, the methods of treatment using the MD Codes for botulinum toxin type A aim to provide the treatment of dynamic lines by blocking excessive facial muscle contraction.

In some examples, the new MD Codes include the concept of treating emotional attributes through equations and formulas which combine the MD Codes for long chains of hyaluronic acid (HA) polymers, the MD Codes for botulinum toxin type A, the MD Codes for HA-based skin boosters, and MD Codes for deoxycholic acid (for reduction of submental fat).

In some examples, set forth herein are methods of consulting a patient. In these examples, the injector determines how the patient's appears is closely related to how she/he feels. To help the patient achieve the look that will make she/he feels and appears the way she/he desires, the injector will have to work together to form a cohesive treatment plan that will help the achievement of the best results possible. To achieve so, the injector has to determine: (i) how the patient would like her/his appearance to make she/he feels; and (ii) the areas that need to be addressed to help achieve that objective. With this determination, the MD Codes are selected for use with the patient.

In some examples, the injector ascertains the following categories of emotional attributes which best reflect how the patient would like to look and feel after the treatment: (1) the patient wants to look less tired, less angry, less sad, to have a less saggy appearance, to look more youthful; (2) the patient wants to look more attractive, (3) the patient wants her/his face to look slimmer, to have softer features.

In some examples, the patient is then advised to identify the top three areas out of the following listed she/he believes will help she/he looks and feels the desired way: (1) on the upper face: forehead lines, forehead shape, frown lines, crow's feet, temple depression, and/or brow shape; (2) on the mid face: under eye area/dark circles, saggy cheeks, nose shape, and/or smile lines; (3) on the lower face: lip volume and definition, lip projection, vertical lines above the lip, and lines around the mouth; (4) with respect to the skin quality: dryness, oiliness, roughness, creepy skin, skin depressions and/or skin pigmentation; (5) on the chin and jawline: fullness under the chin (double chin), chin shape and projection, jowls, and/or jawline; and, (6) on the neck and chest: décolletage and/or neck lines. From this determination, a treatment plan using the MD Codes is provided.

The MD Codes are an advanced treatment approach that divides the face into precise areas and uses a personalized facial aesthetic treatment plan to help create the most desirable look for a particular patient. As an added benefit, the MD Codes, in some examples, address multiple aesthetic goals at once and thereby provide a higher treatment value. By combining advanced techniques and different product types, the MD Codes help the patient to look and feel her/his best. The MD Codes treatment approach is customizable and will vary by person according to age, gender, ethnicity and treatment goals. Each of the following desired outcomes will be based on a treatment plan agreed to between the injector and patient.

In some examples, the MD Codes for botulinum toxin type A cause the relaxation of the muscles that cause lines and wrinkles. They soften frown lines and smooth crow's feet. The MD Codes for long-chain HA products, in some examples, restore lost volume, contours and redefine features and treat unwanted lines. As a consequence, they lift brows and temples, softens dark circles, lift and contour cheeks, soften smile lines, enhance and define lips, soften line around the mouth, and contour chin and jawline. The MD Codes for skin boosters smooth, hydrate and improve the skin elasticity, improving the skin quality on the face and the neck. The MD Codes for deoxycholic acid (for reduction of submental fat) are addressed to treat unwanted fat under the chin, also known as double chin, thus improving the chin profile.

For methods of making a patient look less saggy, the MD Codes equations and formulas thereto lift and project the cheek for a more defined look; soften smile lines; smooth marionette lines; contour the chin and jawline; and, reduce the appearance of a double chin.

For methods of making a patient look less sad, the MD Codes equations and formulas thereto soften frown lines (vertical lines between the eyebrows) and crow's feet; lift and project the cheek for a more defined look; lift and project eyebrows; make the area under the eye look less tired and puffy; add volume to temple area; soften smile lines and marionette lines; add volume to the patient's lips, while forming ideal lip structure; and, improve overall skin quality and hydration.

For methods of making a patient look less tired, the MD Codes equations and formulas thereto soften frown lines (vertical lines between the eyebrows) and crow's feet; lift and project the cheek for a more defined look; make the area under the eye look less tired and puffy, for a more energetic look; lift and project the eyebrow; open up the eye area; and, improve the overall skin quality and hydration.

For low brows (eyebrows, temples): E1+E2+E3+T1+T2

For eye bags, cheeks, and tear trough, Ck1+Ck2+Ck3+Tt1+Tt2+Tt3.

For methods of making a patient look less angry, the MD Codes equations and formulas thereto soften frown lines (vertical lines between the eyebrows) and crow's feet, improve the appearance of deep lines between the eyebrows, lift and project the cheek for a more defined look, and, add volume to your lips, while forming ideal lip structure.

For methods of making a patient have a slimmer face, the MD Codes equations and formulas thereto lift and project the cheek for a more defined look; form the ideal shape for your chin; and, reduce the appearance of a double chin and will create a more defined jawline and an overall slimming appearance.

For methods of making a patient look more feminine/softer, the MD Codes equations and formulas thereto lift and project the cheek for a more defined look; remove sunken look, adding fullness to cheeks; lift and project the eyebrow and open up the eye area; add volume to your lips, while forming ideal lip structure; contour chin and reduce appearance of a double chin; and improve overall skin quality and hydration. If the desired outcome is to look more masculine (for male patients), the MD Codes equations and formulas thereto lift and projects the cheek for a more defined look; lift and project the eyebrow; open up the eye area; contour the chin; and reduce the appearance of a double chin.

For methods of making a patient look younger, the MD Codes equations and formulas thereto soften frown lines (vertical lines between the eyebrows) and crow's feet; lift and project the cheek for a more defined look; remove sunken look, adding fullness to the cheeks; make the area under the eye look less tired and puffy; add volume to temple area, lifts and projects the eyebrow and opens up the eye area; soften smile lines and smooth marionette lines; add volume to your lips, while forming ideal lip structure; contour chin/jawline and reduce appearance of a double chin; improve overall skin quality and hydration.

For methods of making a patient look more attractive (for Caucasian patients), the MD Codes equations and formulas thereto lift and project the cheek for a more defined look; add volume to your lips, while forming ideal lip structure; and, improve overall skin quality and hydration.

For methods of making a patient look more attractive (for Asian patients), the MD Codes equations and formulas thereto lift and project the cheek for a more defined look, form the ideal shape for your chin, and, reduce the appearance of a double chin and create a more defined jawline and overall slimming appearance.

For methods of making a patient look more attractive (for Indian and/or Middle Eastern patients), the MD Codes equations and formulas thereto soften frown lines (vertical lines between the eyebrows) and crow's feet; lift and project the cheek for a more defined look; make the area under the eye look less tired and puffy; lift and project the eyebrow; open up the eye area; and, improve overall skin quality and hydration.

For methods of making a patient look more attractive (for African descent patients), the MD Codes equations and formulas thereto lift and project the cheek for a more defined look; form the ideal shape for your chin; and, make the area under the eye look less tired and puffy.

The MD Codes performed can be written down on a passport so that both patient and injector can follow up the treatment.

In some examples, the conditions treated using the MD Codes include, but are not limited to, looking younger, looking less tired, more attractive, skin booster, reducing underlying fat.

In some examples, the products used with the MD Codes include but are not limited to Delkyra and/or Volet.

F. EXAMPLES

Example 1

In this example, MD Code equations for common facial signs, e.g., look less saggy are shown For the anatomic unit: cheeks. Equation for Saggy Cheeks, $Ck1+Ck2+Ck3+Ck4$.

For the anatomic unit: nasolabial folds. Equation for Deep nasolabial folds, $NL1+NL2+NL3$.

For the anatomic unit: marionette lines. Equation for Marionette Lines, $M1+M2+M3$.

For the anatomic unit: jawline. Equation for Jowls, $C1+C2+C3+JW1+JW2+JW3+JW4+JW5$.

For the anatomic unit: skin. Equation for poor skin quality, $SK$.

For the anatomic unit: submental area. Equation for Submental fat, $SMF$.

In this example, the composition (e.g., Botox) was injected at the sited indicated by the MD Codes.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

Additional embodiments are described below. References are made to the drawings described in this section.

Embodiment 1, a method of treating a subject having a condition or disorder, comprising:
  providing a subject having a condition or disorder;
  selecting at least one or more MD Codes to treat the condition or disorder, wherein the MD Codes indicate injection sites on the face or neck of the subject; and
  injecting a therapeutically effective amount of a pharmaceutical composition at the injection sides.

Embodiment 2, a method of providing a subject with a consultation, comprising:
  identifying a condition or disorder in the subject;
  identifying at least one or more MD Codes useful for treating the condition or disorder;
    wherein the MD Codes indicate injection sites on the face or neck of the subject;
  generating a treatment plan to inject a therapeutically effective amount of a pharmaceutical composition at the injection sides identified by the MD Codes; and
  optionally visualizing the treatment plan on a graphical display.

Embodiment 3, the method of any one of embodiments 1 or 2, wherein the pharmaceutical composition is Botulinum Toxin—Type A.

Embodiment 4, the method of any one of embodiments 1 or 2, wherein the pharmaceutical composition is a long-chain Hyaluronic Acid (HA) product.

Embodiment 5, the method of any one of embodiments 1 or 2, wherein the pharmaceutical composition comprises HA.

Embodiment 6, the method of any one of embodiments 1 or 2, wherein the pharmaceutical composition is deoxycholic acid.

Embodiment 7, the method of any one of embodiments 1 or 2, wherein the MD Codes are substantially as set forth herein.

Embodiment 8, the method of any one of embodiments 1 or 2, wherein the MD Codes are set forth herein.

Embodiment 9, the method of any one of embodiments 1 or 2, comprising visualizing the MD Codes.

Embodiment 10, the method of any one of embodiments 1 or 2, comprising visualizing the MD Codes on a computer screen.

Embodiment 11, the method of any one of embodiments 1, 2, 9, or 10, wherein the visualizing comprises overlaying any of the MD Codes set forth herein with an image of the subject.

Embodiment 12, the method of embodiment 11, wherein the subject suffers from a cosmetic condition, defect, or disease.

Embodiment 13, the method of embodiment 11, wherein the subject suffers from an aesthetic condition, defect, or disease.

Embodiment 14, the method of embodiment 11, wherein the subject suffers from a dermatology condition, defect, or disease.

Embodiment 15, a system for practicing the method of any one of embodiments 1 or 2.

DYNA Codes Methods and Systems

Set forth here are methods and systems, include the DYNA CODES shown in FIGS. 108-111 and 114-116, for treating facial muscle dynamics, wherein the treating includes injecting hyaluronic acid based products, HA derivatives (HA with oligo elements, vitamins, etc.) and non-HA products into the face or neck of a subject in need thereof, at the injection sites indicated in FIGS. 108-111 and 114-116.

In some examples, the methods herein include injecting injectables into the face or next, at the injection sites indicated by the sites in FIGS. 108-111 and 114-116, to improve facial aesthetics. In some examples, the methods result in a natural facial expression.

In some examples, the methods repair an impaired facial expression. For example, the impairment may be facial palsy. For example, the impairment may be poor congenital structures and the effects due to aging.

In an embodiment, set forth herein is a method of treating aging in a subject having an aging condition or disorder, including providing a subject having an aging condition or disorder; selecting at least one or more injection sites set forth in FIGS. 108-111 and 114-116, to treat the condition or disorder, wherein the injection sites are on the face or neck of the subject; and injecting a therapeutically effective amount of a pharmaceutical composition at the injection sides.

In some examples, the methods here are useful for providing dynamic beauty.

In some examples, the methods here are useful for providing dynamic aging.

In an embodiment, set forth herein is a method of rehabilitating facial aesthetics in a subject having an aging condition or disorder, including providing a subject having an aging condition or disorder; selecting at least one or more injection sites, set forth herein, to treat the condition or disorder, wherein the injection sites are on the face or neck of the subject; and injecting a therapeutically effective amount of a pharmaceutical composition at the injection sides. In some examples, this includes maintaining the appearance of an age which is less than the actual age of the subject. In some examples, the rehabilitation is a treatment provided after facial nerve impairment and/or the presence of muscles with suboptimal contraction patterns In some examples, the methods herein include myomodulating facial or neck muscles. Myomodulating includes controlling muscle contraction patterns and movement, for example, to achieve a particular aesthetic result. The methods herein show how to inject compositions at the sites indicated in FIGS. 108-111 and 114-116 to control muscle contraction patterns and movement.

In some examples, the methods herein include rehabilitating the motricity of patients suffering from facial palsy and other disorders that affect facial expression.

In some examples, including any of the foregoing, the methods herein include slowing down aging of a person.

In some examples, including any of the foregoing, the methods herein include slowing down the aesthetic effects of aging of a person.

In some examples, including any of the foregoing, the methods herein include slowing down the aesthetic effects of aging of tissue in a person. In some examples, the tissue is skin tissue.

In some examples, including any of the foregoing, the methods herein include treating volume loss. In some examples, the treatment of volume loss is early enough to block extreme muscle excursion and recruitment of synergists, which slows the formation of hyperdynamic lines.

In some examples, a subject in need of treatment has structural deficiencies which result in unbalanced muscle action which is reflected in a deformation of the skin surface. In some examples, including any of the foregoing, the methods herein include reestablishing natural structural conditions and rebalancing muscle action to restore the facial appearance to that of a subject when they were younger.

In some examples, including any of the foregoing, the methods herein include controlling the future appearance of the face.

As shown in FIGS. 108-111 and 114-116, the DYNA CODES include a list of injection sites based on the topography of the mimetic muscles. Every DYNA CODE is named after the abbreviation of the muscle in the scientific Latin nomenclature for fast recognition. For example, Zygomaticus major muscle is coded as Zmj. The level of injection changes the muscle behavior. If the injection of a given HA product is delivered over the muscle fibers, muscle contraction is reduced and the specific facial area will move less (hypotonic status). On the contrary, if the HA product is delivered under the muscle fiber, a lever effect will result and a more powerful muscle contraction will take place, lifting the facial structure (hypertonic status). If the HA product is delivered within the muscle fibers, muscle isometric status takes place and the facial structures keeps its position and resists gravity, reducing the aspect of saggy skin.

In some examples, including any of the foregoing, the methods herein include injecting an injectable filler treatment, rebalancing muscle activity, and, or, correcting the facial appearance at rest and on animation. Properly placed, a filler injection can alter the mechanical strength of facial muscle fibers, either strengthening a muscle that has lost lifting power or reducing over-contraction. The over-stretching of facial muscle fibers that occurs with an increasing distance between origin and insertion weakens the muscle.

In some examples, including any of the foregoing, the methods herein include injecting a bolus of filler under a muscle to increase the convexity, to bring the origin and the insertion closer together, and to strengthen the muscle contraction.

In some examples, including any of the foregoing, the methods herein include injecting a bolus of filler over a muscle to decrease the convexity, stretching the muscle fibers and, or, reducing its power. In some of these examples, the muscle is a shortened muscle, with a reduced distance between origin and insertion due to a structural deficiency, may have excessive power of contraction.

In some examples, including any of the foregoing, the methods herein include injecting a bolus of filler within the fibers of a given muscle to strengthen isometric contraction, which reduces the pull of the muscle on its antagonists Understanding Muscle Action in the Face Facial mimetic muscles have several characteristics that differentiate them from skeletal muscle, and this may play a role in bone and soft tissue interactions within the aging face. Generally, facial mimetic muscles have their origin in the bone of the face and insert on the skin and among the fibers of other muscles, with no tendons, except for the sphincter muscles. Under histologic examination, smaller fiber size and greater variation in fiber size are observed in facial mimetic muscle compared with limb muscles. Facial mimetic muscles contain predominantly type II (fast-twitch) muscle fibers that typically contract quickly in brief bursts, and are not able to sustain contraction for long periods of time. Finally, facial mimetic muscles appear to lack typical muscle spindles, which function in resetting resting tone.

Together with these characteristics, three key concepts underlie the role of muscle action on facial appearance: length—tension relationship, muscle pulley and lever systems, and the action of synergist muscle groups and antagonist muscle pairs.

Length—Tension Relationship

The pulling force that a muscle produces is described in part by the length—tension relationship. The length—tension relationship relates to two components in a muscle model: a contractile component (active tension, produced by contraction of the muscle) and an elastic component (passive tension, resulting from the elasticity of associated tendon and connective tissues). Peak force is produced by the contractile component of the muscle at resting length, and is reduced if the muscle fiber is either shortened or stretched. Passive tension increases with increasing length in the elastic component: as the connective tissue associated with the muscle is pulled, it resists and pulls back when released. For facial mimetic muscles that have no tendons and insert in the skin, the elasticity of the skin and connective tissue contributes to the elastic component of the length—tension relationship. Elastic and contractile tension together produce the total tension.

Loss of skin elasticity in aging alters the length—tension relationship for facial mimetic muscles. As the elasticity of skin diminishes with age, the contribution of the elastic component to muscle tension decreases and the contractile component must work harder to return to rest after contraction and maintain the resting position of the skin. Moreover, the loss of elasticity results in stretching of the muscle: Loss of elasticity leads to sagging of the skin, and because facial muscles insert in the skin, sagging, together with the decrease in fat compartment and bone bulk, results in an increase in the distance between the origin and insertion of facial muscles. The muscles stretch and lose power. Lacking muscle spindles, the facial mimetic muscles may fail to reset resting tone to compensate for the change in tension.

Muscle Pulley and Lever Systems

Within the body, biomechanical fixed pulley systems alter the angle of action of muscles, and levers increase their mechanical advantage, enhancing muscle force or displacement. An example of such a biomechanical system in the body is the patella (FIG. 112). The patella provides a pivot surface that changes the direction of the pull of quadriceps and acts as a lever fulcrum that increases its mechanical advantage by reducing the amount of force required for the quadriceps muscle to extend the leg. Similar systems are also found in the facial musculature. The lateral sub-orbicularis oculi fat pad (SOOF), located at the lateral/inferior orbital rim and deep to the orbicularis oculi and zygomaticus major, acts as a pulley glide plane 1 and a lever fulcrum for the zygomaticus major muscle (FIG. 112). Pulling over the SOOF provides a mechanical advantage to the zygomaticus major, which lifts the corners of the mouth in a smile. In aging, the loss of structure beneath the muscle, either from loss of bone or the loss and/or ptosis of fat, can diminish the fulcrum effect, reducing the muscle's force.

Muscle Synergists and Antagonists

Antagonist muscle pairs working in balance contribute to a normal youthful appearance of the face. Levators and depressors work in opposition, as explained in Table 1. The interaction between the levators and the depressors underlies facial appearance both at rest and in dynamic expression. In young persons, levators are stronger than depressors, but they are balanced by the action of their depressor antagonists as they also pull against gravity. However, with changes in bone and/or soft tissue in aging, the balance between antagonist muscles can become disrupted, with effects across the face. For example, if a levator muscle loses power due to stretching or loss of underlying structure, the lever effect is diminished and the antagonist (depressor) is freed to act with reduced opposition. This would lead, for example, to a downturn of the oral commissure. Synergist muscles work together as a group, and their relative activity may shift during the aging process. The synergy of the levators of the upper lip is an example. In this example, in a young person, the zygomaticus major and minor muscles play an important role in making the corner of the mouth tilt up in a smile. As the zygomaticus major loses lifting power in aging, the relative role of the risorious muscle increases and produces a more horizontal smile, and contraction of the alaeque nasi labii superioris levator (ANL) muscle leads to upward rotation of the nasal flare and downturn of the tip of the nose. Finally, when zygomaticus major lifting capacity is further diminished, the depressor anguli oris (DAO) muscle predominates, and a "DAO smile," with the corners of the mouth downturned, is observed. In addition to aging effects on the action of muscles themselves, mechanisms that underlie the balancing of activity between synergist and antagonist muscles also decline with age. Effects of the loss of balance between synergist and antagonistic pairs are observed earliest in dynamic facial expression. In dynamic facial expression, hyperdynamic lines resulting from overactive muscles are first apparent when the face is in motion, and subsequently become evident when the face is at rest.

The modulation of muscle action in aging is illustrated through an examination of the effects of aging on the zygomatic smile. In the typical youthful face, intact bony structure and fat pads produce convexities of the face, including the ogee curve formed by the zygomatic arch and malar fat. The SOOF (sub orbicularis oculi fat) provides structure for the zygomaticus major muscle, acting both as a glide plane and as a lever fulcrum that enhances the pulling force of the muscle.

As a person ages, the loss of skin elasticity and volume loss and displacement in midface fat compartments alter zygomaticus major muscle action. The zygomaticus major has its origin in the zygomatic bone and inserts in soft tissue in the modiolus area at the corner of the mouth. The distance between its origin and insertion increases when skin sags and the modiolus falls. See, for example, FIG. 113—Aging and treatment effects on muscle action. The zygomaticus major is stretched and loses resting tension and power in contraction. At the same time, the mechanical advantage of the lever effect over the lateral SOOF is reduced as SOOF volume is depleted. Finally, as the zygomaticus major loses power, it can no longer adequately counterbalance contraction of its antagonist, the DAO.

The result of these changes is alteration in both static facial appearance, due to lax muscle fibers with inadequate resting tone, and in dynamic action, due to inadequate power in contraction and over-action of muscle antagonists. Laxity in the zygomaticus major may be visible at rest as increased nasolabial folds or a downturn of the corners of the mouth. Dynamic effects of the change in zygomaticus muscle power may be reflected in an inability to sustain isometric contraction to maintain a symmetrical smile, a loss of opposition to depressor anguli oris leading to downturned oral commissures and marionette lines, and increased tension in orbicularis oculi resulting in descending lateral eyebrow.

Each DYNA CODE site is represented by letters and symbols. These letters stand for the muscle targeted, the side where the respective muscle is located on the face, and the symbols correspond to the depth of the injection in relation to the muscle addressed. Thus the initial letters represent the referred muscle. The suffixes represented by the "r" or "l" letters indicate the side of the face where the targeted muscle is. The symbols may be either a straight line or a dotted circumference positioned around the letters. The straight line may be positioned either above or under the letters of the targeted muscle. Each of these symbols represents different depth of the injections.

Figure 114:
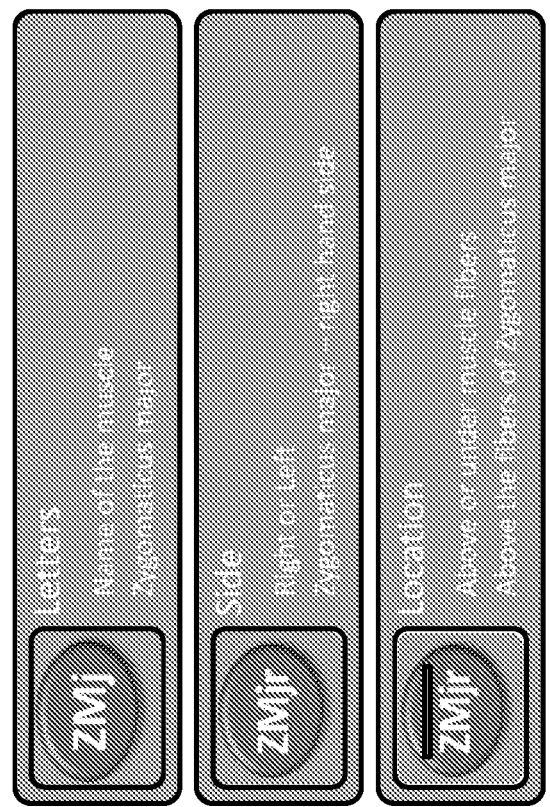
FIG. 114 shows Dyna Code symbols: muscle letters, side location, and injection above the muscle fibers.
Figure 115:
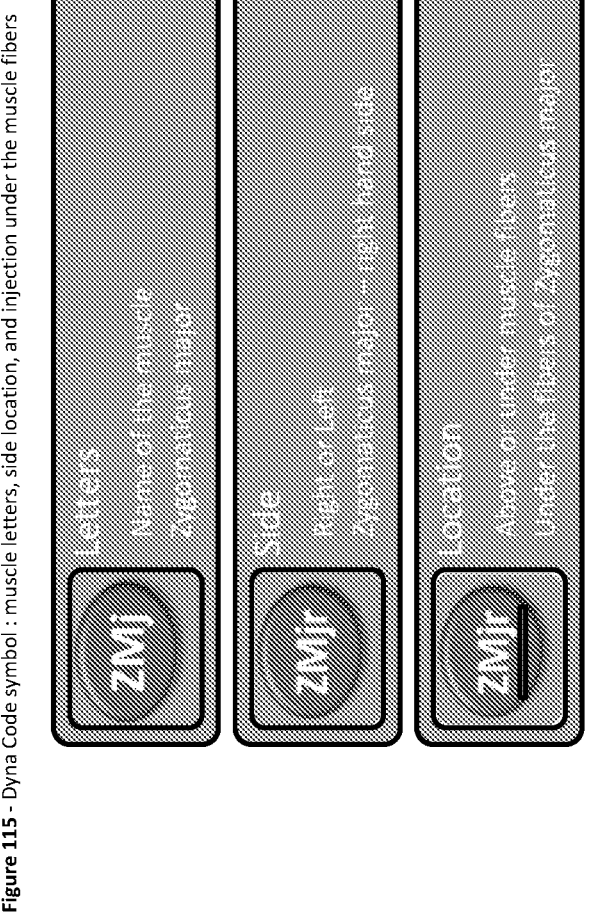
FIG. 115 shows Dyna Code symbols: muscle letters, side location, and injection under the muscle fibers.
Figure 116:
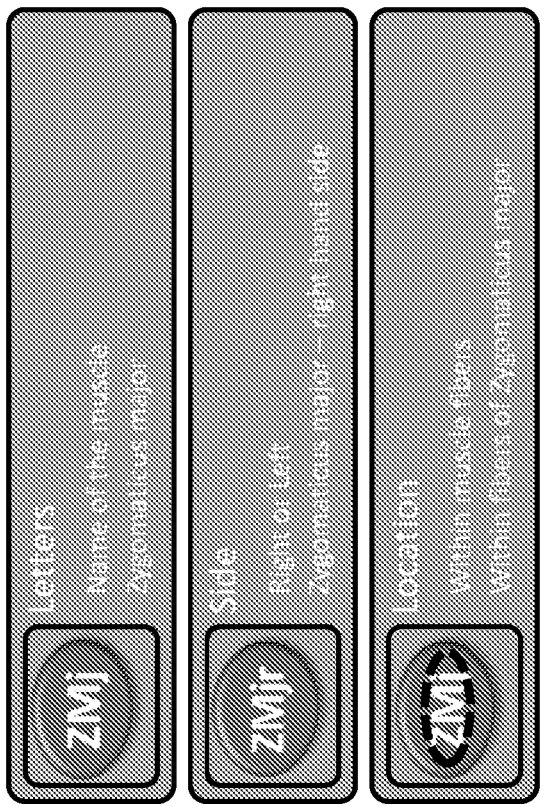
FIG. 116 shows Dyna Code symbols: muscle letters, side location, and injection within the muscle fibers.

In FIGS. 114-116, the first three letters indicate the muscle (ZMj=zygomaticus major). The suffix represented either by the letter "r" or "l" indicates the side of the face where the target muscle is located (ZMjr=zygomaticus major located on the right hand side of the face). The straight line indicates the depth of the injection, which may be either above or under the muscle fibers if positioned above or underneath the Dyna Code symbol, respectively (FIGS. 114 and 115). The dotted circumference around the Dyna Code indicates that HA should be injected within the muscle fibers (FIG. 116).

TABLE 1

| Dyna Codes | Levators | Origin | Insertion | Action |
| --- | --- | --- | --- | --- |
| F | Frontalis | Anterior edge of the galea aponeurotica | Into the forehead skin above the eyebrow | The superior frontalis portion is responsible for the descent of the anterior hairline. The inferior frontalis portion raises the eyebrow |
| C | Corrugator | At the medial portion of the arcus superciliaris of the frontal bone, 0.5 cm from the midline. The origin is about 0.7 to 1.0 cm wide | Into the underside of the frontalis and into the dermis at the junction between the middle and lateral thirds of the eyebrow (the corrugator dimple) 4.2 to 4.5 cm from the midline | The corrugator draws the eyebrow downward and medially, producing the vertical wrinkles of the forehead. It is the "frowning" muscle, and may be regarded as the principal muscle in the expression of suffering |
| P | Procerus | At the aponeurosis of the nasalis pars transversa muscle, the lower part of the nasal bone periosteum and the upper part of the perichondrium of the superior lateral nasal cartilage | Into the skin overlaying the nasal root between the eyebrows. | The procerus draws the medial part of the eyebrow medially downward. |
| OOC | Orbicularis oculi | Pars orbitalis originates on the medial canthal tendon and on the orbital margin extending to the supra orbital foramen in the upper part on the orbital margin (tear trough) in the lower part. Pars palpebralis originates on the medial canthal tendon, the lateral canthal tendon and the posterior lachrymal crest | In its superior portion pars orbitalis inserts into the skin of the eyebrow and inferiorly into the skin of the jugal area. Pars palpebralis adheres directly to the skin since there is neither fat nor subcutaneous tissue. The lateral inferior part of the orbicularis oculi is attached to the posterior portion of the orbital rim by the orbital retaining ligament that represents, along with the tear trough, the distinction between the pars orbitalis and pars palpebralis. This ligament crosses the orbicularis oculi muscle to reach the skin | Pars orbitalis - the sphincter muscle around the eye moves the eyebrow medially and downward and depresses the lateral part of the brow. The orbicularis oculi is the depressor of the lateral part of the eyebrow involved in the lateral muscular balance Pars palpebralis - Involuntary movement to close the eye, i.e., the blink reflex |
| N | Nasalis | At the incisive fossa of the maxila | The pars transversa fibres rise medially forming a triangle to insert into the aponeurosis over the nasal bones, where they merge with the contralateral pars | The pars transversa fibres compress the lateral nasal cartilages and close the nostrils. The pars alaris dilates and opens the nostrils |

TABLE 1-continued

| Dyna Codes | Levators | Origin | Insertion | Action |
|---|---|---|---|---|
| | | | transversa fibres and the aponeurosis of the procerus muscle. The pars alaris inserts into the alar facial crease and adjacent skin of the alar lobule. Laterally, its fibres interdigitate with the levator labii superioris | |
| ANL | Alaeque nasi labii superioris levator | Upper part of the nasal process of the superior maxillary bone | Cartilage of the ala of the nose and upper lip, blended with the orbicularis oris and labii superioris levator | The alaeque nasi labii superioris levator dilates nostril, elevates upper lip |
| LSL | Labii superioris levator | Lower margin of orbit immediately above the infraorbital foramen | Muscle of the upper lip | Elevates upper lip |
| LAO | Levator anguli oris | Canine fossa of maxilla, immediately below the infraorbital foramen | Angle of the mouth, intermingling with the fibers of the zygomaticus major, depressor anguli oris, and oibicularis oris | Raises angle of the mouth |
| B | Buccinator | External alveolar margins of maxilla and mandible by molar teeth, to maxillary tubercle and pterygoid hamulus and posterior mylohyoid line respectively, then via pterygomandibular raphe between bones | It blends into fibers of orbicularis oris | The buccinators compresses cheek against teeth and gums; directs food between molars; retracts cheek from teeth when mouth is closing to prevent biting cheek; expels air and liquid |
| ZMj | Zygomaticus major | Zygomatic bone, in front of the zygomatic suture | Angle of the mouth, blending with the fibers of levator anguli oris, orbicularis oris, and depressor anguli oris | Draws corner of mouth into a smile or grin |
| ZMi | Zygomaticus minor | Zygomatic bone, immediately behind the zygomatic suture | Orbicularis oris, at the outer margin of the labii superioris levator | Draws upper lip upward and outward |
| DSN | Depressor septi nasi | Incisive fossa of the maxilla | Septum and the back part of the ala of the nose | Draws the ala and the tip of the nose downward, constricting the aperture of the nares |
| OO | Orbicularis oris | Near midline on anterior surface of maxilla and mandible and modiolus at angle of mouth | Mucous membrane of margin of lips and raphe with buccinator at modiolus | Closes the lips, protrudes the lips |
| R | Risorius | Risorius arises from zygomatic arch, parotid fascia and masseteric fascia | Risorius blends with other muscles of mouth around lips at its insertion (upper lip, Lip commissure) | The risorius works by expanding and contracting in an upward and outward motion. It works with other facial muscles to create a whole facial motion that pulls the lips and face back. The risorius retracts the angle of the mouth to produce a smile, although an insincere-looking one that does not involve the skin around the eyes. |
| DAO | Depressor anguli oris | External oblique line of lower jaw, continuous with the platysma | Angle of the mouth, continuous with the orbicularis oris and risorius | Depresses the angle of the mouth |
| DLI | Depressor labii inferioris | External oblique line of lower jaw, between the symphysis and mental foramen, continuous with the platysma | Integument of the lower lip, blending with the orbicularis oris and opposite depressor labii inferioris | Draws lower lip downward |
| M | Mentalis (levator menti) | Incisive fossa, external to the symphysis of the lower jaw | Integument of the chin | Raises and protrudes lower lip (pouting) |
| PL | Platysma | Fascia of the upper part of the pectoralis and deltoid muscles | Skin and subcutaneous tissue of the lower part of the face, blending with the muscles at the angle and lower part of the mouth | Depresses the lower jaw, draws lower lip and angle of the mouth downward |

EXAMPLES

Example 1—Case 1

Case 1 involved a mature woman with an asymmetric smile. On the right-hand side, she presented a zygomatic smile, but on the left she showed a DAO pattern. Before treatment, the left cheek sagged due to a lower position of the cheek, yielding a more prominent nasolabial fold. Zygomaticus major had lost its lifting power on her left-hand side and the balance between weakened zygomaticus major and its antagonist, DAO, had been lost. DAO was now free to pull down the corner of the mouth. Case 1 patient was treated with hyaluronic acid (HA) injected in a bolus at the bone at 2 sites on the zygomatic arch under zygomaticus major. Providing structural support to the zygomaticus major increases mechanical advantage, strengthens the muscle, and rebalances activity with its antagonists. The chin was also injected in the labiomental angle on the left-hand side with HA, which mechanically blocked DAO and decreased the power of its downward pull. After treatment, the action of zygomaticus major and DAO was rebalanced. The upward lift of zygomaticus major on the corner of the mouth was increased, the corner of the mouth was lifted up, and the nasolabial fold was less noticeable.

The results of this Example are shown in FIG. 117. Case 1: zygomatic smile. The patient was treated on the left-hand side only. HA was injected at the bone, 0.1 mL at the zygomatic arch and 0.1 mL at the zygomatic eminence, using a 27-g needle. HA was injected in labiomental angle (0.7 mL) and chin apex (0.3 mL) using a 25-g blunt microcannula.)

Example 2—Case 2

A lack of structural support due to bone deficiency can result in aberrant muscular contraction and surface deformation. Case 2 illustrates the contribution of a deficiency of the anterior nasal spine to gummy smile, and correction using injectable filler treatment. In the example the subject was a young Asian patient presented a lack of projection of the anterior nasal spine, retruded underdeveloped columella, and a deficit in the projection of the upper maxilla. The lack of structural support resulted in excessive muscle contraction which was unbalanced by mechanical opponents: on animation, over-contraction of ANLSL, labii superioris levator, and zygomaticus minor resulted in a gummy smile (i.e., a smile which showed a substantial amount of the person's oral gums), shown in FIG. 118. It was observed that the depressor septi nasi was over-contracted due to a lack of support at the level of the bone, which resulted in a collapse of the tip of the nose and a widening of the nasal flare. In this Example, HA was injected into the empty space along the premaxilla at the projection of the anterior nasal spine compensates for the bone deficiency. During smile, there was a reduction in the contraction power of the upper lip levators and the upward retraction of the upper lip is decreased. The aberrant contraction of lip levators and depressor septi nasi was corrected indirectly by mechanical blocking with HA in the anterior nasal spine. The tip of the nose was elevated and the smile line was correctly positioned at the level of the upper part of the central and lateral incisors.

Figure 118:
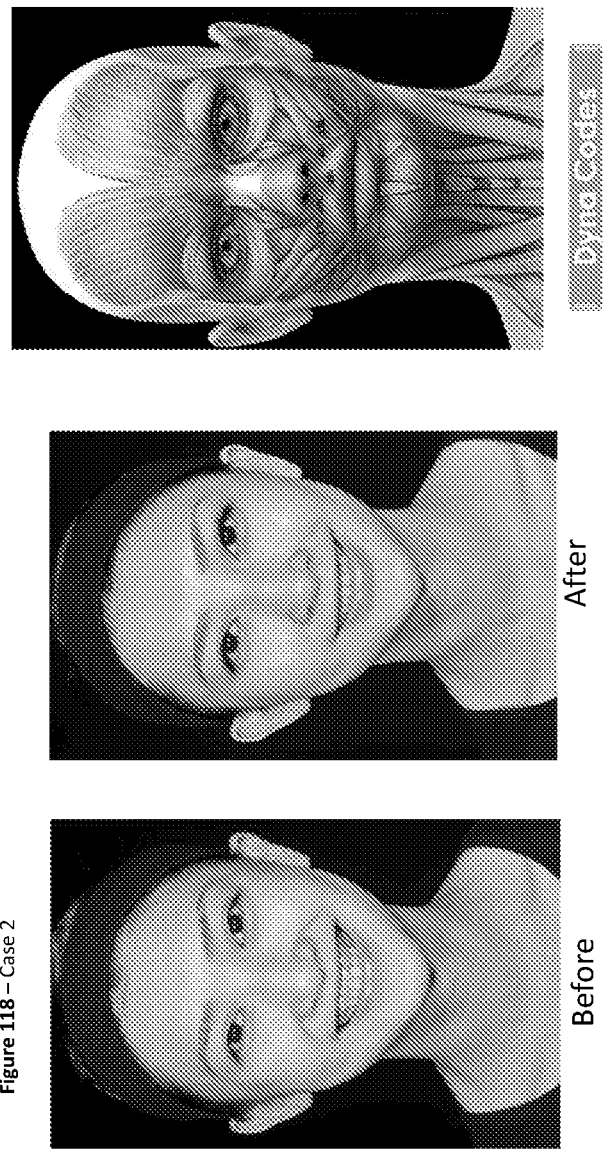
FIG. 118 shows the results of Example 2.

The results of this Example are shown in FIG. 118. Case 2: gummy smile. Treatment was a single bolus of HA (0.7 mL) injected using a 25-g cannula in the pre maxilla, at the bone at the projection of the anterior nasal spine. Before (left) and 6 months after (right) treatment. The lack of support at the premaxilla distorts the nose position and presents a gummy smile. After a mechanical block of depressor septi nasii using HA was provided, the smile was more limited, which corrected both the gummy smile and the distortion of the nose.

Example 3-Case 3

In Case 3, a young woman had no apparent deficiency at rest. However, on animation, a lack of proper bone support in the chin was evident. When pouting, her mentalis was activated and over-contracted, which resulted in an upward rotation of the chin and protrusion of the lower lip with excessive skin wrinkling and deformation. After treatment, the patient's pout was normal. The presence of HA at the labiomental angle and chin apex provided stability for the contracting muscle and blocked the upward rotation and consequent skin wrinkling. Note that the extreme over-contraction of mentalis was corrected while preserving proper mentalis action and the patient was still able to protrude the lower lip. When over-contraction of mentalis was treated with onabotulinumtoxin A, the ability to evert the lower lip can be reduced or lost depending on the dose.

Figure 119:
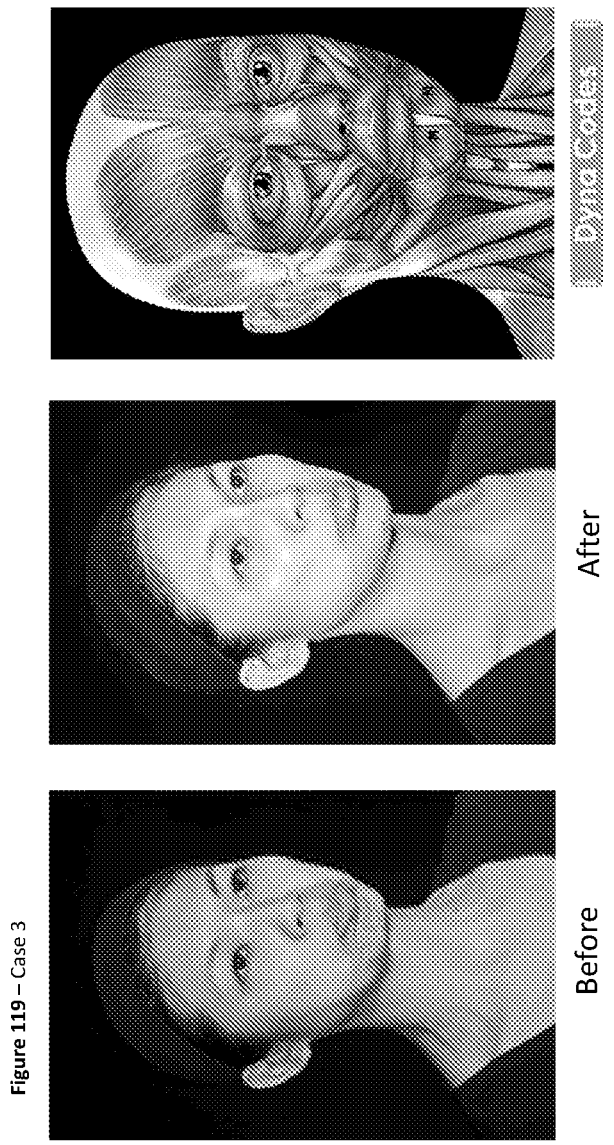
FIG. 119 shows the results of Example 3.

The results of this Example are shown in FIG. 119. Case 3: lack of proper bone support in the chin. The patient was treated with total of 4 mL HA; 1 mL was injected per side into the labiomental angle and 2 mL was injected in the chin apex using a 25-g cannula. Pout; before (left) and 6 months after (right) treatment. Before treatment, the lack of support in the chin caused the mentalis to over-contract and give a peau d'orange appearance. The platysma is also activated when pouting. After mechanical block in her chin, the patient is able to protrude lower lip without skin wrinkling or recruitment of platysma. Controlling over-contraction of the chin also reduces future hypertonic platysmal bands.

Example—Case 4

The fourth case shows a young woman with notable distortion on animation (kissing, pouting). When one purses their lips, the upper and lower lips are directed by the nose and chin position due to the stability at the nasolabial angle and the labiomental angle, respectively. With support at these two sites, the direction of movement in a kiss is horizontal. The patient presented here lacked support at the level of the labiomental angle and chin. Instability at the labiomental angle perturbed the contraction of orbicularis oris. When she was asked to purse her lips (kiss), this instability led to the collapse of obicularis oris during contraction, and both upper and lower lips drop down, resulting in distortion. In pouting, the normal action of mentalis is to protrude the lower lip. In this case, however, her mentalis action lacked coordination due to instability in the labiomental angle. When she asked to pout, the patient couldn't properly protrude the lip. Instead, her lower lip everts toward the oral cavity and hides the upper lip. Treatment with HA in the chin and HA in the lip border allows the patient to produce a natural appearance in a kiss and pout. With support in the soft tissue of chin and lips, her mentalis and orbicularis oris contracted in a more balanced, stable, and organized way. The nose and the chin are very important structural boundaries that enable proper orbicularis oris contraction when pursing. The chin and lower lip are improved by support to mentalis in the labiomental angle and chin apex. The upper lip is improved both directly by HA injection and indirectly by the more organized contraction in the lower lip.

Figure 120:
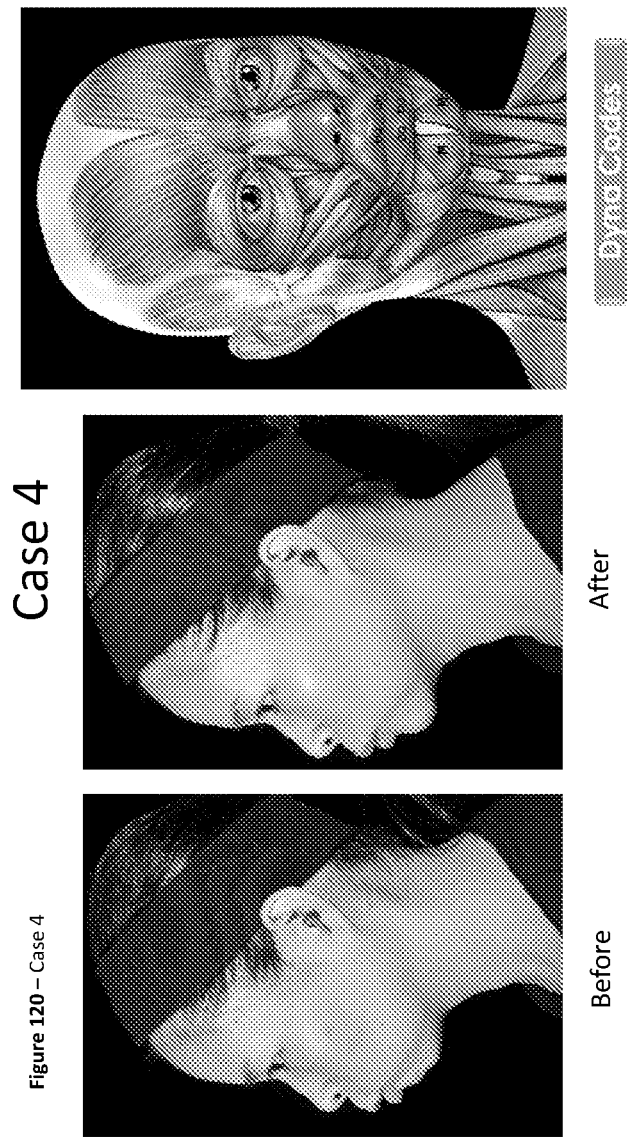
FIG. 120 shows the results of Example 4.

The results of this Example are shown in FIG. 120. Case 4: absence of projection at the chin. HA was injected into the labiomental angle (0.5 mL per side) and chin apex (1 mL) using a 25-g cannula. HA was injected in the lip border (1 mL each in cupid's bow and lip border) using 27-g needle. Purse (kiss); before (left) and 6 months after (right) treatment. Aberrant pursing movement is due to a lack of support of chin and lips. After treatment in the labiomental angle and chin, the patient was able to correctly contract the orbicularis oris without deformation.

Example—Case 5

The fifth case shows a man with facial asymmetry but with a normal facial nerve function observed at rest and on animation. At rest, it was observed that on his left side, the ANL was over-contracting and the upper lip was slightly elevated. Upon animation, both ANL and labii superioris levator were over-contracted. To correct this, the upper lip was pulled higher on the patient's left as he smiles. The labiomental angle was empty on the left-hand side, and this lack of barrier allowed free movement of depressor labii inferioris. Over-contraction of depressor labii inferioris pulled the lower lip down, which resulted in excessive showing of the inferior (i.e., lower) teeth. The subject was also observed to contract his mentalis and rotate the chin slightly upward. HA treatment at the bone on the zygomatic arch increased the pull of zygomaticus major, which in turn reduced the over-contraction of the synergistic medial upper lip levators. Treatment in the labiomental angle and chin apex provided stability and reduced the action of depressor labii inferioris and mentalis, improving the position of the lower lip. After treatment of the cheek and chin, the patient had a more balanced smile with a uniform upper lip smile line and reduced show of the inferior teeth.

Figure 121:
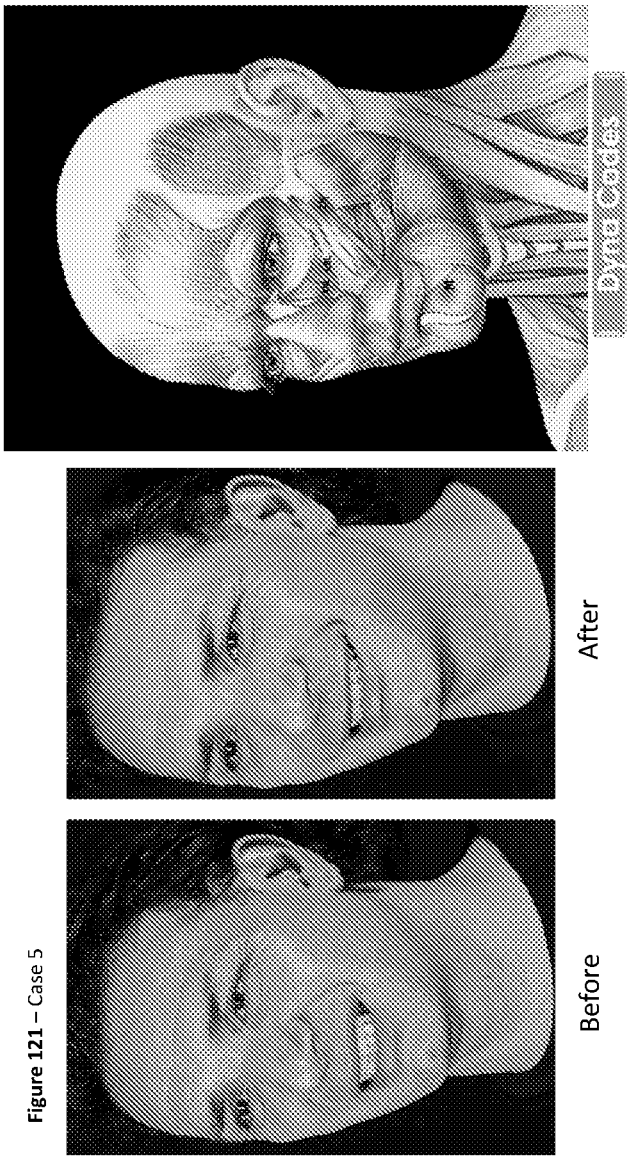
FIG. 121 shows the results of Example 5.
Figure 122:
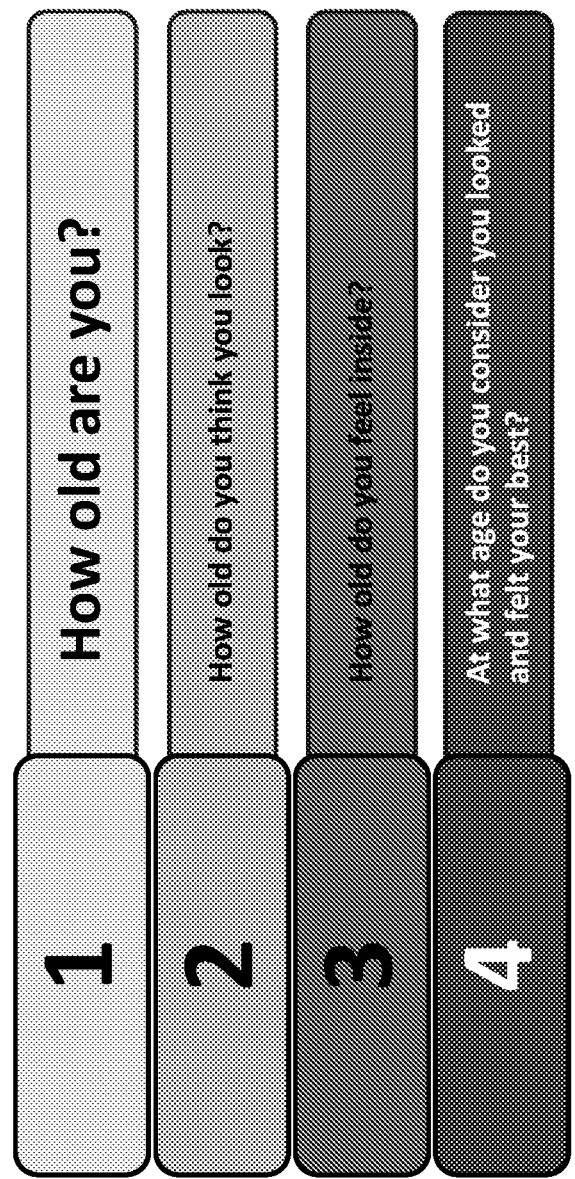
FIG. 122 shows a method of consulting a patient for treatment.

The results of this Example are shown in FIG. 121. Case 7: asymmetry. HA was injected in the left cheek, 0.1 mL at the zygomatic arch and 0.2 mL at the zygomatic eminence, using a 27-g needle. HA was also injected in the labiomental angle (1 mL) on left and at the chin apex (0.5 mL) using a 25-g cannula. Distortion on animation; before (left) and immediately after (right) treatment. Filler treatment of lip levators and depressors controls distortion both at rest and on animation.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

Additional embodiments are described below. References are made to the drawings described in this section.

Embodiment 1, a method of treating a subject in need thereof, the method comprising:
providing a subject;
treating the subject in need thereof by injecting a therapeutically effective amount of a pharmaceutical composition comprising a member selected from the group consisting of hyaluronic acid (HA), HA-based fillers, HA-derivatives, Botulinum Toxin—Type A (Botox), fillers, and combinations thereof,
wherein the treating comprises injecting a patient at sites substantially set forth in any one of FIGS. 108-111 and 114-116.

Embodiment 2, the method of claim 1, wherein the HA-derivatives are selected from the group consisting of vitamins and HA-oligomers.

Embodiment 3, the method of any one of embodiments 1-2, wherein the sites are on the neck or face.

Embodiment 4, the method of any one of embodiments 1-2, wherein the sites are under the facial muscle.

Embodiment 5, the method of any one of embodiments 1-2, wherein the sites are over the facial muscle.

Embodiment 6, the method of any one of embodiments 1-2, wherein the sites are within the facial muscle fiber.

Embodiment 7, the method of any one of embodiments 1-6, wherein the sites are on the chin.

Embodiment 8, the method of any one of embodiments 1-6, wherein the sites are on the chin at the labiomental angle.

Embodiment 9, the method of any one of embodiments 1-6, wherein the sites are on the lower lips.

Embodiment 10, the method of any one of embodiments 1-6, wherein the sites are on the empty space along the premaxilla.

Embodiment 11, the method of any one of embodiments 1-10, wherein the subject is in need of aesthetic treatment.

Embodiment 12, the method of any one of embodiments 1-11, wherein the method further comprises injecting a pharmaceutical composition comprising a member selected from the group consisting of hyaluronic acid (HA), Botox, fillers, and combinations thereof; and repeating the injecting at least once per year for at least five (5) years.

Embodiment 13, the method of any one of embodiments 1-12, wherein the pharmaceutical composition further comprises a member selected from the group consisting of collagen, antibiotics, anti-inflammatory drugs, steroids and combinations thereof.

Embodiment 14, the method of any one of embodiments 1-11, wherein the pharmaceutical composition is Botulinum Toxin—Type A.

Embodiment 15, the method of any one of embodiments 1-11, wherein the pharmaceutical composition is a long-chain Hyaluronic Acid (HA) product.

Embodiment 16, the method of any one of embodiments 1-11, wherein the pharmaceutical composition comprises HA.

Embodiment 17, the method of any one of embodiments 1-11, wherein the pharmaceutical composition is deoxycholic acid.

Embodiment 18, the method of any one of embodiments 1-11, wherein the pharmaceutical composition comprises a vitamin.

Embodiment 19, the method of any one of embodiment 1-18, wherein the injection sites are set forth in any one of FIGS. 108-111 and 114-116.

Figure 108:
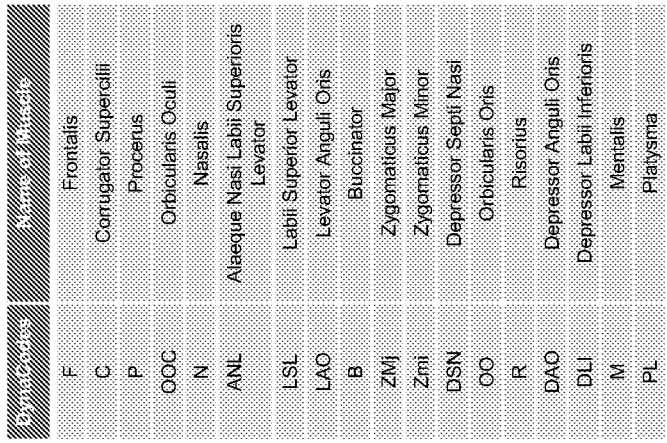
FIG. 108 shows the Dyna Codes muscle location—frontal view.

Embodiment 20, the method of embodiment 19, wherein the injection site is set forth in FIG. 108.

Figure 109:
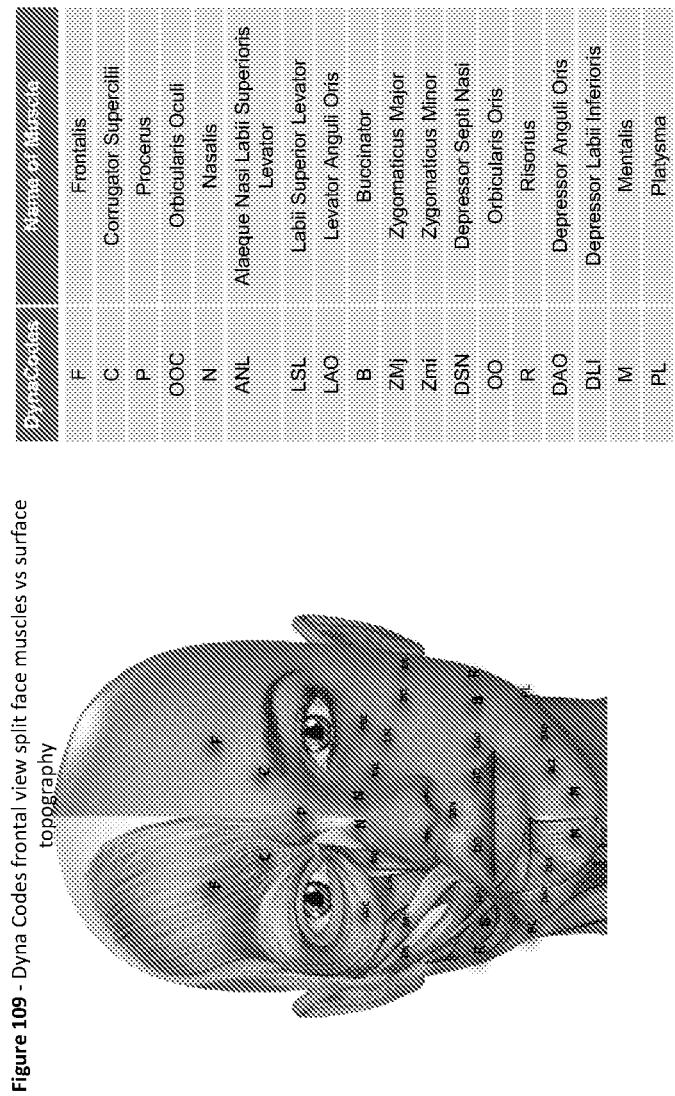
FIG. 109 shows Dyna Codes for split face muscles vs surface topography—frontal view.

Embodiment 21, the method of embodiment 19, wherein the injection site is set forth in FIG. 109.

Embodiment 22, the method of embodiment 19, wherein the injection site is set forth in FIG. 110.

Figure 111:
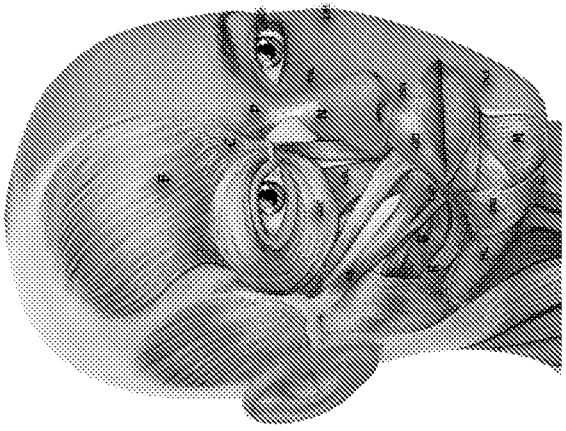

Embodiment 23, the method of embodiment 19, wherein the injection site is set forth in FIG. 111.

Embodiment 24, the method of embodiment 19, wherein the injection site is set forth in FIG. 114.

Embodiment 25, the method of embodiment 19, wherein the injection site is set forth in FIG. 115.

Embodiment 26, the method of embodiment 19, wherein the injection site is set forth in FIG. 116.

Embodiment 27, the method of any one of embodiments 1-25, further comprising visualizing the injection sites.

Embodiment 28, the method of any one of embodiments 1-27, further comprising visualizing the injection sites on a computer screen.

Embodiment 29, the method of any one of embodiments 1-28, wherein the visualizing comprises overlaying any of the injection sites set forth herein with an image of the subject in need thereof.

Embodiment 30, the method of any one of embodiments 1-29, wherein the subject suffers from an aesthetic condition.

Embodiment 31, the method of any one of embodiments 1-29, wherein the subject suffers from a dermatology condition.

Embodiment 32, the method of any one of embodiments 1-31, wherein the method comprising injecting at least 0.5 mL of the therapeutically effective amount of the pharmaceutical composition.

Embodiment 33, the method of any one of embodiments 1-32, wherein the method comprising injecting the therapeutically effective amount of the pharmaceutical composition at a depth of penetration of at least 2-6 mm.

Embodiment 34, the method of any one of embodiments 1-33, wherein pharmaceutical composition is a cellular body.

Embodiment 35, a system for practicing the method of any one of embodiments 1-33.

Embodiment 36, an injector designed for practicing the method of any one of embodiments 1-35.

MD ASA Methods and Systems

MD ASA is an acronym which stands for Multi-dimensional Aesthetic Scan Assessment (FIG. 1).

Using the MD ASA methods herein, facial signs are identified and treated before the negative side effects of aging are apparent, in order to maintain a youthful facial appearance and slow down, and in some examples, reverse the aging process.

In some examples, including any of the foregoing, the methods include visualizing a photo of the patient's face in multiple positions and with specific facial expressions. This process aids in the identification of the facial sites to treat.

In some examples, including any of the foregoing, the methods include a continuous process of facial analysis.

In some examples, including any of the foregoing, the methods include assessing or visualizing facial problems. In some examples, this includes visualizing facial problems a frontal view, right oblique view, left oblique view, right full profile, left full profile, chin down eyes up, and/or chin up eyes up.

In some examples, including any of the foregoing, the methods include assessing or visualizing facial attributes including, but not limited to the following, at rest, angry (frowning), surprise (eyebrows lifted), full smile, kissing (purse the lips), pouting (eversion lower lip), and grimace (neck).

In some examples, including any of the foregoing, the methods include assessing the subject to determine the treatment plant.

In some examples, including any of the foregoing, the methods include providing an aesthetic hierarchy. In methods herein, the aesthetic hierarchy is the first parameter established before other steps set forth herein are practiced. In these examples, the aesthetic hierarchy identifies anatomical facial structures. In some examples, the first hierarchy is the full face and the last one the distractions noticed on each of the facial subunits (see FIG. 3). The aesthetic hierarchy is divided into five (5) different levels, as follows:

The first level is H1. H1 corresponds to the full-face analysis, focusing on its message and perception of overall harmony (FIGS. 4 and 5).

The second level is H2. H2 corresponds to the face's division into thirds, including the neck, and focuses on symmetry, position, and proportion (FIGS. 6 and 7). In methods herein, a fraction of an image of a patient's face is separated from the entire image of the patient's face in order to determine the H2 level.

The third level is H3. H3 corresponds to the facial units which may be divided into five (5) different units, such as but not limited to the forehead and temples, *glabella* and eyebrows, eyelids, cheeks and nose, lips, and chin and neck. H3 also corresponds to the facial units which may be grouped into two (2) major areas—the periorbital and perioral areas as illustrated in FIGS. 8-10.

The forth level is H4. H4 corresponds to facial subunits (FIGS. 11 and 12).

The fifth level is H5. H5 relates to distractions that can be spotted on each of the facial subunits (FIGS. 13 and 14).

Figure 15:
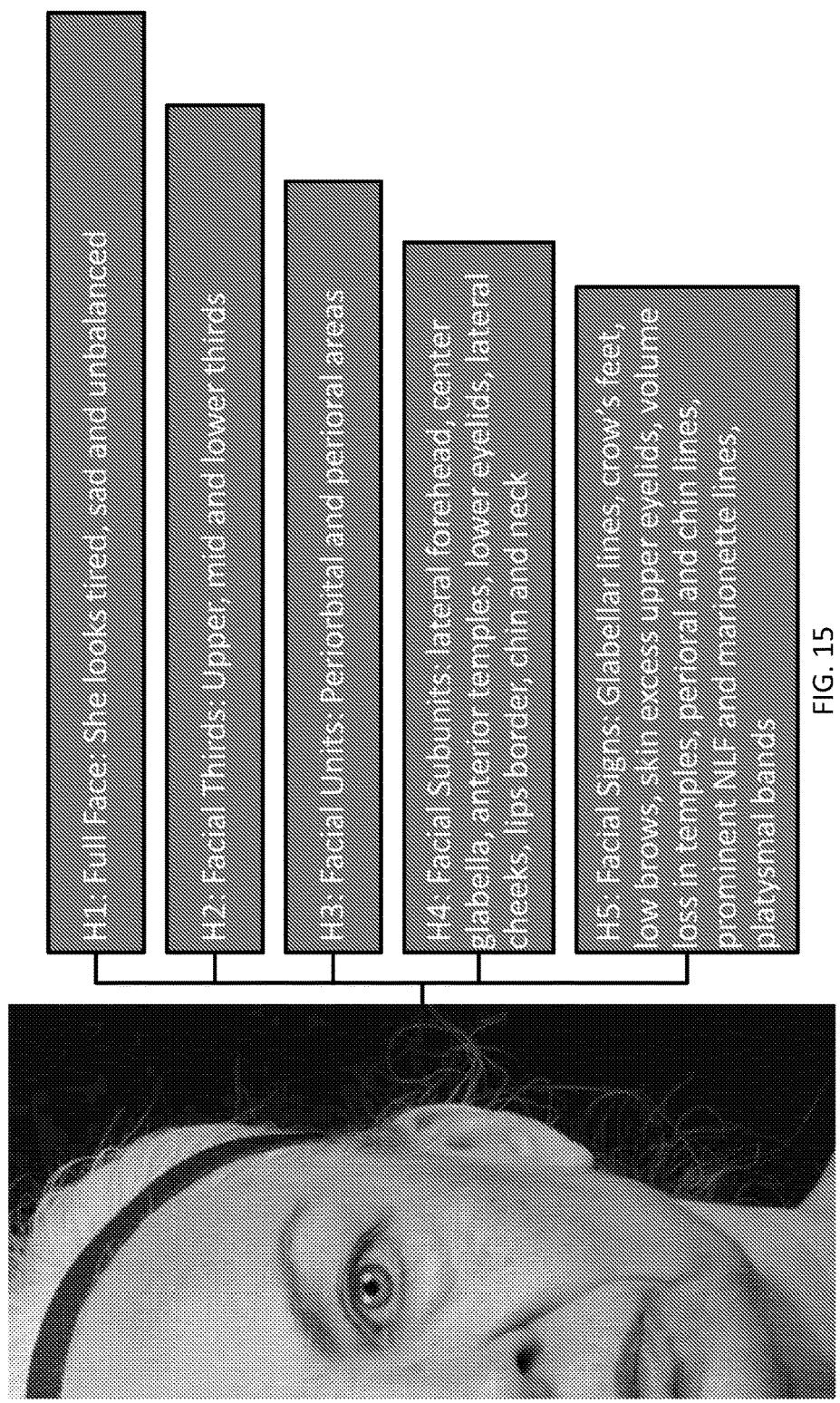
FIG. 15 shows a clinical example: a 56-year-old patient.
Figure 16:
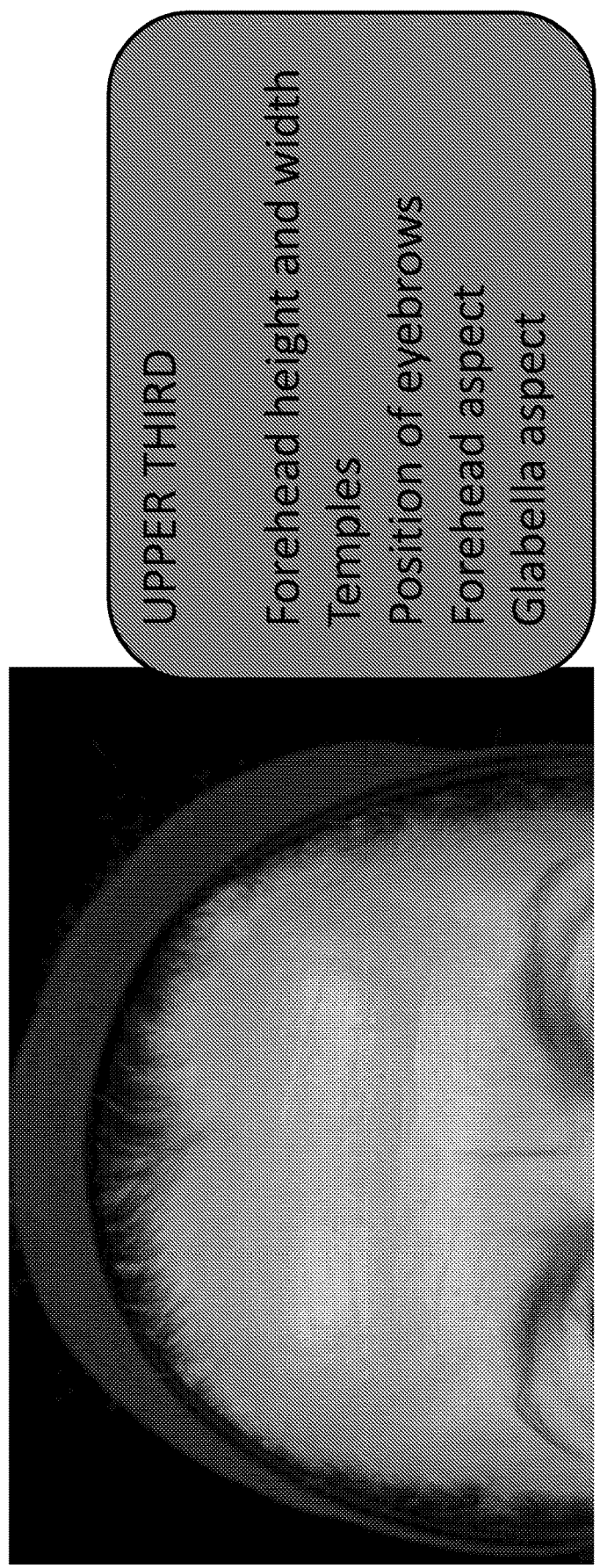
Figure 26:
Figure 27:
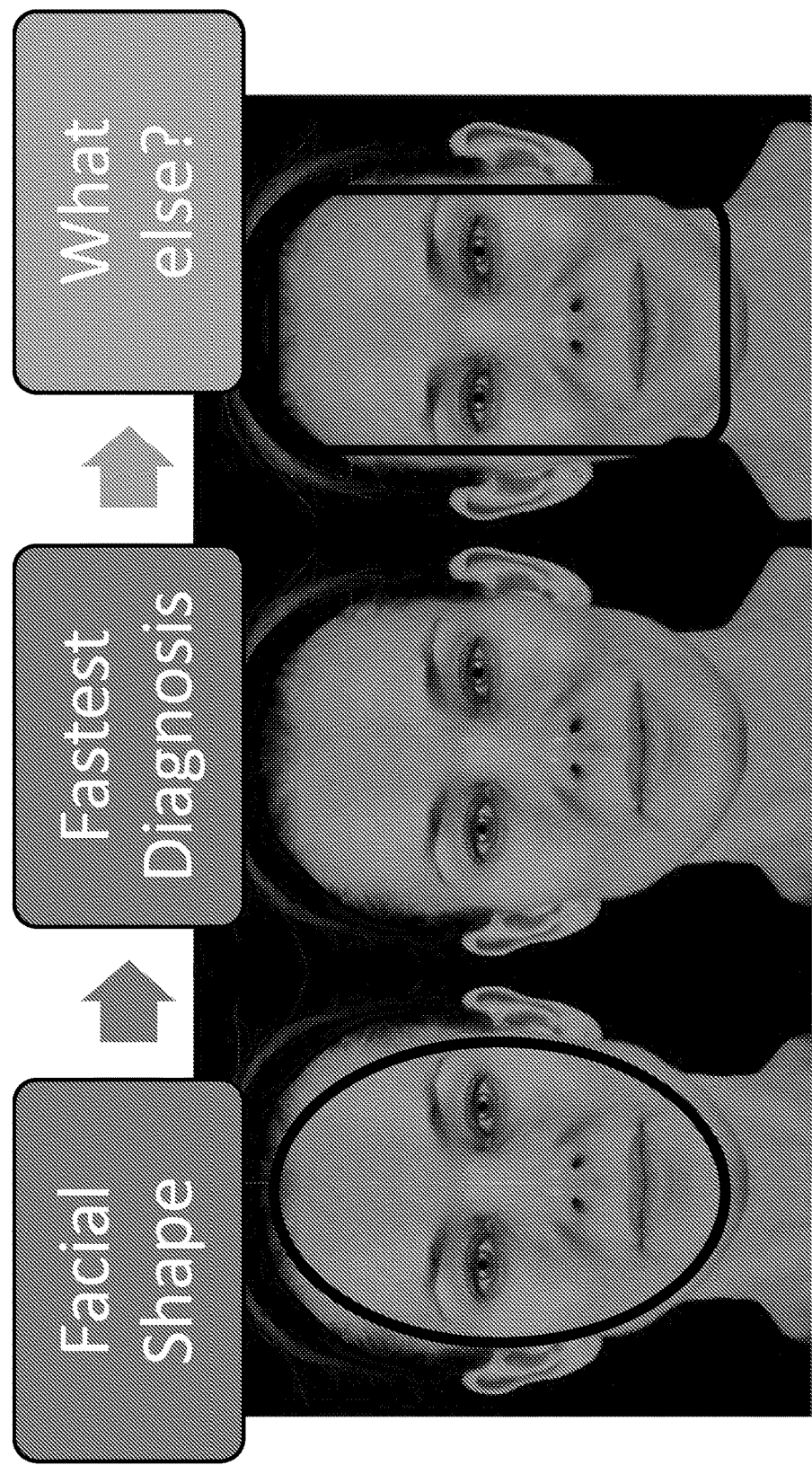
Figure 28:
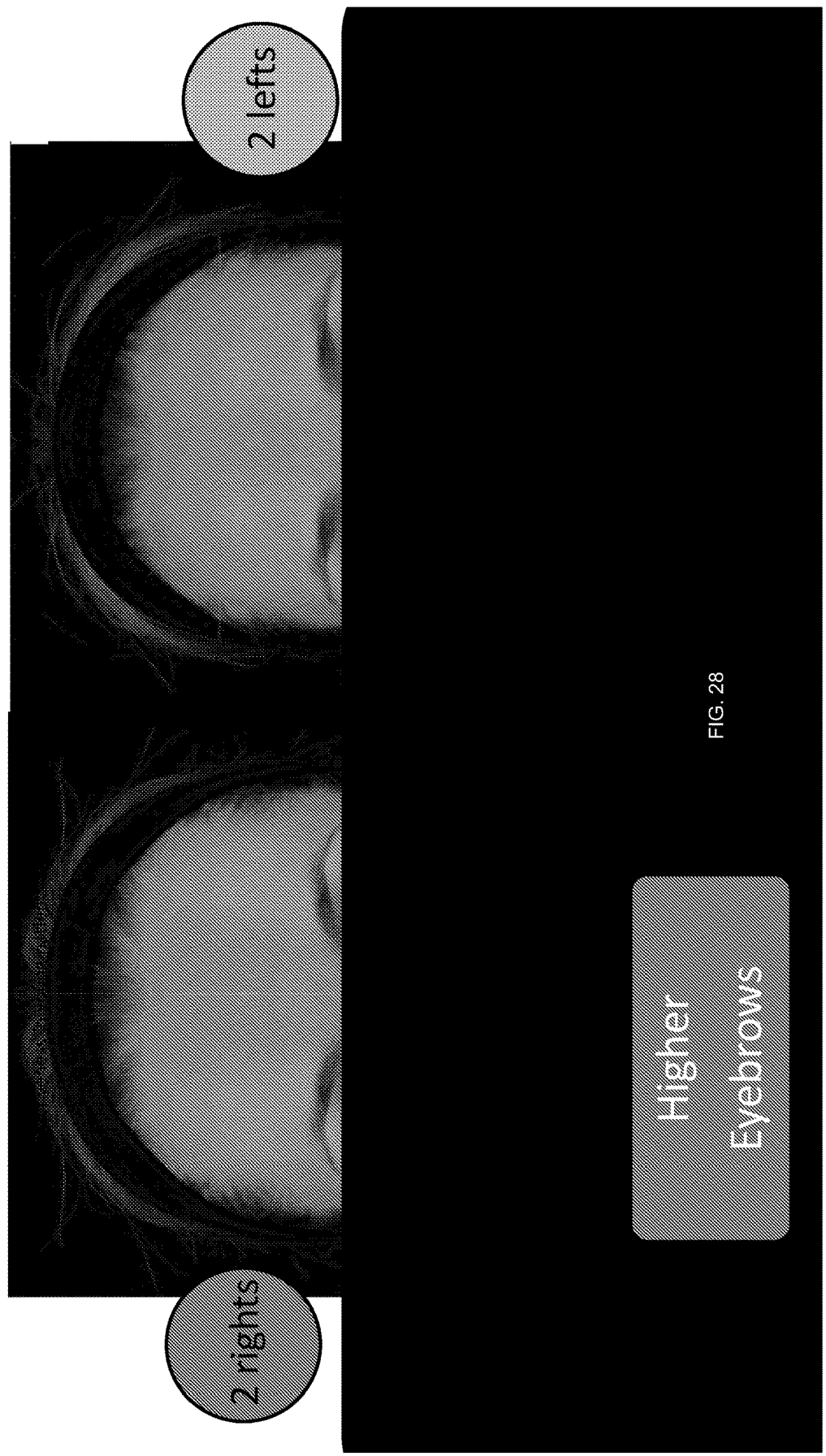
Figure 29:
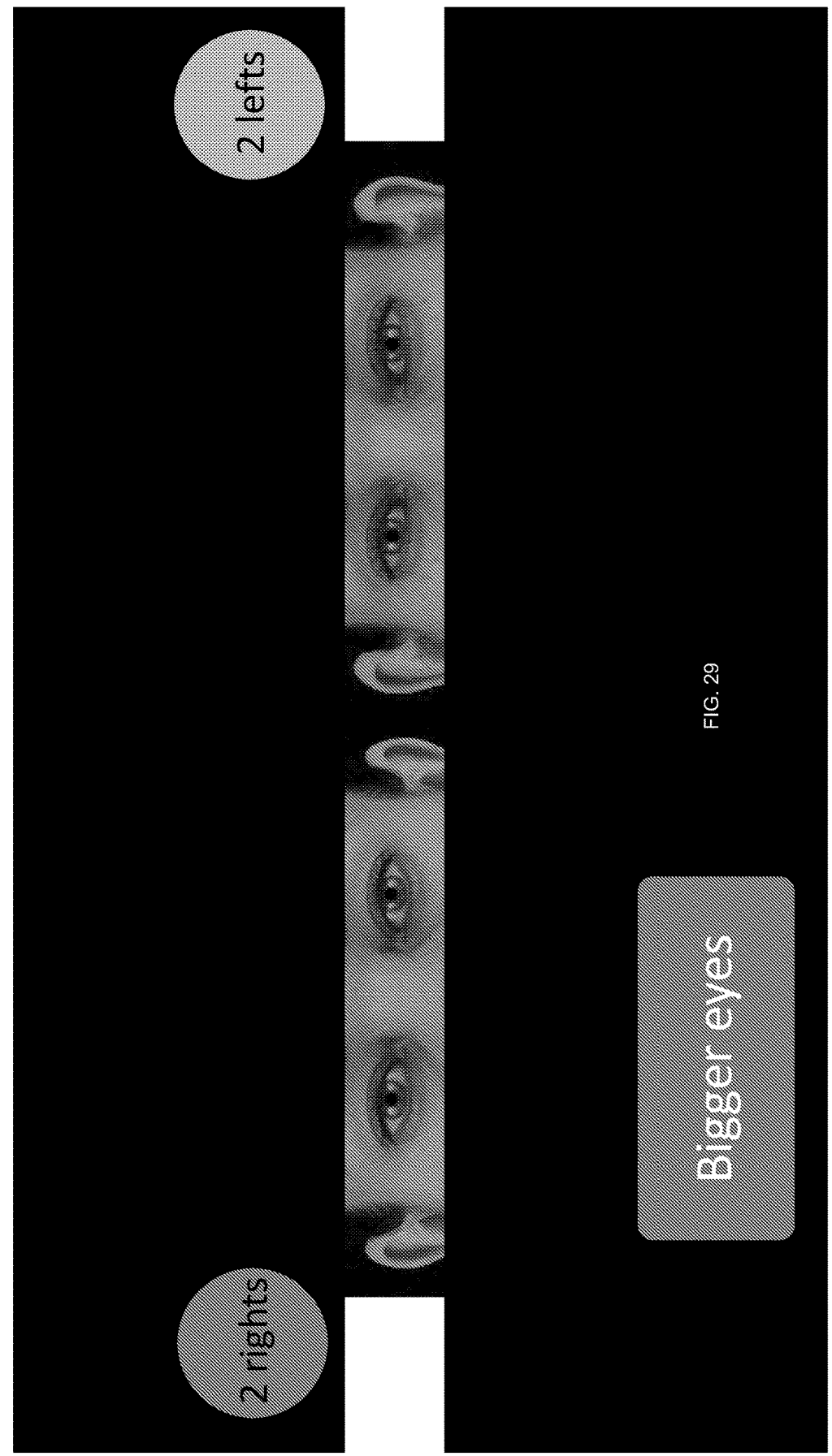
Figure 30:
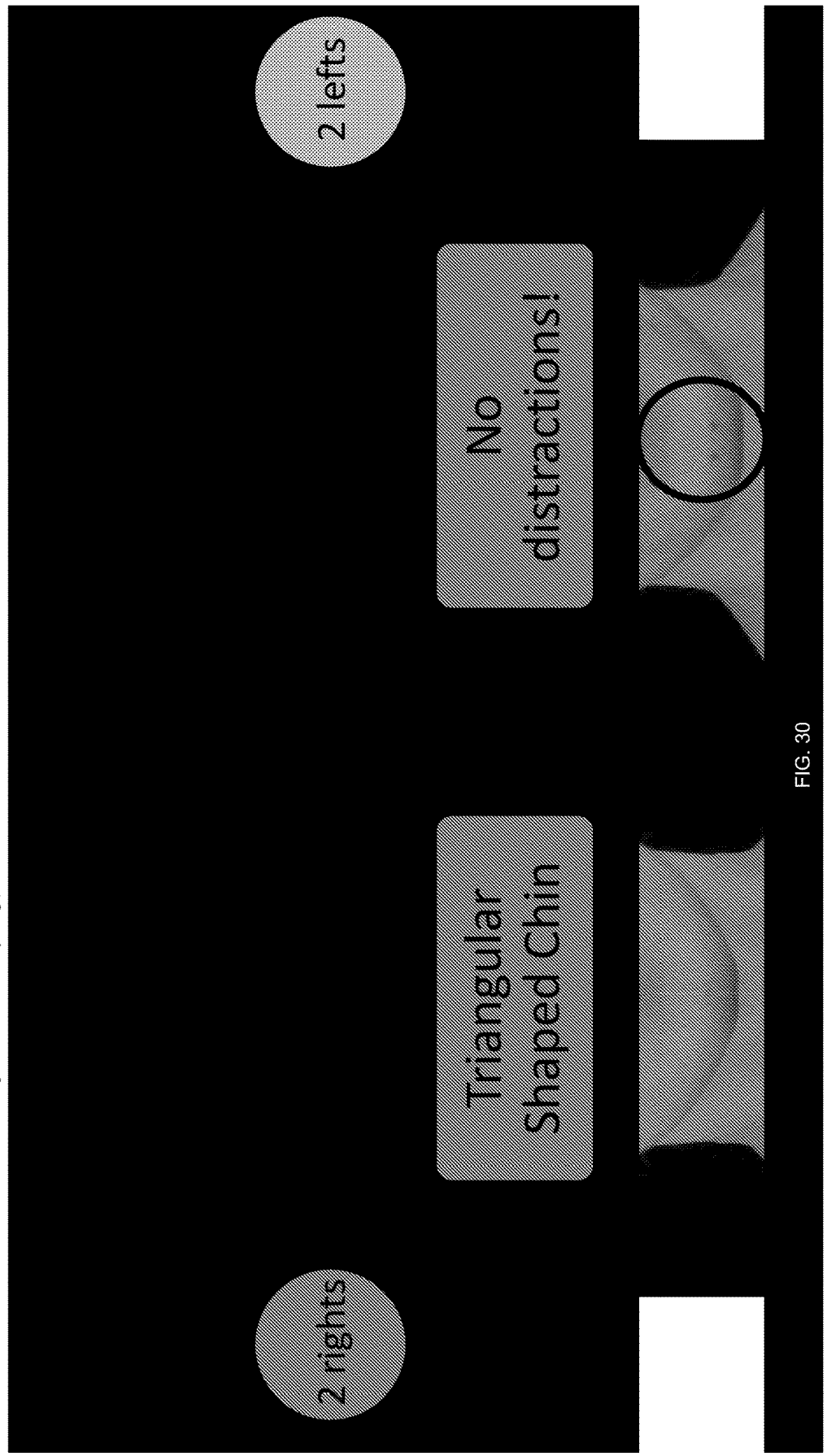
Figure 31:
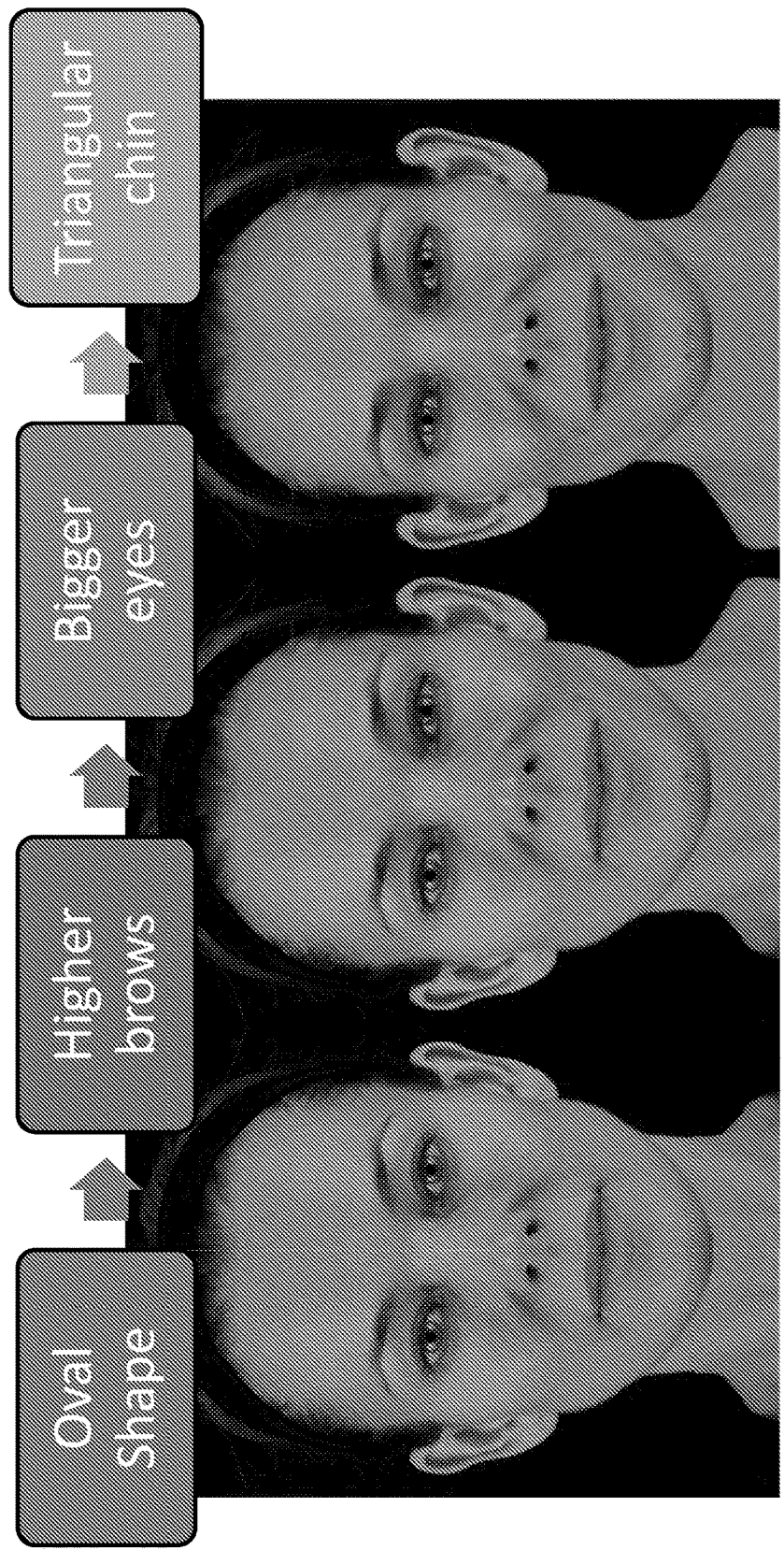
Figure 32:
FIGS. 32 to 35 show "Best side of the face" symmetry analysis on a mature woman.
Figure 33:
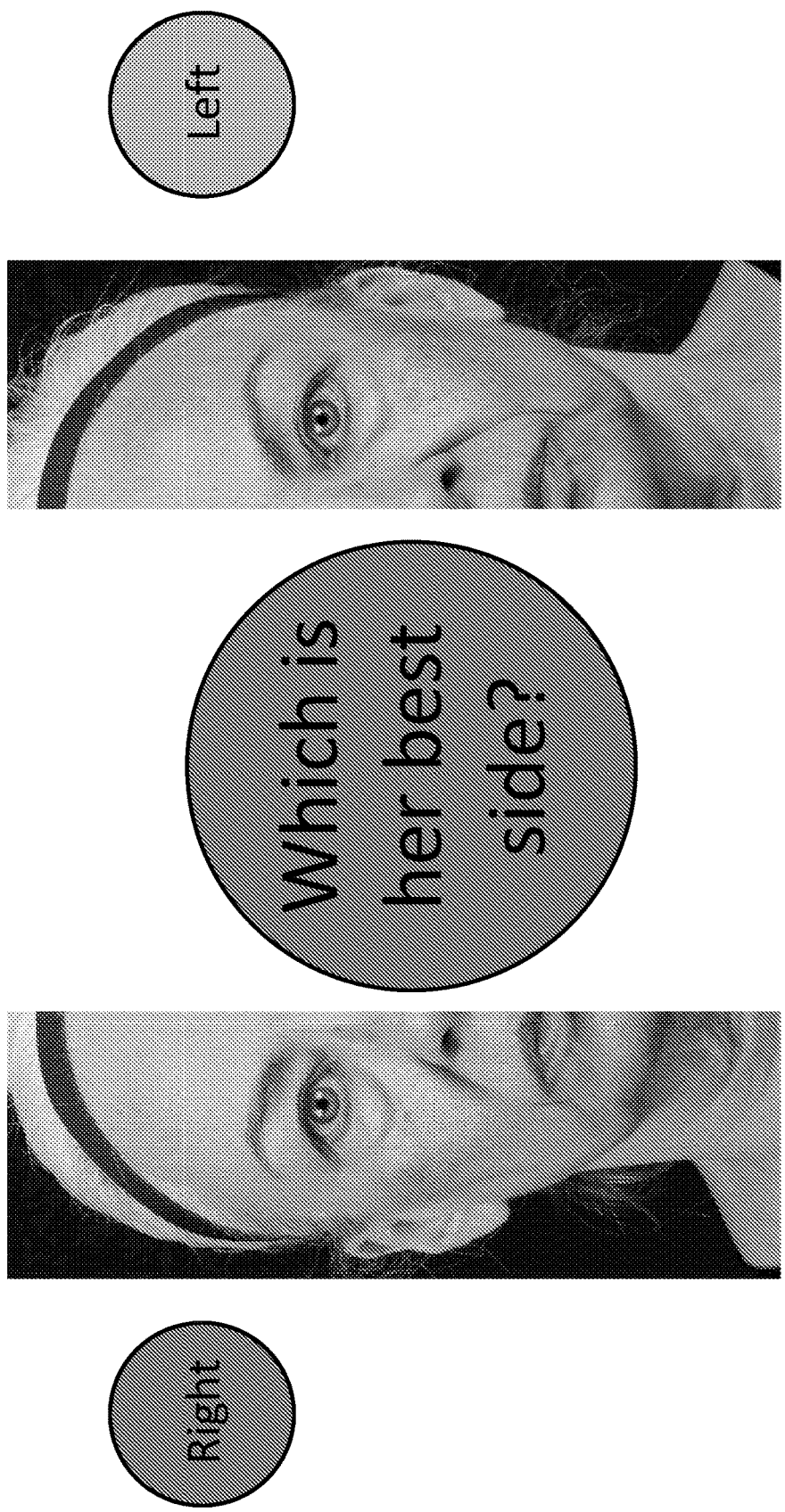
Figure 34:
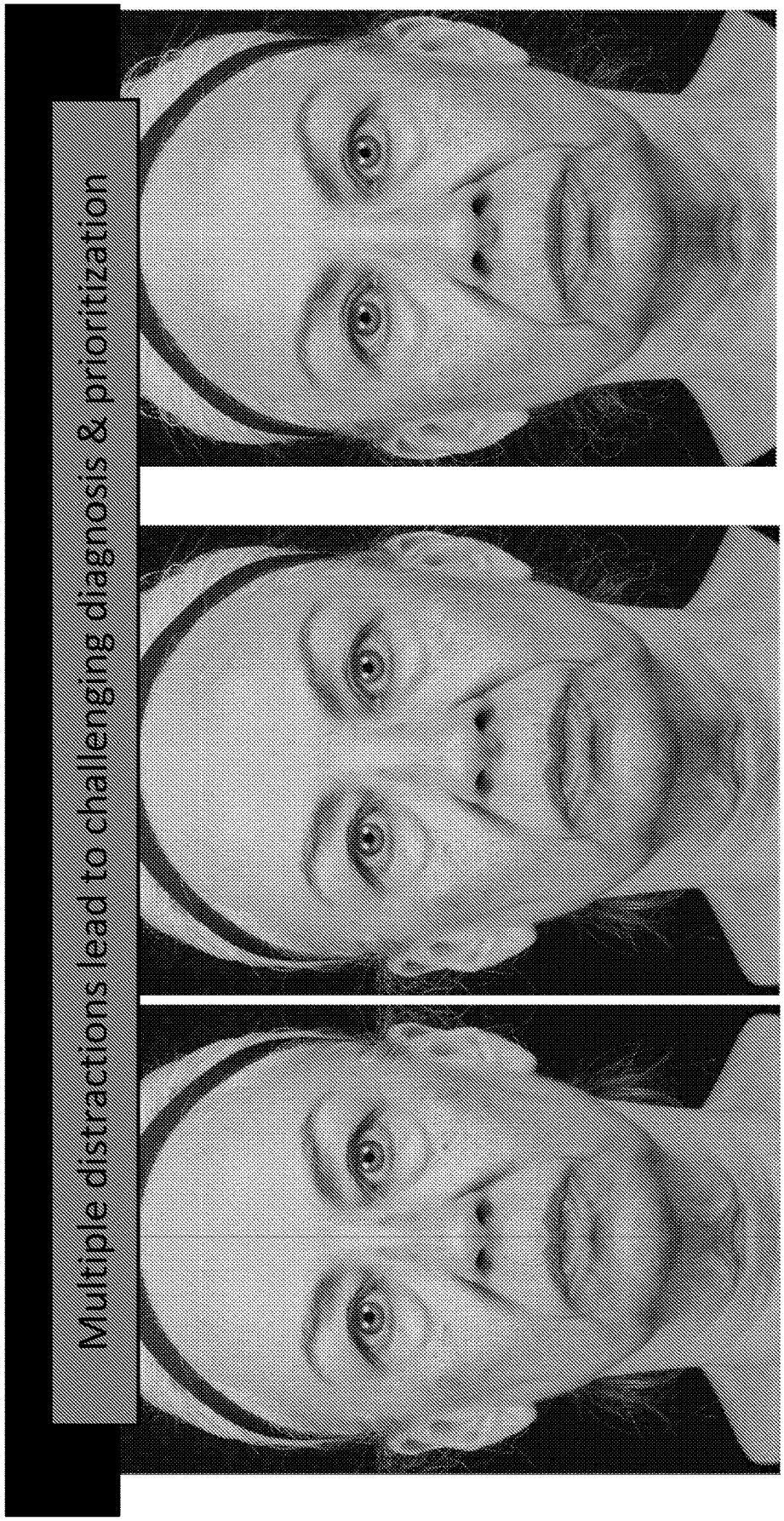
Figure 35:
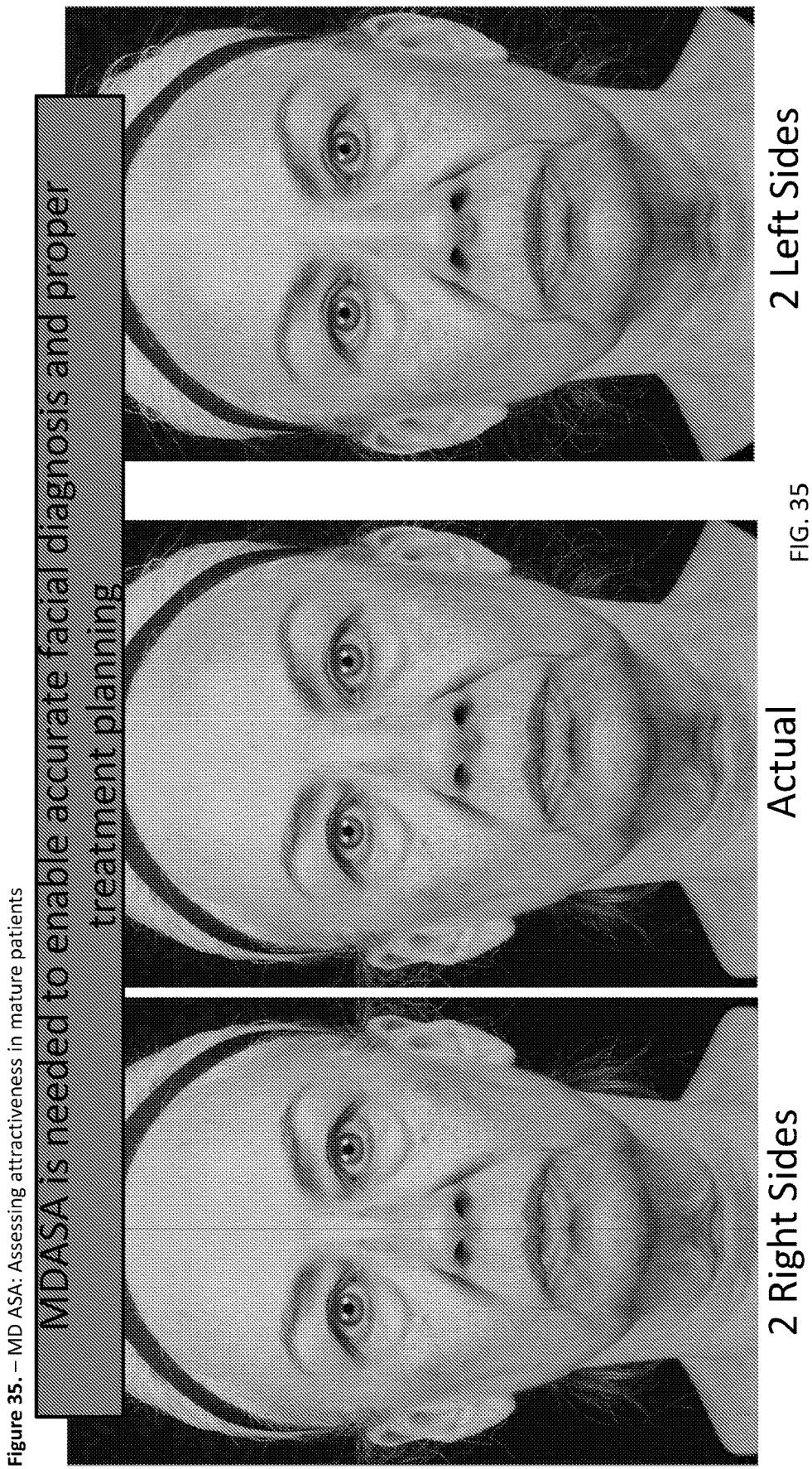
Figure 37:
Figure 38:
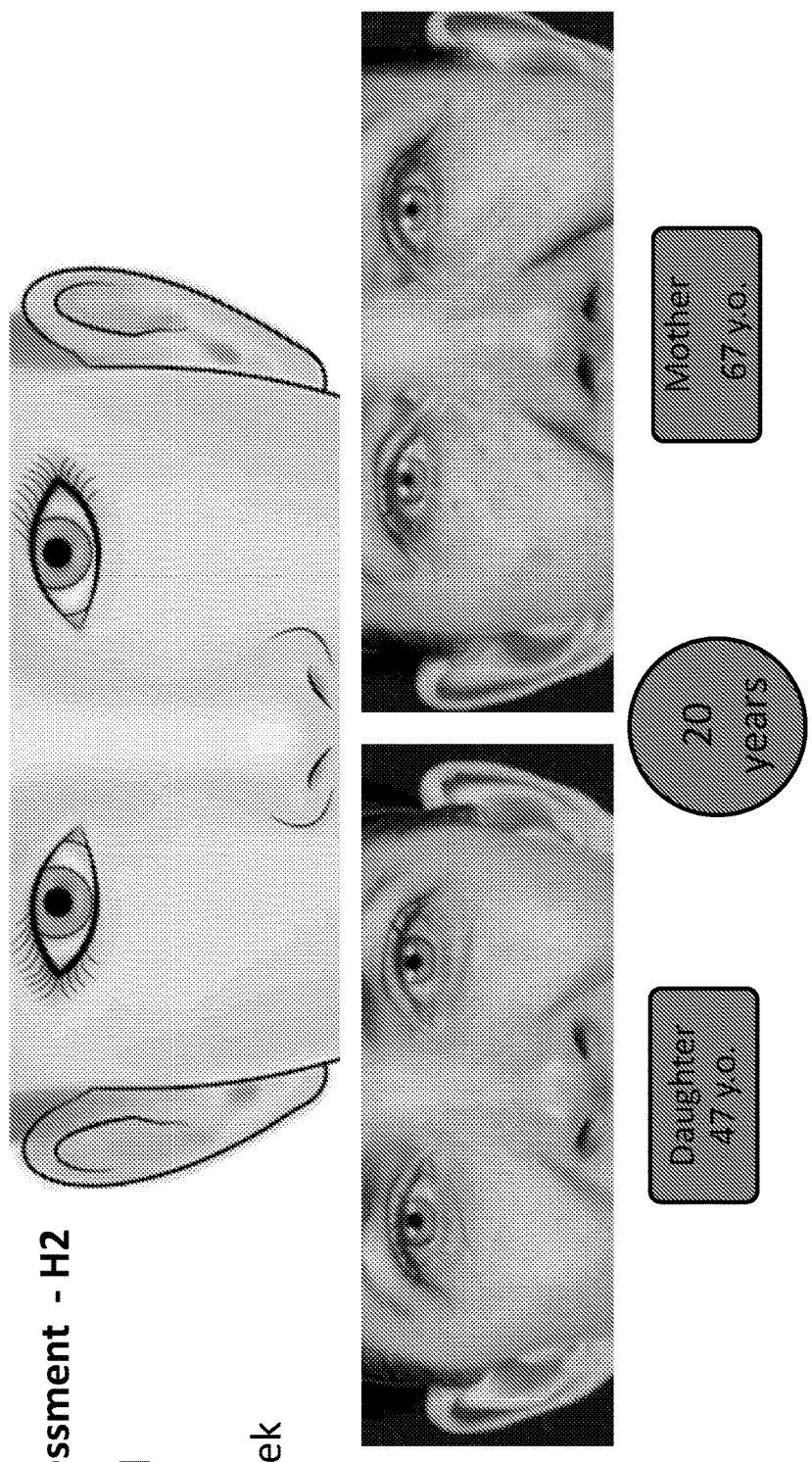
Figure 40:
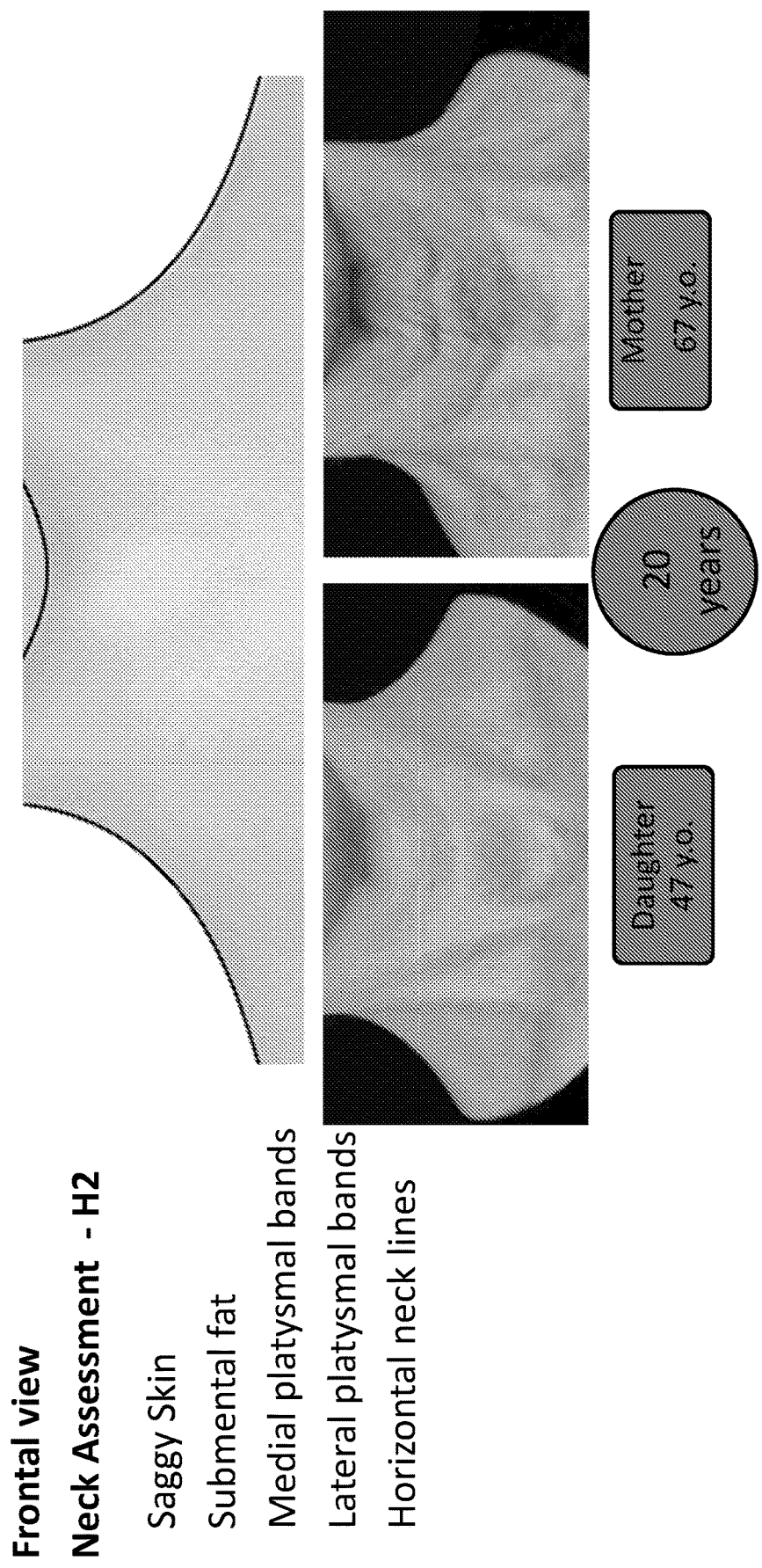
Figure 43:
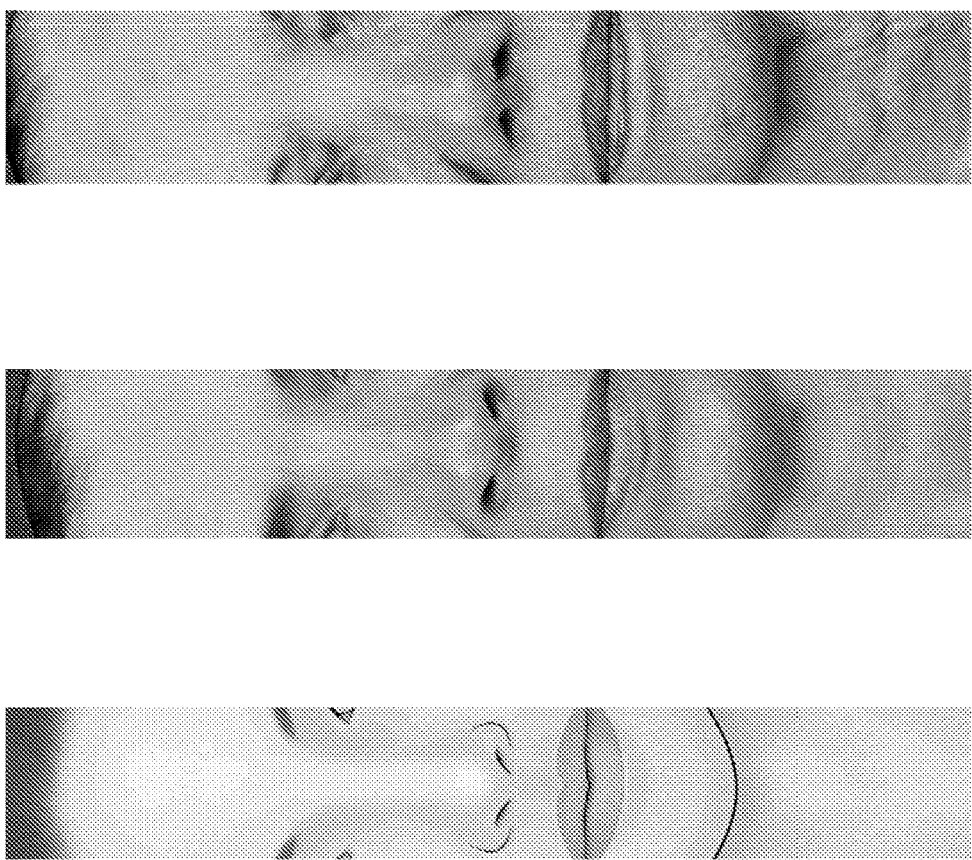
Figure 53:
Figure 54:
Figure 56:
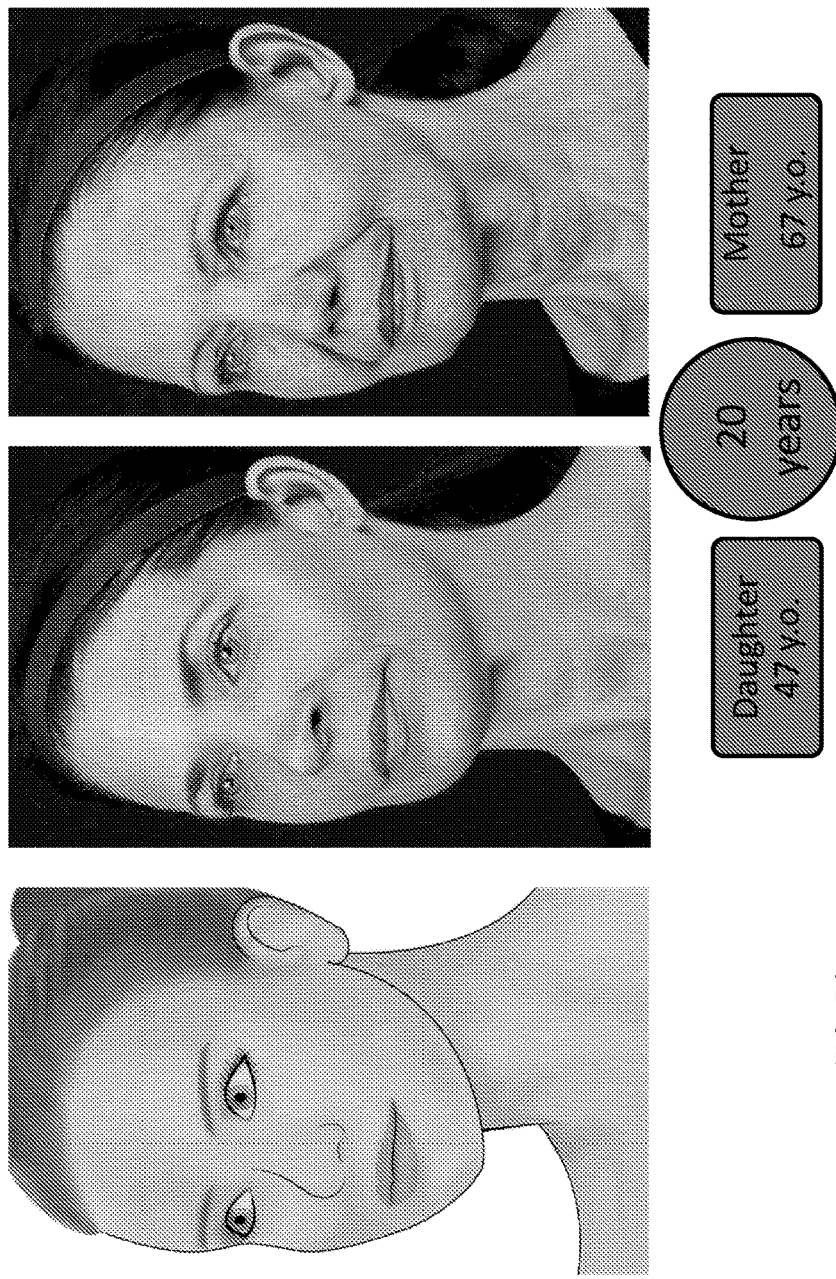
Figure 59:
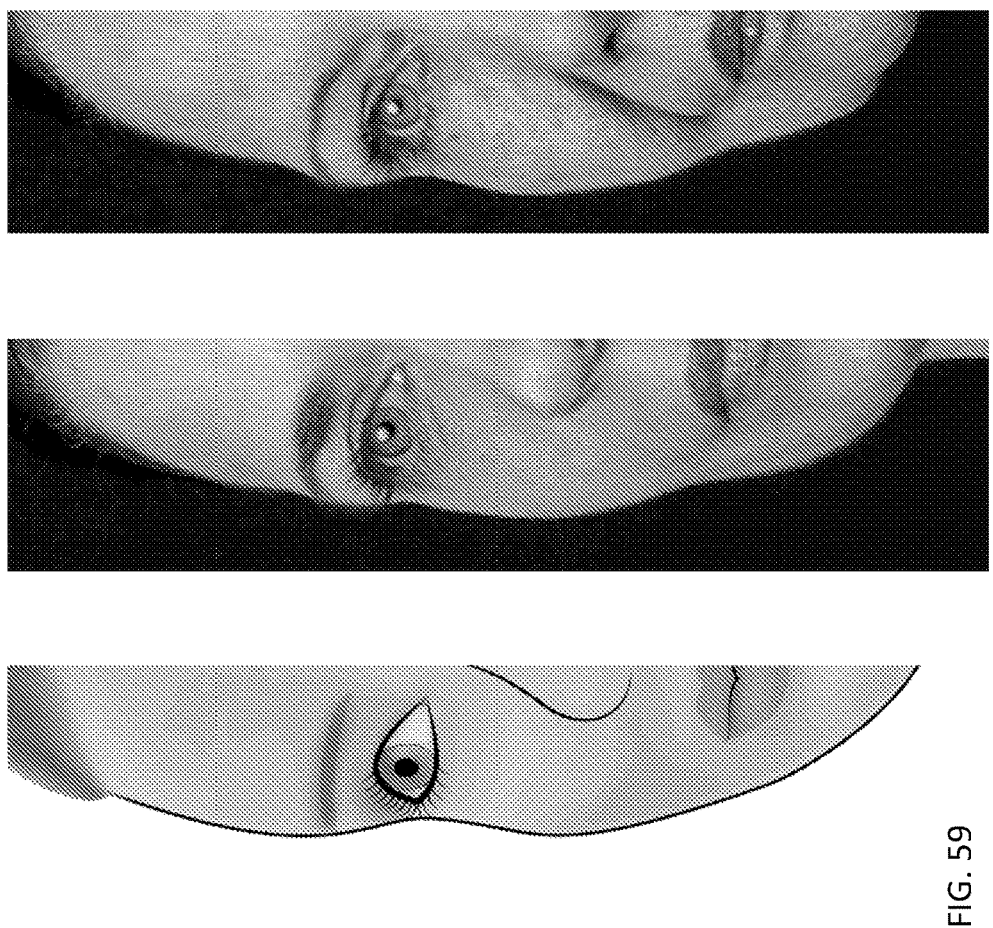
Figure 60:
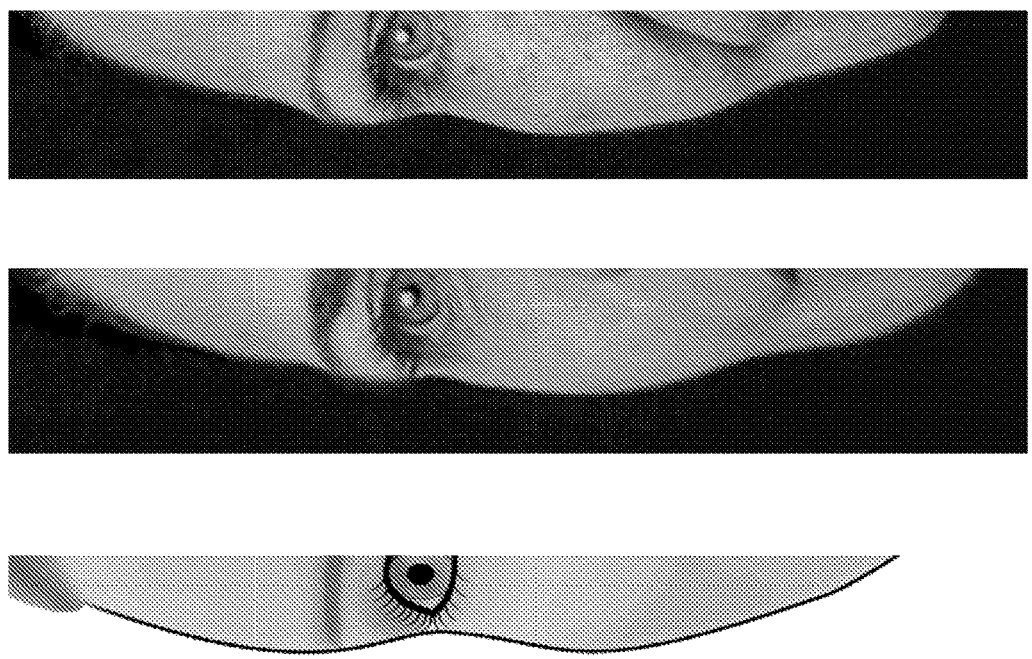
Figure 62:
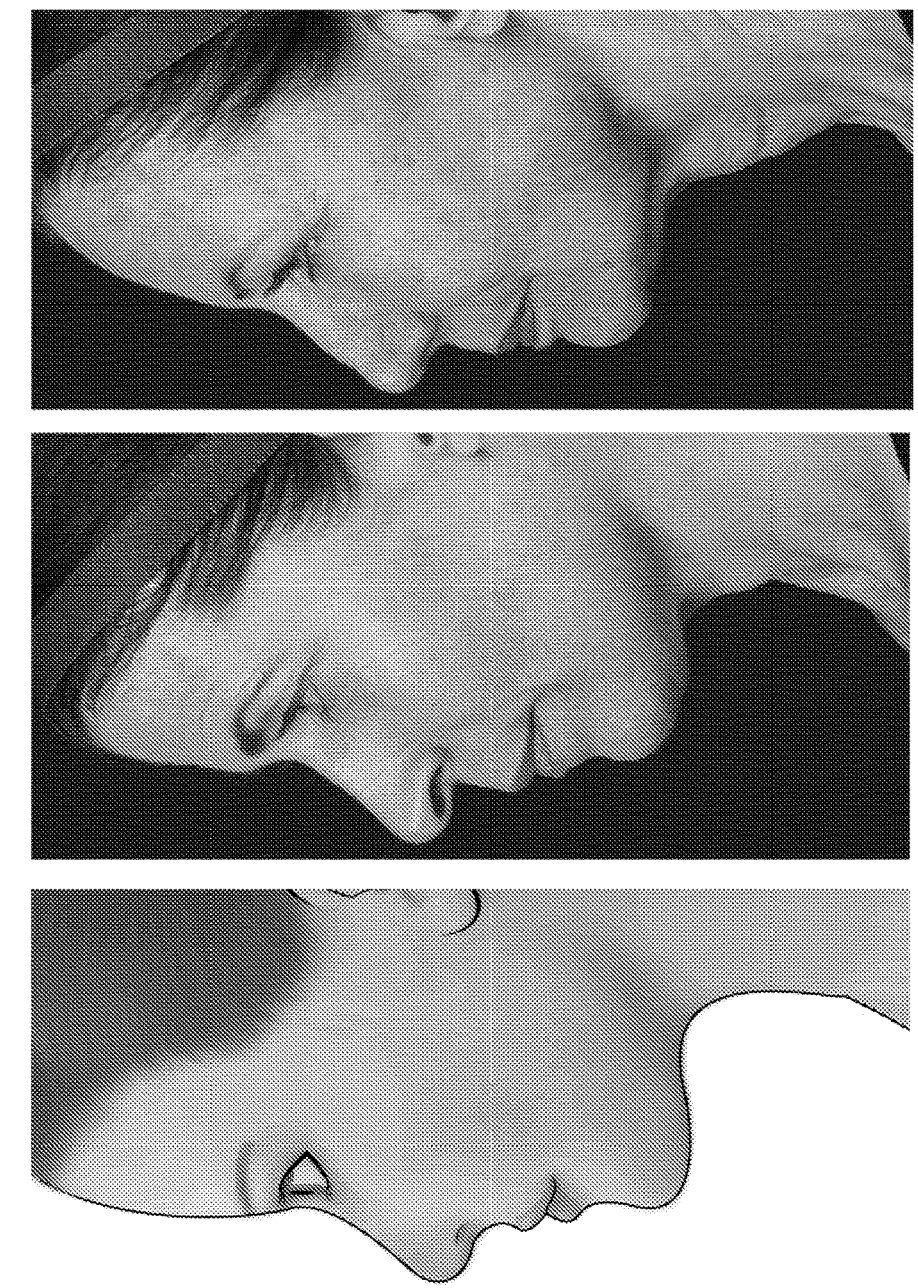
Figure 63:
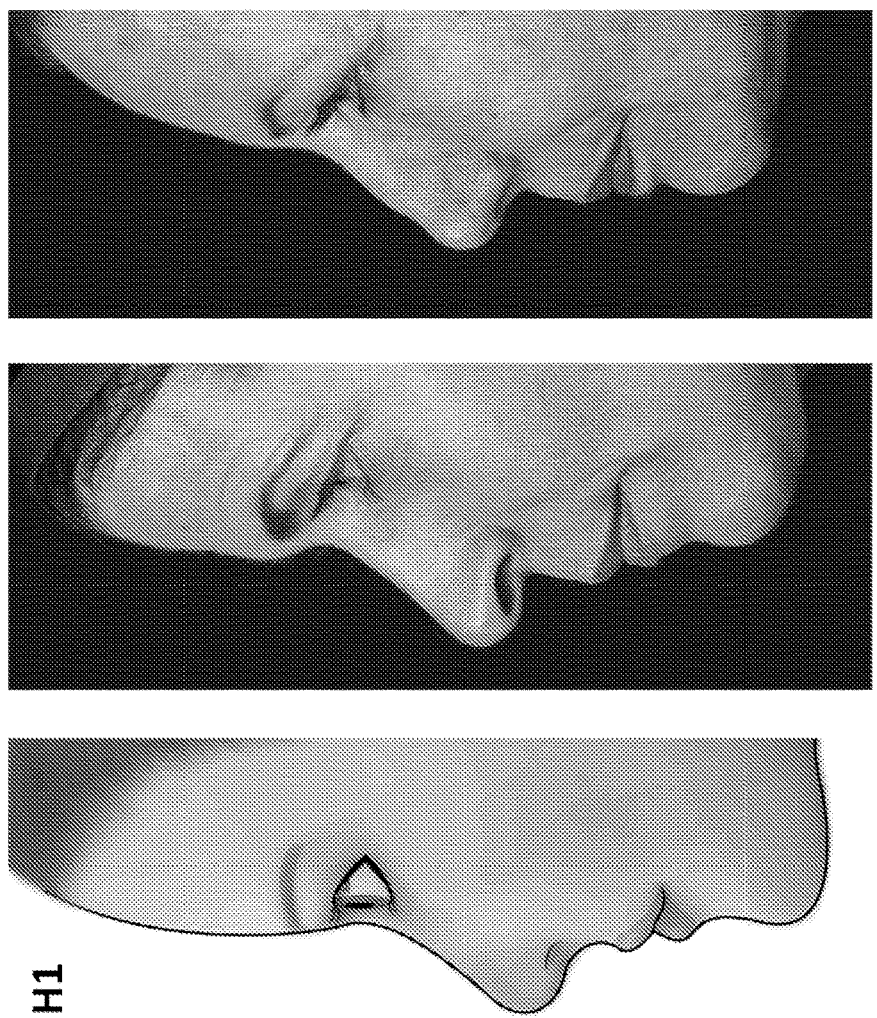
Figure 64:
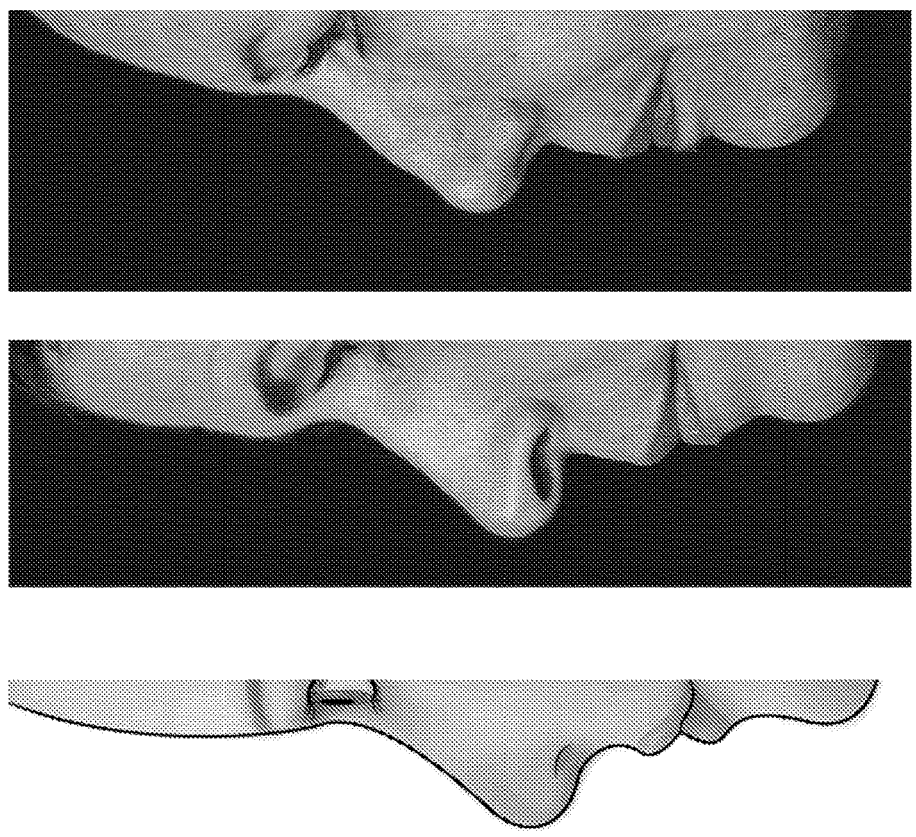

As an example, a 56-year-old patient is shown in FIG. 15. Based on this patient, the following aesthetic hierarchy is provided.

The patient has an H1 which is a tired, sad and unbalanced face.

Once H2, H3, and H4 are duly assessed, it is possible for the injector to identify her facial signs at H5, which comprises glabellar lines, crow's feet, low brows, skin excess in the upper eyelids, volume loss in temples, perioral and chin lines, prominent nasolabial folds, marionette lines, and platysmal bands (FIG. 15).

In some examples, H2 includes facial horizontal scanning, in which all components, proportion, symmetry, volume should be taken into account considering the horizontal classic division of the face into thirds the neck included in it (FIG. 16-19).

In some examples, including any of the foregoing, following the division of the face into horizontal portions, the MD ASA diagram is used to vertically scan the face.

In some examples, including any of the foregoing, the methods include a frontal view wherein the vertical assessment follows the standard division of the face into equal one-fifth slices (herein named after levels—"L"), acting L1 as the focal point, and L2 and L3 mirrored portions on each side of the face (FIGS. 20 and 21).

In some examples, including any of the foregoing, the methods include an oblique view, wherein the one-fifth division is used to analyze on each of the five levels: L1 shows the assessment of the face, its proportion, structure, analysis of jawline and neck; L2 shows the assessment of the forehead, eyebrow, eyes, cheek, nasolabial fold, lip, chin and neck; L3 shows the assessment of the eyebrow-nose outline, as well as the nose-lip-chin complex; L4 shows the assessment of the forehead volume, eyebrow position, upper and lower eyelids, cheek volume, and lip volume; and L5 shows the assessment of the forehead and supraorbital contours, ogee curve and lower cheek shape (FIGS. 22 and 23).

In some examples, including any of the foregoing, the methods include using the MD ASA to generate an ideal face. For example, when analyzing the bony forehead, three important aesthetic characteristics are considered: the general shape, the slope, and the morphology of the supraorbital bar. The outline, in profile and oblique views, varies from round to flat with, sometimes, an inferior concavity defining the supraorbital ridge. In the frontal view, the forehead's ideal width is about twice its height in the frontal view. In the profile view, its shape is slightly more vertical and transversal in convexity in females, whereas it has a more inferior concavity defining the supraorbital ridge in males. Based on this information, the patient is treated.

In some examples, ideal temple shape varies from slightly concave to slightly convex depending on the volume of temporal muscle and subcutaneous fat.

In some examples, ideal eyebrow shape is symmetric one. In the frontal view, the eyebrow presents a gentle curve without angularity. The medial and central portions are wider than the lateral portion. The eyebrow peak is located on a vertical plane passing slightly lateral to or touching the lateral limbus. The eyebrow location should ideally be presented with normal intercanthal distance, the brow head starts just above the medial canthus. The medial brow lies on the orbital ridge, the central brow lies on the ridge and the lateral aspect lies just above the ridge in females. In males, it generally lies along the ridge or below it. In some examples, the methods herein include methods of treating a patient, comprising injecting an injectable comprising a pharmaceutical composition at specific injection sites in the patient's face or neck, thereby maintaining the eyebrow with the any or one of the aforementioned features. In some examples, the methods herein include methods of treating a patient, comprising injecting an injectable comprising a pharmaceutical composition at specific injection sites in the patient's face or neck, thereby reversing the aging process so that the patient obtains an eyebrow with any or at least one of the aforementioned features.

In the frontal view, the eyes should be positioned slightly inclined upwards, with upward lateral canthal tilt. The upper eyelid should cover the iris by approximately 1 to 2 mm, having minimal or even none scleral show between the lower eyelid and iris. In some examples, the methods herein include methods of treating a patient, comprising injecting an injectable comprising a pharmaceutical composition comprising an injectable at specific injection sites in the patient's face or neck, thereby maintaining the eye with any or at least one of the aforementioned features. In some examples, the methods herein include methods of treating a patient, comprising injecting an injectable comprising a pharmaceutical composition at specific injection sites in the patient's face or neck, thereby reversing the aging process so that the patient obtains an eye with any or at least one of the aforementioned features.

In the frontal view, the symmetry of the nose may be assessed by the vertical midline that divides the *glabella*, the nasal bridge, the nasal tip and the Cupid's bow. In the oblique view it should present a graceful outline descending from the supraorbital ridge onto the nasal dorsum and the nasal tip. In the profile view, a gentle outline without an evident hump should be observed. The frontal nasal angle ranges from 115°-135° in females and from 110°-120° in males. The nasal labial angle ranges from 95°—110° in females and from 90°-95° in males. In some examples, the methods herein include methods of treating a patient, comprising injecting an injectable comprising a pharmaceutical composition comprising an injectable at specific injection sites in the patient's face or neck, thereby maintaining the symmetry of the nose with any or at least one of the aforementioned features. In some examples, the methods herein include methods of treating a patient, comprising injecting an injectable comprising a pharmaceutical composition at specific injection sites in the patient's face or neck, thereby reversing the aging process so that the patient obtains a symmetry of the nose having any or at least one of the aforementioned features.

The lip should appear as a complete seal or minimal space between upper and lower lips in its relaxed state. The mean mouth width in Caucasians measures approximately 50 mm. The nasolabial sulcus is almost undetectable at rest. The philtrum columns, the Cupid's bow, and both upper and lower lip borders should be well defined. With respect to volume, the lower lip volume should exceed the upper one. In the profile view, the Ricketts' E-Line should be assessed by means of the fact that the distance of the upper lip should be 4 mm behind and the lower lip should be 2 mm behind this line. While smiling spontaneously, the patient should be able to display the upper anterior teeth, especially due to more upper lip elevation. At the same time, there should be absence or limited display of the inferior teeth, as well as minimal gingiva show. Presence of moderate buccal corridors should be observed. When assessing the patient's teeth, in the frontal view, well-proportioned and aligned teeth should be observed with dental occlusion classified as class I. In some examples, the methods herein include methods of treating a patient, comprising injecting an injectable comprising a pharmaceutical composition comprising an injectable at specific injection sites in the patient's face or neck, thereby maintaining the lips with any or at least one of the aforementioned features. In some examples, the methods herein include methods of treating a patient, comprising injecting an injectable comprising a pharmaceutical composition at specific injection sites in the patient's face or neck, thereby reversing the aging process so that the patient obtains lips having any or at least one of the aforementioned features.

The chin ideal characteristics also depend on the patient's gender. The normal thickness of the chin pad soft tissue is 8-10 mm. In the frontal view, it should be symmetrical and slightly more triangular in females and square in males. The jawline should be uninterrupted and well defined on a younger face, regardless the patient's gender. In some examples, the methods herein include methods of treating a patient, comprising injecting an injectable comprising a pharmaceutical composition comprising an injectable at specific injection sites in the patient's face or neck, thereby maintaining the symmetry of the chin pad with any or at least one of the aforementioned features. In some examples, the methods herein include methods of treating a patient, comprising injecting an injectable comprising a pharmaceutical composition at specific injection sites in the patient's face or neck, thereby reversing the aging process so that the patient obtains a chin pad having any or at least one of the aforementioned features.

In some examples, including any of the foregoing, the methods include overlaying images of a patient's face with their own face, in a different position or showing a different part of the face. In some of these examples, the methods include showing the patient's face by twisting 180° the photo of half of their face and then juxtaposing the two halves to recreate a variation of the patient's face. By doing so the physician will be able to determine on which side the eyebrows are higher positioned, which eye is bigger, and in which side the chin is better outlined. Once this is established, the injector consequently knows what subunits should be addressed to achieve symmetry at least (FIGS. 24 to 31). However, this method may not be useful to assess mature patients as multiple distractions lead to a more challenging assessment and thus diagnostic conclusion. In such a situation other tools and parameters offered within MD ASA will be helpful to proper assess the patient and establish and adequate treatment planning (FIGS. 32 to 35).

FIGS. 36 to 64 show how to use MD ASA to assess the genetic aging in frontal, oblique, and profile views and using the parameters established above.

Therefore in the front view, at H1, the assessment should focus on the messages of the face, i.e. an overall perception of proportion and harmony. At H2 and upper third, the relationship of forehead height and width, temples, position of eyebrows, forehead lines, and the glabellar lines should be observed. At mid third, subunits such as upper and lower eyelids, anterior cheek, nose tip, and upper portion of the nasolabial fold (NLF) are able to be analyzed. The assessment of the lower third should focus on central and lower NLF, upper lip, philtrum columns, vermillion, oral commissure, marionette lines, chin, and prejowl. In some of the methods herein, the methods include provide a H1, H2, H3, H4, and/or H5 determination of a patient.

In some examples, the methods include assessing, on the neck, the existence of saggy skin, submental fat, medial platysmal bands, lateral platysmal bands, and horizontal neck lines.

In some examples, the methods include assessing, from a vertical-scanned perspective, the face symmetry. This symmetry analysis should include the observation of eyebrow position, nose deviation, chin deviation and platysmal bands. At L3, analysis should focus on the impact of the central part of the face showing the relationship between the cheeks and nasolabial folds, as well as on the relationship of eyes-nose-chin complex. At this level, symmetry analysis may include temples, the zygomatic arch, ear, masseter, and facial widths (bitemporal, bizygomatic, and bigonial).

In some examples, L2 analysis focuses on central forehead and *glabella* areas, relationship of the nose and mouth width, chin apex and central neck. At this level, with respect to symmetry, assessment should focus on medial eyebrow, medial canthus, nasal flare, NLF, vermillion volume, prejowl sulcus, central and lateral eyebrow, upper eyelid, lateral canthus, cheek, masseter, and jawline.

In some examples, L1 assesses the symmetry of the head of eyebrow, the intercanthal distance, the nasal base width, the Philtrum columns, the Cupid's bow, the medial and lateral lip tubercles, chin apex, and neck lines.

The analysis of portions of half of the face (hemiface) indicates for the observer how and where to focus on certain relationships among structures, such as: (i) forehead, central brow, lateral canthus, midpupillary line, anterior cheek, and jawline; (ii) forehead height, medial canthus, midpupillary line, NLF, oral commissure, and pre-jowl; and (iii) medial brow, nasal flare, upper and lower lips, and chin.

In some examples, the methods include assessing the triangular and oval central features and relationships between the units of the central face, such as eyes, nose, lips, and chin.

In some examples, in the vertical segmentation, L1 at the oblique view offers the possibility of analyzing the jawline contour and the neck. At L2 the following structures should be focused: Forehead, eyebrow, eyes, cheek, NLF, lip, chin, and neck. At L3 one should observe the eyebrow-nose outline and the nose-lip-chin complex. At L4, details should be under the spot: analysis should focus on forehead volume, eyebrow position, upper and lower eyelids, cheek volume, and lip volume and contour. At L5 in the oblique view, attention should be paid to the outlines: forehead, supraorbital, ogee curve, and lower cheek outline.

The analysis of portions of the face at rest in full profile enables the observer to focus on: (i) eyebrow position, cheek volume, nose projection, lip projection, chin projection, mental cervical angle, mandible angle, and submental area; (ii) forehead outline, nose breakpoint, eye position, cheek projection and position, NLF, oral commissure, marionette lines, and submental area; and (iii) forehead outline, frontal nasal angle, nose projection, nasal labial angle, upper lip projection, lower lip projection, labial mental angle, and chin projection.

Figure 65:
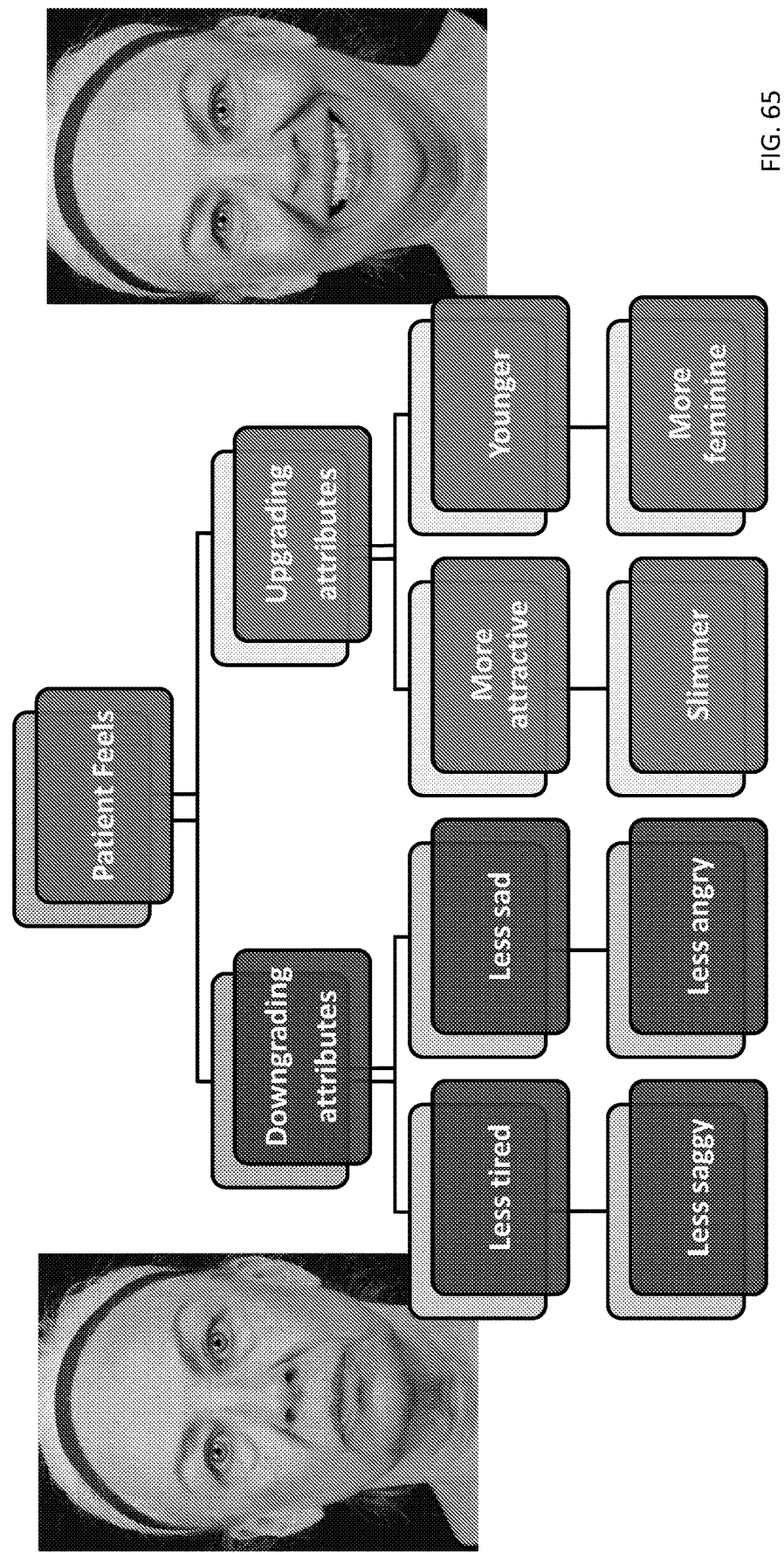
FIG. 65 shows emotional attributes.
Figure 67:
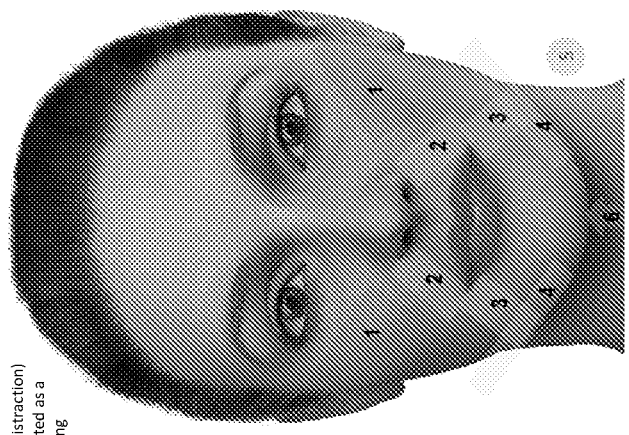
Figure 70:
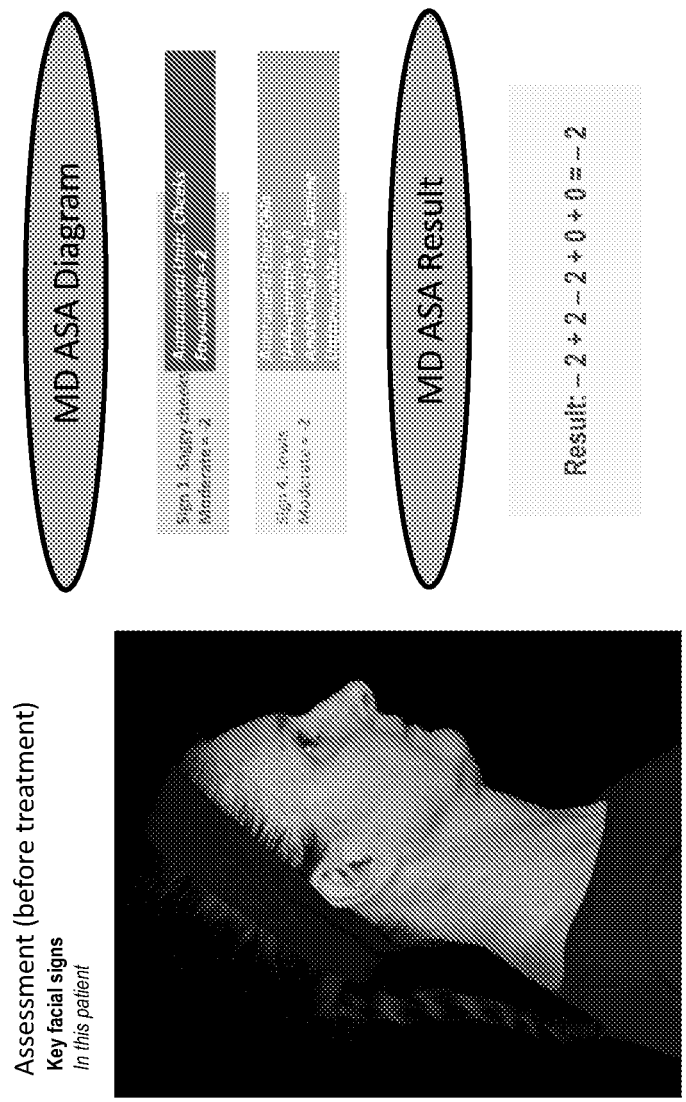
Figure 71:
Figure 72:
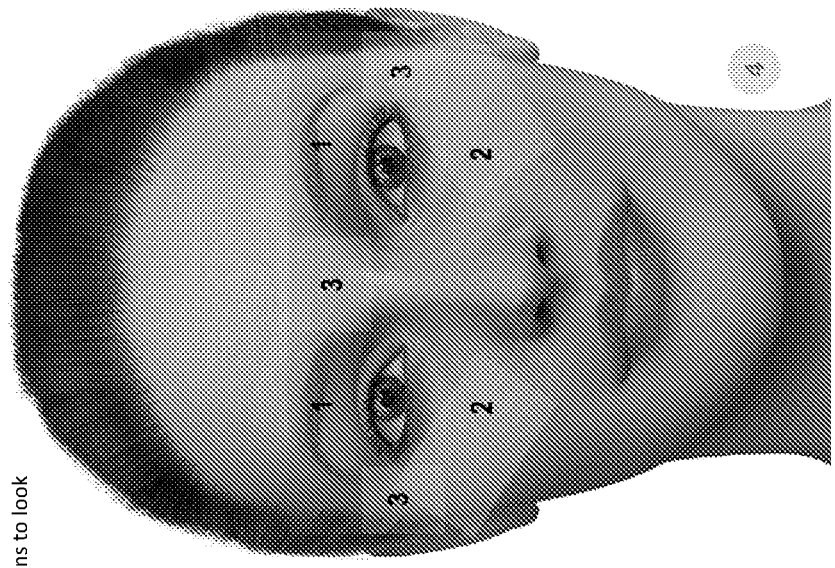
Figure 73:
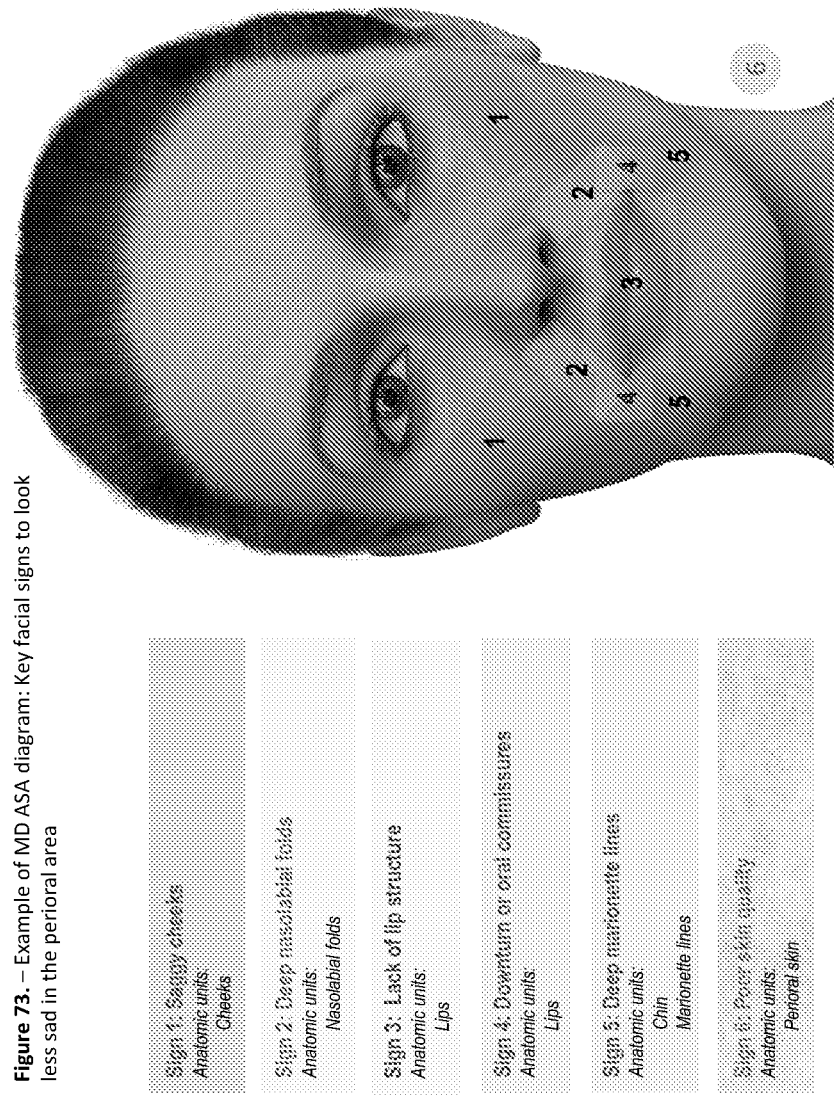
Figure 74:
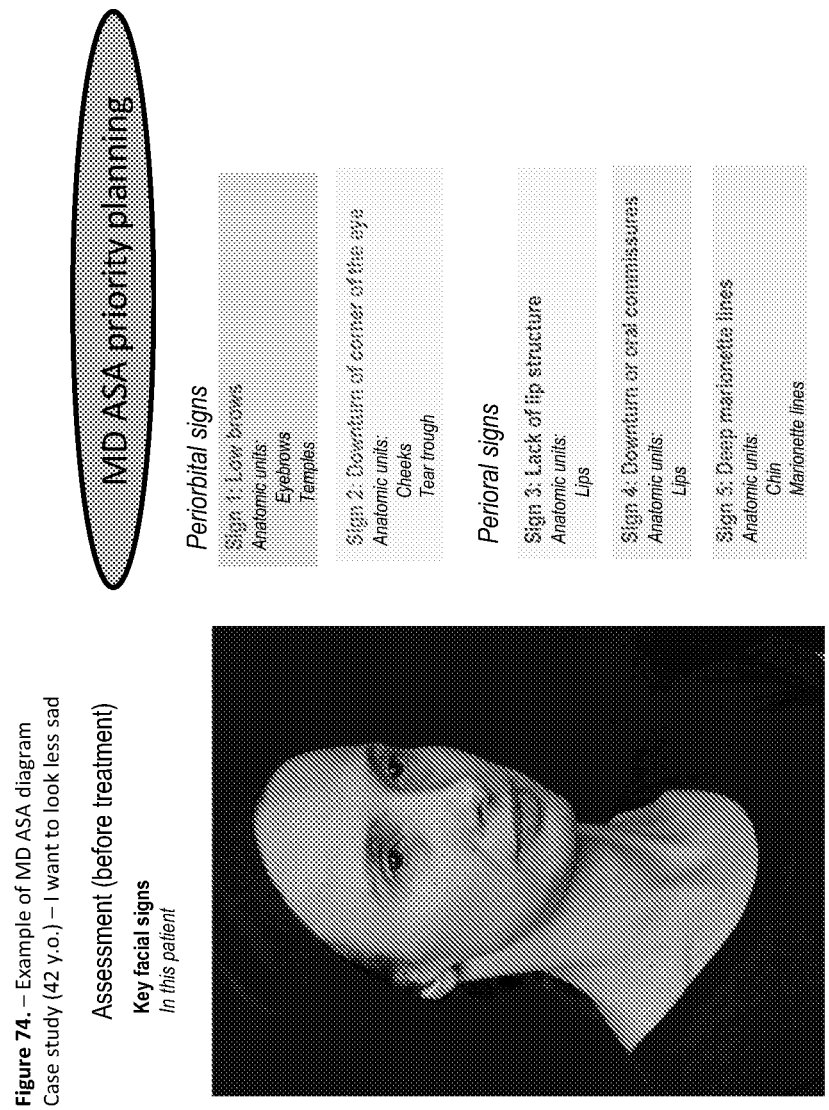
Figure 75:
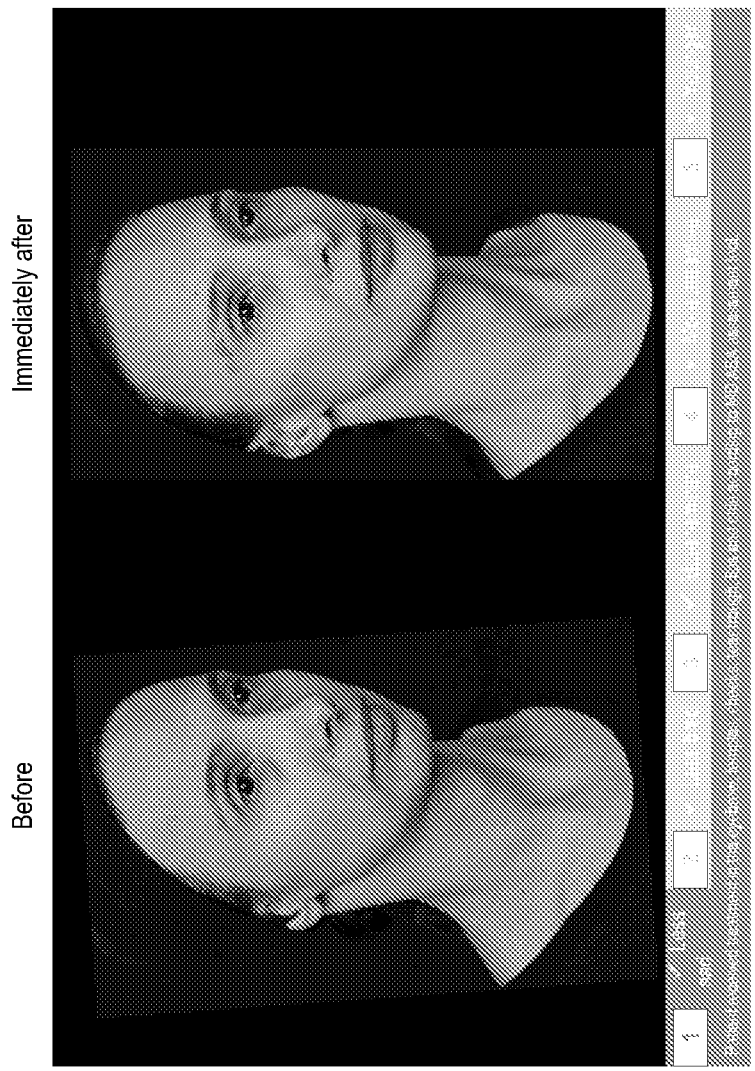

In some examples, set forth herein are methods of provide a method of treatment which first includes consulting a patient. In some of these examples, a health care provide will perform any or at least one of the following steps: Asking patients how they feel about how they look can help unlock the cause of their dissatisfaction and allow physicians to properly assess them and to create a treatment plan that will address their real concerns. "Do they feel like they look tired or sad?" "Do they want to look slimmer or younger?" These emotional attributes provide the clues to the areas and features of the face that may need improvement and present a new, holistic approach in treatments to facial rejuvenation (FIG. 65). The assessment and treatment planning should focus on weakening the downgrading attributes appointed by the patient and at the same time create or reinforce the upgrading ones (FIG. 66).

In some examples, including any of the foregoing, the methods include using the MD ASA to facilitate communication between patient and physician. In some examples, this includes visualizing a treatment plan using a computer to show the patient how the treatment will be administered to the patient and what the expected results of the treatment are.

Using the methods herein, and the MD ASA diagrams, indicators of the face as a primary assessment are used to diagnosis anatomical units and/or features responsible for causing such a negative aesthetic or health condition in a patient. Based on this, a treatment plan is provided to the patient.

In some examples, the following four negative emotional attributes and/or features are treated and thereby improved.

The first negative emotional attribute is a saggy appearance.

The second negative emotional attribute is a sad appearance.

The third negative emotional attribute is a tired appearance.

The fourth negative emotional attribute is an angry appearance.

In some examples, the methods herein include methods of treating a patient, comprising injecting an injectable comprising a pharmaceutical composition comprising an injectable at specific injection sites in the patient's face or neck, to treat and thereby improve or reverse any one or more of the aforementioned negative emotional attributes. In some examples, the methods herein include methods of treating a patient, comprising injecting an injectable comprising a pharmaceutical composition at specific injection sites in the patient's face or neck, to treat and thereby improve or reverse any one or more of the aforementioned negative emotional attributes.

In some examples, the negative emotional attributes also include facial shape which lack uniform proportions.

In some examples, the negative emotional attributes also include facial shape which lack symmetric proportions.

In some examples, the negative emotional attributes also include a less feminine (or soft)/masculine appearance.

In some examples, the negative emotional attributes also include a less youthful appearance as compared to the actual age of the patient.

In some examples, the negative emotional attributes also include a less attractive aesthetic.

In some examples, the negative emotional attributes also include a desire by the patient to have a more attractive aesthetic.

MD ASA Diagram

In some examples, emotional or physical attributes are assessed according to anatomical units and subunits that may be considered unfavourable, acceptable, favourable or very positive. These emotional or physical attributes are rated from 0 to 3 respectively, as follows: 0=unfavourable, 1=acceptable, 2=favourable, and 3=very positive. In some examples, all facial signs are rated as "very positive". For example, all facial signs may be very positive in young and very attractive individuals. The more "3"-grade a given patient is received, the closer this individual is to the ideal look.

In some examples, the facial distractions within the MD ASA diagram are classified as key facial signs may result from structural deficiencies (congenital or acquired) and/or aging process. The facial distractions may range from absent to severe, as follows: 0=absent, 1=mild, 2=moderate and 3=severe. The key facial signs will be considered deductions and will lead to downgrading the overall appearance. Both signs and distractions are built under a 4-point grading. The final result will guide the injector on assessing the right diagnosis and consequently which facial area should be properly addressed and with which priority.

In some examples, the facial assessment is divided into three different steps. In some of these examples, the methods include an assessment by a health care provider or physician.

In some of these examples, the methods include an assessment by the patient him/herself.

In some of these examples, the methods include an assessment which combines the one by the health care provider or physician and the patient.

In some examples, using the MD ASA, the health care provider or physician and the patient communicate about the patient's features, their emotional aesthetic attributes, and the proposed method of treatment.

In some examples, using the MD ASA, the health care provider or physician and/or the patient assesses the aesthetic treatments, In some examples, the methods include treating a point of distraction on their face.

In some examples, the methods include treating a point of distraction on their face such as frown lines.

In some examples, the methods include treating a point of distraction on their face such as prominent nasolabial folds.

In some examples, the methods include treating a point of distraction on their face such as crow's feet. In some examples, the methods include treating a point of distraction on their face such as cheek lines.

In some examples, the methods include treating a point of distraction on their face such as jowls.

In some examples, the methods include treating a point of distraction on their face such as saggy skin in the neck.

EXAMPLES

Example 1—Treating a Sagging Aesthetic

FIGS. 67 to 71 show clinical studies regarding a method of treatment which uses the MD ASA diagram to treat a saggy appearance as well as how to use the diagram rating system with respect to two of the facial indicators associated with that emotional attribute.

The patient was assessed as set forth in FIGS. 67 to 71.

After the assessment, the patient received treatment in the cheeks and chin to improve the saggy appearance.

Example 2—Treating a Sad Aesthetic

FIGS. 72 to 75 show clinical studies regarding a method of treatment which uses the MD ASA diagram to treat a sad appearance.

The patient was assessed as in FIGS. 72 to 75.

Using the MD ASA, patient received treatment in the eyebrows, temples, cheeks, tear trough, lips and chin.

Example 3—Treating a Tired Aesthetic

Figure 77:
Figure 78:
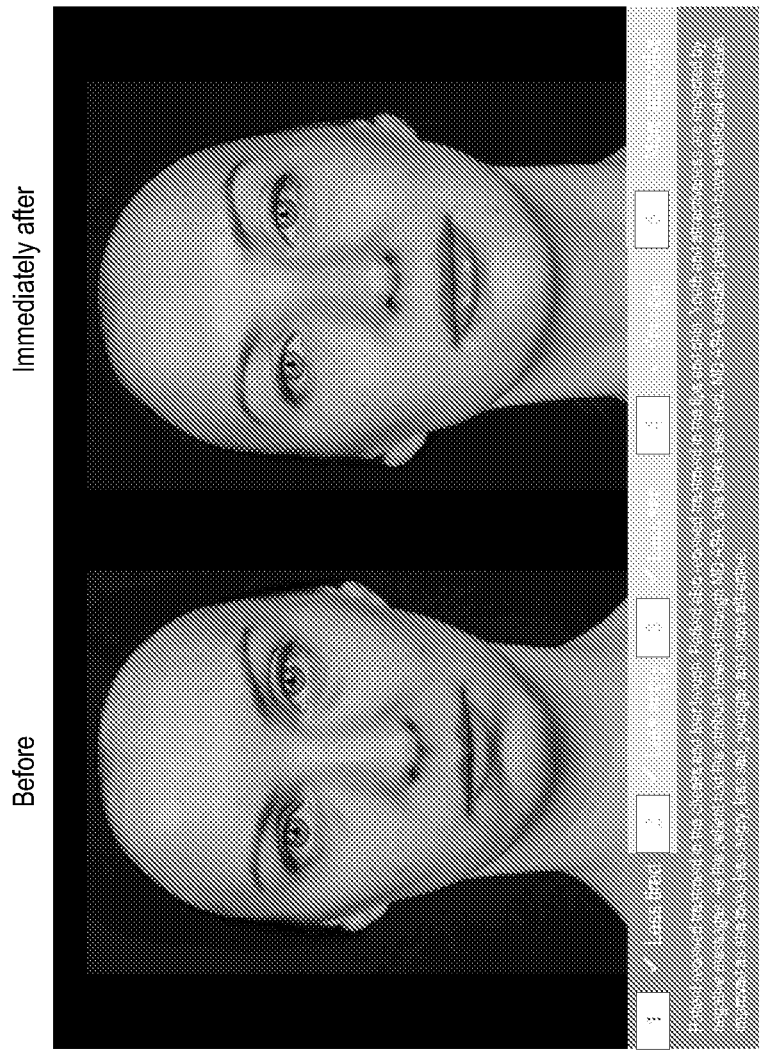
Figure 80:
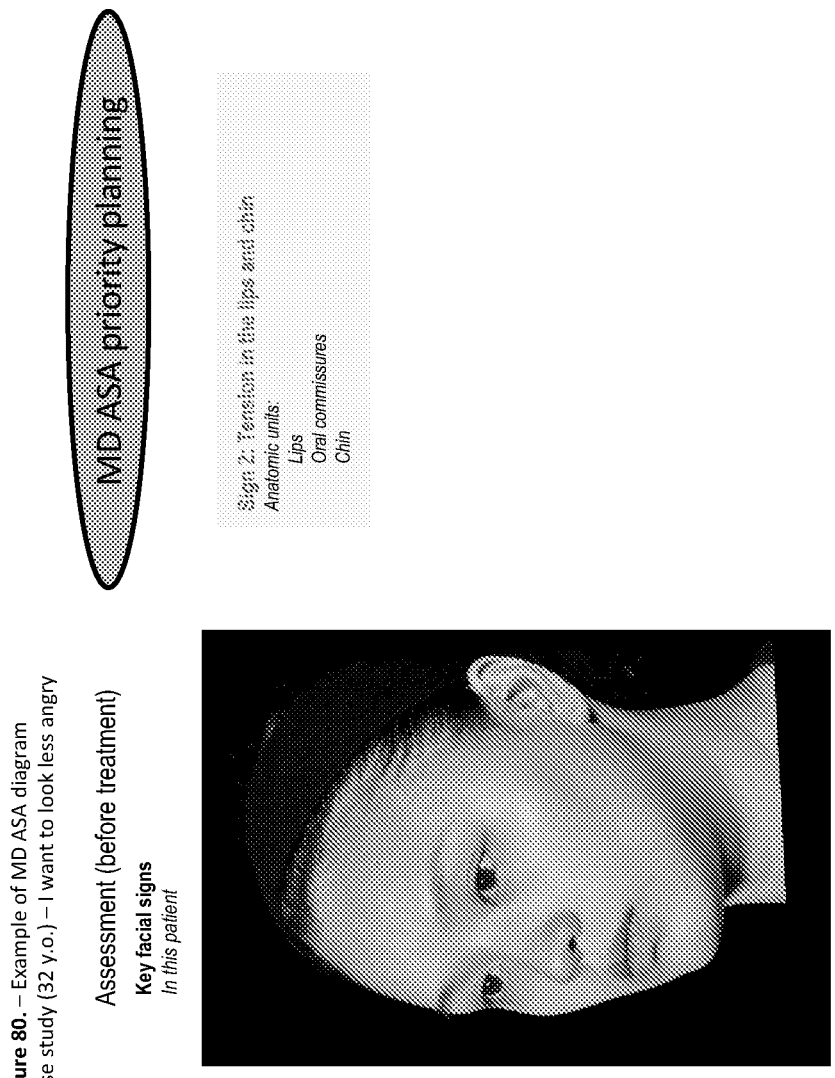
Figure 81:
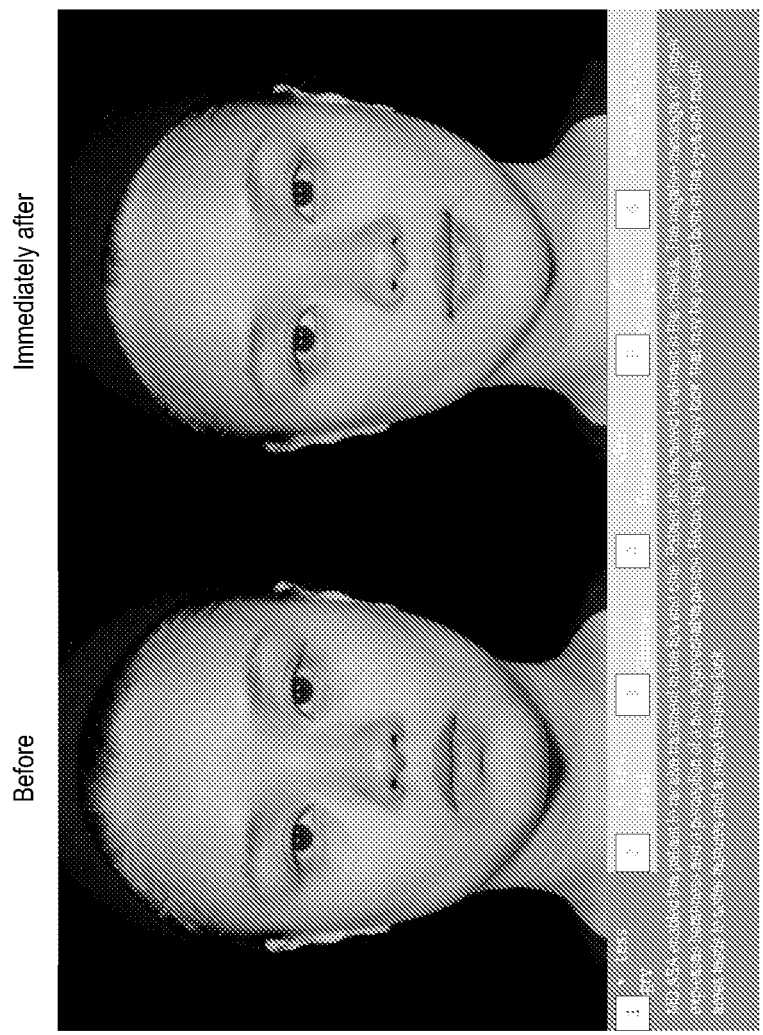
Figure 82:
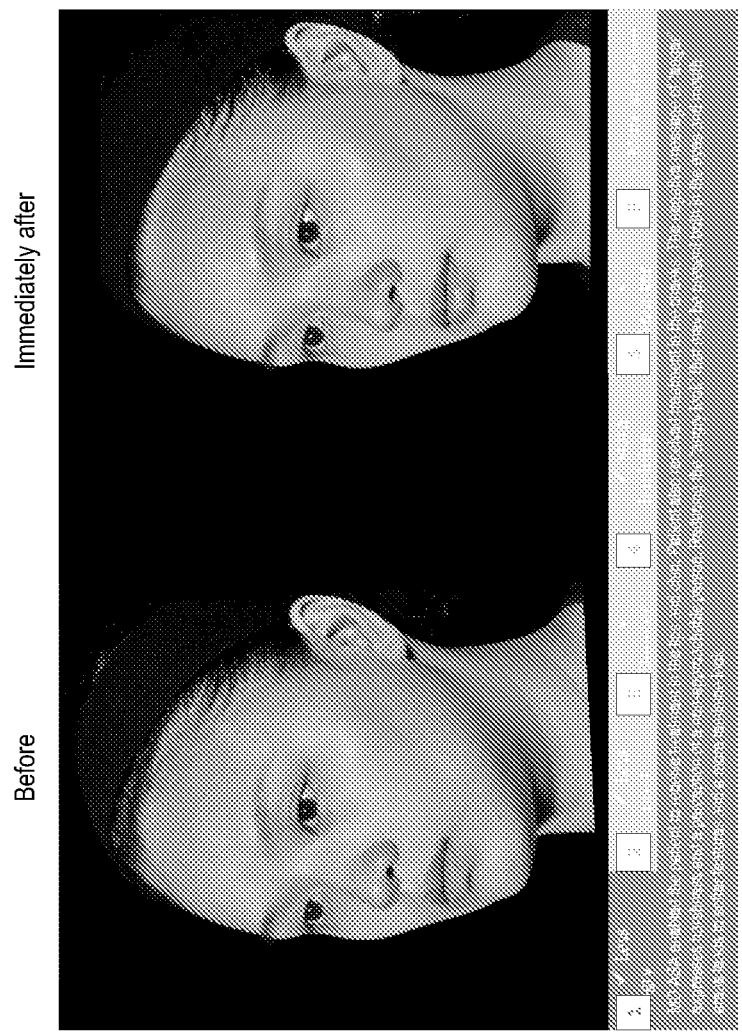

FIGS. 76 to 78 show clinical studies regarding a method of treatment which uses the MD ASA diagram to treat a tired appearance.

The patient's aesthetics had been negatively impacted by age.

The patient was assessed as set forth in FIGS. 67 to 71.

Using the MD ASA diagrams, the patient was treated.

Patient received treatment in the cheeks and tear trough. Patient also received treatment in the lips and chin.

As a result of the treatment, the patient looked less tired.

As a result of the treatment, the patient also had other improved attributes. These improved attributes included looking less angry and less sad. This improved attributes included looking younger and more attractive Example 4—Treating an Angry Aesthetic FIGS. 79 to 82 show clinical studies regarding a method of treatment which uses the MD ASA diagram to treat an angry appearance.

The patient was assessed as set forth in the Figures.

Using the MD ASA diagrams, the patient was treated.

The patient to receive treatment in the lips and chin. Patient also received treatment in the cheeks.

As a result of the treatment, the patient benefited. The aesthetics of the patients' face improved such that she did not look angry or have the appearance of a non-approachable person.

Example 5—Enhancing a Slimmer Aesthetic

Figure 83:
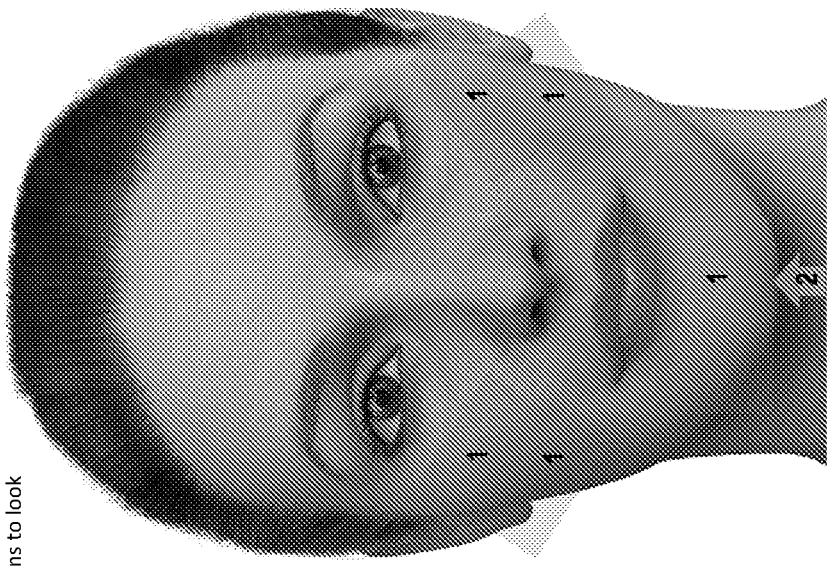
Figure 84:
Figure 85:
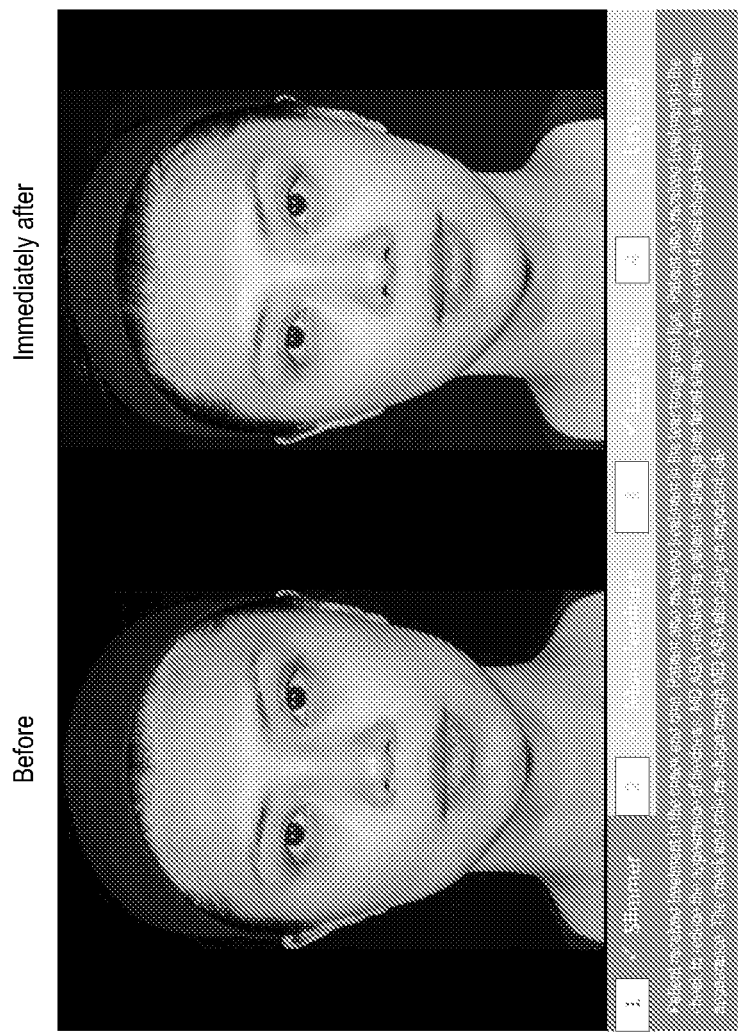
Figure 87:
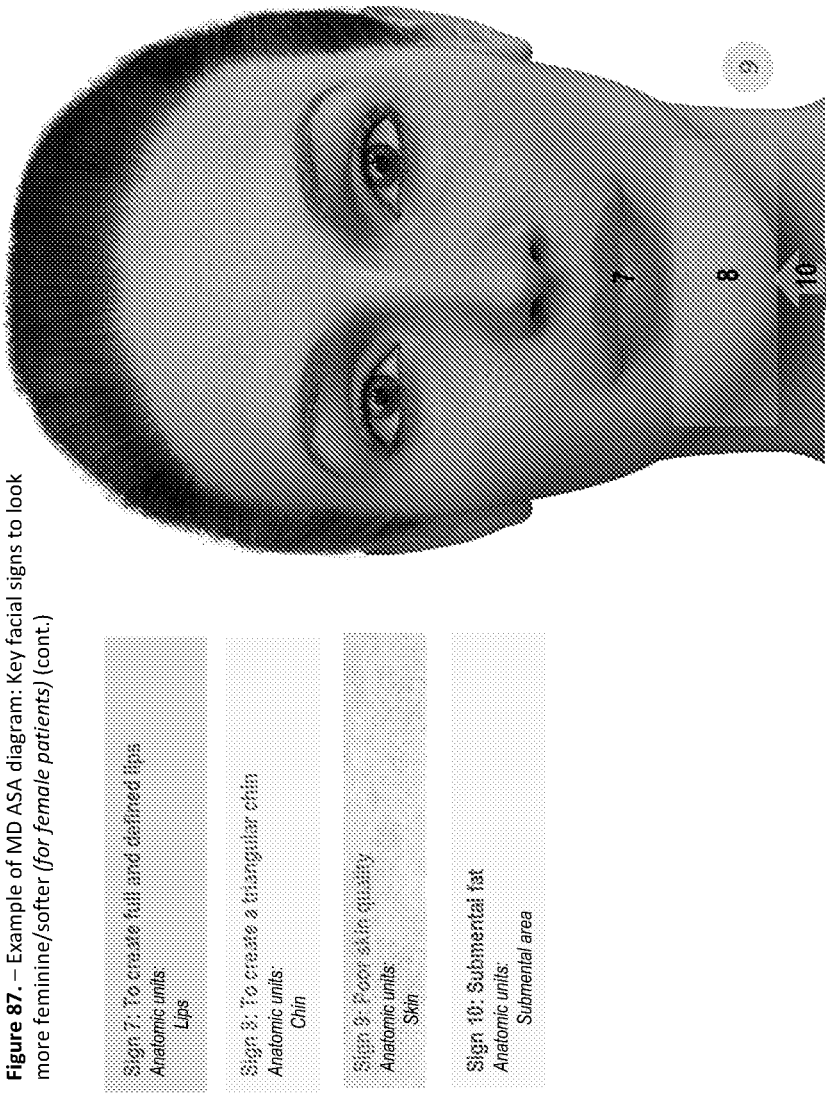
Figure 88:
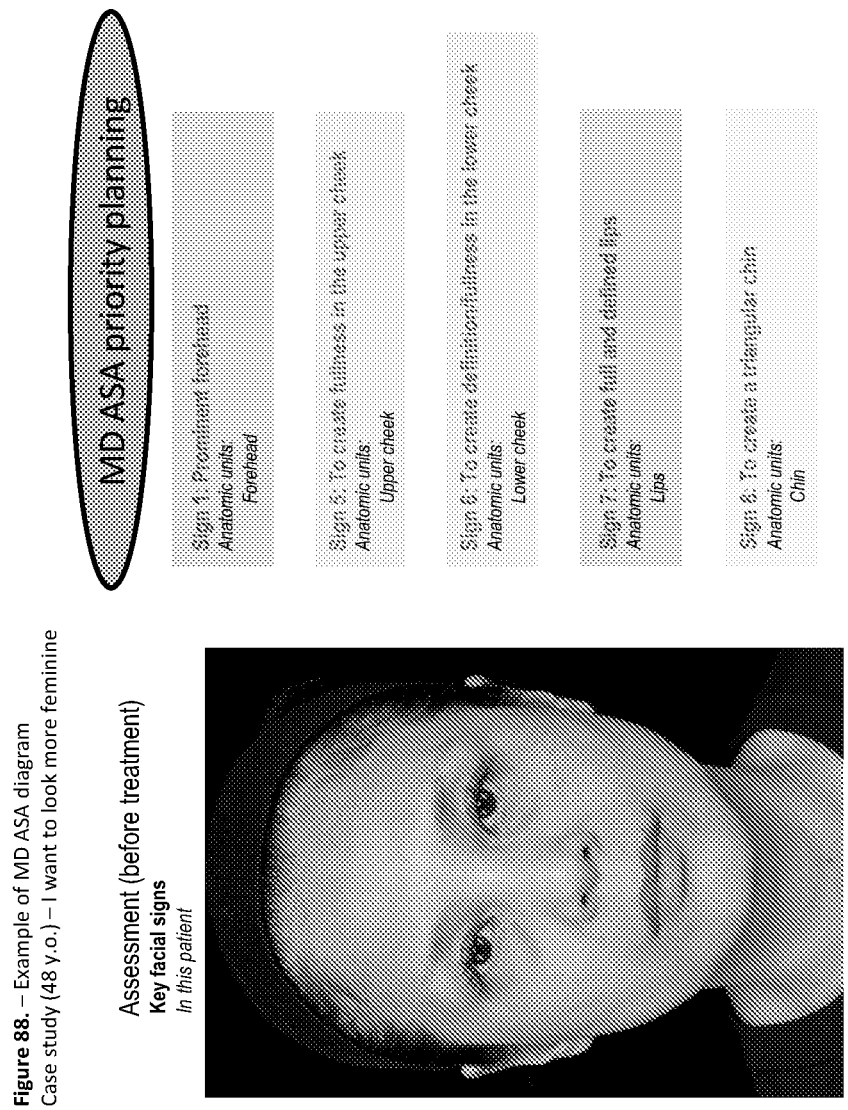
Figure 89:

FIGS. 83 to 85 show clinical studies regarding a method of treatment which uses the MD ASA diagram to treat the slimmer appearance by enhancing it, i.e., by making the slimmer appearance appear more slim.

In this example, the MD ASA diagrams are used to treat the patient resulting in a change in the shape of her face. In this example, the patient obtained a more oval facial shape and a slimmer appearance. The cheek and chin were re-shaped using the MD ASA.

Example 6—Enhancing a More Feminine Aesthetic

FIGS. 86 to 89 show clinical studies regarding a method of treatment which uses the MD ASA diagram to enhance a more feminine (softer) appearance (for female patients).

Using the MD ASA diagrams, improvements in the patient's aesthetics occurred, including rounding the angles of the face, erasing negative messages and providing fuller lips, a and a softer look.

Figure 90:
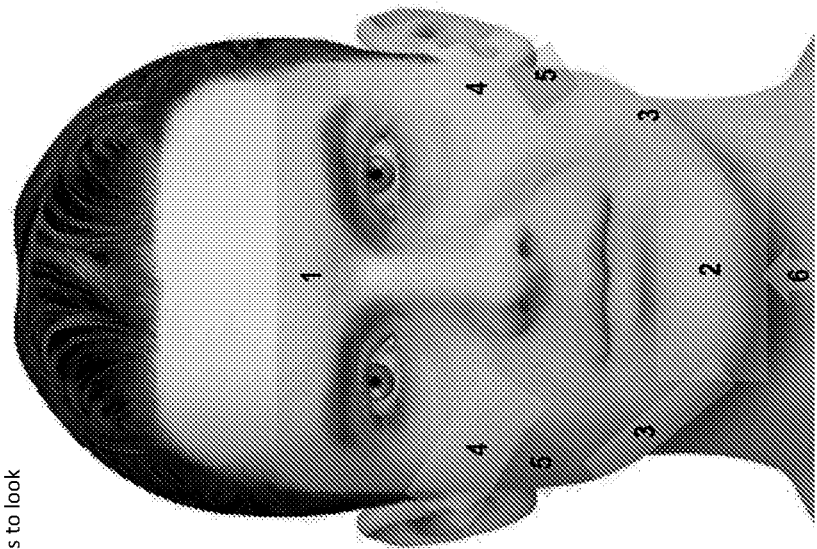
Figure 92:
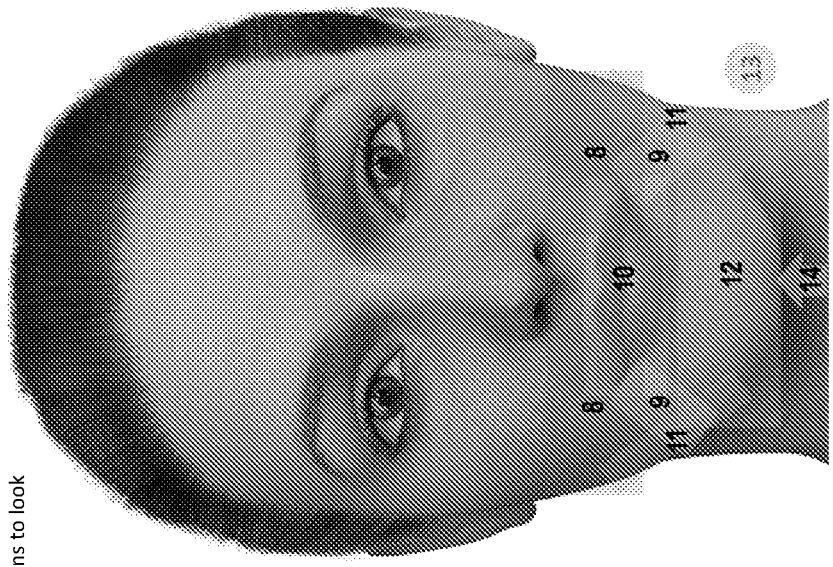
Figure 93:
Figure 94:
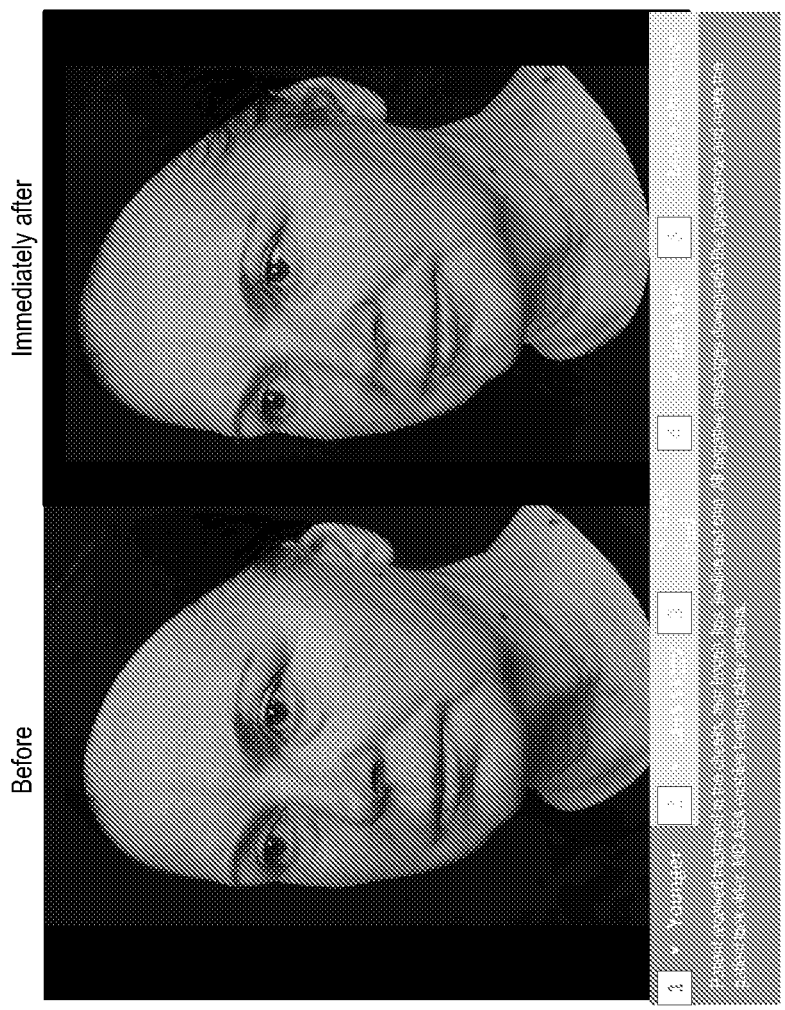
Figure 95:
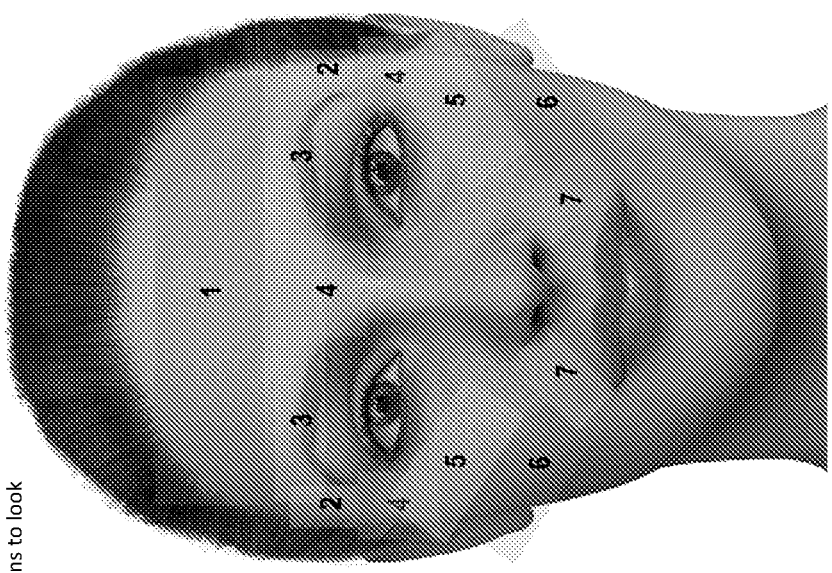
Figure 96:
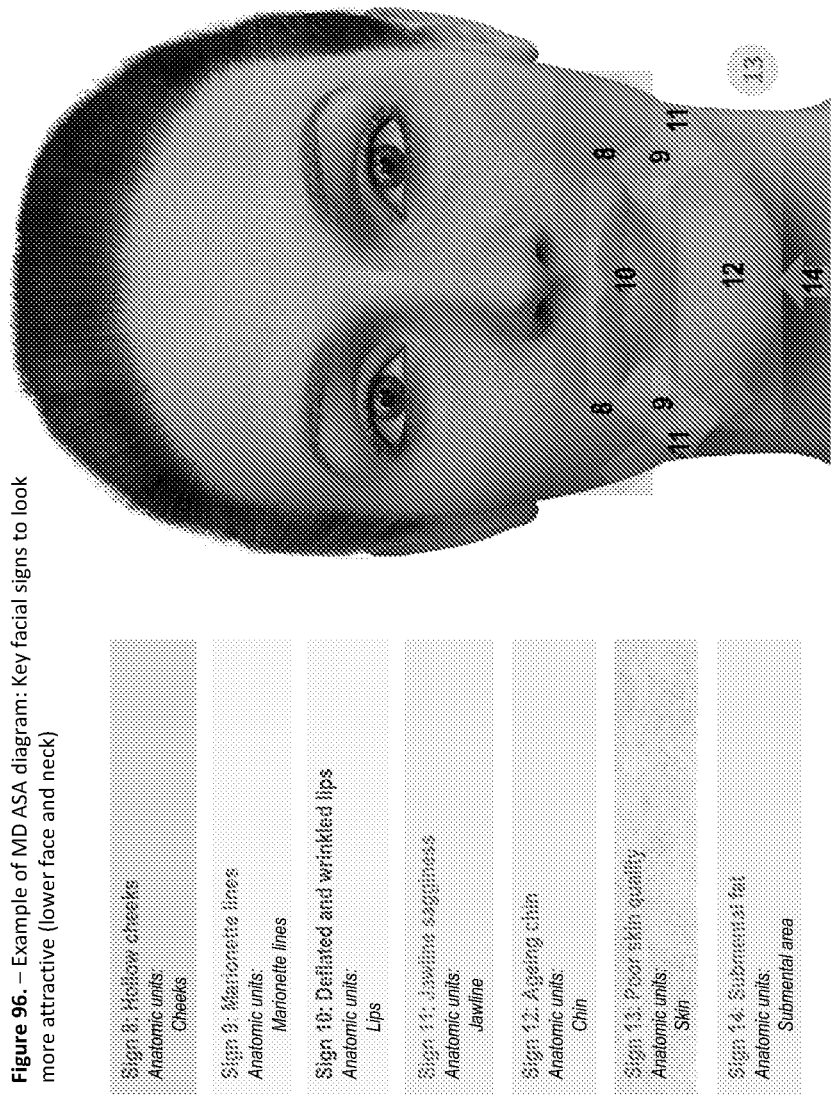
Figure 97:
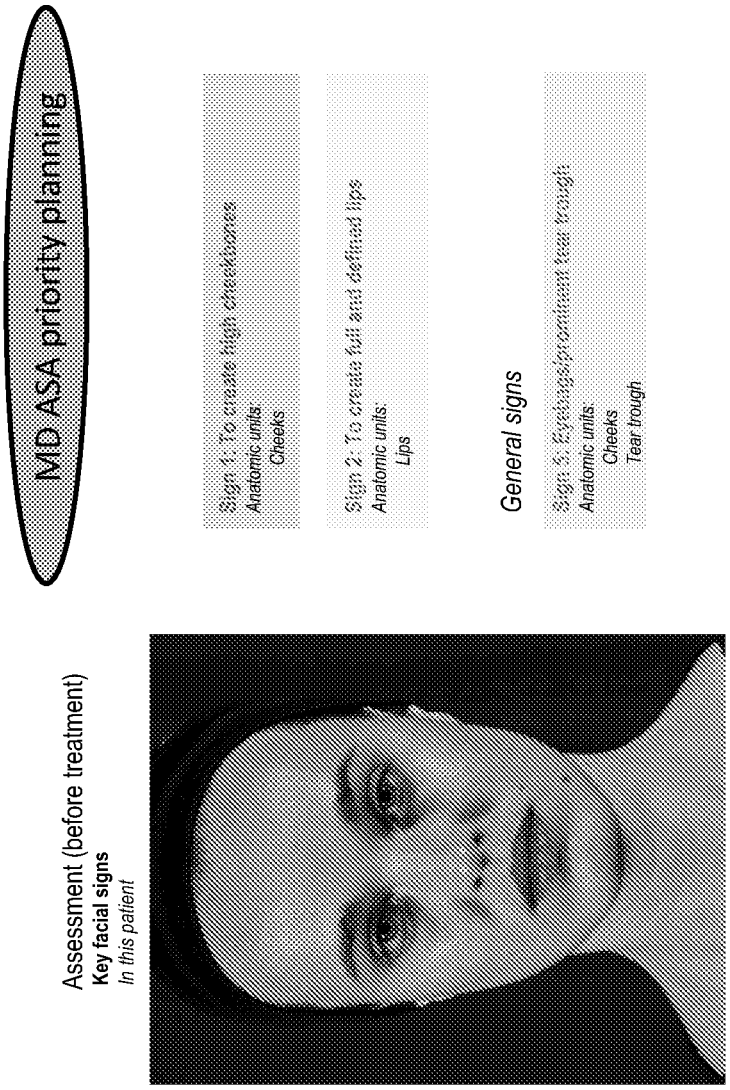
Figure 98:
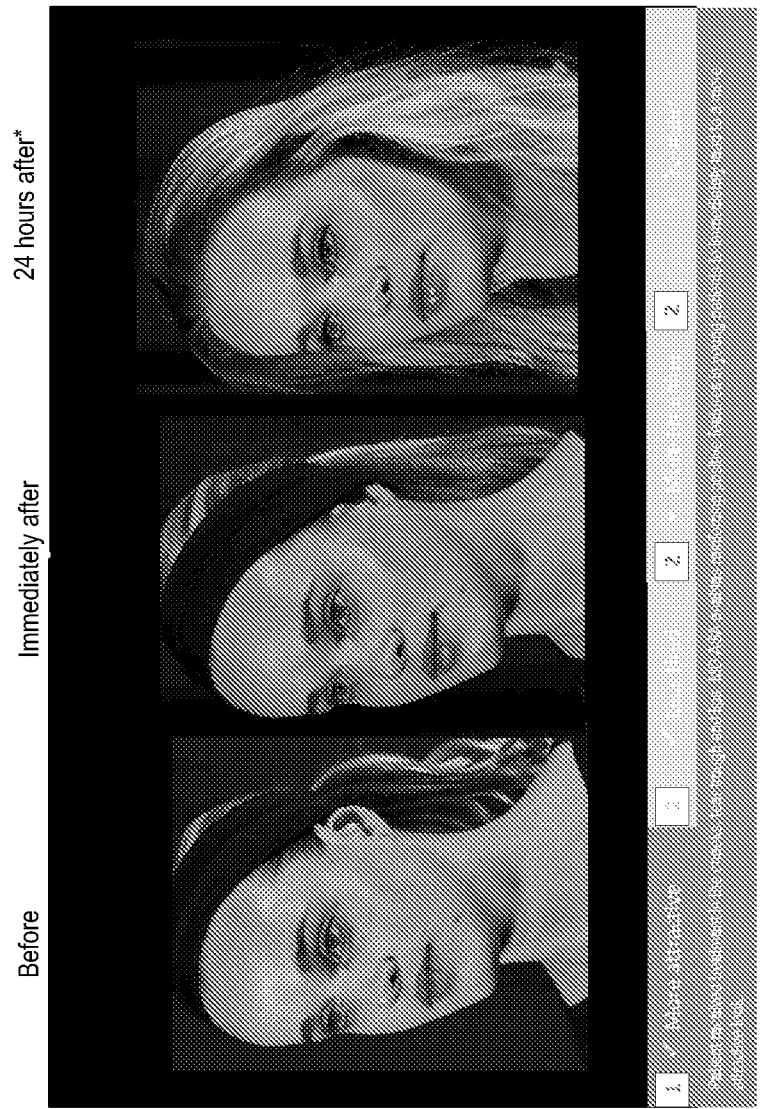
Figure 99:
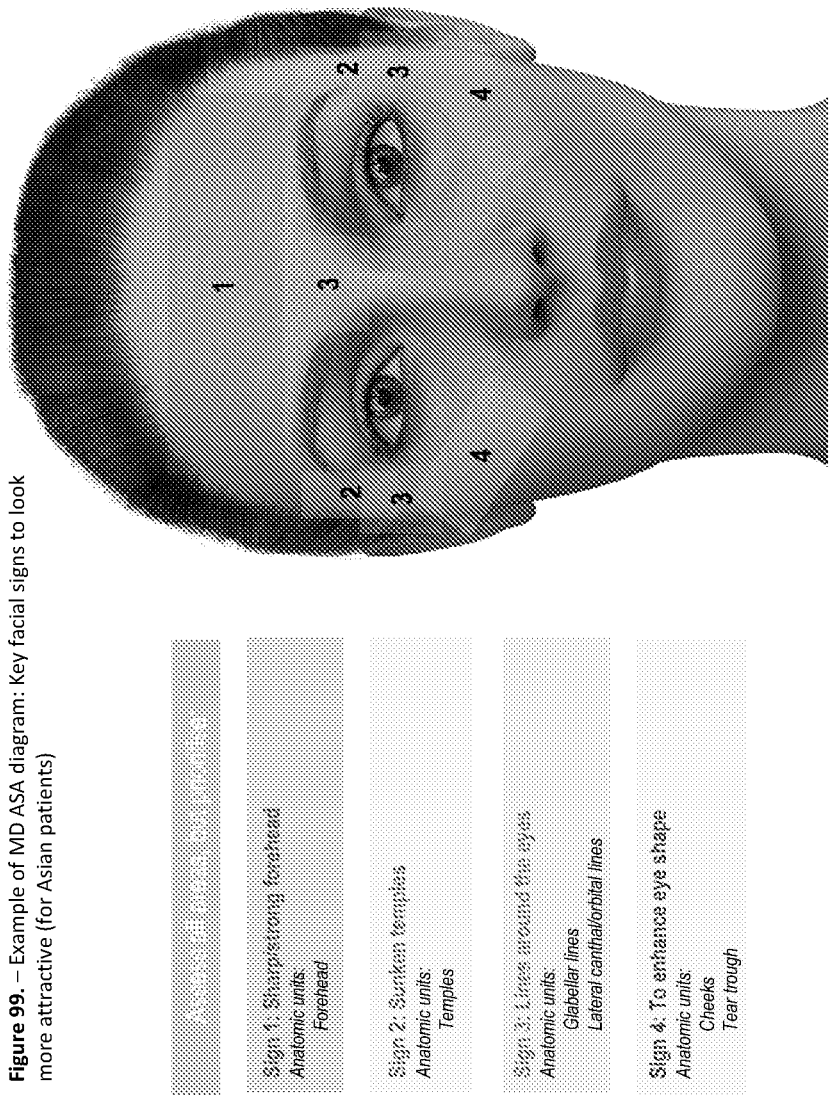
Figure 101:
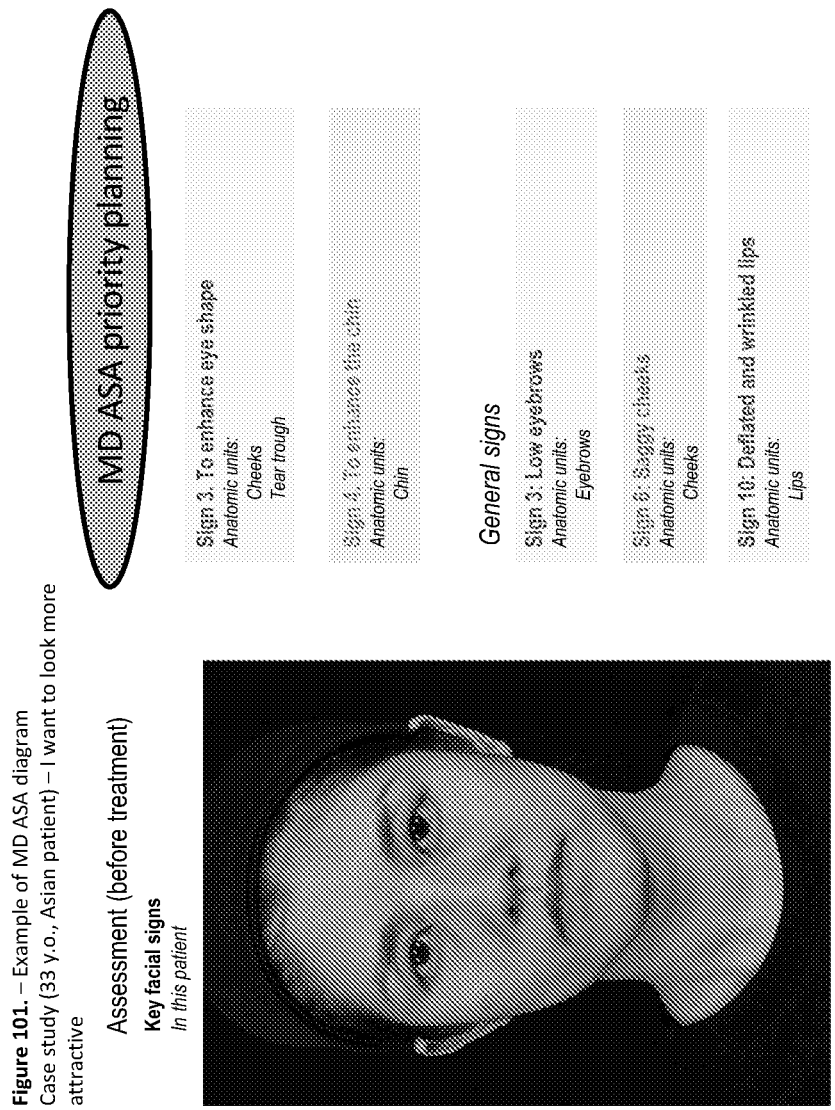
Figure 102:
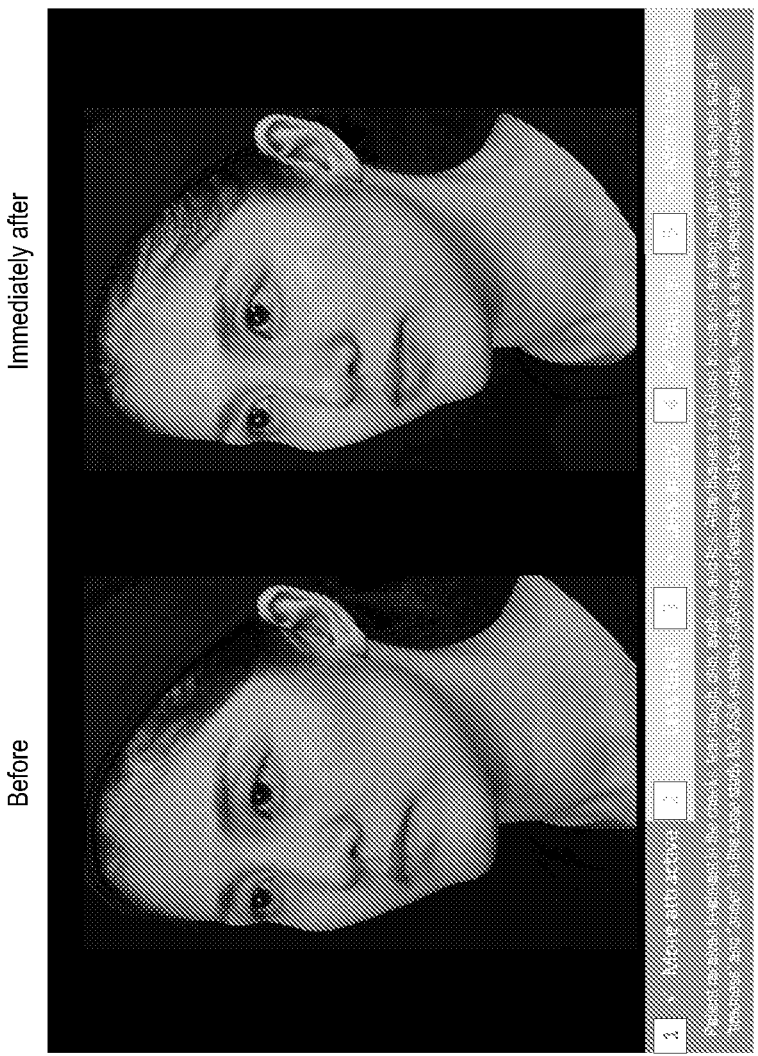
Figure 103:
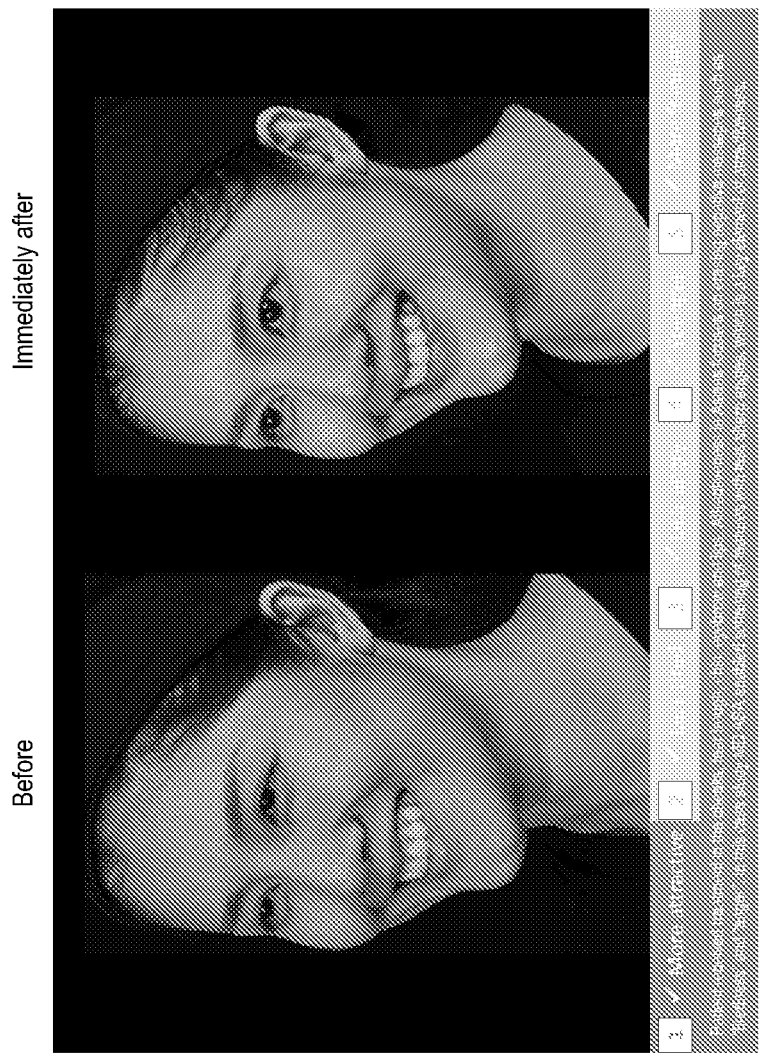

FIG. 90 shows how the MD ASA diagram were used to enhance a more masculine appearance (for male patients).

Example 7—Enhancing a Youthful Aesthetic

FIGS. 91 to 94 show clinical studies regarding a method of treatment which uses the MD ASA diagram to enhance a youthful appearance.

The patient had negative aesthetic attributes such as looking older.

The patient was assessed as set forth in the Figures.

Using the MD ASA diagrams, the patient was treated.

The patient to receive treatment with injectables.

As a result of the treatment, the patient benefited by looking younger.

Example 8—Enhancing a More Attractive Aesthetic

FIGS. 95 to 98 show clinical studies regarding a method of treatment which uses the MD ASA diagram to enhance a more attractive appearance in a Caucasian patient.

The patient was assessed as set forth in the Figures.

Using the MD ASA diagrams, the patient was treated.

The patient to receive treatment in the lips and chin. Patient also received treatment in the cheeks.

As a result of the treatment, the patient benefited by having looking younger and other positive features.

Example 9—Enhancing a More Attractive Aesthetic

FIGS. 99 to 103 show clinical studies regarding a method of treatment which uses the MD ASA diagram to enhance a more attractive appearance in an Asian patient by reducing the appearance of, for example, "tiredness" and "anger".

The patient was assessed as set forth in the Figures.

Using the MD ASA diagrams, the patient was treated.

The patient to receive treatment in the lips and chin. Patient also received treatment in the cheeks.

Example 10—Enhancing a More Attractive Aesthetic

Figure 104:
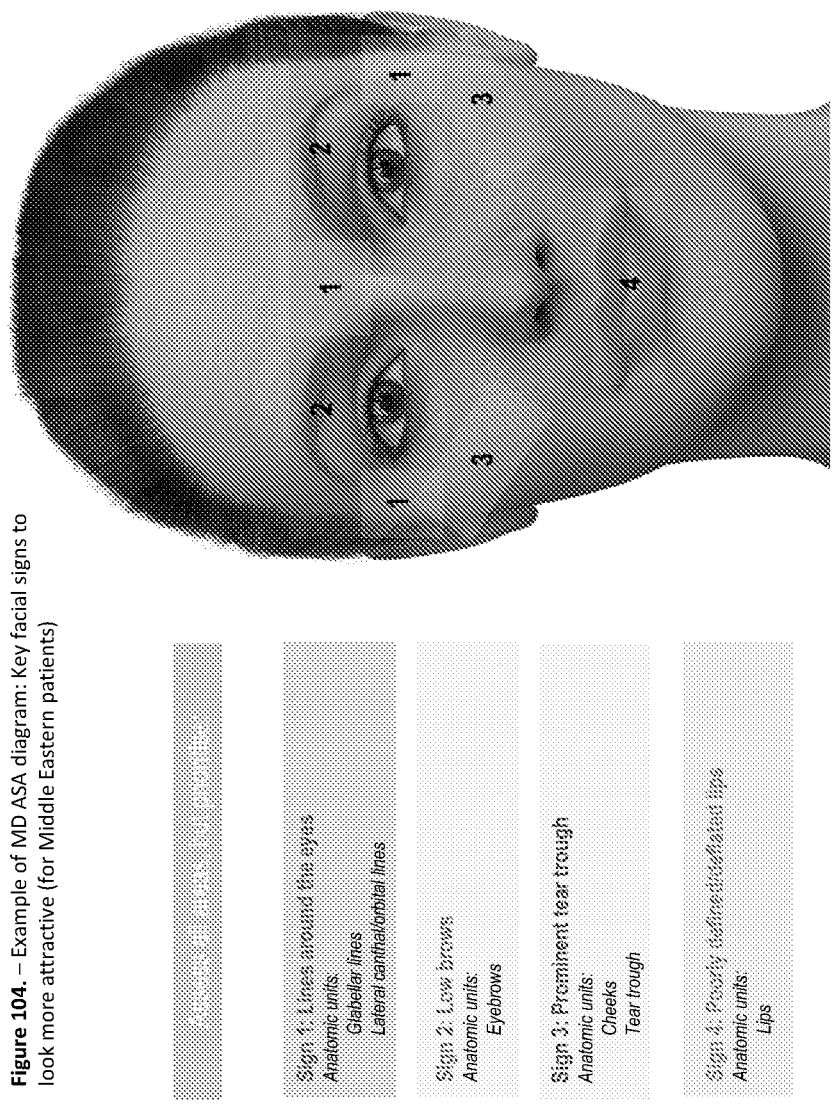
Figure 105:
Figure 106:
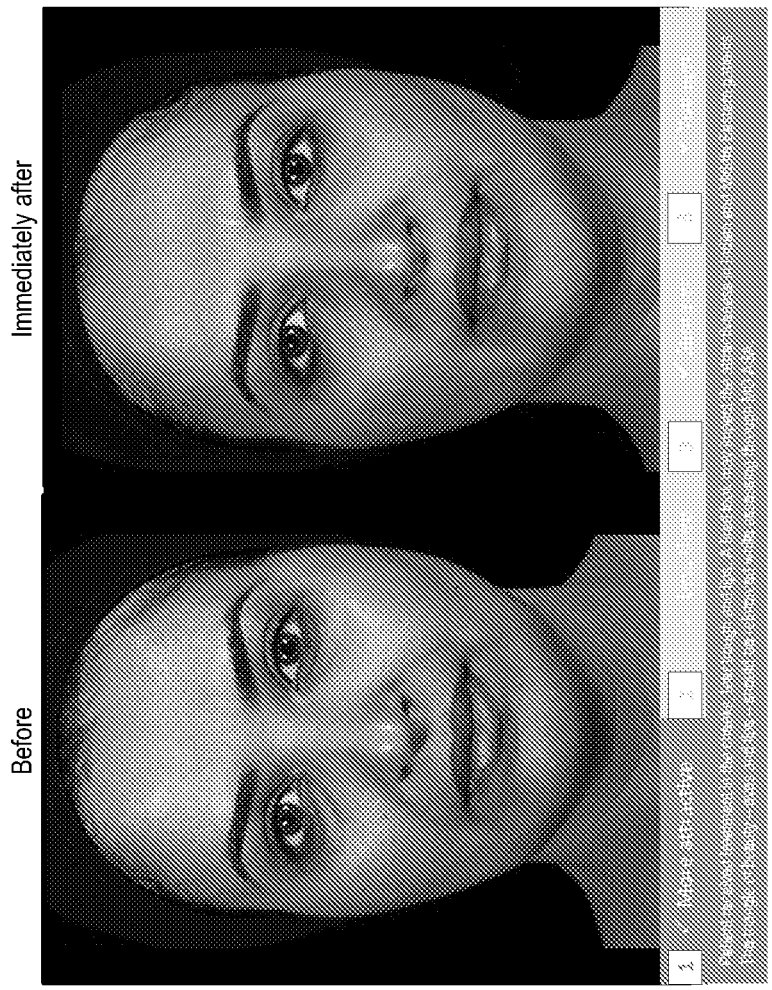

FIGS. 104-106 show clinical studies regarding a method of treatment which uses the MD ASA diagram to enhance a more attractive appearance in a Middle Eastern patient including reducing the appearance of being tired.

In this example, the triangle of beauty—eyes and lips—was reinforced while using the MD ASA diagrams.

The patient was assessed as set forth in the Figures.

Using the MD ASA diagrams, the patient was treated.

The patient to receive treatment in the lips and chin. Patient also received treatment in the cheeks.

Figure 107:
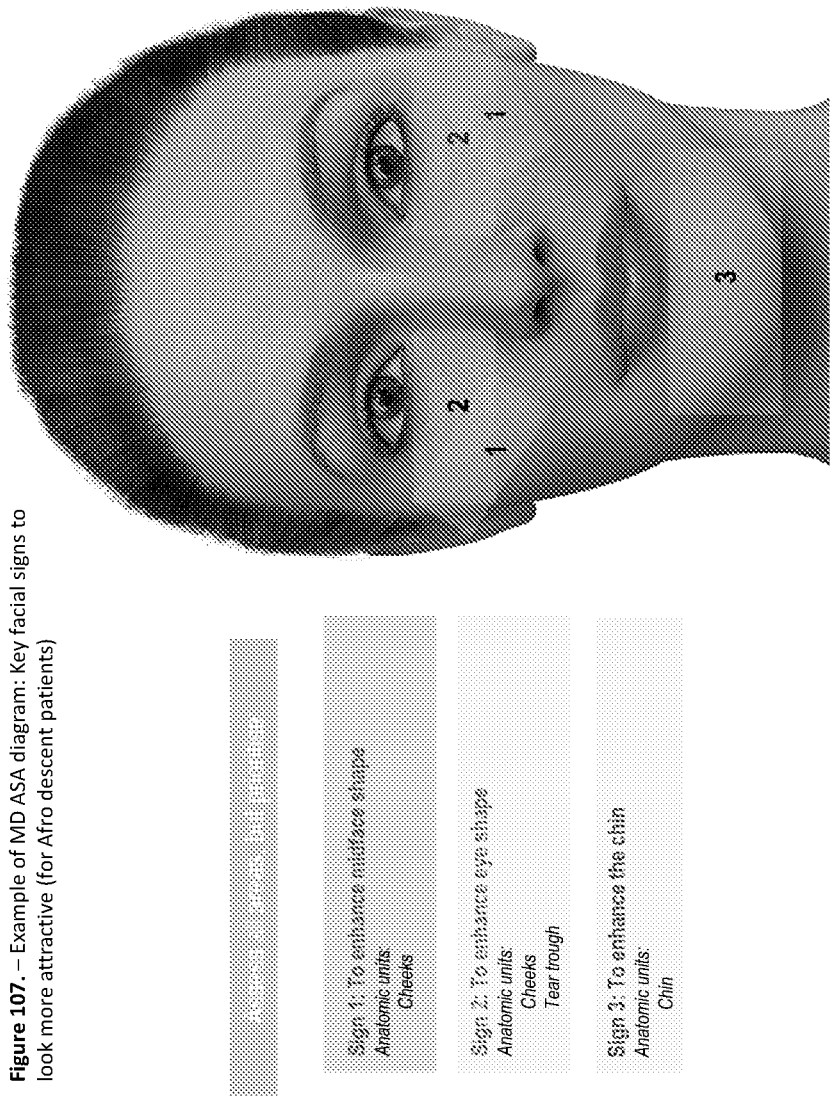

FIG. 107 shows how to use the MD ASA diagram to enhance a more attractive appearance for Afro descent patients.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

Embodiment 1, a method of treating a subject in need thereof, the method comprising:
providing a subject;
assessing the subject based on an MD ASA diagram;
treating the subject in need thereof by injecting a therapeutically effective amount of a pharmaceutical composition comprising a member selected from the group consisting of hyaluronic acid (HA), Botox, fillers, and combinations thereof.

Embodiment 2, the method of embodiment 1, wherein assessing the subject comprising scoring an aesthetic hierarchy.

Embodiment 3, the method of any one of embodiments 1-2, wherein assessing the subject comprising scoring an aesthetic hierarchy substantially as set forth in FIG. 3.

Embodiment 4, the method of any one of embodiments 1-3, wherein the treating comprises injecting a patient at sites set forth herein, in the figures, or incorporated by reference.

Embodiment 5, the method of any one of embodiments 1-4, wherein the sites are on the neck or face.

Embodiment 6, the method of any one of embodiments 1-5, wherein the subject is in need of aesthetic treatment.

Embodiment 7, the method of any one of embodiments 1-6, wherein the method further comprises injecting a pharmaceutical composition comprising a member selected from the group consisting of hyaluronic acid (HA), Botox, fillers, and combinations thereof; and repeating the injecting at least once per year for at least five (5) years.

Embodiment 8, the method of any one of embodiments 1-7, wherein the pharmaceutical composition comprises a member selected from the group consisting of Botulinum Toxin—Type A (Botox), collagen, hyaluronic acid, antibiotics, anti-inflammatory drugs, steroids and combinations thereof Embodiment 9, the method of any one of embodiments 1-7, wherein the pharmaceutical composition is Botulinum Toxin—Type A.

Embodiment 10, the method of any one of embodiments 1-7, wherein the pharmaceutical composition is a long-chain Hyaluronic Acid (HA) product.

Embodiment 11, the method of any one of embodiments 1-7, wherein the pharmaceutical composition comprises HA.

Embodiment 12, the method of any one of embodiments 1-7, wherein the pharmaceutical composition is deoxycholic acid.

Embodiment 13, the method of any one of embodiments 1-7, wherein the pharmaceutical composition comprises a vitamin.

Embodiment 14, the method of any one of embodiments 1-12, wherein the injection sites are set forth in any one of the Figures.

Embodiment 15, the method of any one of embodiments 1-13, further comprising visualizing the injection sites.

Embodiment 16, the method of any one of embodiments 1-14, further comprising visualizing the injection sites on a computer screen.

Embodiment 17, the method of any one of embodiments 1-15, wherein the visualizing comprises overlaying any of the injection sites set forth herein with an image of the subject in need thereof.

Embodiment 18, the method of any one of embodiments 1-16, wherein the subject suffers from an aesthetic condition.

Embodiment 19, the method of any one of embodiments 1-17, wherein the subject suffers from a dermatology condition.

Embodiment 20, the method of any one of embodiments 1-17, wherein the method comprising injecting at least 0.5 mL of the therapeutically effective amount of the pharmaceutical composition.

Embodiment 21, the method of any one of embodiments 1-17, wherein the method comprising injecting the therapeutically effective amount of the pharmaceutical composition at a depth of penetration of at least 2-6 mm.

Embodiment 22, the method of any one of embodiments 1-17, wherein pharmaceutical composition is a cellular body.

Embodiment 23, a system for practicing the method of any one of embodiments 1-20.

Embodiment 24, an injector designed for practicing the method of any one of embodiments 1-20.

Next Human Methods and Systems

Set forth herein is a set of methods and systems useful for designing and generating the NEXT HUMAN, which is a human who has aged but without all of the negative side effects associated with aging.

In some examples, set forth herein are Aging Trigger Points (ATP). These ATP identify subjects or particular areas for a subject that, if treated at an early stage, will slow down the degradation of the facial aesthetic aging process. In some examples, by treating the ATP, the aging process is reversed. In some examples, by treating the ATP, the aging process is stopped.

In some examples, the methods of treatment are provided before the subject has aged beyond the point where his or her aging process can be reversed or stopped.

In some examples, provided herein are health markers (HM).

In some examples, a health-care provider (e.g., a doctor) identifies these HM on a subject to provide a treatment plan for that subject for proactive self-care and early detection of diseases.

In some examples, including any of the foregoing, set forth herein is a method of evaluating the ATP and HM in a subject. A health care provider, such as but not limited to a doctor, may provide this evaluating. In some examples, the ATP are related to aesthetic procedures which are addressed by the HCP.

In some examples, set forth herein is a method of early detection of health risk factors and unfavorable aesthetic aging signs. In some further examples, the methods include treating a subject based on this early detection.

In some examples, the methods include treating a patient to maintain the appearance of that patient when they were 25 years of age.

In some examples, the methods include treating a patient to maintain the appearance of that patient when they were 26 years of age.

In some examples, the methods include treating a patient to maintain the appearance of that patient when they were 27 years of age.

In some examples, the methods include treating a patient to maintain the appearance of that patient when they were 28 years of age.

In some examples, the methods include treating a patient to maintain the appearance of that patient when they were 29 years of age.

In some examples, the methods include treating a patient to maintain the appearance of that patient when they were 30 years of age.

In some examples, the methods include treating a patient to maintain the appearance of that patient when they were 31 years of age.

In some examples, the methods include treating a patient to maintain the appearance of that patient when they were 32 years of age.

In some examples, the methods include treating a patient to maintain the appearance of that patient when they were 33 years of age.

In some examples, the methods include treating a patient to maintain the appearance of that patient when they were 34 years of age.

In some examples, the methods include treating a patient to maintain the appearance of that patient when they were 35 years of age.

In some examples, the methods include treating a patient to maintain the appearance of that patient when they were 36 years of age.

In some examples, the methods include treating a patient to maintain the appearance of that patient when they were 37 years of age.

In some examples, the methods include treating a patient to maintain the appearance of that patient when they were 38 years of age.

In some examples, the methods include treating a patient to maintain the appearance of that patient when they were 39 years of age.

In some examples, the methods include treating a patient to maintain the appearance of that patient when they were 40 years of age.

The NEXT HUMAN system herein includes treating patients based on two basic indicators. The first indicator is referred to herein as Aging Trigger Points (ATP). ATP is subdivided into BATP and SATP. The second indicator is Health Markers (HM).

Bone provides a framework for the soft tissue envelope and structural support. Bone density peaks in early adulthood and then declines at a rate of approximately 1% to 2% per year, and in women bone loss accelerates during the perimenopausal period. Bone loss in facial structure with aging, including in the orbital aperture and mandible, can contribute to the appearance of the aging face. Loss of bone structure or density may result in hypoplasia, and may also affect muscle function and stability, ultimately altering the aesthetic appearance of the face, including its harmony and proportion.

Aging skin is characterized by a decrease in collagen levels, fragmentation of the dermal collagen matrix, an increase in elastogenesis, and accumulation of elastic fibers. Fragmentation of collagen leads to a collapse of fibroblasts, which in turn reduces collagen production. Reduced elasticity is significantly associated with increased sagging. Constant movement of muscles without proper fat and bone support will lead to lines which represent fractures in the dermis represented by lines, folds and depressions.

The SATP refer to topographic locations and are represented as specific surface locations within the aesthetic unit of the face. They are listed from top down and from medial to lateral on the skin surface. On these locations, the appearance of aging signs are visible in the form of lines, folds, shallow depressions and surface displacement of structures such as in saggy skin. There are 16 SATP that must be assessed to identify the presence of negative features (FIGS. 123-126). If those distractions are present at an early stage (20's or 30's) they may result in unfavorable future aging (FIG. 127).

Figure 129:
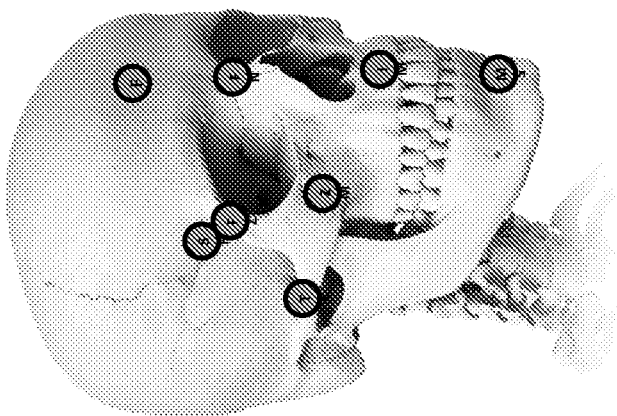
FIG. 129 shows the eight (8) BAPT: Right oblique view.
Figure 130:
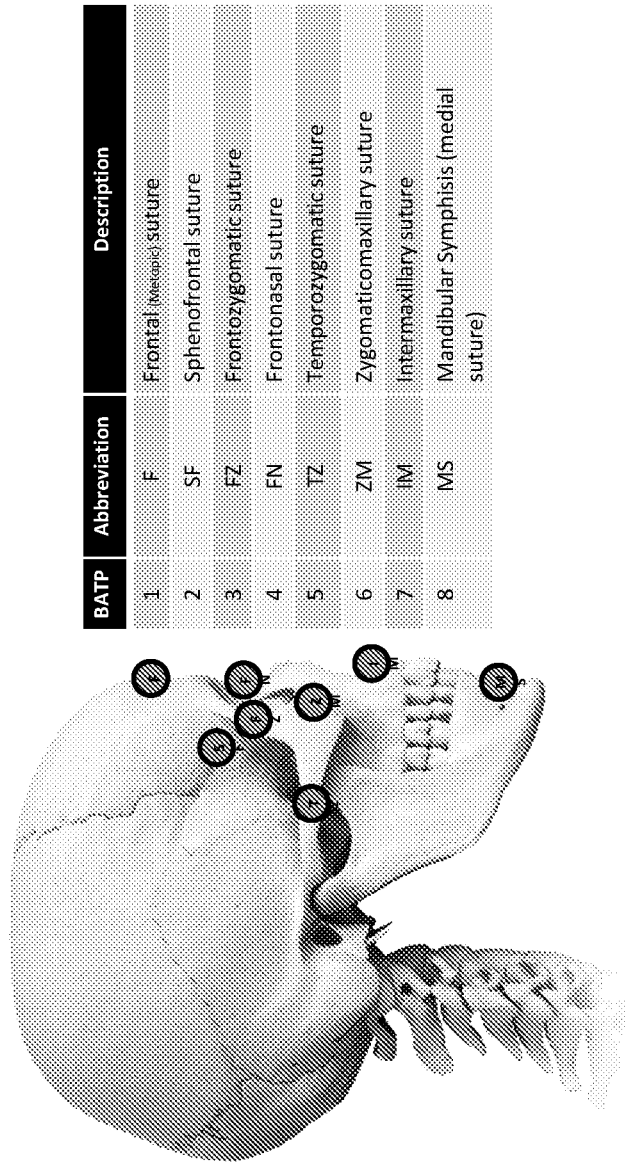
FIG. 130 shows the eight (8) BAPT: Right profile view.

The deep anatomical structures that are found at the bone level (BATP) may influence negatively the aging process and result from unfavorable embryological development or trauma after development. There are 8 BATP at the bone level which represent the bone sutures (FIGS. 128-130). Six sutures perpetuate in adulthood and two are usually fused at birth. Each point is named after the abbreviation of the sutures and is numbered from top down and from medial to lateral in the skull. Structural deficiencies such as chin retrusion, malocclusion are examples of indicators of unfavorable aging if not treated early. The deep fat pads also present an important role in aging. Proper volume and location are desirable. Volume loss and displacement of fat pads lead to exponential domino effect in aging process.

The worse the aesthetic distractions are, even worse and faster they get. Facial aging is a non-stoppable domino effect and does not revert without external help. In Aesthetics, the signal that is commonly seen is the presence of static lines, folds and saggy skin. Although these distractions can be corrected nowadays, timing is really important. Efforts should be made to avoid the exponential decay of the ATP. Early diagnosis and correction of the BATP and SATP may slow down and revert aging signs (FIG. 131).

Aging Trigger Points (ATP)

Humans age at a different pace. Genetics may favorably or unfavorably influence the aging process. The environment may favorably or unfavorably influence the aging process and may deteriorate one's health and aesthetic appearance.

Early assessment of ATP allows for the correction of unfavorable features as soon as possible so that a higher degree of severity is not reached and a more favorable aging process will occur.

The ATP are described at different levels related to aesthetic appearance of the face.

In some examples herein, the methods include two groups of ATP: Deep and superficial.

As used herein, deep ATP is named after BATP and refers to Bone Aging Trigger Points. Superficial ATP are named after SATP and refer to Surface Aging Trigger Points.

Health Markers (HM)

In some examples, the HM are selected from the group consisting of HM1, HM2, HM3, HM4, HM5, HM6, HM7, and HM8. See FIG. 133.

Figure 132:
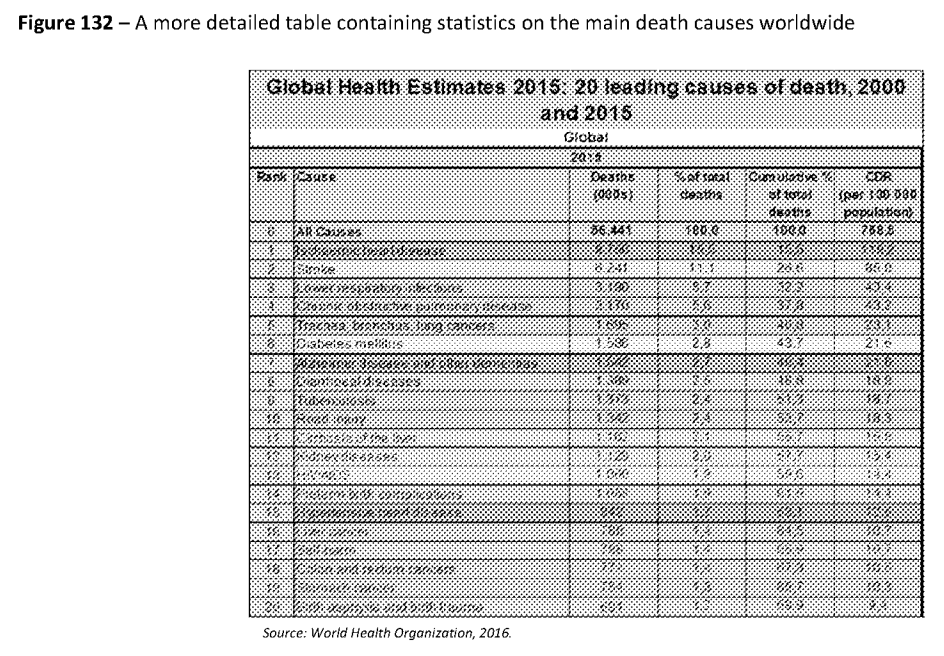

A list of the 10 most current main causes of death is found below (World Health Organization, 2016) (FIG. 132):
1. Heart disease: 9.6M (17.2%)
2. Chronic respiratory diseases: 7.7M (13.7%)
3. Stroke: 6.2M (11.1%)
4. Cancer: 4M (7.1%)
5. Kidney and liver diseases: 2.2M (4.1%)
6. Diabetes: 1.5M (2.8%)
7. Alzheimer's disease: 1.5M (2.7%)
8. Accidents: 1.3M (2.4%)
9. HIV/AIDS: 1M (1.9%)
10. Suicide: 0.7M (1.4%)

There are 8 basic health markers that include metabolic, cardiovascular measurements, and sexual hormones evaluation. Habits such as alcohol intake, smoking and physical exercises are also assessed.

The Aesthetic Consultation with HCP

In some examples, prior to treating a subject, the following steps are performed.

In some examples, a patient is in need of treatment for *glabella* lines and nasolabial folds In some examples, the methods herein include. Step 1: HCP asks the 4 questions after listening to patient's motivation: 1-How old are you?; 2—How old do you think you look?; 3—How old do you feel inside?; and 4—At what age do you consider you looked and felt your best?

In some examples, the patient's responses are recorded.

Figure 136:
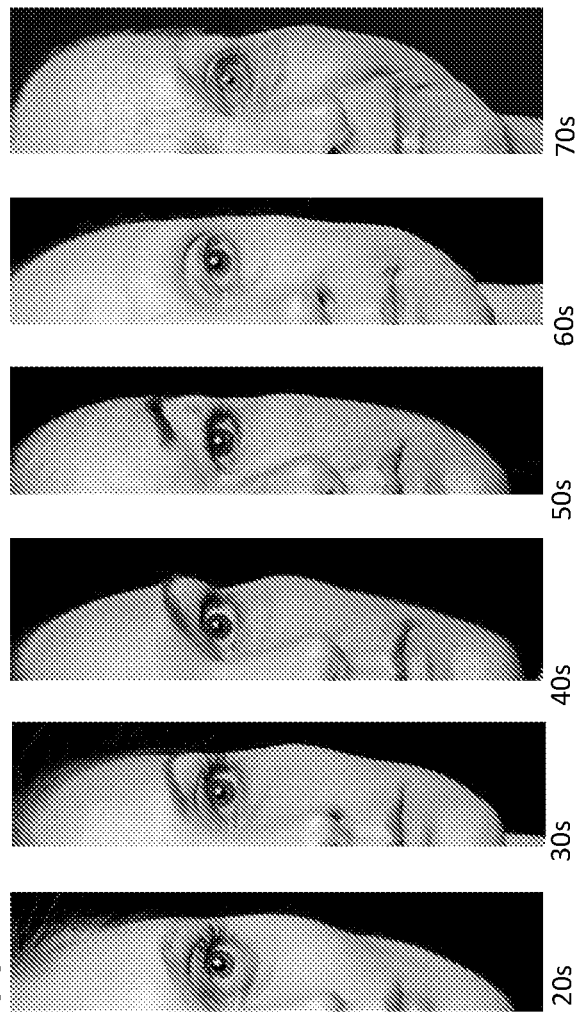
FIG. 136 shows an example of aging sign evolution in non-related female individuals.
Figure 139:
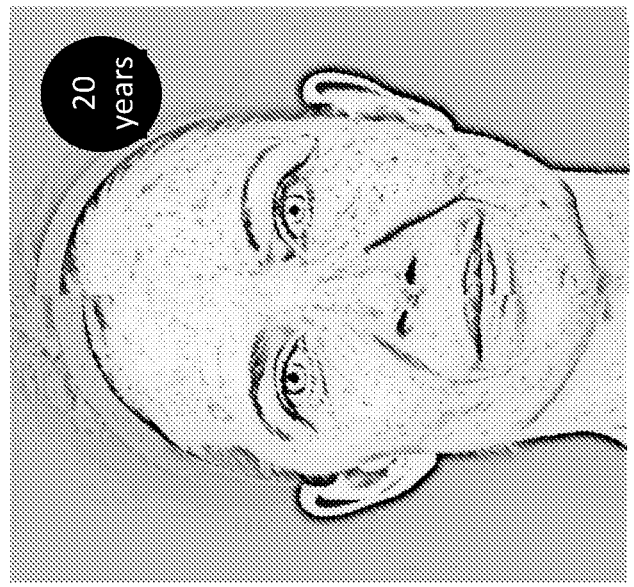
FIG. 139 shows a genetic aging diagram.
Figure 140:
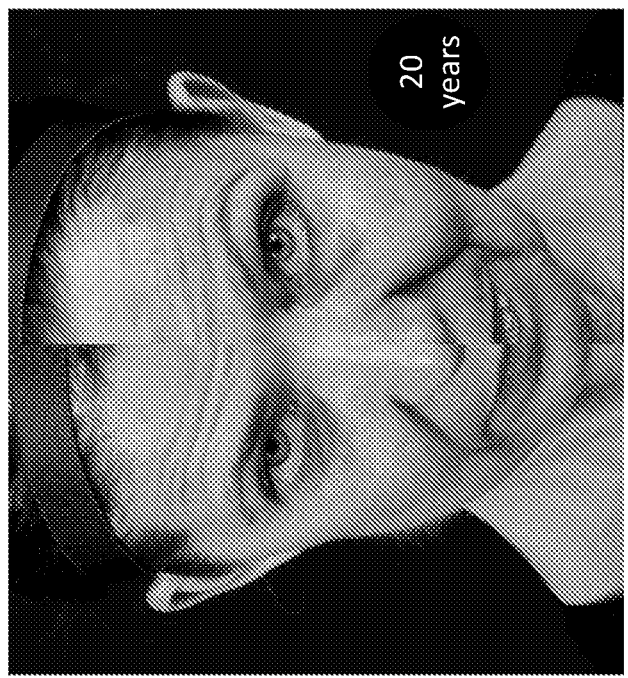
FIG. 140 shows an example of an aging process which is negatively affected by gravity.

In some examples, the methods herein include Step 2: HCP shows the diagram how the aging process evolves and changes according to decades of life (FIGS. 136 and 137). fi In some examples, the methods herein include Step 3: HCP explains genetic aging by showing genetically similar mothers and daughters' assessment in a split face (real patients and/or diagrams) (FIGS. 138 and 139), highlighting the differences in the degree of severity with aging. HCP shows the impact of gravity when the mother and daughter tilt chin down and look up (FIG. 140).

In some examples, the methods herein include Step 4: HCP explains the concept of Active Positive Aging: Patients should be in control of their aging process once they are properly educated and aware of the possible tools (FIG. 140).

Figure 124:
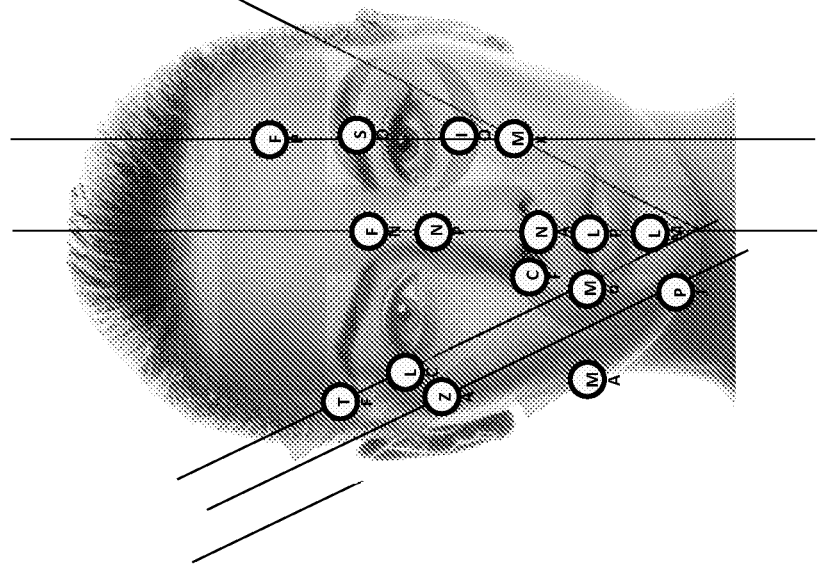
FIG. 124 shows the sixteen (16) SATP: Frontal view.
Figure 125:
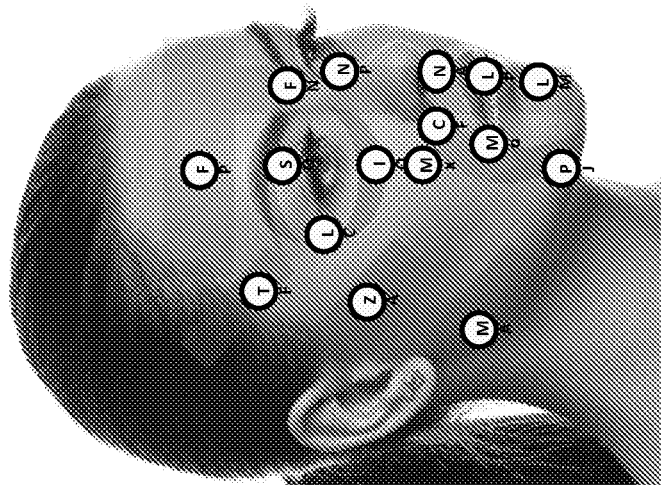
FIG. 125 shows the sixteen (16) SATP: Right oblique view.
Figure 126:
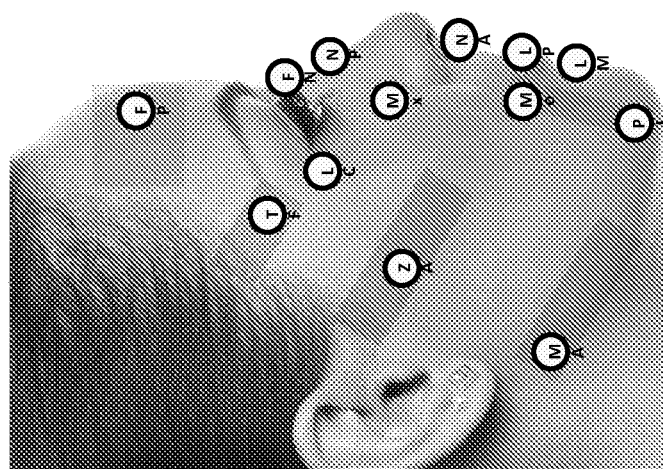
FIG. 126 shows the sixteen (16) SATP: Right profile view.

In some examples, the methods herein include Step 5: Aging Trigger Points. A diagram is shown to describe the location and where injections should be delivered to prevent, correct, and revert ATP (FIGS. 124 and 128).

Figure 148:
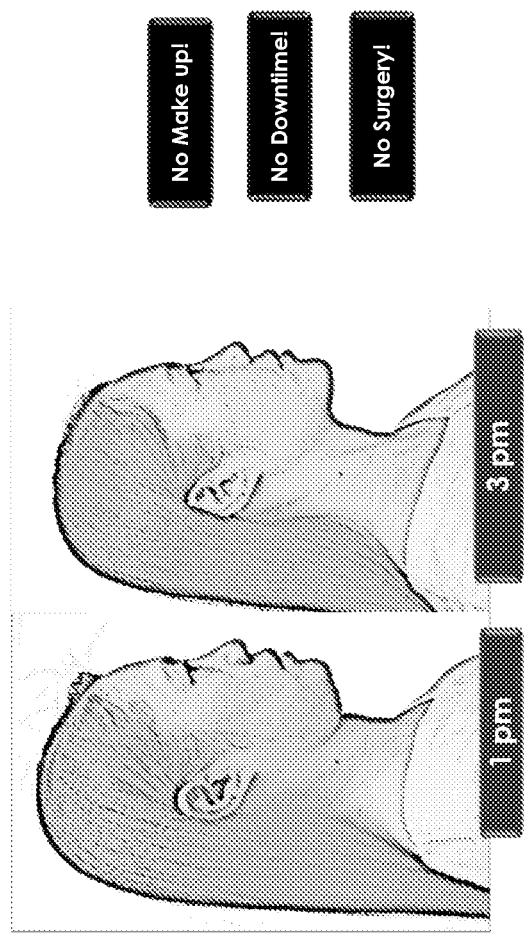
FIG. 148 shows the treatment with ATP described in Example 2.

In some examples, the methods herein include Step 6: HCP shows some pictures (before and after—B&A) of real patients and/or diagrams to clarify the purpose of treatment and what can be achieve. Some potential results are shown in FIGS. 141 and 148.

Figure 149:
FIG. 149 shows the treatment with ATP described in Example 2.
Figure 150:
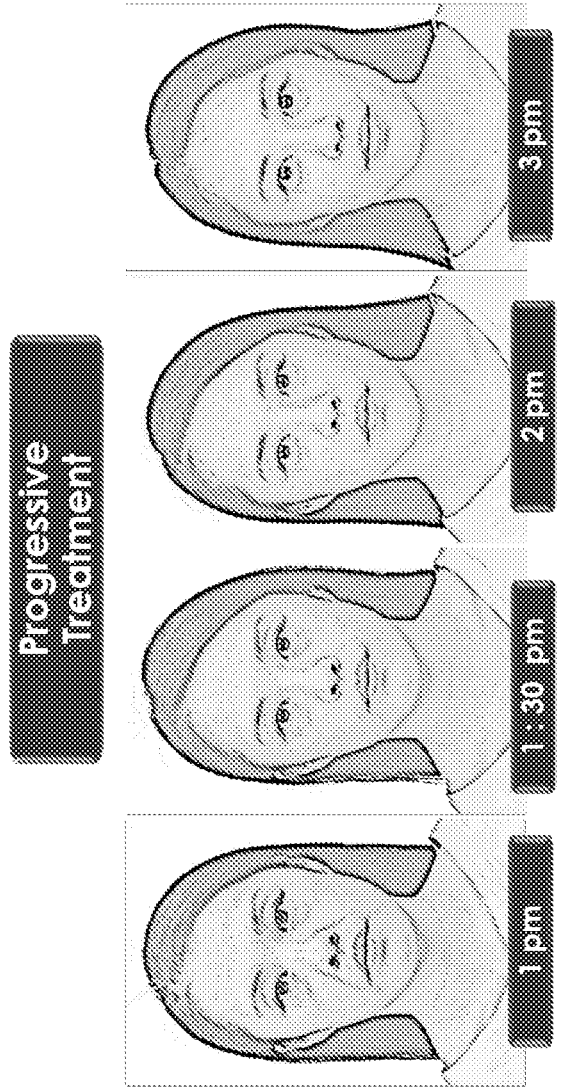

In some examples, the methods herein include Step 7: HCP explains that some patients will require more sessions to achieve the desired outcome. HCP shows some pictures and/or diagrams to demonstrate B&A results (FIGS. 149 and 150).

Figure 133:
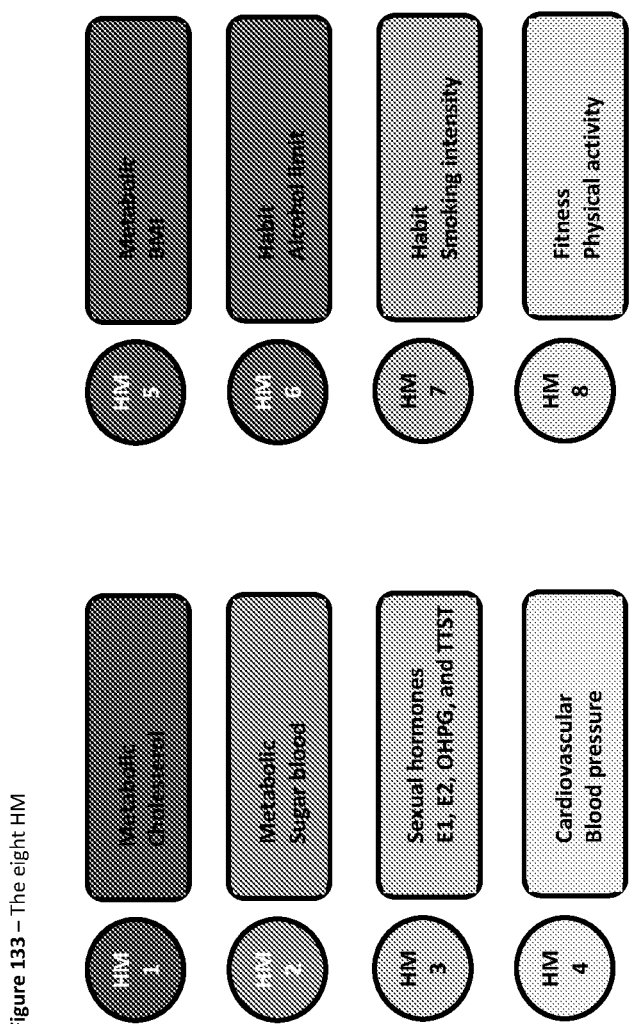
FIG. 133 shows the eight (8) HM.

In some examples, the methods herein include Step 8: HCP introduces the HM diagram and discusses habits and indicates exams (FIG. 133).

Figure 151:
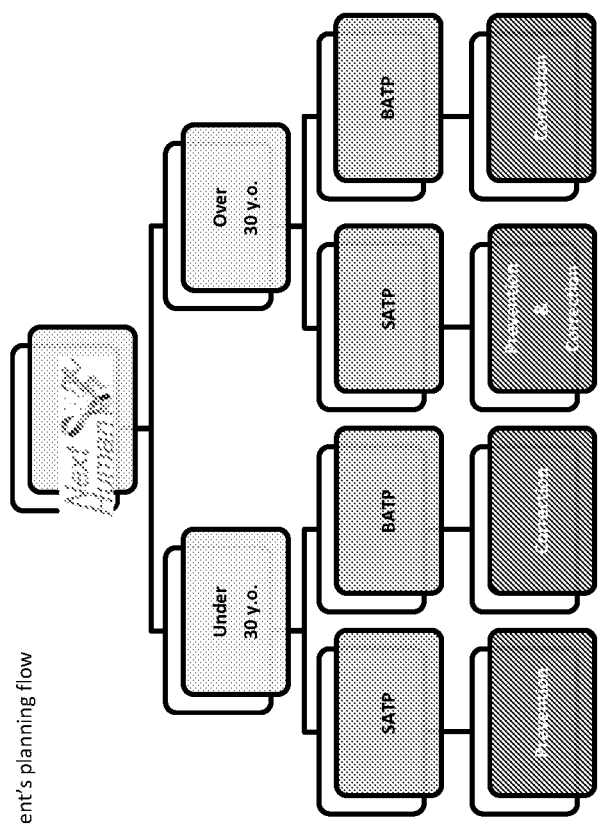
FIG. 151 shows an example treatment plan.

In some examples, the methods herein include Step 9: HCP discusses the aesthetic treatment plan for the patient (FIG. 151) and proceeds identifying and assessing the ATP (SATP and BATP) and their degree of severity.

ATP Assessment

In some examples, set forth herein is a method of treating a patient.

In some examples, a subject is provided. In some of these examples, the subject is a human. In certain examples, the subject is a female. In some other examples, the subject is a male. In some of these examples, the subject is a person between the age of 20 and 30. In some of these examples, the subject is a person between the age of 30 and 40. In some of these examples, the subject is a person between the age of 40 and 50. In some of these examples, the subject is a person between the age of 50 and 60. In some of these examples, the subject is a person between the age of 60 and 70. In some of these examples, the subject is a person between the age of 70 and 80. In some of these examples, the subject is a person between the age of 80 and 30. In some of these examples, the subject is a person between the age of 90 and 100.

In some of these examples, the subject is a male between the age of 20 and 30. In some of these examples, the subject is a male between the age of 30 and 40. In some of these examples, the subject is a male between the age of 40 and 50. In some of these examples, the subject is a male between the age of 50 and 60. In some of these examples, the subject is a male between the age of 60 and 70. In some of these examples, the subject is a male between the age of 70 and 80. In some of these examples, the subject is a male between the age of 80 and 30. In some of these examples, the subject is a male between the age of 90 and 100.

In some of these examples, the subject is a female between the age of 20 and 30. In some of these examples, the subject is a female between the age of 30 and 40. In some of these examples, the subject is a female between the age of 40 and 50. In some of these examples, the subject is a female between the age of 50 and 60. In some of these examples, the subject is a female between the age of 60 and 70. In some of these examples, the subject is a female between the age of 70 and 80. In some of these examples, the subject is a female between the age of 80 and 30. In some of these examples, the subject is a female between the age of 90 and 100.

Figure 152:
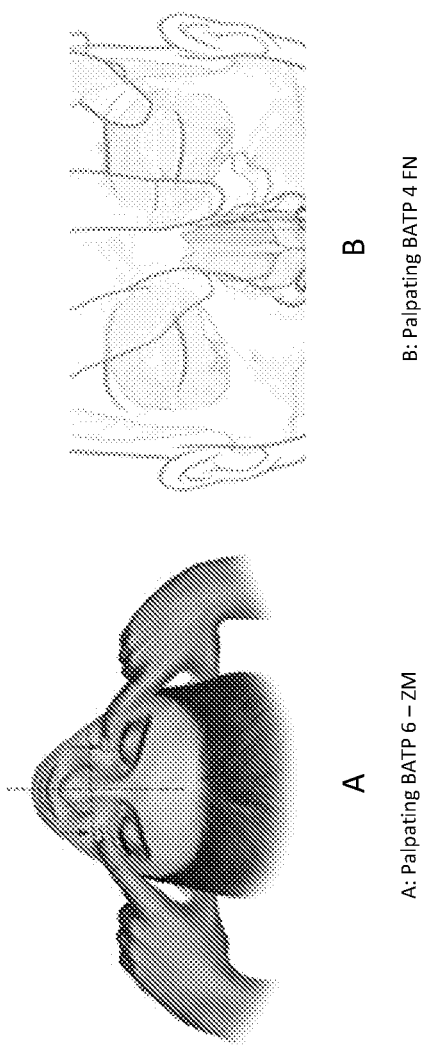
FIG. 152 shows an example method of assessing a subject using palpation.

In some examples, including any of the foregoing, the methods herein include indicators that show if ATP are present on the individual's face. In some of these examples, the SATP are identified through visual assessment in several positions at rest and on animation. In some other of these examples, the BATP are assessed by visual assessment and palpation to verify bone structure and fat pad volume (FIG. 152).

It is noted that fat pads are located superficially and deep to facial muscles. Superficial fat provides volume and mobility to the skin. Deep fat also provides volume to the face, but supplies support and a gliding plane for muscle movement as well. Fat compartments have been identified lying beneath muscles throughout the face, including, for example, the orbicularis oculi and zygomaticus major, the orbicularis *oralis*, and the mentalis. Volume loss, displacement of fat pads, and displacement of fat within fat pads occur in aging, which can alter the action of the overlying muscle. Changes with age differ for different fat pads; some areas increase in volume with age, such as submental and lateral nasolabial fold areas, while age-related volume loss is common in the midface and the periorbital area.

Figure 153:
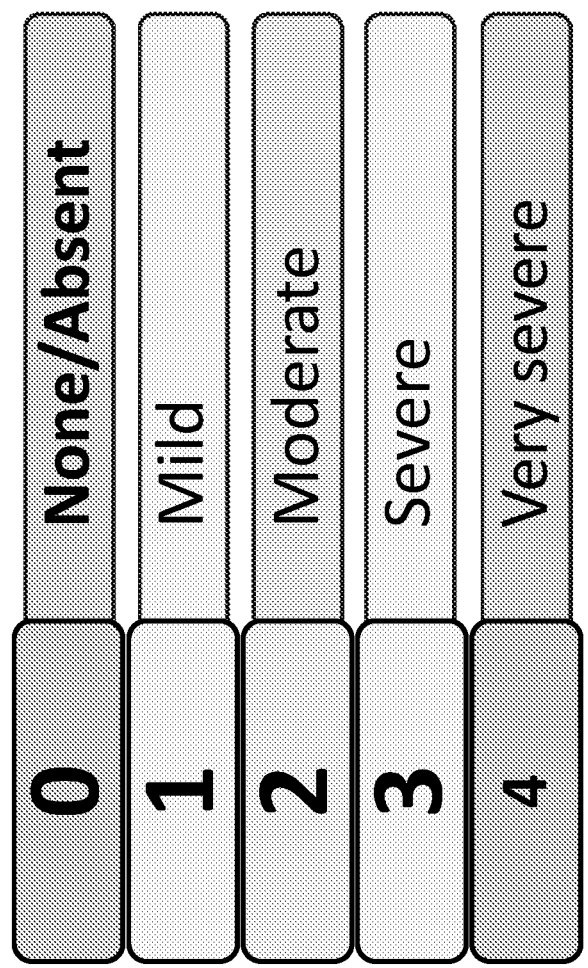
FIG. 153 shows the ATP (SATP and BATP) 5-point scale.

In some examples, including any of the foregoing, the methods herein include assessing the SATP in facial aesthetic units such as forehead, cheeks, lips, among others and neck. The presence of aging signs (lines, folds, saggy skin) are to be assessed and quantified as absent (0), mild (1), moderate (2), severe (3) and very severe (4), varying from 0 up to 4, respectively (FIG. 153).

In some examples, the assessment is made at rest, on animation and tilting down the chin and the eyes looking up. The SATP are rarely present at childhood, however they appear first on animation and tilting down and then at rest. In adulthood, the SATP are worse with tilting down position, on animation and at rest. When a specific SATP is visible at rest and severe in degree at early ages, it denotes bad aesthetic prognosis.

In some examples, including any of the foregoing, the methods herein include assessing the BATP are also assessed in different positions at rest and animation. The frontal view will enable the assessment of proportion and symmetry. The profile view provides the information regarding straight profile (favorable) and challenging convex and concave profiles (unfavorable).

In some examples, including any of the foregoing, the methods herein include identifying the presence of SATP and BATP. In certain examples, the health care provider (HCP) will quantify the degree of severity. There are many validating scales in the literature to assess lines, folds and volume. A 5-point scale is also used to assess the degree of the severity of both ATP, whose range varies between 0 (=none/absent), 1 (=mild), 2 (=moderate), 3 (=severe), and 4 (=very severe).

In some examples, including any of the foregoing, the methods herein include treating the subject to revert aging signs. In some of these examples, the same scale can be used to verify the degree of improvement (FIG. 153).

Figure 154:
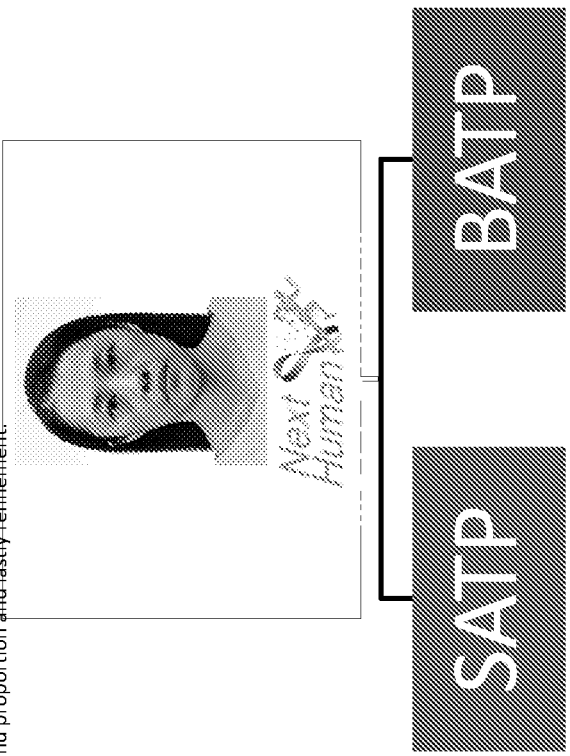
FIGS. 154 and 155 show an example of the NEXT HUMAN follow-up plan.
Figure 155:
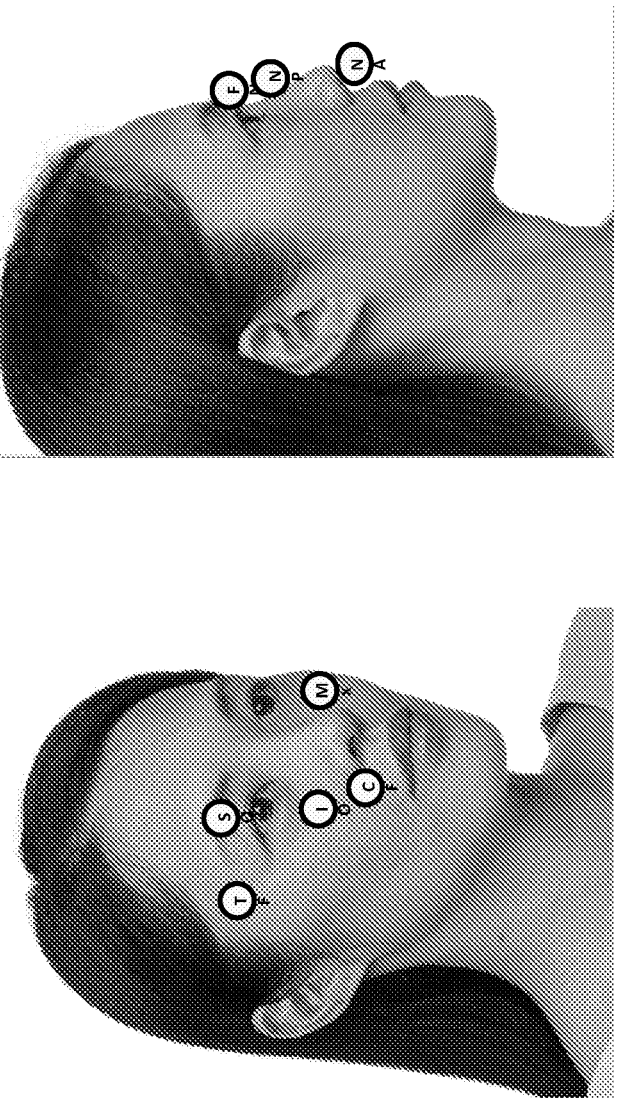

In some examples, including any of the foregoing, the methods herein include assessing the Step 10: Follow up plan to check the improvement based on the five-point scale and address other SATP or BATP (FIGS. 154 and 155).

In some examples, including any of the foregoing, the methods herein include assessing the a continuous follow-up plan based on the methods herein is provided to prevent or revert the aging process.

EXAMPLES

Example 1—General Method of Treatment

A patient is provided. A doctor assesses the patient and determines if the patient possesses certain factors such as those set forth in the figures herein. For example, the patient is assessed as having a small chin.

In view of the small chin assessment, the doctor communicates to the patient that they will eventually get a saggy neck if they do not treat their small chin condition over time.

The doctor then decides that the patient should be injected with hyaluronic acid (HA) at MD ASA sites described be the figures herein.

Example 2—Specific Method of Treatment

Figure 142:
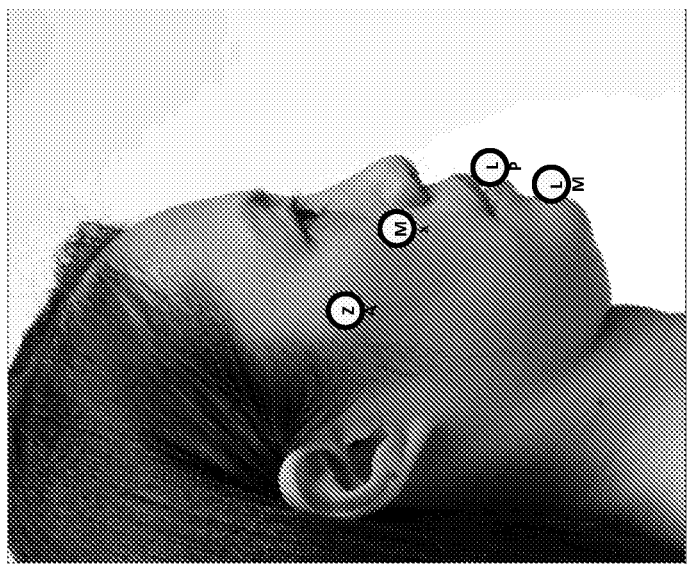
FIG. 142 shows SATP locations suitable for use herein: Profile view.
Figure 144:
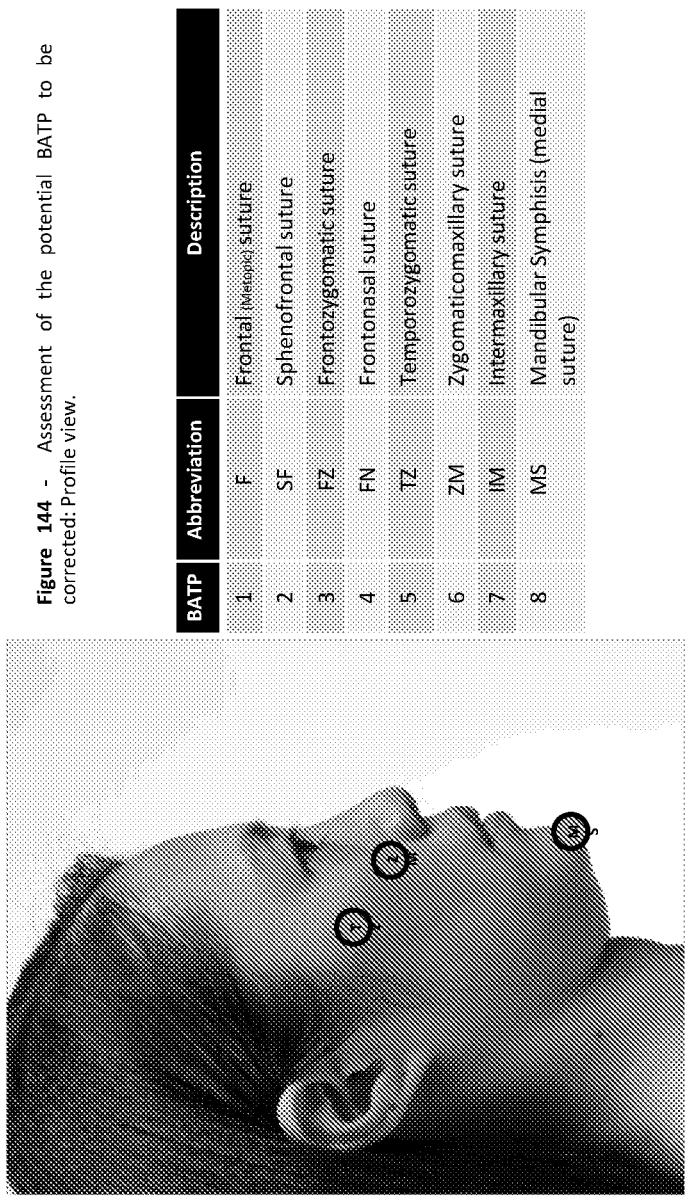
FIG. 144 shows BATP locations suitable for use herein: Profile view.

A patient was provided. See FIG. 141. The patient was assessed as having depressions and/or volume lost condition at sites ZA, IO, Mx, CF, LP, and LM as shown in FIG. 141. The patient was assessed as having a condition at sites ZA, Mx, LP, and LM as shown in FIG. 142. The patient was assessed as having a condition at sites TZ, ZM, and MS as shown in FIG. 143. The patient was assessed as having a condition at sites TZ, ZM, and MS as shown in FIG. 144.

Figure 146:
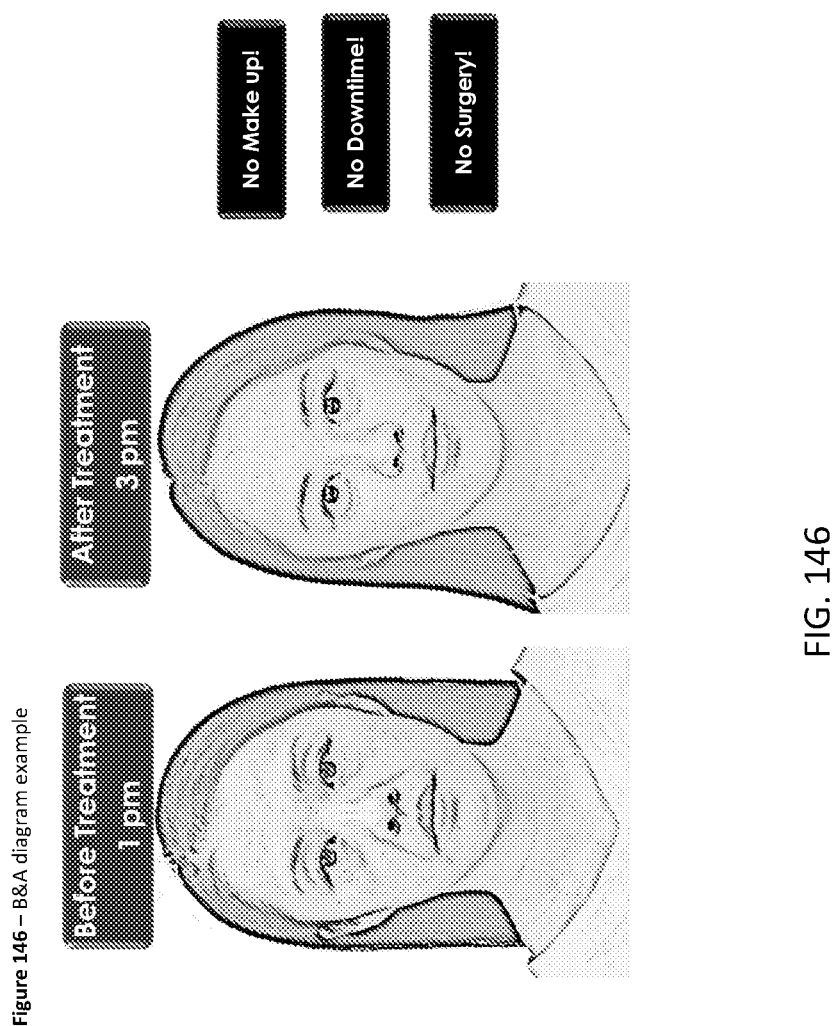
FIG. 146 shows before and after images of a subject treated with a Hyaluronic acid-based injectable. The details are discussed in Example 2.

The results of this treatment are shown in FIG. 145.
The results of this treatment are also shown in FIG. 146.
The results of this treatment are shown in FIG. 147.
The results of this treatment are shown in FIG. 148.
The results of this treatment are shown in FIG. 149.
The results of this treatment are shown in FIG. 150.

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

Embodiment 1, a method of treating a subject in need thereof
providing a map of risk factors;
identifying the risk factors present in a subject in need thereof;
treating the subject in need thereof by injecting a pharmaceutical composition comprising a member selected from the group consisting of hyaluronic acid (HA), Botox, fillers, and combinations thereof.

Embodiment 2, the method of embodiment 1, wherein the risk factors comprise intrinsic factors selected from the group consisting of genetic factors.

Embodiment 3, the method of embodiment 1, wherein the risk factors comprise extrinsic factors selected from the group consisting of environmental factors.

Embodiment 4, the method of embodiment 3, wherein the risk factors comprise family health history.

Embodiment 5, the method of embodiment 3, wherein the risk factors comprise family aesthetic history.

Embodiment 6, the method of any one of embodiments 1-5, wherein the sites are on the neck or face.

Embodiment 7, the method of any one of embodiments 1-6, wherein the subject is in need of aesthetic treatment.

Embodiment 8, the method of embodiment 1, wherein identifying the risk factors comprises overlaying a picture of the subject in need thereof with a picture of the subject's parent of the same gender.

Embodiment 9, the method of embodiment 1, wherein identifying the risk factors comprises overlaying a picture of the subject in need thereof with a picture of the subject's child of the same gender.

Embodiment 10, the method of any one of embodiments 1-9, wherein the method further comprises injecting a pharmaceutical composition comprising a member selected from the group consisting of hyaluronic acid (HA), Botox, fillers, and combinations thereof; and repeating the injecting continually every year or 2 years.

Embodiment 11, the method of any one of embodiments 1-10, wherein the subject in need thereof has an aging condition or disorder.

Embodiment 12, the method of any one of embodiments 1-11, wherein the pharmaceutical composition comprises a member selected from the group consisting of Botulinum Toxin—Type A (Botox), collagen, hyaluronic acid, antibiotics, anti-inflammatory drugs, steroids and combinations thereof.

Embodiment 13, the method of embodiment 12, wherein the pharmaceutical composition is Botulinum Toxin—Type A.

Embodiment 14, the method of embodiment 12, wherein the pharmaceutical composition is a long-chain Hyaluronic Acid (HA) product.

Embodiment 15, the method of embodiment 12, wherein the pharmaceutical composition comprises HA.

Embodiment 16, the method of embodiment 12, wherein the pharmaceutical composition is deoxycholic acid.

Embodiment 17, the method of any one of embodiments 1-16, wherein the injection sites are substantially as set forth in any one of FIGS. 124-126, 128-130, 141-144, and 155.

Embodiment 18, the method of any one of embodiments 1-17, wherein the injection sites are as set forth in any one of FIGS. 124-126, 128-130, 141-144, and 155.

Embodiment 19, the method of any one of embodiments 1-18, comprising visualizing the injection sites.

Embodiment 20, the method of any one of embodiments 1-19, comprising visualizing the injection sites on a computer screen.

Embodiment 21, the method of any one of embodiments 1-20, wherein the visualizing comprises overlaying any of the injection sites set forth herein with an image of the subject.

Embodiment 22, the method of any one of embodiments 1-21, wherein the subject in need thereof suffers from an aesthetic condition.

Embodiment 23, the method of any one of embodiments 1-22, wherein the subject in need thereof suffers from a dermatology condition.

Embodiment 24, the method of any one of embodiments 1-23, wherein the method comprising injecting at least 0.5 mL of the therapeutically effective amount of the pharmaceutical composition.

Embodiment 25, the method of any one of embodiments 1-24, wherein the method comprising injecting the therapeutically effective amount of the pharmaceutical composition at a depth of penetration of at least 2-6 mm or at the level at the bone.

Embodiment 26, the method of any one of embodiments 1-25, wherein pharmaceutical composition is a cellular body.

Embodiment 27, a system for practicing the method of any one of embodiments 1-27.

Embodiment 28, an injector designed for practicing the method of any one of claims 1-27.

MD Codes, MD DYNA Codes, MD ASA

As used herein, the term "MD codes" refers to the codes presented by MD Codes™ The MD Codes™ are the structural codes. They are designed to raise awareness that each aesthetic facial unit (e.g., cheek, chin, lips) comprises subunits that must be respected during injection. These subunits—the MD Codes™—are the structural sites that aim to create or recreate the most desirable facial architecture for patients. The MD codes have the following features: they are the structural codes; they build the foundation by creating facial structure, and they are for facial enhancement at rest.

As used herein, the term "MD DYNA codes" refers to the codes presented by MD DYNA Codes™. The MD DYNA Codes™ are the dynamic codes. They are injection techniques for the precise placement of product of muscle activity, designed to deliver natural facial expression and avoid or correct an abnormal facial appearance on animation. They have the following features: they are dynamic codes; they optimise expression by modulating muscle function; and they are for facial enhancement on animation.

As used herein, the term "MD ASA" refers to the codes represented by MD ASA™ (Multi-Dimensional Aesthetic Scan Assessment) is a facial assessment tool. It introduces a system of aesthetic hierarchy to organise the patient assessment process and train the brain to decipher complex and unveiled signs of the face. MD ASA™ can be administered when the face is at rest and on animation. MD ASA is a system for facial assessment. It trains the brain to decipher complex facial messages. It is used for assessment at rest and on animation.

The above three clinical tools can be used individually or together. A sophisticated approach to facial aesthetics starts with proper assessment and diagnosis. For this MD ASA™ can be applied at rest and on animation. When the face is at rest, MD ASA™ can help to identify the emotional attributes and determine the required structural improvements (the MD Codes™) to enhance overall facial appearance. When the face is animated, MD ASA™ is applied to assess muscle function and determine the proper technique and precise placement of product to optimise facial expression (the MD DYNA Codes™). The above three systems provide refined approach to treatment and provide clear and friendly guidelines for the use of injectables in medical aesthetics.

MD Codes™

The face can be split into separate anatomical units (e.g., eyebrows, cheeks, lips, etc.). The MD Codes™ are a series of precise sites (or subunits) within each unit that are designed to guide injection. They are based on the principle that facial units have to be rebuilt, or treated, in an architectural mode.

Each injection site is represented by a combination of letters and numbers. The letter represents the anatomical unit. The number indicates the subunit and the sequence in which the injections may potentially be delivered. The most important injection site in a particular area is represented by the number 1 and this should usually be the starting point. Injection site 3 is typically an alert zone, and care should be taken in these areas. Every patient will have a specific sequence and may not need all of the MD Codes™ in the anatomical unit—each patient should be assessed and treated individually.

Besides letters and numbers, the injection sites are also coloured and represented by different shapes. The colour red represents an 'alert zone', indicating that the injector should be aware of and avoid important anatomical structures in the area, such as neurovascular bundles. Shapes are used to indicate technical delivery: a triangle indicates fanning; a circle indicates a bolus; and a rectangle indicates linear injection.

SUMMARY

Each code can be depicted with a combination of the following:

Letters: The anatomical area (e.g., Ck=cheeks)
Numbers: The subunits of the anatomical unit (e.g., Ck1=zygomatic arch; Ck2=zygomatic eminence)
Number location: The side of the face (e.g., Ck1r is the zygomatic arch on the right-hand side; Ck1l is the zygomatic arch on the left-hand side)
Number position: Superscript ($X^n$) refers to upper areas (e.g., $Lp^1$=vermillion body of the upper lip); Subscript ($X_n$) refers to lower areas (e.g., $Lp_1$=vermillion body of the lower lip)
Colours: Alert areas denoted in red
Shapes: Technical delivery of the product.
The MD codes are listed below.

| The MD Codes ™ | |
|---|---|
| The 8-point lift, L codes | The 5-point cheek re-shape, Ck codes |
| L1, L2, L3, L4, L5, L6, L7, L8 | Ck1, Ck2, Ck3, Ck4, Ck5 |
| The 3-point forehead reshape, F codes | The 3-point nasolabial reshape, NL codes |
| F1, F2, F3 | NL1, NL2, Nl3 |
| The 2-point temple reshape, T codes | The 8-point lip reshape, Lp codes |
| T1, T2 | Lp1, Lp2, Lp3, Lp4, Lp5, Lp6, Lp7, Lp8 |
| The 3-point eyebrow reshape, E codes | The 3-point marionette lines reshape, M codes |
| E1, E2, E3 | M1, M2, M3 |
| The 2-point glabellar reshape, G codes | The 6-point chin reshape, C codes |
| G1, G2 | C1, C2, C3, C4, C5, C6 |
| The 3-ppint lateral periorbital reshape, O codes | The 5-point jawline reshape, Jw codes |
| O1, O2, O3 | Jw1, Jw2, Jw3, Jw4, Jw5 |
| The 3-point tear trough reshape, Tt codes | The 5-point nose reshape, N codes |
| Tt1, Tt2, Tt3 | N1, N2, N3, N4, N5 |

The codes and the injections corresponding to the codes are described below. The corresponding injection area, product, volume, volume range, injection technique, injection device, targeted structure, and alert area are described.

MD Codes™—L codes, the 8-point lift, L1, L2, L3, L4, L5, L6, L7, L8.

Injection—L1. L1 is the first point of the 8-point lift. The injection site of the L1 is the zygomaticotemporal suture. Injection in L1 is recommended with needle, small bolus technique, 0.1 to 0.5 ml of HA 20 mg/ml, into the bone level. This technique supports the cheek, and therefore, treats sagginess, hollowness of infraorbital area and tear trough. It also gives support to the eyebrow and lower eyelid and improves prominent nasolabial fold, oral commissure and marionette lines. L1 is recommended as the starting point of any treatment. Be wary of the Zygomaticofacial artery. If one bolus is insufficient, injection in L1 can also be delivered in 3 small boluses technique, 0.1 ml each, with needle, into the bone level. This technique improves cheek support and give more lifting effect.

Injection—L2. L2 is the second point of the 8-point lift. The injection site of the L2 is the zygomatic eminence. Alert Area is Zygomaticofacial artery. Aspiration is highly recommended when injecting with needle. Injection in L2 is recommended with needle, bolus technique, 0.2 to 0.4 ml of HA 20 mg/ml, into the bone level. The injection described above is per side. This technique will provide projection of the cheek, shortening of palpebrar-malar sulcus, improvement of eye shape and nasolabial fold.

Injection—L3. L3 is the third point of the 8-point lift. The injection site of the L3 is in the anteromedial cheek. It improves the medial lid-cheek junction and softens the tear trough. Alert Area is infraorbital foramen. Injection in L3 can be delivered in different layers. The layers to be considered include bone, the deep malar fat pad and the medial SOOF—sub orbicularis oculi fat. Needles should be used when bone structure is needed and it must be delivered laterally to the mid pupillary line, small bolus technique with 0.3 to 0.5 ml into the bone. The treatment of the medial SOOF should be performed with blunt cannulas, to restore the deep malar fat pad, especially over the projection of the infraorbital foramen, 0.2 to 1.0 ml, fanning technique into the fat pad. The product selection in L3, HA 20 mg/ml or HA 17.5 mg/ml, will depend on the degree of retrusion in the L3 area which should be assessed in the profile view. If the cheek covers the nasal flare, HA 17.5 mg/ml is recommended to give support to the lower eyelid. Also, ask the patient to smile. If there is excessive projection of the L3 area (the ping pong ball), HA 17.5 mg/ml is preferable. HA 20 mg/ml should be used when L3 area presents a significant concavity, even when smiling.

Injection—L4. L4 is the fourth point of the 8-point lift. It is located at the nasolabial fold. Inject L4 with HA 17.5 mg/ml, 0.1 to 0.5 ml with a cannula or needle, linear technique into the dermal level. *Injections with needles at the subcutaneous level present high risk of complication such as necrosis if facial artery is hit. In case of bone retrusion, HA 20 mg/ml can be used. A small bolus of 0.1 to 0.3 ml should be delivered with needle into the bone level. Aspiration is mandatory. Be wary of the facial artery. Injecting slightly medial to the nasolabial crease is highly recommended. In Asian patients the facial artery may lie in the nasolabial fold.

Injection—L5. L5 is the fifth point and is located at the marionette lines. Inject L5 with HA 17.5 mg/ml, 0.1 to 0.5 ml, linear technique with needle or cannula into sub dermal level. Be wary of the facial artery.

Injection—L6. L6 is the sixth point of the 8-point lift. The injection site of the L6 is the pre jowl sulcus. Inject L6 with HA 20 mg/ml, 0.5 to 1.0 ml, using fanning or linear technique, with cannula into the fat pad. L6 can also be injected using small bolus technique with needle. L6 reduces the prominence of the prejowl sulcus.

Injection—L7. L7 is the first point of the jawline. The injection site of the L7 is in the mandibular angle. Inject L7 with HA 20 mg/ml, 0.5 to 1.0 ml, using small bolus or fanning technique with needle into the fat pad for lifting effect (indicated for females.) L7 with HA 20 mg/ml, 0.5 to 1.0 ml, using small bolus with needle into the bone for widening the jaw line (usually recommended for man). L7 can also be injected with cannula, 0.5 to 1.0 ml, into the fat pad.

Injection—L8. L8 is the eighth point of the 8-point-lift. L8 is located in parotid and submalar region. The injection addresses the sunken area at the parotid level, preauricular volume loss and lifts the jawline. Alert Area: Parotid gland, buccal nerve and facial vein and artery. In large areas the use of a cannula is preferable. Inject L8 with a needle in small areas or a cannula for larger ones, fanning technique, 0.5 to 1.0 ml, into the subcutaneous layer. Pinch the skin first, if the skin is movable HA 20 mg/ml is recommended, if the skin is not easily movable and attached to deep planes, HA 17.5 mg/ml should be used.

MD Codes™—F codes, Forehead F1, F2, F3.

Injection—F1. F1 is the first point of the forehead, located in the medial forehead. When line treatment is required, inject HA 15 mg/ml, 0.1 to 0.3 ml, micro-aliquot with needle, into dermal level. When contour treatment is required, inject 0.1 to 0.5 ml of HA 17.5 mg/ml with cannula, fanning technique, into the bone level. Or small bolus technique with needle into the bone level, massage is mandatory. Be wary of the supraorbital artery.

Injection—F2. F2 is the second point of the forehead, located in the lateral forehead. When line treatment is required, inject HA 15 mg/ml, 0.1 to 0.3 ml, micro-aliquot with needle, into dermal level. When contour treatment is required, inject 0.1 to 0.5 ml of HA 17.5 mg/ml with cannula, fanning technique, into the bone level. Or small bolus technique with needle into the bone level, massage is mandatory. Be wary of the superficial temporal artery.

Injection—F3. F3 is the third point of the forehead, located in the central forehead. When line treatment is required, inject HA 15 mg/ml, 0.1 to 0.3 ml, micro-aliquot with needle, into dermal level. When contour treatment is required, inject 0.1 to 0.5 ml of HA 17.5 mg/ml with cannula, fanning technique, into the bone level. Or small bolus technique with needle into the bone level, massage is mandatory. Be wary of the supratrochlear artery. The injection described above is in midline.

MD Codes™—T codes, Temple T1, T2.

Injection—T1. T1 is the first point of the temple. It is located in the anterior temple. T1 should be injected with HA 20 mg/ml from 0.5 to 1.0 ml for visible results. Anterior temple should be addressed performing small bolus technique with needle into the bone level. Be wary of the frontal artery, superficial temporal artery and deep temporal arteries. When injected, patients may feel bearable pain in maxilla.

Injection—T2. T2 is the second point. It is located in the posterior temple. T2 is indicated with HA 20 mg/ml from 0.5 to 2.0 ml, small bolus technique with needle into the bone level. Alert Zone: Superficial temporal artery and deep temporal arteries.

MD Codes™—E codes, Eyebrow E, E1, E2, E3.

Injection—E1+E2+E3. E1 is the first point, it is the tail of the eyebrow. Inject in the eyebrow codes are recommended with HA 15 mg/ml, 0.1 to 0.4 ml, micro-aliquot technique with cannula, into the fat pad (ROOF). E1 can be injected alone, with needle, into the bone level. E2 is located in the center eyebrow. Inject in the eyebrow codes are recommended with HA 15 mg/ml, 0.1 to 0.3 ml, linear technique. With cannula, into the fat pad (ROOF). E3 is the head eyebrow. Inject in the eyebrow codes are recommended with HA 15 mg/ml, 0.1 to 0.3 ml, linear technique with cannula, into the fat pad (ROOF). Inject slowly and protect the upper eyelid with your finger. Be wary of the supraorbital and supratrochlear foramens.

MD Codes™ G codes, *Glabella* G, G1, G2.

Injection—G1+G2. G1 is used for the treatment of static glabela lines. Injections must be very superficial with needles in micro-aliquots. G2 is for *glabella* reshape and must be addressed with cannulas at the supraperiosteal level. Be wary of the supratrochlear artery. Injection to G1 is per side. Injection to G2 is in midline.

MD Codes™—O codes, Lateral periorbital O1, O2, O3.

Injection—O1+O2+O3. O1 is located in the central lateral periorbital area. Inject with HA 15 mg/ml, 0.2 to 0.5 ml, micro aliquot technique with cannula into the submuscular compartment. O2 is in the lower lateral periorbital area. Inject with HA 15 mg/ml, 0.2 to 0.5 ml, micro aliquot technique with cannula into the submuscular compartment. O3 is the upper lateral periorbital area. Inject with HA 15 mg/ml, 0.1 to 0.5 ml, micro aliquot technique with cannula into the submuscular compartment. Orbital codes improve the appearance of lines and volume loss in the lateral periorbital area. Be wary injecting into the lower and upper eyelid. If lines are to be directly addressed, the use of needles into deep dermal level is advisable.

MD Codes™—Tt codes, Tear trough Tt1, Tt2, Tt3.

Injection—Tt1. Tt1 is the first point of the tear trough, located in the central infraorbital area. The use of cannula into the fat pad is preferable to reduce bleeding and risk of intravascular injury. Always use your finger to control where the tip of the cannula is and protect the eye globe, vessels or any other dangerous structure. Inject 0.1 to 0.4 ml of HA 15 mg/ml with cannula or needle into bone level, using micro-aliquot technique. In this code we must be wary of the infraorbital artery.

Injection—Tt2. Tt2 is the second point, located in the lateral infraorbital area, or, the palpebral malar sulcus. Be wary of the eye globe. Inject with HA 15 mg/ml, 0.1 to 0.3 ml with cannula or needle into bone level, using micro-aliquot technique. Alert Zone: Eye globe.

Injection—Tt3. Tt3 is the third point, its injection site is the medial infraorbital. Inject with HA 15 mg/ml, 0.1 to 0.3 ml with cannula or needle into bone level, using micro-aliquot. Be wary of the angular artery.

MD Codes™—Ck codes, Cheek, Ck1, Ck2, Ck3, Ck4, Ck5.

Injection—Ck1-3 points. Ck1 is the first point of the cheek. The injection site of the Ck1 is the zygomaticotemporal suture. The zygomatic arch, or cheek bone, is formed by the zygomatic process of temporal bone and the temporal process of the zygomatic bone. Injection in Ck1 is recommended with needle, small bolus technique, 0.1 to 0.5 ml of HA 20 mg/ml, into the bone level. This technique supports the cheek, and therefore, treats sagginess, hollowness of infraorbital area and tear trough. It also gives support to the eyebrow and lower eyelid and improves prominent nasolabial fold, oral commissure and marionette lines. Ck1 is recommended as the starting point of any treatment. Be wary of the Zygomaticofacial artery. If one bolus is insufficient, injection in Ck1 can also be delivered in 3 small boluses technique, 0.1 ml each, with needle, into the bone level. This technique improves cheek support and give more lifting effect.*

Injection—Ck1—Top Model Look. After injecting with needle, one may also consider the "top model look" delivered with cannula, linear technique, 0.5 to 1.0 ml of HA 20 mg/ml, into the fat pad, to create structure along the zygomatic arch. This technique achieves a more sophisticated look. Be wary of the Zygomaticofacial artery.

Injection—Ck2. Ck2 is the second point of the cheek. The injection site of the Ck2 is the zygomatic eminence. The zygomatic is a diamond shaped bone that forms the anterior and lateral projection to the mid face. Alert Area: Zygomaticofacial artery. Aspiration highly recommended when injecting with needle. Injection in Ck2 is recommended with needle, small bolus technique, 0.1 to 0.4 ml of HA 20 mg/ml, into the bone level. This technique will provide projection of the cheek, shortening of palpebrar-malar sulcus, improvement of eye shape and nasolabial fold.

Injection—Ck3—Needle. Ck3 is the third point of the cheek. The injection site of the Ck3 is in the anteromedial cheek. Alert Area: Infraorbital foramen. Ck3 injection improves the medial lid-cheek junction and softens the tear trough. Injection in Ck3 can be delivered in different layers. The layers to be considered include bone, the deep malar fat pad and the medial SOOF—sub orbicularis oculi fat. Needles should be used when bone structure is needed and it must be delivered laterally to the mid pupillary line, small bolus technique 0.2 to 0.5 ml into the bone. HA 20 mg/ml should be used.

Injection—Ck3—Cannula. In Ck3, the treatment of the medial SOOF should be performed with blunt cannulas, to restore the deep malar fat pad, especially over the projection of the infraorbital foramen, 0.5 to 1.0 ml, fanning technique into the fat pad. The product selection in Ck3, HA 20 mg/ml or HA 17.5 mg/ml, will depend on the degree of retrusion in the Ck3 area which should be assessed in the profile view. If the cheek covers the nasal flare, HA 17.5 mg/ml is recommended to give support to the lower eyelid. Also, ask the patient to smile. If there is excessive projection of the Ck3 area (the ping pong ball), HA 17.5 mg/ml is preferable. HA 20 mg/ml should be used when Ck3 area presents a significant concavity, even when smiling. Alert Area: Infraorbital foramen.

Injection—Ck4. Ck4 is the fourth point of the cheek. Ck4 is located in submalar region, under the zygomatic arch, in the lateral lower cheek, parotid area. The Ck4 injection addresses the sunken area at the parotid level, preauricular volume loss and lifts the jawline. The temporal-cheek fat is the most lateral compartment of the cheek. This fat lies in direct contact with the parotid gland and connects the temporal fat to the cervical subcutaneous fat. Alert Area: Parotid gland. In large areas the use of a cannula is preferable. Inject Ck4 with a needle in small areas or a cannula for larger ones, fanning technique, 0.5 to 1.5 ml, into the subcutaneous layer. Pinch the skin first, if the skin is movable HA 20 mg/ml is recommended, if the skin is not easily movable and attached to deep planes, HA 17.5 mg/ml should be used.

Injection—Ck5. Ck5 is the fifth point of the cheek. The location of the Ck5 is the submalar area. It is an inverted triangular area of midfacial depression and is limited superiorly by the prominence of the zygoma, medially by the nasolabial fold, and laterally by the body of the masseter muscle. Alert Area: Be aware of the location of facial artery and buccal nerve. Inject Ck5 preferably with a cannula, fanning technique, 0.5 to 1.0 ml, into subcutaneous layer. HA 20 mg/ml should be used when there is too much volume loss in the sunken area of Ck5. Otherwise, HA 17.5 mg/ml is recommended. Intraoral massage is advisable after injecting Ck5.

MD Code-NL codes, Nasolabial fold NL1, NL2, NL3.

Injection—NL1 (Needle). The injection site of NL1 is the upper part of the nasolabial fold. In case of bone retrusion, HA 17.5 mg/ml can be used. A small bolus of 0.1 to 0.3 ml should be delivered with needle into the bone level. Aspiration is mandatory. Be wary of the facial artery. Injecting slightly medial to the nasolabial crease is highly recommended. In Asian patients the facial artery may lie in the nasolabial fold.

Injection—NL1+NL2+NL3. Cannula: Severe nasolabial folds should be addressed with subcutaneous approach and injections should be delivered with cannulas using HA 17.5 mg/ml. Inject NL1 with HA 17.5 mg/ml, 0.2 to 0.5 ml with a cannula lineartechnique into the subcutaneous. NL2 is the central nasolabial fold. Inject NL2 with HA 17.5 mg/ml, 0.2 to 0.4 ml linear technique with needle into sub dermal level and cannula into the subcutaneous. Needle: NL3 the lower nasolabial fold. Inject NL3 with HA 17.5 mg/ml, 0.1 to 0.2 ml, linear technique, with needle into sub dermal level. Alert Area: Facial Artery. Injections with needles at the subcutaneous level present high risk of complication such as necrosis if facial artery is hit.

MD Codes™—Lp codes, Lips, Lp1, Lp2, Lp3, Lp4, Lp5, Lp6, Lp7, Lp8.

Injection—Lp1. Lp1 is the first point of the lip. The injection site of the Lp1 is the upper and lower vermillion body. Lp1 superscript is the vermillion body of the upper lip and Lp1 subscript is in the lower lip. Lp1 is injected with HA 17.5 mg/ml into the vermillion body, at the mucosa or submucosa level, 0.05 to 0.25 ml per quadrant, with linear anterograde technique, with cannula, to promote lip augmentation and avoid vascular injury. If needle is to be chosen, HA 17.5 mg/ml should be delivered in aliquots of 0.05-0.25 ml per point into the vermillion body, more superficially. Lp1 promotes lip augmentation and projection. Massage is advisable to reduce irregularities. Be wary of the labial arteries.

Injection—Lp2. Lp2 is the second point of the lip. The injection site of the Lp2 is the cupid's bow. Inject Lp2 with HA 17.5 mg/ml, 0.02 to 0.1 ml, retrograde linear technique, with a needle into the mucosa. Gives structure to the cupid's bow area.

Injection—Lp3. Lp3 is the third point of the lip. The injection site of the Lp3 is the lip border. Lp3 superscript refers to upper lip and subscript to the lower lip. Lp3 is injected with HA 17.5 mg/ml, linear technique, into the mucosa. Inject 0.05 to 0.3 ml per quadrant with retrograde linear technique, with needle into the mucosa for more precise contouring. Lp3 gives structure to the white line/lip border. Indirectly decreases perioral lines.

Injection—Lp4. Lp4 is the fourth point of the lip. The injection site of the Lp4 is the medial tubercle of the upper lip. Lp4 is injected with HA 17.5 mg/ml, 0.05 to 0.1 ml, small bolus technique into the mucosa. Needle is recommended for precise injection. The entry points may either be from the mucosa or skin. Cannula can be used when the entry point is lateral and when the treatment of Lp1 is being performed. Lp4 provides projection or fullness of the medial tubercle of the upper lip. Be wary of the superior labial artery when injecting with needles.

Injection—Lp5. Lp5 is the fifth point of the lip. The injection site of the Lp5 are the lateral tubercles of the lower lip. Lp5 is injected with HA 17.5 mg/ml, 0.05 to 0.1 ml, small bolus technique into the mucosa. Needle is recommended for precise injection. The entry point is usually through the skin. Cannula can be used when the entry point is lateral and when the treatment of Lp1 is being performed. Provides projection or fullness of the lateral tubercles of the lower lip. Be wary of the inferior labial artery when injecting with needles.

Injection—Lp6. Lp6 is the sixth point of the lip. The injection site of the Lp6 is the oral commissure. Inject Lp6 with HA 17.5 mg/ml, 0.05 to 0.15 ml, linear or fanning technique with a cannula (deep plane), or linear with needle (superficial plane) into the mucosa. Lp6 lifts and corrects the downturn of the corner of the mouth.

Injection—Lp7. Lp7 is the seventh point of the lip. The injection site of the Lp7 is the philtrum column. Lp7 is injected with HA 17.5 mg/ml, 0.02 to 0.1 ml, linear technique, with needle into the subdermal level. Lp7 gives structure and defines philtrum columns.

Injection—Lp8. Lp8 is the eighth point of the lip. The injection sites of the Lp8 are the cutaneous part of the upper and lower lips where the perioral lines are. Inject Lp8 with HA 15 mg/ml, 0.1 to 0.2 ml per quadrant, micro aliquot technique with a cannula or needle, into the subdermal level. Another option is HA 17.5 mg/ml, 0.2 to 0.5 ml per quadrant, fanning technique with a cannula, into the subcutaneous layer when the perioral area is deflated or advancement of the cutaneous part of the upper and lower lips is desirable. Lp8 corrects the perioral lines. It may also correct the deflated aspect of the perioral area. Lp8 should also be addressed when advancement of upper (Lp8) and lower (Lp8) is required. Over injection into Lp8 may lead to flattening, elongation and widening of the upper lip producing an aged appearance.

MD Codes™—M codes, Marionette line M1, M2, M3.

Injection—M1+M2+M3. M1 is the first point and is located at the upper part of the marionette line. Inject M1 with HA 17.5 mg/ml, 0.1 to 0.2 ml, linear technique with needle into sub dermal level. M2 is the second point located at the central part. Inject M2 with HA 17.5 mg/ml, 0.2 to 0.4 ml, linear technique with needle into sub dermal level. M3, the third point, is the lower part of the marionette line. Inject M3 with HA 17.5 mg/ml, 0.2 to 0.4 ml, linear technique with needle into sub dermal level.

MD Codes™—C codes, Chin C1, C2, C3, C4, C5, C6.

Injection—C1. C1 is the first point of the chin. The injection site of the C1 is the labiomental sulcus. Inject C1 with 0.5 ml to 1.0 ml using linear or fanning technique, preferably with cannulas into the subcutaneous level. HA 20 mg/ml is used in C1. The injection reduces the protrusion of the lower lip, gives support to the oral commissure and elongates the chin.

Injection—C2 with Cannula. C2 is the second point of the chin. The injection site of the C2 is the chin apex. Inject C2 with HA 20 mg/ml, 0.3 to 0.5 ml per side, using small bolus technique into the subcutaneous. Cannula is used when C1 also needs to be treated, needle is used when a single point in the midline is required. C2 improves chin height, that is, the vertical dimension.

Injection—C2 with Needle.

Injection—C3. C3 is the third point of the chin. The injection site of the C3 is the anterior chin, to project the pogonion. Inject C3 with HA 20 mg/ml, 0.3 ml to 0.5 ml, using small bolus technique into the bone level. It improves anterior projection of the chin. Be wary of the mental artery, do not go too lateral.

Injection—C4. C4 is the fourth point of the chin. The entry point of the C4 is the submental, area and the product is delivered in midline of the soft tissue menton. Inject C4 with HA 20 mg/ml, 0.3 to 0.5 ml, small bolus technique, with needle into the fat pad. C4 shortens the long chin by rotating it upwards. It improves anterior projection and creates the sulcus in a flat labial-mental angle.

Injection—C5. C5 is the fifth point of the chin. The injection site of the C5 is the lateral lower chin. Inject C5 with HA 20 mg/ml, 0.2 to 0.5 ml, small bolus technique, needle into the bone level. C5 widens the chin and gives lateral support, producing a squarer chin. This point is recommended for men.

Injection—C6. C6 is the sixth point of the chin. The injection site of the C6 is the pre jowl area and sulcus. Inject C6 with HA 20 mg/ml, 0.5 to 1.0 ml, using fanning technique with cannula into the fat pad. C6 can also be injected using small bolus technique with needle into the bone to improve the sulcus. C6 reduces the prominence of the prejowl area and sulcus.

MD Codes™—Jw codes, Jawline Jw1, Jw2, Jw3, Jw4, Jw5.

Injection—Jw1. Jw1 is the first point of the jawline. The injection site of the Jw1 is in the mandibular angle. Inject Jw1 with HA 20 mg/ml, 0.5 to 1.0 ml, using small bolus or fanning technique with needle into the fat pad for lifting effect (indicated for females). Jw1 with HA 20 mg/ml, 0.5 to 1.0 ml, using small bolus with needle into the bone for widening the jaw line (usually recommended for man). Jw1 can also be injected with cannula, 0.5 to 1.0 ml, linear technique into the fat pad.

Injection—Jw2. Jw2 is the second point of the jawline. The injection site of the Jw2 is the pre-auricular area. Injection at Jw2 area in recommended with HA 20 mg/ml or HA 17.5 mg/ml, 0.5 to 1.0 ml, using fanning technique with cannula into the subcutaneous level. Pinch the skin first, if the skin is movable HA 20 mg/ml is recommended; if the skin is not easily movable and attached to deep planes, HA 17.5 mg/ml should be used. Alert Zone: Be wary of the parotid gland.

Injection—Jw3. Jw3 is the third point of the jawline, it is located at the mandible body. Injection at Jw3 area is recommended with HA 20 mg/ml or HA 17.5 mg/ml, 0.5 to 1.0 ml, using linear technique with cannula into the subcutaneous level. HA 20 mg/ml is used when more volume is required, while HA 17.5 mg/ml gives support. Alert Zone: Be wary of facial artery.

Injection—Jw4. Jw4 is the fourth point of the jawline. The injection site of the Jw4 is the prejowl. Injection in Jw4 is recommended with HA 20 mg/ml, 0.5 to 1.0 ml, using linear technique with cannula, into the fat pad.

Injection—Jw5. Jw5 is the fifth point of the jawline. The injection site of the Jw5 is the chin. Jw5 is injected with HA 20 mg/ml, 0.5 to 1.0 ml, with cannula into the fat pad. Small bolus technique is used for projection and linear technique is used for contour.

MD Codes™—N codes, Nose, N1, N2, N3, N4, N5.

Injection—N1. N1 is the first point of the nose. The injection site of the N1 is the anterior nasal spine. N1 is injected with HA 20 mg/ml, 0.1 to 0.3 ml, small bolus technique, with needle at the bone level. N1 lifts the tip of the nose. Be wary of the columellar artery.

Injection—N2. N2 is the second point of the nose. The injection site of the N2 is the anterior septum. N2 is injected with HA 20 mg/ml, 0.1 to 0.3 ml, small bolus technique, with needle at the septum cartilage level. N2 corrects a retruded columella. Be wary of the columellar artery.

Injection—N3. N3 is the third point of the nose. The injection site of the N3 is the frontal nasal angle. N3 is injected with HA 20 mg/ml, 0.1 to 0.3 ml, small bolus technique, with needle at the bone level. N3 improves the nasal hump. Be wary of the supratrochlear artery.

Injection—N4. N4 is the fourth point of the nose. The injection site of the N4 is the frontal nasal angle. N4 is injected with HA 20 mg/ml, 0.1 to 0.2 ml, linear technique, with needle into the bone level. N4 projects the bony nasal dorsum. Be wary of the dorsal nasal artery.

Injection—N5. N5 is the fifth point of the nose. The injection site of the N5 is the cartilaginous dorsum. N5 is injected with HA 20 mg/ml, 0.1 to 0.2 ml, linear technique, with needle into the bone level. N5 projects the cartilaginous dorsum. Be wary of the dorsal nasal artery.

MD CODES Equations

As used herein, the term "MD CODES equations" refers to equations presented by the MD CODES™ Equations.

The MD CODES™ Equations focus on a specific unit of the face and consist of the MD Codes™ that guide treatment of a specific facial sign or deficiency. For example, one facial sign that contributes to an appearance of tiredness is low brows. To improve low brows we must treat both the eyebrows and temples. Therefore, the MD Codes™ Equation for low brows contains the MD Codes™ for the eyebrows and temples. The MD Codes™ Equations are for guidance only and treatment must always be tailored to the individual needs of the patient.

MD CODES Formulas

As used herein, the term "MD CODES formulas" refers to the formulas represented by The MD Codes™ Formulas.

The MD Codes™ Formulas combine all of the MD Codes™ Equations that commonly define a specific emotional attribute. There is one Formula per emotional attribute. Each Formula includes all of the facial units that should be assessed and considered for treatment, and all of the product options available. To look less tired, we may need to treat beyond low eyebrows, we should also address, where appropriate, eyebags, nasolabial folds etc. While most of the MD Codes™ Formulas may be applied universally to patients of all ethnicities and genders, there are some Formulas where specific guidance is given for different patient populations.

The MD Codes™ Formulas are not ready-made treatment plans. The patient may not need every Code listed in the Formula, and there may be other areas of the face that are also having a negative impact on appearance. Treatment plans should always be tailored to the individual needs of the patient. The Formulas are a guide that can help identify the facial areas most likely to be deficient in a patient with a specific attribute and provide a starting point when creating an individualised, holistic treatment plan.

Provided herein is a MD Codes formula to achieve a less saggy look, as follows:
 Sign 1: Saggy cheeks—Anatomic units: Cheeks, Equation=Ck1+Ck2+Ck3+Ck4
 Sign 2: Deep nasolabial folds—Anatomic units: Nasolabial folds, Equation=NL1+NL2+NL3
 Sign 3: Marionette lines—Anatomic units: Marionette lines, Equation=M1+M2+M3
 Sign 4: Jowls Anatomic units: Chin Jawline, Equation=C1+C2+C6 and Jw1+Jw2+Jw3+Jw4+Jw5
 Sign 5: Poor skin quality, —Anatomic units: Skin, Equation=SK
 Sign 6: Submental fat—Anatomic units: Submental area, Equation=SMF Provided herein is an example, a case study (50 years old): I want to look less saggy.

Provided herein is a MD Codes formula to achieve a less sad look in the perioral area, as follows:
 Sign 1: Saggy cheeks—Anatomic units: Cheeks, Equation=Ck1+Ck2+Ck3+Ck4
 Sign 2: Deep nasolabial folds—Anatomic units: Nasolabial folds, Equation=NL1+NL2+NL3
 Sign 3: Lack of lip structure—Anatomic units: Lips, Equation=Lp1+Lp2+Lp3+Lp4+Lp5+Lp7+Lp8
 Sign 4: Downturn or oral commissures—Anatomic units: Lips, Equation=Lp6.
 Sign 5: Deep marionette lines—Anatomic units: Chin, Marionette lines, Equation=C1+C2+C6, and M1+M2+M3.
 Sign 6: Poor skin quality—Anatomic units: Perioral skin, Equation=SK.

Provided herein is a MD Codes formulas to achieve a less sad look in the periorbital area, as follows:
 Sign 1: Low brows—Anatomic units: Eyebrows, Temples, Equation=E1+E2+E3, T1+T2
 Sign 2: Downturn of corner of the eye—Anatomic units: Cheeks, Tear trough, Equation=Ck1+Ck2+Ck3, Tt1+Tt2+Tt3
 Sign 3: Lines around the eyes—Anatomic units: Glabellar lines, Lateral canthal/orbital lines, Equation=G1+G2, O1+O2+O3
 Sign 4: Poor skin quality—Anatomic units: Periorbital skin, Equation=SK Provided herein is an example, a case study (42 years old): I want to look less sad (periorbital and perioral areas).

Provided herein is a MD Codes formula to achieve a less tired look, as follows:
 Sign 1: Low brows—Anatomic units: Eyebrows, Temples, Equation=E1+E2+E3, T1+T2
 Sign 2: Eyebags—Anatomic units: Cheeks, Tear trough, Equation=Ck1+Ck2+Ck3, Tt1+Tt2+Tt3
 Sign 3: Saggy cheeks—Anatomic units: Cheeks, Equation=Ck1+Ck2+Ck3+Ck4
 Sign 4: Lines around the eyes—Anatomic units: Glabellar lines, Lateral canthal/orbital lines, Equation=G1+G2, O1+O2+O3
 Sign 5: Poor skin quality—Anatomic units: Skin, Equation=SK Provided herein is an example, a case study (27 years old): I want to look less tired.

Provided herein is a MD Codes™ formula to achieve a less angry look, as follows:
 Sign 1: Lines around the eyes—Anatomic units: Glabellar lines, Lateral canthal/orbital lines, Equation=G1+G2, O1+O2+O3
 Sign 2: Tension in the lips and chin—Anatomic units: Lips, Oral commissures, Chin, Equation=Lp1+Lp2+Lp3+Lp6, C1+C2+C3

Provided herein is an example, a case study (32 years old): I want to look less angry.

Provided herein is a MD Codes formula to achieve a slimmer look, as follows:

Sign 1: To modify a square, round or heavy face—Anatomic units: Upper cheek, Lower cheek, Chin, Equation=Ck1+Ck2+Ck4, C1+C2+C3+C4+C6.

Sign 2: Submental fat—Anatomic units: Submental area, Equation=SMF

Provided herein is an example, a case study (37 years old): I want to look slimmer.

Provided herein is a MD Codes formula to achieve a more feminine/softer look, as follows:

Sign 1: Prominent forehead—Anatomic units: Forehead, Equation=F1+F2+F3

Sign 2: Sunken temples—Anatomic units: Temples, Equation=T1+T2

Sign 3: Lines around the eyes—Anatomic units: Glabellar lines, Lateral canthal/orbital lines, Equation=G1+G2, O1+O2+O3

Sign 4: To create higher brows—Anatomic units: Eyebrow, Equation=E1+E2+E3

Sign 5: To create fullness in the upper cheek—Anatomic units: Upper cheek, Equation=Ck1+Ck2+Ck3

Sign 6: To create definition/fullness in the lower cheek—Anatomic units: Lower cheek, Equation=Ck4+Ck5

Sign 7: To create full and defined lips—Anatomic units: Lips, Equation=Lp1+Lp2+Lp3+Lp4+Lp5+Lp6+Lp7

Sign 8: To create a triangular chin—Anatomic units: Chin, Equation=C1+C2.

Sign 9: Poor skin quality—Anatomic units: Skin, Equation=SK

Sign 10: Submental fat—Anatomic units: Submental area, Equation=SMF

Provided herein is an example, a case study (48 years old): I want to look more feminine.

Provided herein is a MD Codes formulas to achieve a more masculine look, as follows:

Sign 1: To create a projected supraorbital ridge—Anatomic units: Eyebrows, Equation=E1+E2+E3

Sign 2: To create a square chin—Anatomic units: Chin, Equation=C1+C2+C5

Sign 3: To create a strong jawline—Anatomic units: Jawline, Equation=Jw1+Jw2+Jw3+Jw4+Jw5

Sign 4: To create strong cheekbones—Anatomic units: Cheeks, Equation=Ck1+Ck2

Sign 5: To define and slim the face—Anatomic units: Cheeks, Equation=Ck4

Sign 6: Submental fat—Anatomic units: Submental area, Equation=SMF

Provided herein is an example, a case study (40 years old): I want to look more masculine.

Provided herein is a MD Codes formula to achieve a younger look (upper and midface), as follows:

Sign 1: Volume loss in the forehead—Anatomic units: Forehead, Equation=F1+F2+F3

Sign 2: Volume loss in the temples—Anatomic units: Temples, Equation=T1+T2

Sign 3: Low eyebrows—Anatomic units: Eyebrows, Equation=E1+E2+E3

Sign 4: Lines around the eyesAnatomic units: Glabellar lines, Lateral canthal/orbital lines, Equation=G1+G2, O1+O2+O3

Sign 5: Eyebags—Anatomic units: Cheeks, Tear trough, Equation=Ck1+Ck2+Ck3, Tt1+Tt2+Tt3

Sign 6: Saggy cheeks—Anatomic units: Cheeks, Equation=Ck1+Ck2+Ck3+Ck4

Sign 7: Deep nasolabial folds—Anatomic units: Nasolabial folds, Equation=NL1+NL2+NL3.

Sign 8: Deflated and hollow cheeks—Anatomic units: Cheeks, Equation=Ck1+Ck2+Ck3+Ck4+Ck5

Sign 9: Marionette lines—Anatomic units: Marionette lines, Equation=M1+M2+M3

Sign 10: Deflated and wrinkled lips—Anatomic units: Lips, Equation=Lp1+Lp2+Lp3+Lp4+Lp5+Lp6+Lp7+Lp8

Sign 11: Jawline sagginess—Anatomic units: Jawline, Equation=Jw1+Jw2+Jw3+Jw4+Jw5.

Sign 12: Ageing chin—Anatomic units: Chin, Equation=C1+C2+C3+C4+C6

Sign 13: Poor skin quality—Anatomic units: Skin, Equation=SK

Sign 14: Submental fat—Anatomic units: Submental area, Equation=SMF

Provided herein is an example, a case study (52 years old): I want to look younger.

Provided herein is a MD Codes formulas to achieve a more attractive look for Caucasian patients, as follows:

Sign 1: To create high cheekbones—Anatomic units: Cheeks, Equation=Ck1+Ck2+Ck3.

Sign 2: To create full and defined lips—Anatomic units: Lips, Equation=Lp1+Lp2+Lp3+Lp4+Lp5+Lp6+Lp7.

Sign 3: Lines around the eyes—Anatomic units: Glabellar lines, Lateral canthal/orbital lines, Equation=G1+G2, O1+O2+O3

Provided herein is an example, a case study (25 years old, Caucasian): I want to look more attractive.

Provided herein is a MD Codes formulas to achieve a more attractive look for Asian patients, as follows:

Sign 1: Sharp/strong forehead—Anatomic units: Forehead, Equation=F1+F2+F3

Sign 2: Sunken temples—Anatomic units: Temples, Equation=T1+T2

Sign 3: Lines around the eyes—Anatomic units: Glabellar lines, Lateral canthal/orbital lines, Equation=G1+G2, O1+O2+O3

Sign 4: To enhance eye shape—Anatomic units: Cheeks, Tear trough, Equation=Ck1+Ck2+Ck3, Tt1+Tt2+Tt3.

Sign 5: To slim the face—Anatomic units: Lower cheek, Equation=Ck4

Sign 6: To enhance the chin—Anatomic units: Chin, Equation=C1+C2+C3+C4+C6.

Provided herein is an example, a case study (33 years old, Asian): I want to look more attractive.

Provided herein is a MD Codes formula to achieve a more attractive look for Indian or Middle Eastern patients, as follows:

Sign 1: Lines around the eyes—Anatomic units: Glabellar lines, Lateral canthal/orbital lines, Equation=G1+G2, O1+O2+O3.

Sign 2: Low brows—Anatomic units: Eyebrows, Equation=E1+E2+E3.

Sign 3: Prominent tear trough—Anatomic units: Cheeks, Tear trough, Equation=Ck1+Ck2+Ck3, Tt1+Tt2+Tt3.

Sign 4: Poorly defined/deflated lips—Anatomic units: Lips, Equation=Lp1+Lp2+Lp3+Lp4+Lp5+Lp6+Lp7.

Provided herein is an example, a case study (39 years old, Middle Eastern): I want to look more attractive.

Provided herein is MD Codes™ Formulas to achieve a more attractive look for African patients, as follows:

Assess all areas, but prioritise:
Sign 1: To enhance midface shape—Anatomic units: Cheeks, Equation=Ck1+Ck2+Ck4.
Sign 2: To enhance eye shape—Anatomic units: Cheeks, Tear trough Equation=Ck1+Ck2+Ck3, Tt1+Tt2+Tt3.
Sign 3: To enhance the chin—Anatomic units: Chin, Equation=C1+C2+C3+C4+C6.

Provided herein is a method of using MD Codes™ through the emotional atributes. Patients often point to an area or feature of their face that they want to correct. However, this is rarely the cause of their dissatisfaction with their appearance. They look in the mirror and see something they don't like and identify a line or fold that they believe is the cause. Treating only this line or fold will not solve their problem and can lead to disappointment.

Asking patients how they feel about how they look can help unlock the cause of their dissatisfaction and allow you to create a treatment plan that will address their real concerns. Do they feel like they look tired or sad? Do they want to look slimmer or younger? These emotional attributes provide the clues to the areas and features of the face that may need improvement and present a new, holistic approach to facial revitalisation.

Reduce Negative Emotional Attributes
I want to look less saggy
I want to look less sad
I want to look less tired
I want to look less angry
Enhance Positive Emotional Attributes
I want to look slimmer
I want to look more feminine/softer
I want to look younger
I want to look more attractive Provided herein is a method for treating emotional attributes. It is not unusual that a patient will request the improvement of positive emotional attributes first. However, a practioner need to educate them about proper treatment sequence. Practioners need to "clean the house" and reduce the negative messages first, before enhancing the positive attributes. There are eight different emotional attributes that patients may want or need to improve, but how does this impact their treatment? What are the treatment options for someone who wants to look less tired, for example?

Patients with a particular attribute often have deficiencies in the same facial areas or units. For example, an appearance of tiredness often results from deficiencies in periorbital and infraorbital subunits. By identifying the facial architecture that contributes most often to the appearance of a particular attribute, we can identify the MD Codes™ that would most likely benefit these patients.

EXAMPLES

Example 1, How to use the emotional attributes and the MD Codes™ to fulfill the patient's demand to look more attractive.
Example 2, How to use the emotional attributes and the MD Codes™ to fulfill the patient's demand to look younger.
Example 3, How to use the emotional attributes and the MD Codes™ to fulfill the patient's demand to look younger, less tire, and less saggy.
Example 4, How to use the emotional attributes and the MD Codes™ to fulfill the patient's demand to look less saggy, less tire, and look slimmer.
Example 5, How to use the emotional attributes and the MD Codes™ to fulfill the patient's demand to look less sagyy, less sad, and Younger.

MD DYNA Codes™

The MD DYNA Codes™ are the dynamic codes. It is a friendly system with clear and precise information to deliver injection techniques for the precise placement of product impacting muscle activity, designed to deliver natural facial expression and avoid or correct an abnormal facial appearance on animation.

The MD DYNA Codes™ provide for tools that move beyond facial revitalisation at rest. People are used to assessing the face at rest and are skilled at optimising static features and deficiencies. The emotional attributes approach has taught that resting faces often portray messages or emotions that do not reflect how people feel on the inside. The MD Codes™ and MD Codes™ Formulas have provided the tools to help us improve these emotional attributes and consequently outcomes for patients. But the effect facial expression has on people's appearance and on how people portray themselves to others must be considered.

It is not enough to only improve appearance when the face is at rest. A common fear patients have is that their results will look unnatural, and this usually occurs when doctors do not consider the effect of the treatment on facial animation. Patients are looking for natural results at rest and on animation, which is the most challenging aspect to deliver with injectables.

With this in mind, a new concept—patient expresses should be considered, for example what are the favourable signs that are present on animation but absent at rest? What does this tell about patient's aesthetic needs? Are there unfavourable signs that could be improved? How should the treatment plans be adapted to preserve the favourable signs, optimise the unfavourable signs, and maintain natural expression?

The present invention provides four concepts to help individualize treatment aiming to provide the best possible treatment for each patient. As discussed herein, Multi-Dimensional Aesthetic Scan Assessment (MD ASA™) assesses the following:

Patient wants—Patient perceptions of their appearance
Patient needs—Expert opinion of clinical priorities
Patient feels—Patient's emotional motivation for seeking treatment
Patient expresses—Facial dynamics of natural expression Beauty is dynamic. People think one should look better when smile. But it is not true for everyone. Patients who upgrade their appearance when they smile are generally easier to treat than those who do not. A key feature of dynamic beauty is symmetrical animation, as well as the absence of distracting lines on the skin. A patient at rest, at age 58, she presents negative messages such as tiredness, sadness and sagginess. When the face animates into a smile, all of these messages disappear. Why? Because her cheeks are fuller, her jowls and marionette lines disappear and her eyebags reduce in severity. This indicates what need to done to improve her appearance at rest, and which areas are at risk of looking unnatural on animation after treatment if an injector is not careful with his/her technique? This example clearly shows the power of dynamic beauty even in mature patients. The challenge for injectors is to treat her at rest and maintain the attractiveness that she had on animation without any treatment.

Ageing is a dynamic process. The ageing process affects multiple facial layers: the bony skeleton, fat pads, mimetic muscles and skin. Volume loss at the bone and fat pad levels may impact muscle behaviour by reducing soft tissue support, reducing the facial height and altering the distance from muscle origin and insertion points. Over the years, the impact of constant muscle activity on the skin may produce localised fractures known as lines. Ageing leads to an increment of facial lines both at rest and on animation. Ageing is a dynamic process and its impact may be reduced if patients are assessed on animation. In youth, lines will first appear when the face is animated but with age these same lines will gradually become visible and aesthetic at rest as skin changes become permanent. The concept of dynamic ageing will help us understand the role of muscle activity during the ageing process and to find treatments to reduce the negative impact of muscles on the skin surface.

Facial expressions change with age. Although the human face can express a multitude of positive and negative emotions, herein the present invention focus on the most common features that can be improved with injectables.

The mimetic muscles of the face are involved in expression of emotions. Emotions are often revealed through the gestures of face and body rather than verbal communication, and may be conveyed through a range of microexpressions. Because of this complexity of movement the face must be viewed as a three-dimensional moving unit, not an isolated photograph.

Facial (mimetric) muscles are responsible for expression and appearance of a face. Mimetic muscles work differently in comparison with the other skeletal muscles because they move skin instead of joints, which may play a role in bone and tissue interactions within the ageing face. They are thin, flat muscles that act either as dilators, as elevators and depressors of the eyebrows and mouth, or as sphincters of facial orifices. Generally, facial mimetic muscles have their origin in the bone of the face and insert on the skin and among the fibres of other muscles, with no tendons, except for the sphincteric muscles.

Differences may also be seen under histologic examination, where smaller fibre sizes and greater variation in fibre size may be observed in facial mimetic muscle compared with limb muscles. Facial muscles contain mostly type II muscle fibres that typically contract quickly in brief bursts. These muscles are not able to sustain contraction for long periods of time. Finally, facial mimetic muscles appear to lack typical muscle spindles, which function in resetting resting tone. Three key concepts affect the role of muscle action on facial appearance: muscle pulley and lever systems, length—tension relationship and the action of synergist muscle groups and antagonist muscle pairs. Facial expressions communicated via mimetic muscles are most visible in two key regions—the periorbital and perioral areas.

MD DYNA Codes™ with the respective muscle are as follows:

| MD DYNA Codes ™ | Name of Muscle |
|---|---|
| F | Frontalis |
| C | Corrugator Supercilii |
| P | Procerus |
| OOc | Orbicularis Oculi |
| N | Nasalis |
| LAN | Levator Labii Superioris Alaeque Nasi |
| LLS | Levator Labii Superior |
| ZMj | Zygomaticus Major |
| Zmi | Zygomaticus Minor |
| DSN | Depressor Septi Nasi |
| OO | Orbicularis Oris |

-continued

| MD DYNA Codes ™ | Name of Muscle |
|---|---|
| R | Risorius |
| DAO | Depressor Anguli Oris |
| DLI | Depressor Labii Inferioris |
| M | Mentalis |
| PL | Platysma |

The superficial musculo-aponeurotic system (SMAS) is a fibrofatty superficial facial fascia first consisting of an envelope of collagen fibres, elastic fibres, and fat cells where the mimetic muscles and overlying dermis are enveloped and interconnected. Considerable variability exists in the histologic appearance of the SMAS. It plays an important functional role in appearance and in facial expression, as it is responsible for connecting the facial muscles to the dermis.

Muscles function in synergist/antagonist pairs plays a crucial role in facial expression. The role of functional synergist and antagonist muscle groups and pairs is understood to be crucial in biomechanical efficiency of movement around joints. Consideration of this concept is largely limited in literature to the opposing actions of brow elevators and depressors, which has guided clinical practice. The role of muscle synergists and antagonists in other facial areas has historically received less attention, perhaps because their effects are not immediately obvious. Muscles rarely act in total isolation. Antagonistic muscle action may be defined as muscles working together to allow coordinated movement, while muscles that hold a steady position so that the muscle flexing action is more effective are said to be synergistic. Throughout the face, the action of functional synergist and antagonist muscles contribute to facial movement and appearance. Contraction of the *frontalis* muscle with its synergistic occipitalis and antagonistic action of the procerus, corrugator supercilii, orbicularis oculi is illustrated.

Ageing can disrupt the synergist/antagonist relationship. The fine balance that exists between synergistic and antagonistic mimetic muscles pairs allows for a myriad of facial expressions. If the action of one muscle is completely eliminated, it can cause an imbalance that significantly changes the face's emotive ability. In the mimetic muscles, such an imbalance, may result from structural deficiencies or changes in muscle action due to natural ageing, and is articulated in both the appearance and the expressive ability of the face.

Control and alteration of facial expression can be a powerful tool, which is why it is so important to learn how to observe the face in motion. In spite of this, facial aesthetic literature often avoids fully discussing how aging affects the numerous synergist and antagonist pairs and how changing interactions in the facial musculature should be considered in planning and manipulation of facial aesthetic treatments. Understanding the complex interactions of facial muscles and the effects of loss of stability on muscle action will help physicians better assess the basic morphology of the aging characteristics that are specific to each individual face. This should allow the physician to personalize a course of treatment with neuromodulators and fillers to achieve an aesthetically pleasing outcome adapted to suit each patient.

In contrast, failure to fully understand the interplay between mimetic muscular components and failure to take those interactions into account in a developing a treatment plan, can result in inadequate or inappropriate treatment. The outcome of such treatment may result in an unnatural appearance with negative secondary effects distant from the site of injection. The complex musculature and variable anatomy of the well-balanced face as well as its many expressive functions suggest that planning and careful technique are critical for achieving optimal aesthetic outcomes.

The anatomy of facial expression and periorbital muscle relationships are illustrated in various figures disclosed herein.

MD DYNA Codes™ for periorbital expression (including corresponding mucles and actions) and the corresponding treatments are provided below.

| MD DYNA Codes ™ | Name of Muscle | Action |
|---|---|---|
| F | Frontalis | Elevator: Lifts of the eyebrows and creates the forehead horizontal lines. Expresses surprise or fear |
| C | Corrugator Supercilii | Depressor: Depresses the brow and pulls it medially, as in frowning. Expresses concentration or anger |
| P | Procerus | Depressor: Depresses lower forehead skin in the midline to create a horizontal crease at the bridge of the nose. Expresses concentration |
| OOc | Orbicularis Oculi | Sphincter muscle of the eyelids plays a role in various ocular reflexes. Action of the orbital portion is voluntary and includes furrowing above the bridge of the nose, narrowing of the palpebral fissure, and bunching and protrusion of the eyebrows and eyelid closure. |

The anatomy of facial expression and perioral muscle relationships are illustrated in various figures disclosed herein.

MD DYNA Codes™ for perioral expression (including corresponding mucles and actions) and the corresponding treatments are provided below.

| MD DYNA Codes ™ | Name of Muscle | Action |
|---|---|---|
| N | Nasalis | Assists in widening the nares and in elongating the nose |
| LAN | Levator Labii Superioris Alaeque Nasi | Levator: Dilates the nostril and elevates the upper lip in a snarling appearance of disgust or distain |
| LLS | Levator Labii Superior | Elevator: Elevates the upper lip |
| ZMj | Zygomaticus Major | Elevator: Elevates the upper lip, exposing the maxillary teeth and assists in deepening the nasolabial furrow |
| Zmi | Zygomaticus Minor | Elevator: Draws the corner of the mouth into a smile or grin |
| DSN | Depressor Septi Nasi | Pulls the nasal tip downward |
| OO | Orbicularis Oris | Depressor: Acts as a sphincter around the mouth and its fibres interlace with all other facial muscles that act on the mouth. The 'kissing muscle' |
| R | Risorius | Pulls the mouth corners laterally into a grin or smile |
| DAO | Depressor Anguli Oris | Draws the angle of the mouth sideways and downwards, expressing sadness |
| DLI | Depressor Labii Inferioris | Depresses the lower lip laterally and assists in eversion to express sadness |
| M | Mentalis | Everts the lower lip and rotates the chin upwards, expressing doubt or disdain |

-continued

| MD DYNA Codes ™ | Name of Muscle | Action |
|---|---|---|
| PL | Platysma | Draws the corners of the mouth inferiorly and widens it (as in expressions of sadness and fright). Also draws the skin of the neck superiorly when teeth are clenched |

In some embodiments, the MD DYNA Codes™ is provided for chemical myomodulation.

Underlying principles of chemical myomodulation include neuromodulation: producing flaccid muscle paralysis through chemical denervation. Neuromodulators are used to reduce muscle movement in overacting muscles, for example to diminish hyperdynamic lines or correct position or asymmetry by reducing muscle activity. For BOTOX®/VISTABEL® to work, the neurotoxin BoNTA undergoes a 4 steps process of 1) cell binding; 2) internalisation; 3) translocation and cleavage; and 4) blockage of acetylcholine release.

Practice of chemical myomodulation of the present invention are provided in the following cases studies.

Provided herein is a method of chemical myomodulation, comprising
  Step 1: Diagnosis: Presence of *glabella* and forehead lines
  Step 2: Objective: Lines reduction
  Step 3: MD DYNA Codes™ selection: C+F
  Step 4: After treatment assessment.
Provided herein is a method of chemical myomodulation, comprising:
  Step 1: Diagnosis: Presence of chin and neck lines
  Step 2: Objective: Lines reduction
  Step 3: MD DYNA Codes™ selection, M+PL
  Step 4: After treatment assessment.
Provided herein is a method of chemical myomodulation, comprising:
  Step 1: Diagnosis: Presence of downturn of the corners of the mouth
  Step 2: Objective: Downturn correction
  Step 3: MD DYNA Codes™ selection: DAO
  Step 4: After treatment assessment Hyaluronic acid injectables replace lost volume. Precise injection of hyaluronic acid can return structures to their correct location. A hyaluronic acid bolus replaces lost volume to rebuild the fulcrum, increasing the mechanical advantage of the levator muscle and strengthening its power of contraction. The extra volume reduces sagging, but also indirectly balances contraction of the depressor muscle, reversing some of the changes triggered by ageing. Thus, the impact of dynamic ageing can be reduced with mechanical myomodulation with injectables.

In some embodiments, the MD DYNA Codes™ is provided for mechanical myomodulation. Practice of mechanical myomodulation of the present invention are provided in the following cases studies.

Provided herein is a method of mechanical myomodulation-correction of chin wrinkling, comprising:
  Step 1: Diagnosis: Skin wrinkling when pouting.
  Step 2: Objective: Reduce skin lines
  Step 3: MD DYNA Codes™ selection: M
  Step 4: After treatment assessment.
Correction of chin wrinkling with mechanical myomodulation may preserve mentalis activity.

Provided herein is a method of mechanical myomodulation-correction of gummy smile, comprising:
Step 1: Diagnosis: Presence of gummy smile.
Step 2: Objective: Correct gummy smile+Lift nose tip
Step 3: MD DYNA Codes™ selection: DSN+LAN
Step 4: After treatment assessment.
Correction of gummy smile with mechanical myomodulation is longer lasting than with chemical one.

Provided herein is a method of mechanical myomodulation—correction of asymmetrical smile, comprising:
Step 1: Diagnosis: Presence of asymmetrical smile.
Step 2: Objective: Lift the corner of the mouth, specially her left side.
Step 3: MD DYNA Codes™ selection: Zmj+Zmi
Step 4: After treatment assessment.
Both mouth corners are lifted and a symmetrical smile was obtained.

MD ASA™

Provided herein is a facial assessment tool called MD ASA. As used herein, the term "MD ASA" refers to the facial assessment tool or system represented by MD ASA™

MD ASA™ stands for Multi-Dimensional Aesthetic Scan Assessment. It is a facial assessment tool and consists a system of aesthetic hierarchy. It is developed for organizing the patient's assessment and diagnosis. It systematically defines the process of facial evaluation, helping injectors to decipher the complex and unveiled signs of the face both at rest and on animation. MD ASA™ is a system created to organize the assessment process and train the brain to focus on the unveiled signs of the face.

In social and professional relationships, people relate to each other through the messages of our faces. This is how we speak with the world. However, when people turn eyes onto oneself, people often zoom in on the tiny distractions seen in the magnifying mirror. This is noticeable when injectors consult with their patients. When asked what bothers them, or what they want to improve, they usually point to a distraction that they see in frontal view when they look at themselves in the mirror. However, they are often unaware that this will not change the overall message of the face or how they are perceived by others. Therefore, treatment of this distraction is unlikely to give them the satisfaction with their appearance that they are looking for. The MD ASA provides for treatment of the message, not the distraction.

It is time to understand that every line or distraction people see in their faces is not caused only by a local problem, but has started elsewhere. A classical example is of prominent nasolabial folds that result from a saggy cheek. The challenge is to read the library of different books that visit healthcare professionals in their clinics and are often written in unfamiliar languages. Faces of different genders, ages, ethnicities and genetic structures, and with diverse triggers of environmental ageing are seen. How can the treatment areas be prioritised? How can injectors become the expert that can educate patients on the need to treat "the cause" and not "the symptom"? The MD ASA provides for treatment of the cause of a problem, not the symptom.

The MD ASA™ system stands for Multi-Dimensional Aesthetic Scan Assessment, and was created to organise the assessment process. To achieve this, it is needed to re-train the brain to focus on the cause of the symptoms that patients present—the lines, dark circles or folds. MD ASA™ will help the injector expand the patient's understanding of what we can do to improve not only a distraction but also the message of the face.

Currently, there is a lack of proper diagnosis in medical aesthetics, which can negatively impact patient outcomes and restrict the growth of the aesthetic industry. MD ASA™ was developed to help injectors to feel more confident in their treatment approach and better apply their scientific artistry.

MD ASA™ introduces a new system of aesthetic hierarchy for facial assessment that retrains the brain to decipher facial messages at rest and on animation, and to translate the emotional attributes into key areas for pre- and post-treatment assessment. MD ASA™ teaches injectors how to indirectly treat problem areas and helps patients to understand the need for a full-face approach.

The MDA ASA™ aesthetic hierarchy methodically assesses different areas and features of the face, both in isolation and as part of the overall message of the face. This new system evaluates symmetry and proportion within different facial units, assesses structural deficiencies within facial subunits and identifies distractions that can negatively impact patient satisfaction.

As patients often have a limited budget, the MD ASA™ system is a useful tool to facilitate treatment prioritisation. By combining clinical assessment of severity with patient perceptions of acceptability, a measured and focused discussion of priorities can be had.

It is needed to take patients on a challenging journey that will make them shift focus from the tiny distractions on their faces and expand their vision to the overall message. For this specialist clinical tools—MD ASA™, the MD DYNA Codes™, and the MD Codes™—are needed.

During the ageing process, human face changes faster than people's inner perception of chronological ageing. There is a disconnect or misalignment between what we feel inside and what our face transmits to the world. The concept of "the face speaks" is a landmark in facial assessment and will provide the clues as to which direction we should go in with our treatment plans. The face speaks clearly but it is not always easy to interpret. Faces are books written in foreign languages, and therefore, there is a need for a "dictionary" to help decipher the puzzle of the "ageing process."

The aesthetic hierarchy forms the basis of MD ASA™ and defines the systematic process of facial evaluation, all the way from full facial assessment to assessment of individual distractions of the face. Each section combines patient wants and needs with clinical opinion, ensuring both high-quality aesthetic outcomes and patient satisfaction.

The aesthetic hierarchy are as the follows in the following order: H1: Full face, H2: Facial thirds and neck, H3: Periorbital and Perioral analysis, H4: Facial Units, H5: Facial Subunits/Distractions.

What is to be analysed according to the aesthetic hierarchy is as follows:
H1: Full face: Analysis, Patient feels: Emotional attributes
H2: Facial thirds and neck: Analysis, Patient presents: Symmetry and proportion
H3: Periorbital and Perioral: Analysis, Patient expresses: Animation
H4: Facial Units: Analysis, Patient needs: Key facial areas
H5: Subunits/Distractions: Analysis, Patient wants Combining patient wants with clinical opinion of patient needs will allow an injector to develop an accurate and satisfying treatment plan. Both the patient and the injector should use the qualitative checklist below to rate each area within the aesthetic hierarchy before treatment.
Patient* scale: love, like, live with, hate (* Patient subjective assessment)
Injector scale: ideal, favourable, acceptable, unfavorable ( Related to patient's age, gender and ethnicity)

Prioritizing treatment areas can be based on the above scales. A "priority scale" will help an injector to identify which areas of each aesthetic hierarchy you should focus on first, enabling successful priority planning for treatment. For example, when assessing the facial thirds and neck, an injector should prioritize each area on a scale of 1-4, with 1 being the highest priority and 4 the lowest.

It is important for patients to understand their own aesthetic journey and how a full facial assessment approach will lead to their best possible outcome. Therefore, with patients the ultimate aim of MD ASA™ is to move patients up the hierarchy to H1, where they observe the face as a complete message and understand the need for a full-face treatment approach. It is important for injectors to understand the different elements that contribute to a negative or suboptimal facial message, and learn how to indirectly treat problem areas. Therefore, with injectors the ultimate aim of MD ASA™ is to move down the hierarchy to H5, where the facial messages—the emotional attributes they are so familiar with now—are systematically broken down into the key areas and issues for improvement.

When assessing the full face it is important to take into account the emotional attributes that patients may want to improve (patient feels). Some attributes are negative (downgrading) and should be erased or weakened. Some are positive (upgrading) and should be created or enhanced. Downgrading attributes include but not limited to less tired, less sad, less angry, less saggy. Upgrading attributes include but not limited to younger, more attractive, more feminine, slimmer.

H1: Full face Patient feels For each patient, one must begin at the basics, by ranking the top three most important emotional attributes. Focus on the full face to identify the overall facial messages, the presence of upgrading or downgrading attributes, and the key emotional attributes that should be corrected or enhanced. Does the patient look tired or sad, saggy or angry? Which positive attribute is easier to reach? Youth? Attractiveness? Feminine features? Slim appearance?

Full face assessment should also determine overall facial harmony, proportion and symmetry. What is the injector's general impression of these aspects—are they ideal, favourable, acceptable or unacceptable? Does this change when the face is animated into a smile? As a general rule, patients that "upgrade" their appearance when they smile are usually technically easier to treat than those who downgrade or remain the same. Focusing on H1 it can be difficult for detailing the areas—the facial units—needed to inject to achieve our treatment goals. Therefore, there is a need to look at the face from a different perspective, and move on to the next part of the aesthetic hierarchy: H2.

The injector can use the following scale to assess each facial area/unit: ideal, favourable, acceptable, unacceptable.

H2: Facial thirds and neck, Patient presents This section of the aesthetic hierarchy splits the face into thirds (upper, mid, lower) and the neck. This allows an injector to assess each third in isolation, and pinpoint precise areas of asymmetry or unbalanced proportion, such as the relationship of forehead height and width in the upper face or the position of the upper and lower eyelids in the mid face. An injector should focus on each third and the neck as individual areas, instead of in relation to each other, to ensure objective assessment of each section. The facial elements an injector should assess in each section are listed below. Assessment of the facial thirds and neck should be combined with completion of both the qualitative checklist and the priority scale.

Upper third: forehead height and width; temples; position of eyebrows; forehead lines; glabellar lines.

Mid third: upper eyelid; lower eyelid; anterior cheek; nose tip;

upper nasolabial fold.

Lower third: central and lower nasolabial folds; upper lip; lower lip; philtrum columns; vermilion; oral commissure; marionette lines; chin; prejowl.

Neck: saggy skin; submental fat; medial platysmal bands; lateral platysmal bands; horizontal neck lines.

H3: Periorbital and Perioral analysis, Patient expresses This section of the hierarchy focuses on the periorbital and perioral units, which are the most expressive of the face. Aging signs often appear when the face is animated before they become visible at rest, giving the injector a glimpse into the future and an opportunity to take action early. By analysing the face when it is animated into different expressions, such as smiling or kissing, one can evaluate the impact on appearance and identify which unit should be prioritised for treatment. As a general rule, patients that "upgrade" their appearance when they smile are usually easier to treat than those who downgrade or remain the same.

Facial units can be assessed as follows:

H3: Periorbital: Relationship between eyebrows and eye size, Horizontal eye proportion.

H2: Lower third: Symmetry and Proportion, Does patient improve on animation?

H3: Perioral: Nose-to-lip distance, Lip-to-chin distance, Which is the patient's 'best side'?

H4: Facial Units Patient needs—Splitting the face into its facial subunits allows the injector to assess the patients' needs, combining his/her clinical opinion with their personal treatment objectives (patient needs and wants). One should focus on each MD Codes™ subunit individually, as opposed to in relation to each other, to ensure objective assessment of each section. Facial elements an injector should assess in each subunit are Forehead, Eyebrow, Tear trough, Cheek sagginess, Nasolabial fold, Chin shape. Assessment of each facial subunit should be combined with completion of both the qualitative checklist and the priority scale.

H5: Facial subunits/Distractions, Patient wants—Patients focus on the specific distractions on their faces (patient wants=lines and folds), which are the triggers that lead them to seek treatment. Those distractions should be assessed at rest and on animation. One should aim to verify the degree of severity and how much those distractions downgrade the overall appearance of the patient. Important distractions should be identified and an understanding of the patient's acceptability (in particular 'live with' versus 'hate') will help to prioritise treatment and facilitate patient education. In H5 the experts can focus on the areas that received "acceptable" or "unfavourable" ratings. The objective of treating an area which is considered "acceptable" is to try to make it "favourable" or "ideal." This is a beautification or transformation. Treatment of the areas that received "unfavourable" remarks are the top priority for correction. Sometimes what the patient asks for is not treatable or is much more complex than the patient may think. At this point proper patient education is needed.

An example of some of the distractions the injector should assess in the full face is described. Assessment of each distraction should be combined with completion of both the qualitative checklist and the priority scale.

In some embodiments, the MDA ASA™ is used to assess a saggy look as follows. How to assess a saggy look: Assess all areas, but prioritise
- Sign 1: Saggy cheeks—Anatomic units: Cheeks
- Sign 2: Deep nasolabial folds—Anatomic units: Nasolabial folds
- Sign 3: Marionette lines—Anatomic units: Marionette lines
- Sign 4: Jowls—Anatomic units: Chin, Jawline
- Sign 5: Poor skin quality—Anatomic units: Skin
- Sign 6: Submental fat—Anatomic units: Submental area Rate each area on the scale of: ideal, favourable, acceptable, unacceptable.

In some embodiments, the MDA ASA™ is used to assess a sad look in the periorbital area as follows. How to assess a sad look in the periorbital area: Assess all areas, but prioritize
- Sign 1: Low brows—Anatomic units: Eyebrows, Temples
- Sign 2: Eyebags/Downturn of corner of the eye—Anatomic units: Cheeks, Eyelids, Tear trough.
- Sign 3: Lines around the eyes—Anatomic units: Glabellar lines, Lateral canthal/orbital lines.
- Sign 4: Poor skin quality—Anatomic units: Periorbital skin Rate each area on the scale of: ideal, favourable, acceptable, unacceptable.

In some embodiments, the MDA ASA™ is used to assess a sad look in the periorbital area as follows. How to assess a sad look in the perioral area: Assess all areas, but prioritize:
- Sign 1: Saggy cheeks—Anatomic units: Cheeks
- Sign 2: Deep nasolabial folds—Anatomic units: Nasolabial folds
- Sign 3: Lack of lip structure—Anatomic units: Lips
- Sign 4: Downturn or oral commissures—Anatomic units: Lips
- Sign 5: Deep marionette lines—Anatomic units: Chin, Marionette lines
- Sign 6: Poor skin quality—Anatomic units: Perioral skin Rate each area on the scale of: ideal, favourable, acceptable, unacceptable.

In some embodiments, the MDA ASA™ is used to assess a tired look as follows. How to assess a tired look: Assess all areas, but prioritise:
- Sign 1: Low brows—Anatomic units: Eyebrows, Temples
- Sign 2: Eyebags—Anatomic units: Cheeks, Tear trough
- Sign 3: Saggy cheeks—Anatomic units: Cheeks
- Sign 4: Lines around the eyes—Anatomic units: Glabellar lines, Lateral canthal/orbital lines.
- Sign 5: Poor skin quality—Anatomic units: Skin Rate each area on the scale of: ideal, favourable, acceptable, unacceptable In some embodiments, the MDA ASA™ is used to assess an angry look as follows. How to assess an angry look: Assess all areas, but prioritise
- Sign 1: Lines around the eyes—Anatomic units: Glabellar lines, Lateral canthal/orbital lines
- Sign 2: Tension in the lips and chin—Anatomic units: Lips, Oral commissures, Chin Rate each area on the scale of: ideal, favourable, acceptable, unacceptable In some embodiments, the MDA ASA™ is used to assess the facial shape as follows. How to assess the facial shape:
- Sign 1: To modify a square, round or heavy face—Anatomic units: Upper cheek, Lower cheek, Chin
- Sign 2: Submental fat—Anatomic units: Submental area
  Rate each area on the scale of: ideal, favourable, acceptable, unacceptable In some embodiments, the MDA ASA™ is used to assess the need of a more feminine/softer look as follows. How to assess the need of a more feminine/softer look: Assess all areas, but prioritise:
- Sign 1: Prominent forehead—Anatomic units: Forehead
- Sign 2: Sunken temples—Anatomic units: Temples
- Sign 3: Lines around the eyes—Anatomic units: Glabellar lines, Lateral canthal/orbital lines
- Sign 4: To create higher brows—Anatomic units: Eyebrows
- Sign 5: To create fullness in the upper cheek—Anatomic units: Upper cheek
- Sign 6: To create definition/fullness in the lower cheek—Anatomic units: Lower cheek
- Sign 7: To create full and defined lips—Anatomic units: Lips
- Sign 8: To create a triangular chin—Anatomic units: Chin
- Sign 9: Poor skin quality—Anatomic units: Skin
- Sign 10: Submental fat—Anatomic units: Submental area Rate each area on the scale of: ideal, favourable, acceptable, unacceptable In some embodiments, the MDA ASA™ is used to assess the need of a more masculine look as follows. How to assess the need of a more masculine look: Assess all areas, but prioritise:
- Sign 1: To create a projected supraorbital ridge—Anatomic units: Eyebrows
- Sign 2: To create a square chin—Anatomic units: Chin
- Sign 3: To create a strong jawline—Anatomic units: Jawline
- Sign 4: To create strong cheekbones—Anatomic units: Cheeks
- Sign 5: To define and slim the face—Anatomic units: Cheeks
- Sign 6: Submental fat—Anatomic units: Submental area Rate each area on the scale of: ideal, favourable, acceptable, unacceptable In some embodiments, the MDA ASA™ is used to assess the need of a more attractive look (upper and midface) as follows. How to assess the need of a more attractive look (upper and midface): Assess all areas, but prioritise
- Sign 1: Volume loss in the forehead—Anatomic units: Forehead
- Sign 2: Volume loss in the temples—Anatomic units: Temples
- Sign 3: Low eyebrows—Anatomic units: Eyebrows
- Sign 4: Lines around the eyes—Anatomic units: Glabellar lines, Lateral canthal/orbital lines.
- Sign 5: Eyebags/prominent tear trough—Anatomic units: Cheeks, Tear trough.
- Sign 6: Saggy cheeks—Anatomic units: Cheeks
- Sign 7: Deep nasolabial folds—Anatomic units: Nasolabial folds.

In some embodiments, the MDA ASA™ is used to assess the need of a more attractive look (low face and neck) as follows. How to assess the need of a more attractive look (low face and neck): Assess all areas, but prioritise
- Sign 8: Hollow cheeks—Anatomic units: Cheeks
- Sign 9: Marionette lines—Anatomic units: Marionette lines
- Sign 10: Deflated and wrinkled lips—Anatomic units: Lips
- Sign 11: Jawline sagginess—Anatomic units: Jawline
- Sign 12: Ageing chin—Anatomic units: Chin
- Sign 13: Poor skin quality—Anatomic units: Skin
- Sign 14: Submental fat—Anatomic units: Submental area Rate each area on the scale of: ideal, favourable, acceptable, unacceptable In some embodiments, the MDA ASA™ is used to assess the need of a more attractive look with ethnicity specificities as follows.

Patient's desires relating to attractiveness may vary depending on their ethnicity. There are some common desires requested by patients of Caucasian, Asian, Indian or Middle Eastern and African descent and MD ASA™ provides specific assessment for each ethnicity.

In some embodiments, the MDA ASA™ is used to assess the need of a more attractive look for Caucasian patient as follows. How to assess the need of a more attractive look for Caucasian patients: Assess all areas, but prioritise Sign 1: To create high cheekbones—Anatomic units: Cheeks Sign 2: To create full and defined lips—Anatomic units: Lips Sign 3: Lines around the eyes—Anatomic units: Glabellar lines, Lateral canthal/orbital lines Rate each area on the scale of: ideal, favourable, acceptable, unacceptable In some embodiments, the MDA ASA™ is used to assess the need of a more attractive look for Asian patients as follows. How to assess the need of a more attractive look for Asian patients: Assess all areas, but prioritize Sign 1: Sharp/strong forehead—Anatomic units: Forehead Sign 2: Sunken temples—Anatomic units: Temples Sign 3: Lines around the eyes—Anatomic units: Glabellar lines, Lateral canthal/orbital lines Sign 4: To enhance eye shape—Anatomic units: Cheeks, Tear trough Sign 5: To slim the face—Anatomic units: Lower cheek Sign 6: To enhance the chin—Anatomic units: Chin Rate each area on the scale of: ideal, favourable, acceptable, unacceptable In some embodiments, the MDA ASA™ is used to assess the need of a more attractive look for Indian or Middle Easter patients as follows. How to assess the need of a more attractive look for Indian or Middle Easter patients, Assess all areas, but prioritise:

Sign 1: Lines around the eyes—Anatomic units: Glabellar lines, Lateral canthal/orbital lines Sign 2: Low brows—Anatomic units: Eyebrows Sign 3: Prominent tear trough—Anatomic units: Cheeks, Tear trough Sign 4: Poorly defined/deflated lips—Anatomic units: Lips Rate each area on the scale of: ideal, favourable, acceptable, unacceptable In some embodiments, the MDA ASA™ is used to assess the need of a more attractive look for patiens of African descente as follows. How to assess the need of a more attractive look for patiens of African descente: Assess all areas, but prioritise Sign 1: To enhance midface shape—Anatomic units: Cheeks Sign 2: To enhance eye shape—Anatomic units: Cheeks, Tear trough Sign 3: To enhance the chin—Anatomic units: Chin Rate each area on the scale of: ideal, favourable, acceptable, unacceptable

EXAMPLES

Example 1, Example of a clinical use of MD ASA™.

Example 2, How to assess the need of a younger look (upper and midface).

Example 3, How to assess the need of a younger look (lower face and neck).

Example 4, Case study (52 years old): I want to look younger.

What is claimed is:

1. A method of providing a subject with a consultation by means of a facial assessment tool, comprising:
   identifying a condition or disorder in the subject,
      wherein the identifying a condition or disorder in the subject comprises:
         accessing the facial assessment tool and performing a first facial assessment of the subject, and
         accessing the facial assessment tool and performing a second facial assessment of the subject;
   identifying at least one or more treatment codes useful for treating the condition or disorder,
      wherein the at least one or more treatment codes are identified from at least one between the first facial assessment and the second facial assessment of the subject;
      wherein each one of the treatment codes indicate injection sites on the face or neck of the subject,
      wherein each one of the treatment codes further provides at least one injection instruction, and
      wherein the treatment codes are represented by at least one of letters, numbers and symbols;
   generating a treatment plan to inject a therapeutically effective amount of a pharmaceutical composition at the injection sites identified by the treatment codes and according to the at least one injection instruction provided by the at least one or more treatment codes; and
   optionally visualizing the treatment plan on a graphical display.

2. The method of claim 1, wherein the treatment codes are selected from the group consisting of one or more MD Codes and one or more MD Dyna codes,
   wherein each one of the MD Codes is directed to an anatomical area,
   wherein each one of the MD Codes is represented at least by a letter and a number,
   wherein each one of the MD Dyna codes is directed to a muscle, and
   wherein each one of the MD Dyna codes are represented at least by a letter and a symbol.

3. The method of claim 2, wherein the letters of the MD Codes are divided into anatomical areas,
   wherein the numbers of the MD Codes refer to subunits of the anatomical areas, and
   wherein the numbers of the MD Codes further indicate a delivery sequence of the pharmaceutical composition at the injection sites.

4. The method of claim 3, wherein each one of the MD Codes is further represented by a color and a shape,
   wherein the color indicates an alert area,
   wherein the shape indicates a technical delivery,
   wherein the symbol of the MD Dyna Codes indicates the depth of the injection to be performed, and
   wherein the symbol of the MD Dyna Codes may be a straight line positioned above the letters of the MD Dyna Codes, a straight line positioned under the letters of the MD Dyna Codes, or a dotted circumference positioned around the letters of the MD Dyna Codes.

5. The method of claim 4, wherein the at least one injection instruction is provided by the letters, numbers, colors, shapes, and symbols of at least one or more treatment codes selected from the group consisting of the MD Codes and the MD Dyna Codes.

6. The method of claim 5, wherein the MD codes are selected from the group consisting of: L codes, F codes, T codes, E codes, G codes, O codes, Tt codes, Ck codes, NL codes, Lp codes, M codes, C codes, Jw codes, and N codes;
wherein the L codes are selected from the group consisting of L1, L2, L3, L4, L5, L6, L7, and L8;
wherein the F codes are selected from the group consisting of F1, F2, and F3;
wherein the T code are selected from the group consisting of T1 and T2;
wherein the E codes are selected from the group consisting of E1, E2, and E3;
wherein the G codes are selected from the group consisting of G1 and G2;
wherein the O codes are selected from the group consisting of O1, O2, and O3;
wherein the Tt codes are selected from the group consisting of Tt1, Tt2, and Tt3;
wherein the Ck codes are selected from the group consisting of Ck1, Ck2, Ck3, Ck4, and Ck5;
wherein the NL codes are selected from the group consisting of NL1, NL2, and NL3;
wherein the Lp codes are Lp1, Lp2, Lp3, Lp4, Lp5, Lp6, Lp7, and Lp8;
wherein the M codes are selected from the group consisting of M1, M2, and M3;
wherein the C codes are selected from the group consisting of C1, C2, C3, C4, C5, and C6;
wherein the Jw codes are selected from the group consisting of Jw1, Jw2, Jw3, Jw4, and Jw5; and
wherein the N codes are selected from the group consisting of N1, N2, N3, N4, and N5.

7. The method of claim 6, wherein the MD DYNA codes for periorbital expression are selected from the group consisting of F, C, P, and 00c,
wherein the MD DYNA Codes for perioral expression are selected from the group consisting of N, LAN, LLS, ZMi, Ami, DSN, 00, R, DAO, DLI, M, and PL;
wherein the injection is for chemical myomodulation; and
wherein the pharmaceutical composition is botulinum toxin-type A.

8. The method of claim 7, wherein if *glabella* and forehead lines are identified, then MD DYNA Codes C+F are selected to reduce the *glabella* and forehead lines;
wherein if chin and neck lines are identified, MD DYNA Codes M+PL are selected to reduce the chin and neck lines; and
wherein if downturn of the corners of the mouth is identified, MD DYNA Codes DAO are selected to correct the downturn of the corners of the mouth.

9. The method of claim 2, wherein the MD Codes are grouped to form at least one MD Codes equation, and wherein each MD Codes equation guides the injection of the pharmaceutical composition at the injection sites.

10. The method of claim 1, wherein if skin wrinkling when pouting is identified, the MD DYNA Code M is selected to reduce skin lines;
wherein if gummy smile is identified, the MD DYNA Codes DSN+LAN are selected to correct gummy smile and to lift nose tip; and
wherein if asymmetrical smile is identified, the MD DYNA Codes Zmj+Zmi are selected to lift a corner of the mouth.

11. The method of claim 1, wherein the identifying at least one or more treatment codes and the generating a treatment plan are performed by the facial assessment tool.

12. The method of claim 1, wherein the first facial assessment of the subject is a condition wherein the subject's face is at rest and the second facial assessment of the subject is a condition wherein the subject's face is animated.

13. The method of claim 12, wherein it further comprises displaying the injection sites at a graphical display of the facial assessment tool, and
wherein the displaying the injection sites at a graphical display of the facial assessment tool further comprises overlaying any of the injection sites with an image of the subject in need.

14. The method of claim 1, wherein the MD codes are identified by the facial assessment tool from the first facial assessment of the subject and the MD Dyna codes are identified by the facial assessment tool from the second facial assessment of the subject.

15. The method of claim 14, wherein the treatment plan is generated by the facial assessment tool from an aesthetic hierarchy; wherein the aesthetic hierarchy is divided into five different levels H1, H2, H3, H4, and H5; and
wherein:
the first level (H1) of the aesthetic hierarchy is a full-face analysis,
the second level (H2) of the aesthetic hierarchy corresponds to a face's division into thirds,
the third level (H3) of the aesthetic hierarchy corresponds to a periorbital and perioral analysis,
the fourth level (H4) of the aesthetic hierarchy splits the face into its facial subunits, and
the fifth level (H5) of the aesthetic hierarchy considers at least one distraction of the face, wherein the distractions are considered at rest and on animation.

16. The method according to claim 1, further comprising:
determining if an indicator of at least one aging trigger point (ATP) is present in the individual's face,
quantifying the presence of at least one aging trigger point; and
developing the treatment plan based on the quantified aging trigger point;
wherein the at least one aging trigger point is subdivided into at least one bone aging trigger point (BATP) and at least one surface aging trigger point (SATP),
wherein the determining is performed with a feature selected from the group consisting of:
a visual assessment of the individual's face, wherein the visual assessment is performed in several positions of the individual's face, at rest and on animation, and
a palpitation on the individual's face to verify bone structure and fat pad volume.

17. The method according to claim 16, wherein the visual assessment of the individual's face compares a picture of the individual's face with a picture of the individual's parent's face of the same gender.

18. A system for providing a subject with a consultation, the system having means to identify a cosmetic, and aesthetic and/or a dermatologic condition or disorder in the subject and by means of a facial assessment tool;
wherein the system is configured to perform a first facial assessment of the subject and a second facial assessment of the subject, wherein the first and second facial assessments are performed by means of the facial assessment tool,
wherein the system is configured to identify, by means of the facial assessment tool, at least one or more treatment codes useful for treating the condition or disorder;
wherein the at least one or more treatment codes are identified from at least one between the first facial assessment and the second facial assessment of the subject;
wherein each one of the treatment codes indicate injection sites on the face or neck of the subject,
wherein each one of the treatment codes further provides at least one injection instruction,
wherein the treatment codes are represented at least by one of letters, numbers and symbols,
wherein the system is configured to generate a treatment plan to inject a therapeutically effective amount of a pharmaceutical composition at the injection sites identified by the treatment codes and according to the at least one injection instruction provided by the treatment codes; and
wherein the system is configured to visualize the treatment plan on a graphical display.

19. The system of claim 18, wherein the treatment codes are selected from the group consisting of one or more MD Codes and one or more MD Dyna codes,
wherein each one of the MD Codes is directed to an anatomical area,
wherein each one of the MD Codes is represented at least by a letter and a number,
wherein each one of the MD Dyna codes is directed to a muscle, and
wherein each one of the MD Dyna codes are represented at least by a letter and a symbol.

20. The system of claim 19, wherein the letter of the MD Codes is directed to a name of the anatomical area and the number of the MD Codes refer to subunits of the anatomical area, and wherein the numbers further indicate a delivery sequence of the pharmaceutical composition at the injection sites.

21. The system of claim 20, wherein each one of the MD Codes is further represented by a color and a shape,
wherein the color indicates an alert area, and wherein the shape indicates a technical delivery,
wherein the symbol of the MD Dyna Codes indicates the depth of the injection to be performed, and
wherein the symbol of the MD Dyna Codes is a straight line positioned above the letters of the MD Dyna Codes, a straight line positioned either above or under the letters of the MD Dyna Codes, or a dotted circumference positioned around the letters of the MD Dyna Codes.

22. The system of claim 21, wherein the MD Codes are grouped to form at least one MD Codes equation, and wherein each MD Codes equation guides the injection of the pharmaceutical composition at the injection sites.

23. The system of claim 21, wherein the at least one injection instruction is provided by the letters, numbers, colors, shapes, and symbols of at least one or more treatment codes selected from the group consisting of the MD Codes and the MD Dyna Codes.

24. The system of claim 23, wherein it comprises means for visualizing overlying any of the injection sites of one or more treatment codes with an image of the subject.

25. The system of claim 24, further comprising visualizing the injection sites on the facial assessment tool.

26. The system of claim 25, wherein the facial assessment tool is further configured to perform at least one of the following:
identifying the at least one or more treatment codes, and generating the treatment plan.

27. The system of claim 26, wherein the treatment plan is generated by the facial assessment tool from an aesthetic hierarchy;
wherein the aesthetic hierarchy is divided into five different levels H1, H2, H3, H4, and H5; and
wherein:
the first level (H1) of the aesthetic hierarchy is a full-face analysis,
the second level (H2) of the aesthetic hierarchy corresponds to a face's division into thirds,
the third level (H3) of the aesthetic hierarchy corresponds to a periorbital and perioral analysis,
the fourth level (H4) of the aesthetic hierarchy splits the face into its facial subunits, and
the fifth level (H5) of the aesthetic hierarchy considers at least one distraction of the face, wherein the distractions are considered at rest and on animation.

28. The system of claim 25, wherein the first facial assessment of the subject is a condition wherein the subject's face is at rest and the second facial assessment of the subject is a condition wherein the subject's face is animated.

29. The system of claim 28, wherein the first facial assessment of the subject identifies the MD codes, and wherein the second facial assessment of the subject identifies the MD Dyna codes.

30. The system of claim 25, wherein the facial assessment tool comprises a graphical display configured to display the injection sites, and wherein the facial assessment tool is further configured to overlay any of the injection sites with an image of the subject in need.

31. The system according to claim 19, wherein the visual assessment of the individual's face compares a picture of the individual's face with a picture of the individual's parent' face of the same gender.

32. The system of claim 18, wherein the MD Codes are selected from the group consisting of: L codes, F codes, T codes, Lp codes, E codes, M codes, G codes, C codes, O codes, Jw codes, Tt codes, and N codes;
wherein the L codes are selected from the group consisting of L1, L2, L3, L4, L5, L6, L7, and L8;
wherein F codes are selected from the group consisting of F1, F2, and F3;
wherein T codes are selected from the group consisting of T1 and T2;
wherein E codes are selected from the group consisting of E1, E2, and E3;
wherein G codes are selected from the group consisting of G1 and G2;
wherein O codes are selected from the group consisting of O1, O2, and O3;
wherein T codes are selected from the group consisting Tt1, Tt2, and Tt3;
wherein Ck codes are selected from the group consisting of Ck1, Ck2, Ck3, Ck4, and Ck5;
wherein NL codes selected from the group consisting of are NL1, NL2, and NL3;
wherein Lp codes are selected from the group consisting of Lp1, Lp2, Lp3, Lp4, Lp5, Lp6, Lp7, and Lp8;
wherein M codes are selected from the group consisting of M1, M2, and M3;
wherein C codes are selected from the group consisting of C1, C2, C3, C4, C5, and C6;

wherein Jw codes are selected from the group consisting of Jw1, Jw2, Jw3, Jw4, and Jw5; and wherein N codes are selected from the group consisting of N1, N2, N3, N4, and N5.

33. The system of claim 18, wherein the MD Dyna Codes for periorbital expression are selected from the group consisting of F, C, P, and OOc; and wherein the MD DYNA Codes for perioral expression are selected from the group consisting of N, LAN, LLS, ZMi, Ami, DSN, OO, R, DAO, DLI, M, and PL.

34. The system according to claim 18, wherein it is further configured to determine if an indicator of at least one aging trigger point (ATP) is present in the individual's face by performing at least one selected from the group consisting of:
   a visual assessment of the individual's face, wherein the visual assessment is performed in several positions of the individual's face, at rest and on animation, and
   a palpitation on the individual's face to verify bone structure and fat pad volume;
   wherein the at least one aging trigger point is subdivided into at least one bone aging trigger point (BATP) and at least one surface aging trigger point (SATP); and
   wherein the system is further configured:
   to quantify the presence of at least one aging trigger point, and
   to develop the treatment plan further based on the quantified aging trigger point.

35. A method of treating a subject in need thereof, comprising:
   diagnosing a subject thereby identifying a condition or disorder; and
   selecting a treatment using MD DYNA codes;
   wherein MD DYNA codes indicate injection sites on face or neck of the subject and injecting an effective amount of a pharmaceutical composition at each of the injection sites;
   wherein the condition or disorder is an aesthetic condition or disorder;
   wherein the pharmaceutical composition is selected from the group consisting of hyaluronic acid (HA), HA-based fillers, HA-derivatives, botulinum toxin-type A (BoNT-A), fillers, and combinations thereof;
   wherein the MD DYNA codes for periorbital expression are selected from the group consisting of F, C, P, and 00c; wherein the MD DYNA Codes for perioral expression are selected from the group consisting of N, LAN, LLS, ZMi, Ami, DSN, 00, R, DAO, DLI, M, and PL; wherein the injection is for chemical myomodulation, and the pharmaceutical composition is botulinum toxin-type A;
   wherein if presence of *glabella* and forehead lines is identified, MD DYNA Codes C+F are selected to reduce lines; wherein if presence of chin and neck lines is identified, MD DYNA Codes M+PL are selected to reduce lines; wherein if presence of downturn of the corners of the mouth is identified, MD DYNA Codes DAO are selected to correct downturn;
   wherein the injection is for mechanical myomodulation, and the pharmaceutical composition is HA, HAbased fillers, or HA-derivatives;
   wherein if skin wrinkling when pouting is identified, MD DYNA Codes M is selected to reduce skin lines; wherein if presence of gummy smile is identified, MD DYNA Codes DSN+LAN are selected to correct gummy smile and Lift nose tip; and wherein if presence of asymmetrical smile, MD DYNA Codes Zmj+Zmi are selected to lift the corner of the mouth.

36. The method of any of claims 35, wherein MD ASA is used to assess a saggy look comprising assessing all facial areas, but prioritizing the following:
   Sign 1: Saggy cheeks—Anatomic units: Cheeks
   Sign 2: Deep nasolabial folds—Anatomic units: Nasolabial folds
   Sign 3: Marionette lines—Anatomic units: Marionette lines
   Sign 4: Jowls—Anatomic units: Chin, Jawline
   Sign 5: Poor skin quality—Anatomic units: Skin
   Sign 6: Submental fat—Anatomic units: Submental area.

37. The method of any of claims 36, wherein MDA ASA is used to assess a sad look in the periorbital area comprising assess all areas, but prioritizing the following:
   Sign 1: Low brows—Anatomic units: Eyebrows, Temples
   Sign 2: Eyebags/Downturn of corner of the eye—Anatomic units: Cheeks, Eyelids, Tear trough
   Sign 3: Lines around the eyes—Anatomic units: Glabellar lines, Lateral canthal/orbital lines
   Sign 4: Poor skin quality—Anatomic units: Periorbital skin.

38. The method of claim 37, wherein MDA ASA is used to assess a sad look in the periorbital area, comprising assessing all areas and prioritizing the following:
   Sign 1: Saggy cheeks—Anatomic units: Cheeks
   Sign 2: Deep nasolabial folds—Anatomic units: Nasolabial folds
   Sign 3: Lack of lip structure—Anatomic units: Lips
   Sign 4: Downturn or oral commissures—Anatomic units: Lips
   Sign 5: Deep marionette lines—Anatomic units: Chin, Marionette lines
   Sign 6: Poor skin quality—Anatomic units: Perioral skin.

39. The method of claim 38, wherein MDA ASA is used to assess a tired look, comprising assessing all areas and prioritizing the following:
   Sign 1: Low brows—Anatomic units: Eyebrows, Temples
   Sign 2: Eyebags—Anatomic units: Cheeks, Tear trough
   Sign 3: Saggy cheeks—Anatomic units: Cheeks
   Sign 4: Lines around the eyes—Anatomic units: Glabellar lines, Lateral canthal/orbital lines
   Sign 5: Poor skin quality—Anatomic units: Skin.

40. The method of claim 39, wherein MDA ASA is used to assess an angry look, comprising assessing all areas and prioritizing the following:
   Sign 1: Lines around the eyes—Anatomic units: Glabellar lines, Lateral canthal/orbital lines
   Sign 2: Tension in the lips and chin—Anatomic units: Lips, Oral commissures, Chin.

41. The method of claim 40, wherein MDA ASA is used to assess the facial shape, comprising assessing all areas and prioritizing the following:
   Sign 1: To modify a square, round or heavy face—Anatomic units: Upper cheek, Lower cheek, Chin
   Sign 2: Submental fat—Anatomic units: Submental area.

42. The method of claim 41, wherein MDA ASA is used to assess the need of a more feminine/softer look, comprising assessing all areas, but prioritizing the following:
   Sign 1: Prominent forehead—Anatomic units: Forehead
   Sign 2: Sunken temples—Anatomic units: Temples
   Sign 3: Lines around the eyes—Anatomic units: Glabellar lines, Lateral canthal/orbital lines
   Sign 4: To create higher brows—Anatomic units: Eyebrows Sign 5: To create fullness in the upper cheek—Anatomic units: Upper cheek Sign 6: To create definition/fullness in the lower cheek—Anatomic units: Lower cheek Sign 7: To create full and defined lips—Anatomic units: Lips Sign 8: To create a triangular chin—Anatomic units: Chin Sign 9: Poor skin quality—Anatomic units: Skin Sign 10: Submental fat—Anatomic units: Submental area.

43. The method of claim 42, wherein MDA ASA is used to assess the need of a more masculine look, comprising assessing all areas, but prioritizing the following:

Sign 1: To create a projected supraorbital ridge—Anatomic units: Eyebrows Sign 2: To create a square chin—Anatomic units: Chin Sign 3: To create a strong jawline—Anatomic units: Jawline Sign 4: To create strong cheekbones—Anatomic units: Cheeks Sign 5: To define and slim the face—Anatomic units: Cheeks Sign 6: Submental fat—Anatomic units: Submental area.

44. The method of claim 43, wherein MDA ASA is used to assess the need of a more attractive look (upper and midface), comprising assessing all areas, but prioritizing the following:

Sign 1: Volume loss in the forehead—Anatomic units: Forehead

Sign 2: Volume loss in the temples—Anatomic units: Temples

Sign 3: Low eyebrows—Anatomic units: Eyebrows

Sign 4: Lines around the eyes—Anatomic units: Glabellar lines, Lateral canthal/orbital lines Sign 5: Eyebags/prominent tear trough—Anatomic units: Cheeks, Tear trough Sign 6: Saggy cheeks—Anatomic units: Cheeks Sign 7: Deep nasolabial folds—Anatomic units: Nasolabial folds Sign 8: Hollow cheeks—Anatomic units: Cheeks Sign 9: Marionette lines—Anatomic units: Marionette lines Sign 10: Deflated and wrinkled lips—Anatomic units: Lips Sign 11: Jawline sagginess—Anatomic units: Jawline Sign 12: Ageing chin—Anatomic units: Chin Sign 13: Poor skin quality—Anatomic units: Skin Sign 14: Submental fat—Anatomic units: Submental area.

45. The method of any of claim 44, wherein MDA ASA is used to assess the need of a more attractive look with ethnicity specificities including the following:

(i) to assess the need of a more attractive look for a Caucasian subject, comprising assessing all areas, but prioritizing the following:

Sign 1: To create high cheekbones—Anatomic units: Cheeks

Sign 2: To create full and defined lips—Anatomic units: Lips

Sign 3: Lines around the eyes—Anatomic units: Glabellar lines, Lateral canthal/orbital lines;

(ii) to assess the need of a more attractive look for an Asian subject, comprising assessing all areas, but prioritizing the following:

Sign 1: Sharp/strong forehead—Anatomic units: Forehead

Sign 2: Sunken temples—Anatomic units: Temples

Sign 3: Lines around the eyes—Anatomic units: Glabellar lines, Lateral canthal/orbital lines Sign 4: To enhance eye shape—Anatomic units: Cheeks, Tear trough Sign 5: To slim the face—Anatomic units: Lower cheek Sign 6: To enhance the chin—Anatomic units: Chin;

(iii) to assess the need of a more attractive look for an Indian or Middle Easter subject, comprising assessing all areas, but prioritizing the following:

Sign 1: Lines around the eyes—Anatomic units: Glabellar lines, Lateral canthal/orbital lines Sign 2: Low brows—Anatomic units: Eyebrows Sign 3: Prominent tear trough—Anatomic units: Cheeks, Tear trough Sign 4: Poorly defined/deflated lips—Anatomic units: Lips; or (iv) to assess the need of a more attractive look for a subject of African descent, comprising assessing all areas, but prioritizing the following:

Sign 1: To enhance midface shape—Anatomic units: Cheeks

Sign 2: To enhance eye shape—Anatomic units: Cheeks, Tear trough

Sign 3: To enhance the Anatomic units: Chin.

\* \* \* \* \*